US012622901B2

(12) United States Patent
Gray et al.

(10) Patent No.: US 12,622,901 B2
(45) Date of Patent: May 12, 2026

(54) COMPOUNDS FOR TAU PROTEIN DEGRADATION

(71) Applicants: Dana-Farber Cancer Institute, Inc., Boston, MA (US); The General Hospital Corporation, Boston, MA (US)

(72) Inventors: Nathanael S. Gray, Boston, MA (US); Stephen J. Haggarty, Gloucester, MA (US); Quan Cai, Shanghai (CN); Tinghu Zhang, Brookline, MA (US); Maria Catarina Telo Baptista Lima da Silva, Revere, MA (US); Fleur M. Ferguson, Cambridge, MA (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 18/200,950

(22) Filed: May 23, 2023

(65) Prior Publication Data

US 2024/0091213 A1 Mar. 21, 2024

Related U.S. Application Data

(63) Continuation of application No. 16/630,294, filed as application No. PCT/US2018/041787 on Jul. 12, 2018, now abandoned.

(60) Provisional application No. 62/531,773, filed on Jul. 12, 2017.

(51) Int. Cl.

| | |
|---|---|
| ***A61K 31/4545*** | (2006.01) |
| ***A61K 31/437*** | (2006.01) |
| ***A61K 38/05*** | (2006.01) |
| ***A61K 51/04*** | (2006.01) |
| ***A61P 25/28*** | (2006.01) |
| ***C07D 471/04*** | (2006.01) |
| ***C07K 5/062*** | (2006.01) |
| ***G01N 33/534*** | (2006.01) |
| ***G01N 33/68*** | (2006.01) |

(52) U.S. Cl.

CPC ........ *A61K 31/4545* (2013.01); *A61K 31/437* (2013.01); *A61K 38/05* (2013.01); *A61K 51/0455* (2013.01); *A61P 25/28* (2018.01); *C07D 471/04* (2013.01); *C07K 5/06034* (2013.01); *G01N 33/534* (2013.01); *G01N 33/6896* (2013.01)

(58) Field of Classification Search

CPC .. A61K 31/4545; A61K 31/437; A61K 38/05; A61K 51/0455; A61P 25/28; C07D 471/04; C07K 5/06034; G01N 33/534; G01N 33/6896

USPC ........................................................ 424/1.65

See application file for complete search history.

(56) References Cited

U.S. PATENT DOCUMENTS

| | | | |
|---|---|---|---|
| 6,274,119 | B1 | 8/2001 | Barrio et al. |
| 8,691,187 | B2 | 4/2014 | Szardenings et al. |
| 9,249,101 | B2 | 2/2016 | Kudo et al. |
| 9,402,082 | B2 | 7/2016 | Deshpande |
| 9,694,084 | B2 | 7/2017 | Bradner et al. |
| 9,993,472 | B2 | 6/2018 | Laberge et al. |
| 2012/0302755 | A1 | 11/2012 | Szardenings et al. |
| 2015/0239878 | A1 | 8/2015 | Iguchi et al. |
| 2015/0291562 | A1 | 10/2015 | Crew et al. |
| 2016/0058872 | A1 | 3/2016 | Crew et al. |
| 2016/0207919 | A1 | 7/2016 | Gobbi et al. |
| 2016/0228586 | A1 | 8/2016 | Attardo et al. |
| 2016/0244411 | A1 | 8/2016 | Kudo et al. |
| 2017/0121321 | A1 | 5/2017 | Crews et al. |
| 2018/0215731 | A1 | 8/2018 | Crew et al. |
| 2019/0290778 | A1 | 9/2019 | Nomura et al. |

(Continued)

FOREIGN PATENT DOCUMENTS

| | | | |
|---|---|---|---|
| CN | 106543185 | A | 3/2017 |
| EP | 3535265 | A2 | 9/2019 |
| JP | 2016-531851 | A | 10/2016 |

(Continued)

OTHER PUBLICATIONS

Bondeson et al., "Lessons in Protac design from selective degradation with a promiscuous warhead," Cell Chem Biol., 25(1):78-87 (2018).

(Continued)

*Primary Examiner* — Michael G. Hartley
*Assistant Examiner* — Sean R Donohue
(74) *Attorney, Agent, or Firm* — Fish & Richardson P.C.

(57) ABSTRACT

Provided herein are bifunctional compounds that bind tau protein and/or promote targeted ubiquitination for the degradation of tau protein. In particular, provided are compounds that can bind tau protein, a protein whose aggregation is implicated in a variety of neurodegenerative disease (e.g., tauopathies), and can promote its degradation by recruiting an E3 ubiquitin ligase (e.g., Cereblon), which can ubiquitinate tau protein, marking it for proteasomal degradation. Also provided are radiolabeled forms of the bifunctional compounds, pharmaceutical compositions comprising the bifunctional compounds, methods of detecting and/or diagnosing neurological disorders, methods of detecting and/or diagnosing pathological aggregation of tau protein (e.g., in the central nervous system), methods of treating and/or preventing neurological disorders, and methods of promoting the degradation of tau protein by E3 ubiquitin ligase activity in a subject by administering a compound or composition described herein.

13 Claims, 17 Drawing Sheets

(56) References Cited

U.S. PATENT DOCUMENTS

2023/0133538 A1 5/2023 Ferguson et al.

FOREIGN PATENT DOCUMENTS

| | | | |
|---|---|---|---|
| WO | WO 2008/016893 | A1 | 2/2008 |
| WO | WO 2008/128171 | A2 | 10/2008 |
| WO | 2014028445 | A2 | 2/2014 |
| WO | WO 2014/060767 | A1 | 4/2014 |
| WO | WO 2014/060768 | A1 | 4/2014 |
| WO | WO 2015/047902 | A1 | 4/2015 |
| WO | WO 2015/060365 | A1 | 4/2015 |
| WO | WO 2015/092420 | A1 | 6/2015 |
| WO | 2016105518 | A1 | 6/2016 |
| WO | WO 2016/197032 | A1 | 12/2016 |
| WO | 2017011590 | A1 | 1/2017 |
| WO | 2017024318 | A1 | 2/2017 |
| WO | 2017030814 | A2 | 2/2017 |
| WO | 2018102067 | A2 | 6/2018 |
| WO | WO 2018/237026 | A1 | 12/2018 |
| WO | 2019014429 | A1 | 1/2019 |
| WO | WO 2021/011913 | A1 | 1/2021 |
| WO | WO 2021/097243 | A1 | 5/2021 |

OTHER PUBLICATIONS

Caplus Accession No. 2017:229794, 4 pages, Bradner et al., "Using heterobifunctional compounds for targeted CAR protein degradation to attenuate adoptive immunotherapy associated adverse inflammation."
Chu et al., "Specific knockdown of endogenous tau protein by peptide-directed ubiquitin-proteasome degradation," Cell Chem Biol., 23(4):453-61, DOI:10.1016.j.chembiol.2016.02.016 (Apr. 21, 2016).
Flach et al., "Axotrophin/March7 acts as an E3 ubiquitin ligase and ubiquinates tau protein in vitro impairing microtubule binding," Biochim Biophys Acta., 1842(9):1527-38, DOI:10.1016/j.bbadis.2014.05.029, Epub 2014 (Sep. 2014).
Galdeano et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities," J. Med Chem., 57(20):8657-63, DOI:10.1021/jm5011258, Epub Oct. 6, 2014 (Oct. 23, 2014).
Lai et al., "Modular Protac Design for the Degradation of Oncogenic BCR-ABL," Agnew Chem Int Ed Engl., 55(2):807-810 (2016).
Li et al., "Proteolysis-targeting chimera (PROTAC) for targeted protein degradation and cancer therapy," Journal of Hematology & Oncology, 13:50, 14 pages (2020).
Silva et al., "Human iPSC-derived neuronal model of tau-A152T frontotemporal dementia reveals tau-mediated mechanisms of neuronal vulnerability," Stem Cell Reports, 7(3):325-340, DOI:10.1016/j.stemcr.2016.08.001, Epub Sep. 1, 2016 (Sep. 13, 2016).
Silva et al., "Targeted degradation of aberrant tau in frontotemporal dementia patient-derived neuronal cell models," Biochemistry and Chemical Biology Neuroscience, 8:e45457, DOI:10.7554/eLife.45457 (2019).
Extended European Search Report mailed Jun. 6, 2021, for European Application No. 18831849.7 (14 pages).
International Search Report and Written Opinion in Application No. PCT/US2018/041787 dated Sep. 11, 2018 (9 pages).
International Preliminary Report on Patentability in Application No. PCT/US2018/041787 dated Jan. 14, 2020 (7 pages).
Ariza et al., "Tau Positron Emission Tomography (PET) Imaging: Past, Present, and Future," J Med Chem., Jun. 2015, 58(11):4365-82.
Chang and Stewart, "What is the functional role of the thalidomide binding protein cereblon?," Int. J. Biochem. Mol. Biol., 2011, 2(3):287-94.
Cleveland et al., "Purification of tau, a microtubule-associated protein that induces assembly of microtubules from purified tubulin," J. Mol. Biol., Oct. 1977, 116(2):207-225.
Duan et al., "Characterization of the VHL tumor suppressor gene product: localization, complex formation, and the effect of natural inactivating mutations," Proc. Natl. Acad. Sci. US.A. 1995, 92(14):6459-63.
Extended European Search Report in European Appln. No. 23195169.0, mailed on Oct. 31, 2024, 19 pages.
Glick et al., "Autophagy: cellular and molecular mechanisms," J. Pathol., May 2010, 221(1):3-12.
Hartmann et al., "Structural Dynamics of the Cereblon Ligand Binding Domain," PLoS One, May 2015, 10(5):e0128342, 16 pages.
Hashimoto et al., "Radiosynthesis, Photoisomerization, Biodistribution, and Metabolite Analysis of $^{11}$C-PBB3 as a Clinically Useful PET Probe for Imaging of Tau Pathology," J. Nucl. Med., Sep. 2014, 55(9):1532-1538.
Higgins et al., "A mutation in a novel ATP-dependent Lon protease gene in a kindred with mild mental retardation," Neurology, Nov. 2004, 63(10):1927-31.
International Preliminary Report on Patentability in International Appln. No. PCT/US2021/022758, mailed on Sep. 29, 2022, 6 pages.
International Search Report and Written Opinion in International Appln. No. PCT/US2021/022758, mailed on Jun. 14, 2021, 8 pages.
Matyskiela et al., "A novel cereblon modulator recruits GSPT1 to the CRL4$^{CRBN}$ ubiquitin ligase," Nature, Jul. 2016, 535(7611):252-257.
Minervini et al., "Isoform-specific interactions of the von Hippel-Lindau tumor suppressor protein," Sci. Rep., Jul. 2015, 5:12605, 9 pages.
Notice of Allowance in Japanese Appln. No. 2020-501505, mailed on Mar. 7, 2023, 6 pages (with English translation).
Office Action in Australian Appln. No. 2018300982, mailed on Mar. 20, 2024, 4 pages.
Office Action in Canadian Appln. No. 3069181, mailed on Dec. 4, 2023, 4 pages.
Office Action in European Appln. No. 18831849.7, mailed on Jun. 23, 2022, 4 pages.
Office Action in Japanese Appln. No. 2020-501505, mailed on Aug. 5, 2022, 14 pages (with English translation).
Office Action in Japanese Appln. No. 2023-062212, mailed on Jun. 5, 2024, 12 pages (with English translation).
Okamura et al., "The development and validation of tau PET tracers: current status and future directions," Clin. Transl. Imaging, 2018, 6(4):305-316.
Orr et al., "A Brief Overview of Tauopathy: Causes, Consequences, and Therapeutic Strategies," Trends Pharmacol. Sci., Jul. 2017, 38(7):637-648.
Partial European Search Report in European Appln. No. 23195169.0, mailed on Aug. 8, 2024, 22 pages.
Stebbins et al., "Structure of the VHL-ElonginC-ElonginB Complex: Implications for VHL Tumor Suppressor Function," Science, Apr. 1999, 284(5413):455-61.
Tai et al., "Tau Reduction Prevents Key Features of Autism in Mouse Models," Neuron, May 2020, 106(3):421-437.e11, 29 pages.

COMPOUNDS FOR TAU PROTEIN DEGRADATION

RELATED APPLICATIONS

This application is a continuation of U.S. application Ser. No. 16/630,294, filed on Jan. 10, 2020, which is a national stage application, filed under 35 U.S.C. § 371, of International Application No. PCT/US2018/041787, filed Jul. 12, 2018, which claims the benefit of priority under 35 U.S.C. § 119 (e) to U.S. Provisional Application, U.S. Ser. No. 62/531,773, filed Jul. 12, 2017, the entire contents of which are incorporated herein by reference.

FIELD OF THE INVENTION

The present invention relates generally to bifunctional compounds that bind tau protein and promote its degradation via recruitment of an E3 ubiquitin ligase, and uses of the compounds in the treatment of neurological diseases (e.g., Alzheimer's disease).

BACKGROUND OF THE INVENTION

Alzheimer's disease (AD) is characterized by progressive loss of memory and other mental functions. Worldwide, nearly 35 million people suffer from AD. The exact mechanism for AD is not fully understood, but two characteristic protein deposits, senile plaques and neurofibrillary tangles (NFT), have been defined as causative events for AD. While senile plaques include extracellular aggregation of amyloid-β peptides (Aβ), the NFTs are composed of hyperphosphorylated tau protein. Since tau accumulation begins before extensive neuronal loss, targeting tau protein has become a strategy for treating AD. Hence, tau is not only a drug target but also a biomarker for early diagnosis of AD by measurement of brain tau loading. Positron emission tomography (PET) is a molecular imaging technique that provides a non-invasive diagnostic method for the detection of tau aggregation. Thus, several tau radiotracers have been developed and tested in humans.

Recently, a new therapeutic strategy to reduce and/or eliminate proteins associated with certain pathological states, PROTAC (proteolysis targeting chimeras; e.g., see U.S. patent application U.S. Ser. No. 14/792,414, filed Jul. 6, 2015), was developed by creating bifunctional compounds that recruit target proteins to E3 ubiquitin ligases, which subsequently induce proteasome-mediated degradation of the target protein. E3 ubiquitin ligases are proteins that, in combination with an E2 ubiquitin-conjugating enzyme, promote the attachment of ubiquitin to a lysine on a target protein via an isopeptide bond (e.g., an amide bond that is not present on the main chain of a protein). The ubiquitination of the protein commonly results in degradation of the target protein by the proteasome.

Currently, there are no clinically approved compounds that target tau for the treatment of AD, and overall clinical failure is much higher for AD compared to other diseases. Accordingly, an ongoing need exists to identify drugs that effectively treat neurological disorders, such as AD. In particular, drugs that can take advantage of cellular machinery involved in protein homeostasis (e.g., ubiquitination and proteasome degradation) may find use as therapeutic agents.

SUMMARY OF THE INVENTION

PROTAC relies on a strategy of recruiting target protein to an E3 ubiquitin ligase and subsequently inducing proteasome-mediated degradation of the target protein. The present disclosure describes the conjugation of tau binding moieties with an E3 ubiquitin ligase binding moiety (e.g., lenalidomide, thalidomide) to provide compounds that can induce the ubiquitination of tau protein and promote its degradation in cells. Accordingly, the present disclosure stems from the recognition that the aggregation of tau protein, in particular hyperphosphorylated tau protein, causes certain neurological disorders (e.g., tauopathies such as AD), and that by targeting both tau protein, or any post-translationally modified form of tau, and recruiting an E3 ubiquitin ligase (e.g., Cereblon) to ubiquitinate the tau protein and mark it for proteasome degradation, a single bifunctional compound can promote the degradation of tau protein, thus providing new compounds, compostions, and methods for the treatment of neurological disease (e.g., tauopathies such as AD). Thus, the present disclosure represents an important advance in the treatment of neurological disease, particularly tauopathies.

In one aspect, provided are compounds of Formula I:

$$\text{T-L-E,} \qquad \text{I}$$

or pharmaceutically acceptable salts, co-crystals, tautomers, stereoisomers, solvates, hydrates, polymorphs, isotopically enriched derivatives, or prodrugs thereof, wherein:

T is a tau protein binding moiety;

E is an E3 ubiquitin ligase binding moiety;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, a bond, —O—, —N($R^A$)—, —S—, —C(═O)—, —C(═O)O—, —C(═O)N$R^A$—, —N$R^A$C(═O)—, —N$R^A$C(═O)$R^A$—, —C(═O)$R^A$— —N$R^A$C(═O)O—, —N$R^A$C(═O)N($R^A$)—, —OC(═O)—, —OC(═O)O—, —OC(═O)N($R^A$)—, —$S(O)_2$N$R^A$—, —N$R^A$$S(O)_2$—, or a combination thereof; and each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two $R^A$ groups are joined to form a substituted or unsubstituted heterocyclic ring.

In certain embodiments, T is of Formula T-I:

T-I

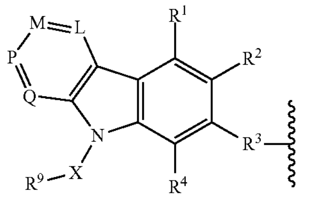

wherein:

L is N or $CR^5$;

M is N or $CR^6$;

P is N or $CR^7$;

Q is N or $CR^8$;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or C1-6 alkyl;

$R^9$ is hydrogen, $—N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is $—(CH_2)_n$, —O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$ -A-(C═O)$NR^A$—, -A-$NR^A$—$(CH_2)_n$—(C═O)$NR^A$—, —$(CH_2)_n$—$S(O)_2NR^A$—, -A-$(CH_2)_n$—$S(O)_2$ $NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each of $R^1$, $R^2$, and $R^4$-$R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^2$;

$R^{12}$ is hydrogen, —$CH_3$, aryl, or heteroaryl; and n is 0-12;

wherein one or more carbon of $R^{1-8}$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments of Formula T-I:

L is N or $CR^5$;

M is N or $CR^6$;

P is N or $CR^7$;

Q is N or $CR^8$;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, $—N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$, —O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each of $R^1$, $R^2$, and $R^4$-$R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^{12}$;

$R^2$ is hydrogen, —$CH_3$, aryl, or heteroaryl; and n is 0-12;

wherein one or more carbon of $R^{1-8}$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments, T is of formula T-II:

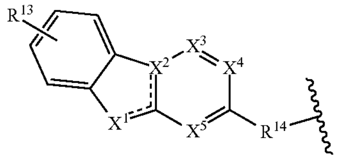

T-II wherein:

$X^1$ is CH, N, NH, O, or S;

$X^2$ is CH, C, or N;

$X^3$ is $CR^{15}$ or N;

$X^4$ is $CR^5$ or N;

$X^5$ is $CR^5$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, -A-O—$(CH_2)_n$— (C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$—, —$(CH_2)_n$-A-(C═O) $NR^A$—, —$(CH_2)_n$—$S(O)_2NR^A$—, -A-$(CH_2)_n$—$S(O)_2$ $NR^A$—, or —$(CH_2)_n$-A-$S(O)_2NR^A$—;

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}$ alkyl$)_2$.

In certain embodiments of Formula T-II:

$X^1$ is CH, N, O, or S;

$X^2$ is CH, C, or N;

$X^3$ is $CR^{15}$ or N;

$X^4$ is $CR^{15}$ or N;

$X^5$ is $CR^{15}$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl; $R^{14}$ is —$(CH_2)_n$ —O—, -A-$(CH_2)_n$—O—, —$(CH_2)_n$-A-O—, —$(CH_2)_n$ —S—, -A-$(CH_2)_n$—S—, —$(CH_2)_n$-A-S—, —$(CH_2)_n$ —$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O) $NR^A$—, —$(CH_2)_n$-A-(C═O)$NR^A$—, —$(CH_2)_n$—S $(O)_2$ $NR^A$—, -A-$(CH_2)_n$—$S(O)_2NR^A$—, or —$(CH_2)_n$ A-$S(O)_2NR^A$—;

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}$ alkyl$)_2$.

In certain embodiments, T is of formula T-III or T-IV:

T-III

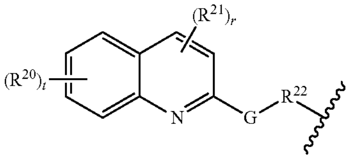

or

T-IV

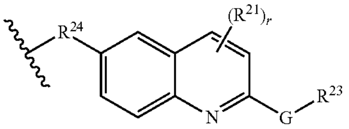

wherein:

$R^{20}$ and $R^{21}$ are independently halogen, —OH, —COOH, —$SO_3H$, —$NO_2$, —SH, —$NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$ $S(O)_2$ $NR^A$—;

$R^{23}$ is halogen, —OH, —COOH, —$SO_3H$, —$NO_2$, —SH, —$NR^xR^y$, substituted or unsubstituted alkyl, or substituted or unsubstituted alkoxy;

$R^{24}$ is unsubstituted alkylene, alkylene substituted with one or more halogen or hydroxy groups, unsubstituted alkoxylene, or alkoxylene substituted with one or more halogen or hydroxy groups;

$R^x$ and $R^y$ are independently hydrogen, or substituted or unsubstituted alkyl;

n is 0-12;

t is 0, 1, 2, 3, or 4; and r is 0, 1, or 2.

In certain embodiments, E is a cereblon E3 ubiquitin ligase binding moiety or a VHL E3 ubiquitin ligase binding moiety.

In certain embodiments, E is a cereblon E3 ubiquitin ligase binding moiety.

Exemplary compounds of Formula I include, but are not limited to:

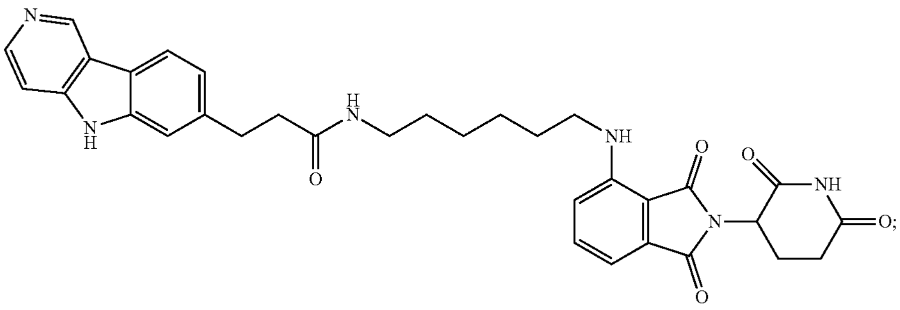

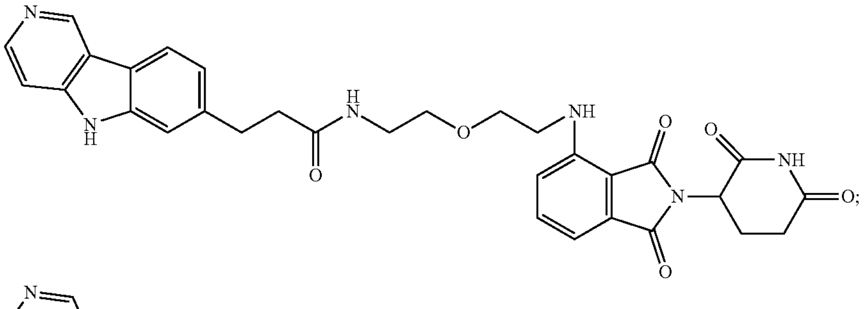

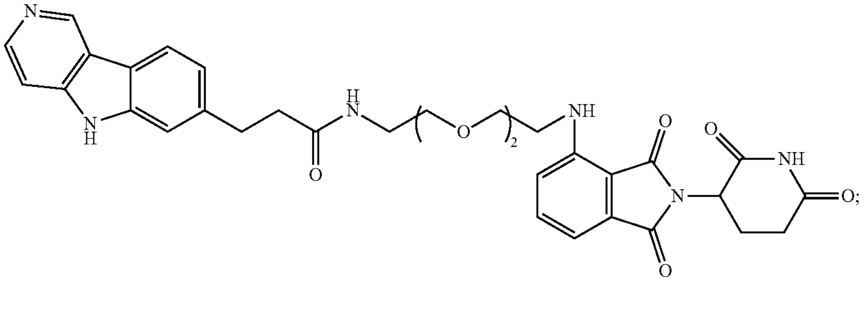

-continued
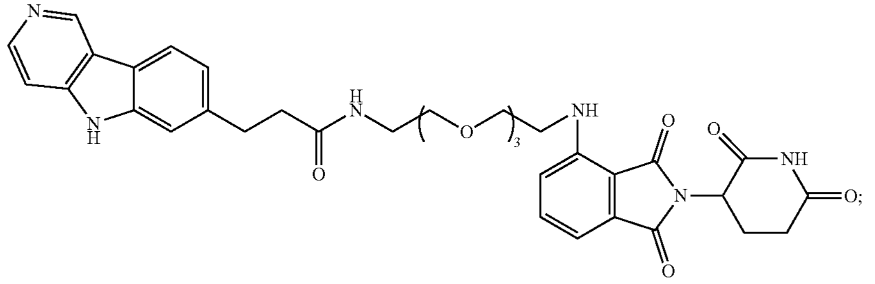
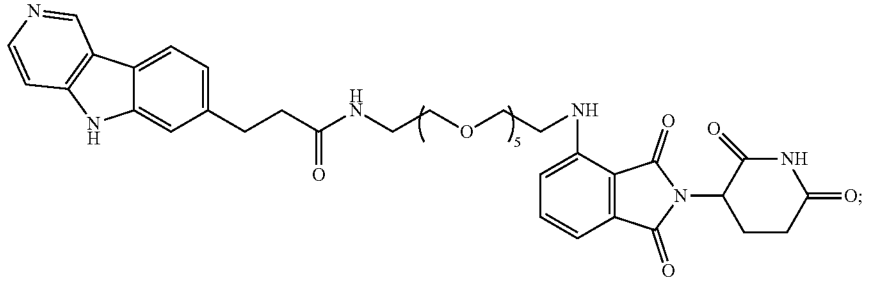
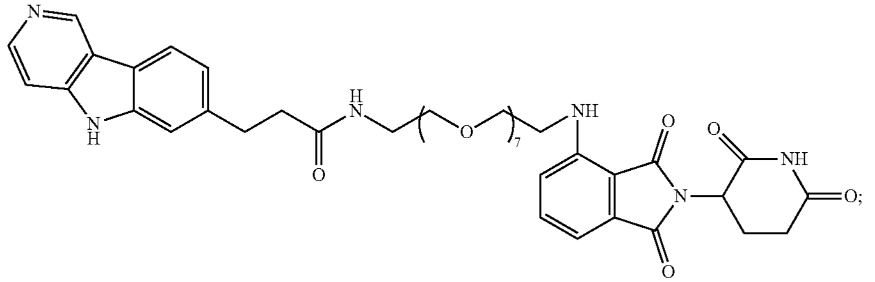
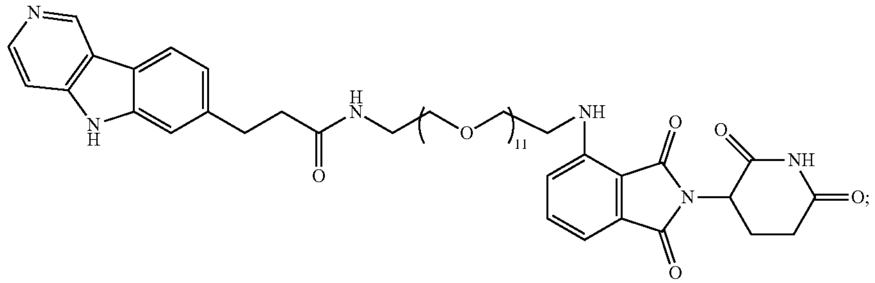
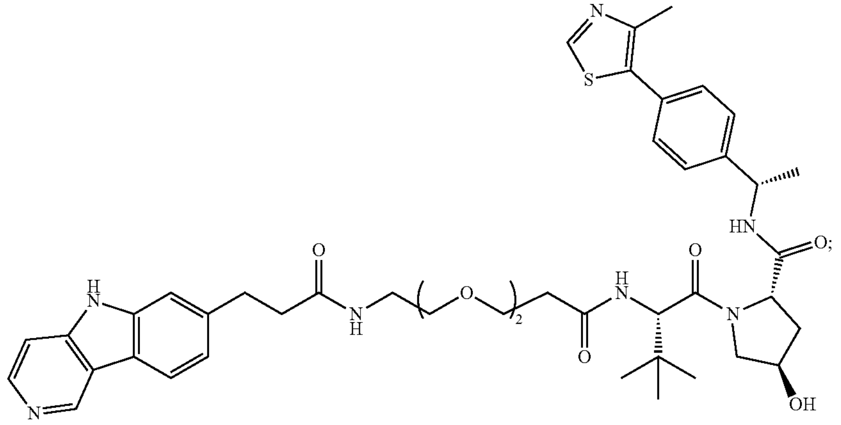

-continued
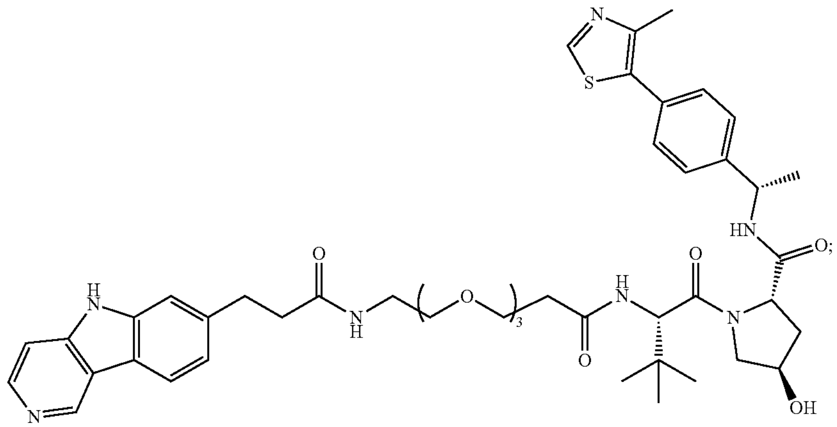
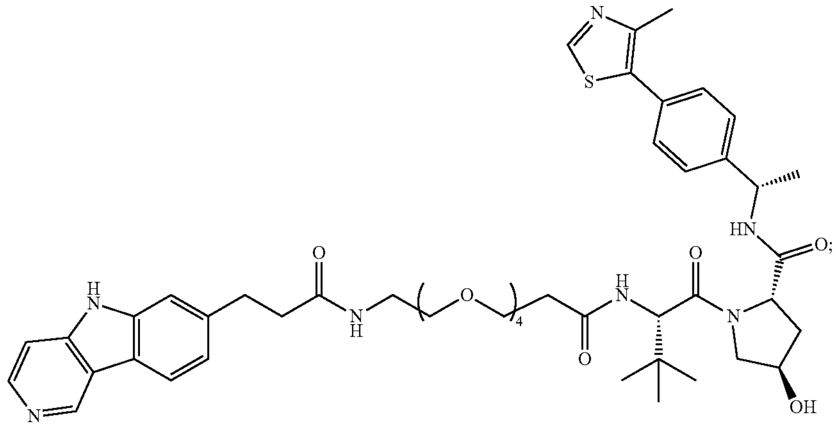
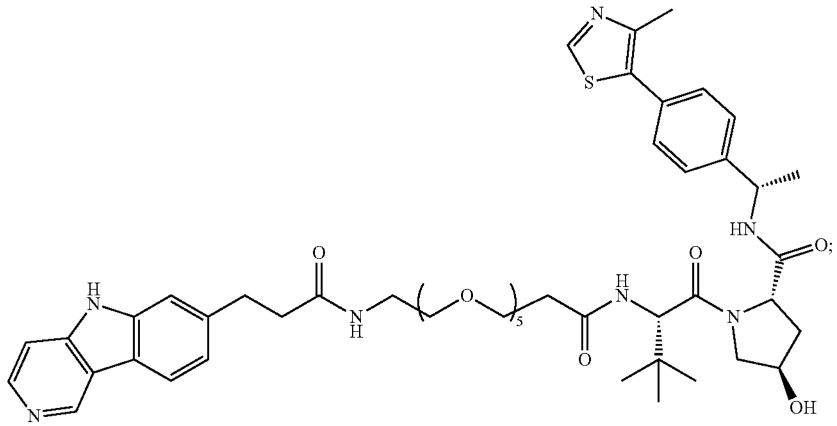
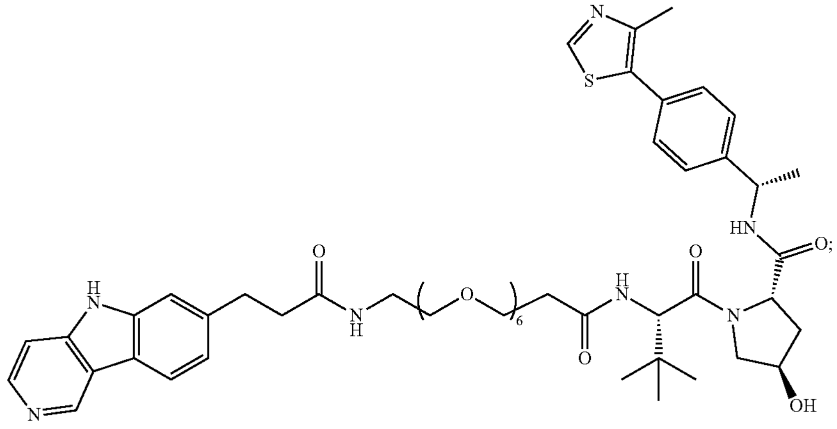

-continued
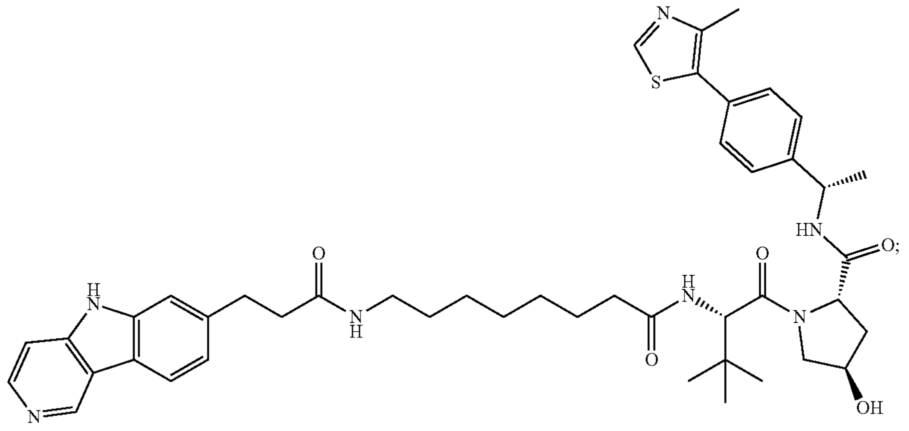
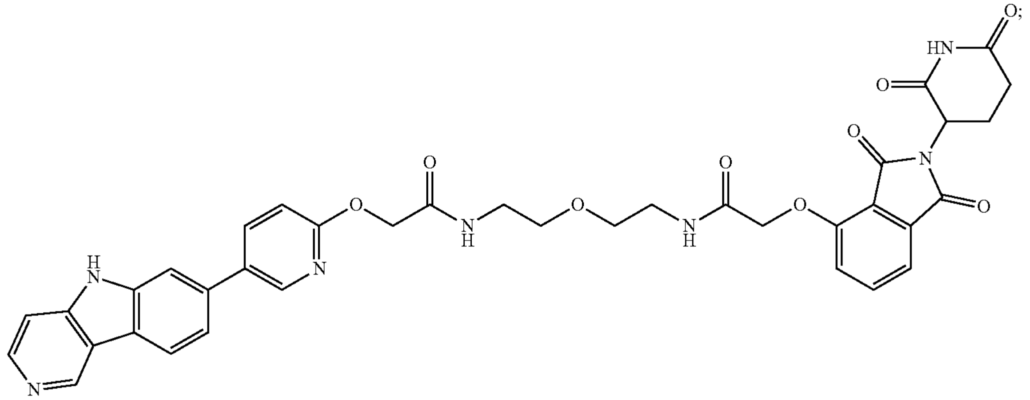
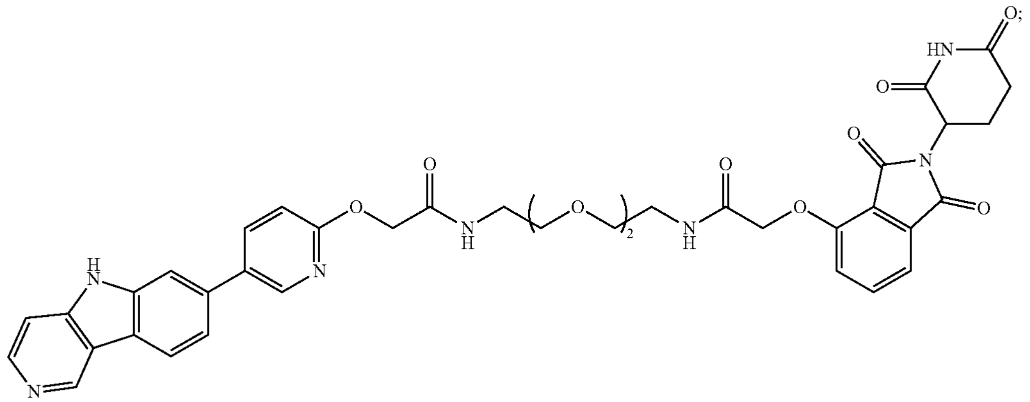
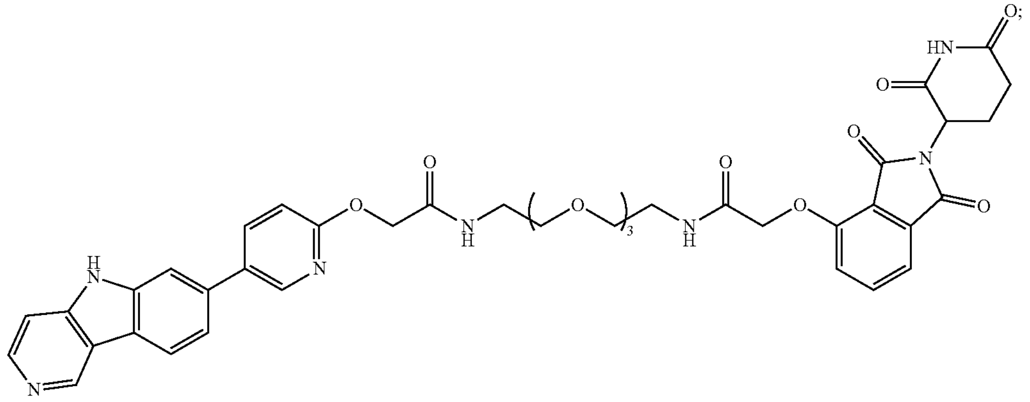

-continued
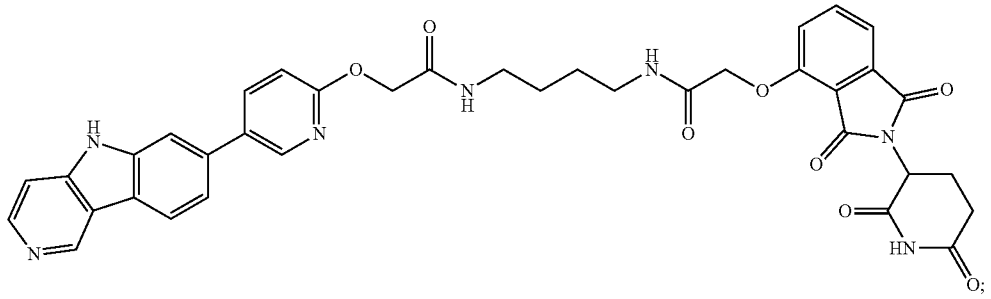
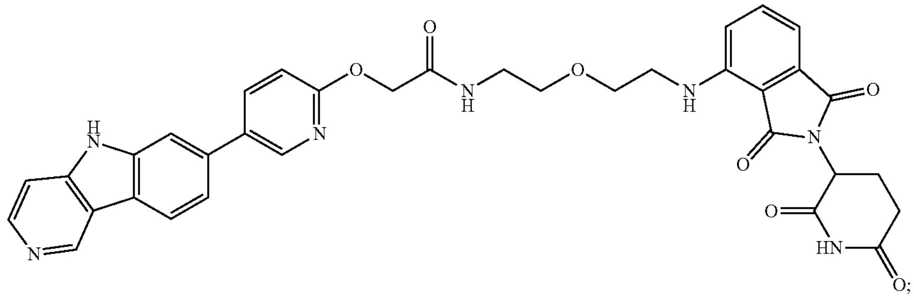
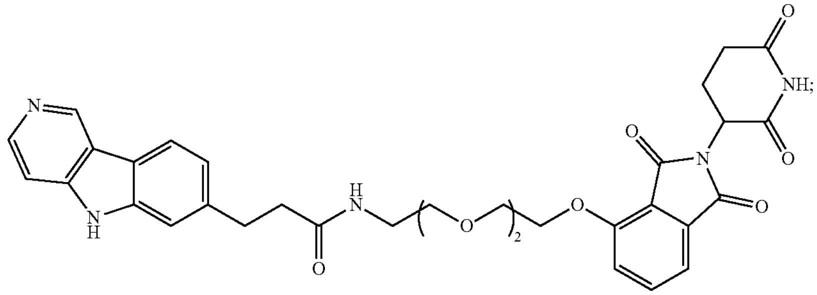
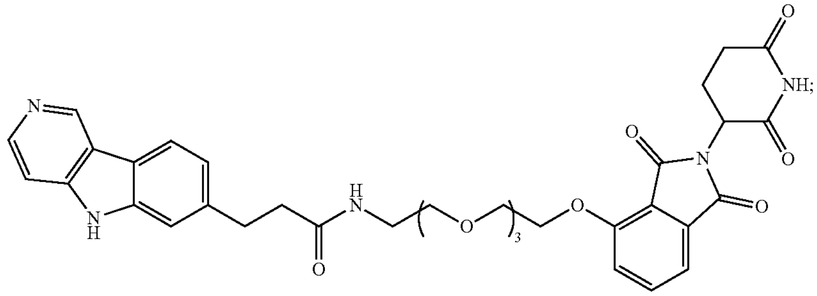
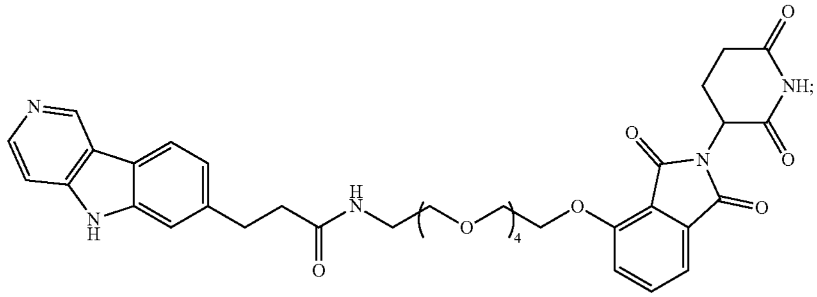

-continued

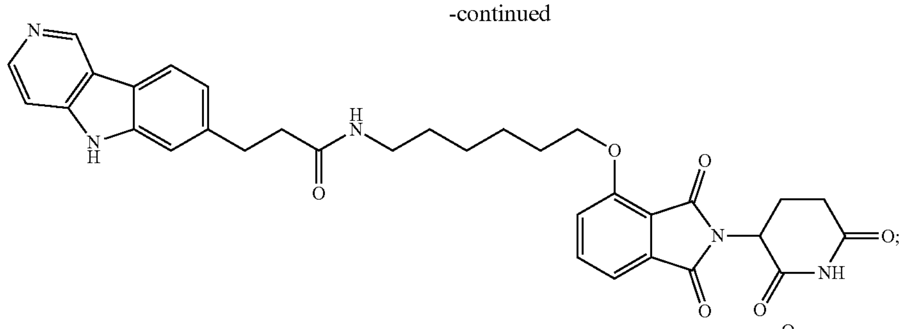

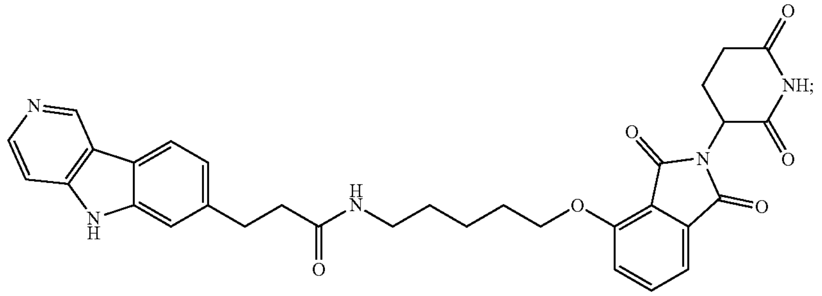

and pharmaceutically acceptable salts thereof.

In another aspect, provided are radiolabeled compounds comprising a compound of Formula I, or a pharmaceutically acceptable salt thereof, enriched with a radionuclide.

In another aspect, provided are pharmaceutical compositions comprising a compound of Formula I, or a pharmaceutically acceptable salt thereof, and a pharmaceutically acceptable excipient.

In another aspect, provided are methods of treating a neurological disorder in a subject in need thereof, the method comprising administering a compound of Formula I, or a pharmaceutically acceptable salt thereof, or a pharmaceutical composition comprising a compound of Formula I, to the subject. In certain embodiments, the neurological disorder is a neurodegenerative disease. In certain embodiments, the neurodegenerative disease is a tauopathy (e.g. Alzheimer's disease).

In another aspect, provided are methods of promoting the degradation of tau protein in a subject in need thereof, the method comprising administering a compound of Formula I, or a pharmaceutically acceptable salt thereof, or a pharmaceutical composition comprising a compound of Formula I, to the subject.

In another aspect, provided are methods of detecting a neurological disorder, the method comprising contacting a compound of Formula I, or a pharmaceutically acceptable salt thereof, or a pharmaceutical composition comprising a compound of Formula I, with a tissue.

In another aspect, provided are methods of detecting pathological aggregation of tau protein in tissue, the method comprising contacting a compound of Formula I, or a pharmaceutically acceptable salt thereof, or a pharmaceutical composition comprising a compound of Formula I, with a tissue.

In another aspect, provided are methods of diagnosing a neurological disorder in a subject, the method comprising contacting a compound of Formula I, or a pharmaceutically acceptable salt thereof, or a pharmaceutical composition comprising a compound of Formula I, with a tissue of the subject.

In another aspect, provided are compounds of Formula I, or pharmaceutically acceptable salts thereof, or pharmaceutical compositions comprising a compound of Formula I, for use in treating a neurological disorder in a subject in need thereof; and/or promoting the degradation of tau protein.

In another aspect, provided are kits comprising a compound of Formula I, or a pharmaceutically acceptable salt thereof, or a pharmaceutical composition comprising a compound of Formula I. In certain embodiments, the kit further comprises instructions for administration (e.g., human administration) and/or use.

The details of certain embodiments of the invention are set forth in the Detailed Description of Certain Embodiments, as described below. Other features, objects, and advantages of the invention will be apparent from the Definitions, Examples, Figures, and Claims.

DEFINITIONS

Chemical Definitions

Figure 1A:
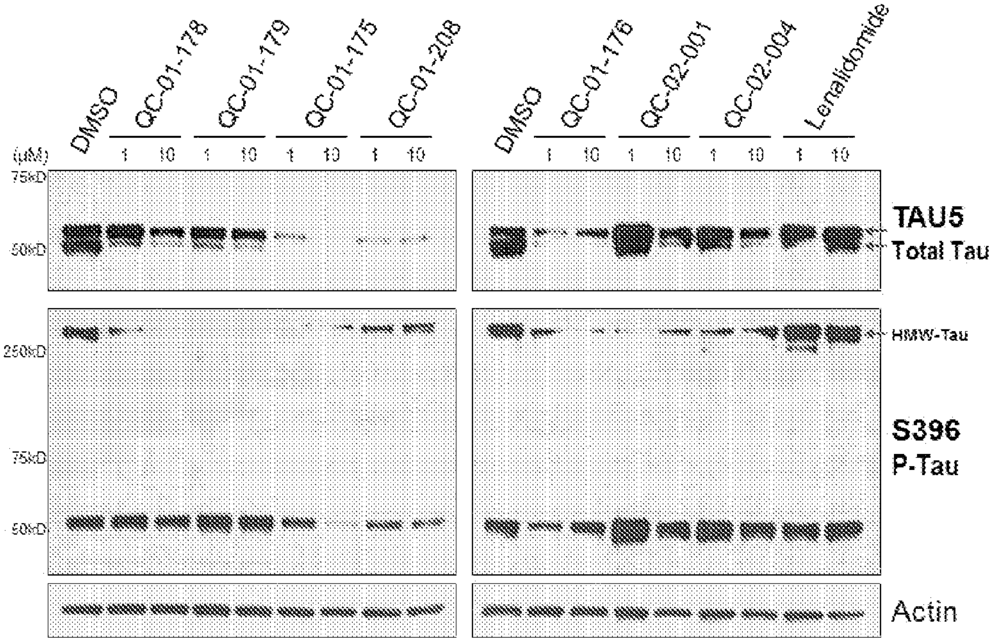
FIG. 1A is a series of western blot stains showing the effect of exemplary compounds on levels of tau protein in a human tau-A152T neuronal model, after 24 h treatment.
Figure 1B:
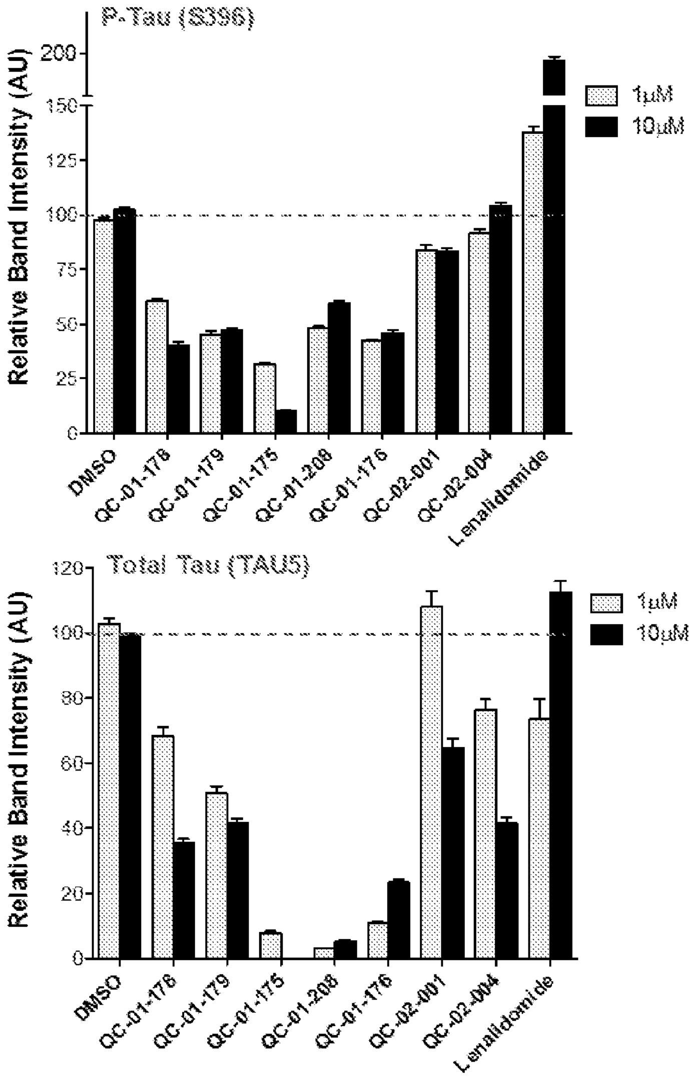
FIG. 1B is a series of bar graphs quantifying the total tau and hyperphosphorylated tau from the western blots in FIG. 1A. These figures demonstrate the significant tau lowering effects of the exemplary compounds, but not lenalinomide, a CRBN-only binding compound.
Figure 2A:
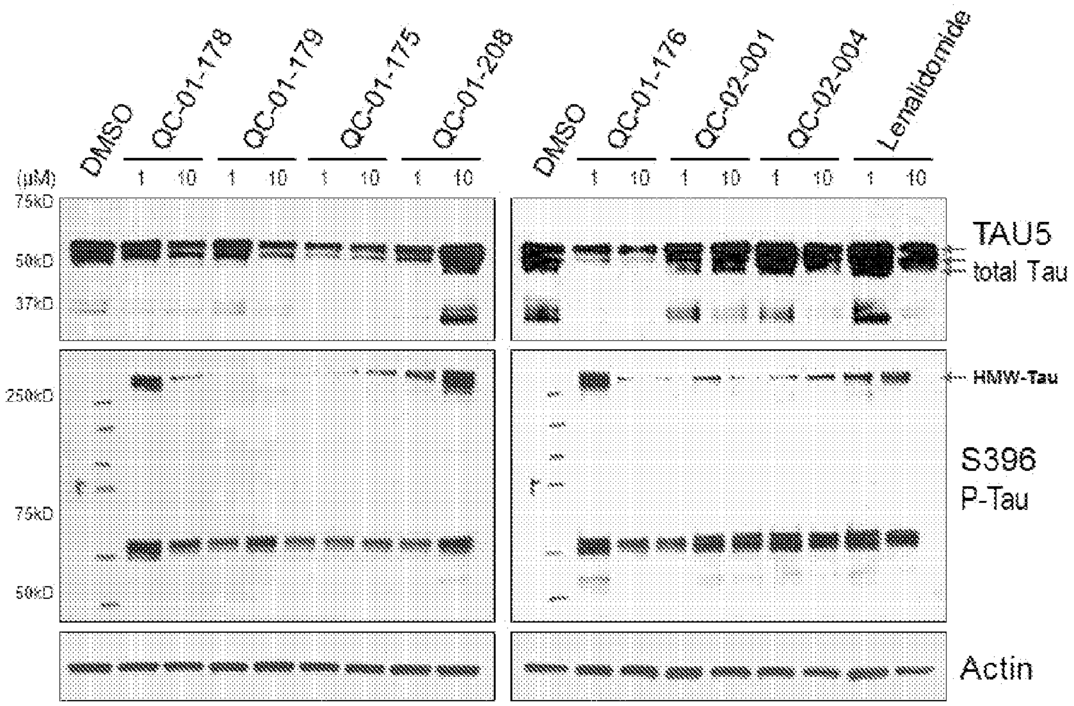
FIG. 2A is a series of western blot stains showing the effect of exemplary compounds on levels of tau protein in a human tau-P301L neuronal model, after 24 h treatment.
Figure 2B:
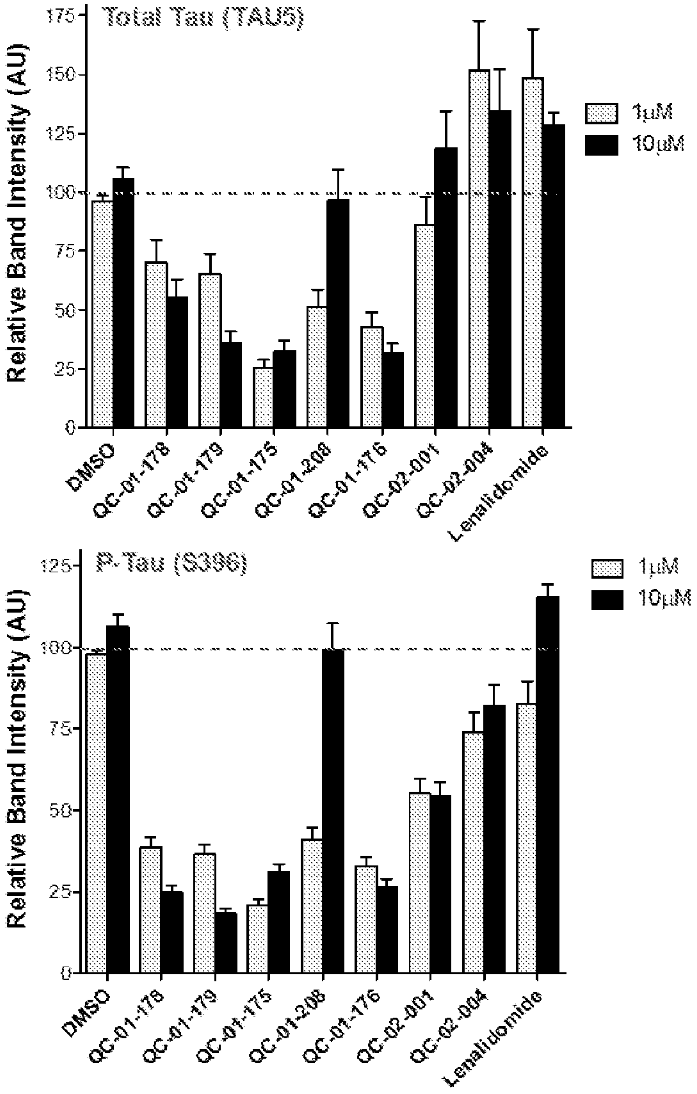
FIG. 2B is a series of bar graphs quantifying the total tau and hyperphosphorylated tau from the western blots in FIG. 2A. These figures demonstrate the significant tau lowering effects of the exemplary compounds, but not lenalinomide, a CRBN-only binding compound.

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, $\sim\sim\sim$ is a single bond where the stereochemistry of the moieties immediately attached thereto is not specified, - - - is absent or a single bond, and $\underline{- - -}$ or $\underline{- - -}$ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{2}C$ with $^{3}C$ or 14C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1_18}$ alkyl"). In some embodiments, a heteroalkyl group is a saturated group having 1 to 16 carbon atoms and 1 or more heteroatoms within the parent chain ("hetero$C_{1_16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

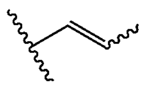

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_2$ 7 alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{24}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl (C), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl (CQ). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $SSR^{cc}$, $—C(=O)R^{aa}$, $—CO_2H$, —CHO, $—C(OR^{cc})_3$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{ab}SO_2R^{aa}$, $—SO_2N(R^{bb})_2$, $—SO_2R^{aa}$, $—SO_2OR^{aa}$, $—OSO_2R^{aa}$, $—S(=O)R^{aa}—OS(=O)R^{aa}$, $—Si(R^{aa})_3$, $—OSi(R^{aa})_3—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}P(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR)_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{aa})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups; wherein X is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two RC° groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups;

each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $C(=O)R^{ee}$, $—CO_2H$, $—CO_2R^{ee}$, $OC(=O)R^{ee}$, $—OCO_2R^{ee}$, $—C(=O)N(R^{ff})_2$, $—OC(=O)N(R^{ff})_2$, $—NR^{ff}C(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(Re)_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)(OR^{ee})_2$, $—P(=O)(R^{ee})_2$, $—OP(=O)(R^{ee})_2$, $—OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X is a counterion;

each instance of $R^{ee}$ is, independently, selected from $C_{1-6}$alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(=NH)NH($C_{1-6}$ alkyl), —OC(=NH)$NH_2$, —NHC(=NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2$($C_{1-6}$ alkyl), —$SO_2$O($C_{1-6}$ alkyl), —$OSO_2$($C_{1-6}$ alkyl), —SO($C_{1-6}$ alkyl), —Si($C_{1-6}$ alkyl)$_3$, —OSi($C_{1-6}$ alkyl)$_3$—C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^9$ substituents can be joined to form =O or =S; wherein X is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR—, —ON($R^{bb}$)$_2$, —OC(=O)S$R^{aa}$, —OC(=O)$R^{aa}$, —$OCO_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)R—, —$OSO_2R^{aa}$, —OSi($R^{aa}$)$_3$, —OP($R^{cc}$)$_2$, —OP($R^{cc}$)$_3^+X^-$, —OP(O$R^{cc}$)$_2$, —OP(O$R^{cc}$)$_3^+X^-$, —OP(=O)($R^{aa}$)$_2$, —OP(=O)(O$R^{cc}$)$_2$, and —OP(=O)(N($R^{bb}$)$_2$)$_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, NHC(=N$R^{bb}$)N($R^{bb}$)$_2$, —$NHSO_2R^{aa}$, —NHP(=O)(O$R^{cc}$)$_2$, and —NHP(=O)(N($R^{bb}$)$_2$)$_2$, wherein RV, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$$CO_2R^{aa}$, —N$R^{bb}$(=O)N($R^{bb}$)$_2$, —N$R^{bb}$C(=N$R^{bb}$)N($R^{bb}$)$_2$, —N$R^{bb}$ $SO_2R^{aa}$, —N$R^{bb}$p(=O)(O$R^{cc}$)$_2$, and —N$R^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and X are as defined herein.

The term "sulfonyl" refers to a group selected from —$SO_2$N($R^{bb}$)$_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, —C(=S)O($R^{X1}$), —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphatiethioxy, heteroaliphatiethioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (e.g., —C(═O)$R^{aa}$), carboxylic acids (e.g., —$CO_2$H), aldehydes (—CHO), esters (e.g., —$CO_2R^{aa}$, —C(═O)$SR^{aa}$, —C(═S)$SR^{aa}$), amides (e.g., —C(═O)N($R^{bb}$)$_2$, —C(═O)$NR^{bb}SO_2R^{aa}$, —C(═S)N($R^{bb}$)$_2$), and imines (e.g., —C(═$NR^{bb}$)$R^{aa}$ C(═$NR^{bb}$)$OR^{aa}$), —C(═$NR^{bb}$)N($R^{bb}$)$_2$), wherein $R^{aa}$ and $R^{bb}$ are as defined herein.

The term "silyl" refers to the group —Si(R')$_3$, wherein $R^a$ is as defined herein.

The term "oxo" refers to the group ═O, and the term "thiooxo" refers to the group ═S.

Nitrogen atoms can be substituted or unsubstituted as valency permits, and include primary, secondary, tertiary, and quatemary nitrogen atoms. Exemplary nitrogen atom substituents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups, and wherein $R^{aa}$, $R^{bb}$, $R^{cc}$, and Rd are as defined herein.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3 edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4- pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —RV, —N(R$^{bb}$)$_2$, —C(═O)SR$^{aa}$, —C(═O)R$^{aa}$, —CO$_2$, R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —S(═O)R$^{aa}$, —SO$_2$R$^{aa}$, —Si(R$^{aa}$)$_3$, —P(R$^{cc}$)$_2$, —P(Re)$_3$$^+$X$^-$, —P(OR$^{cc}$)$_2$, —P(OR$^{cc}$)$_3$$^+$X$^-$, —P(═O)(R$^{aa}$)$_2$, —P(═O)(OR$^{cc}$)$_2$, and —P(═O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3{}^+X^-$, $—P(OR^{cc})_2$, $—P(OR^{cc})_3{}^+X^-$, $—P(=O)(R^{aa})_2$, $—P(=O)(OR^{cc})_2$, and $—P(=O)(N(R^{bb})\ 2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $F^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, -OMs), p-bromobenzenesulfonyloxy (brosylate, —OBs), $—OS(=O)_2(CF_2)_3CF_3$ (nonaflate, —ONf), or trifluoromethanesulfonate (triflate, —OTf). In some cases, the leaving group is a brosylate, such asp-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., $—OC(=O)SR^{aa}$, $—OC(=O)R^{aa}$, $—OCO_2R^{aa}$, $—OC(=O)N(R^{bb})_2$, $—OC(=NR^{bb})R^{aa}$, $—OC(=NR^{bb})OR^{aa}$, $—OC(=NR^{bb})N(R^{bb})_2$, $—OS(=O)R^{aa}$, $—OSO_2R^{aa}$, $—OP(R^{cc})_2$, $—OP(R^{cc})_3$, $—OP(=O)_2R^{aa}$, $—OP(=O)(R^{aa})_2$, $—OP(=O)(OR^{cc})_2$, $—OP(=O)_2N(R^{bb})_2$, and $—OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for tau protein binding and/or promoting the degradation of tau protein. In certain embodiments, a therapeutically effective amount is an amount sufficient for treating a neurological disorder (e.g., AD). In certain embodiments, a therapeutically effective amount is an amount sufficient for tau protein binding and/or promoting the degradation of protein and treating a neurological disorder (e.g., AD).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for tau protein binding and/or promoting the degradation of tau protein. In certain embodiments, a prophylactically effective amount is an amount sufficient for treating a neurological disorder (e.g., AD). n certain embodiments, a prophylactically effective amount is an amount sufficient for tau protein binding and/or promoting the degradation of tau protein and treating a neurological disorder (e.g., AD).

The term "neurological disorder" refers to any disorder, disease, or condition of the nervous system.

The term "tau protein" refers to a class of proteins that stabilize microtubules. They are abundant in neurons of the central nervous system and are less common elsewhere, but are also expressed at very low levels in CNS astrocytes and oligodendrocytes. The tau proteins are the product of alternative splicing from a single gene that in humans is designated MAPT (microtubule-associated protein tau) and is located on chromosome 17. Tau protein described herein include all post-translationally modified forms of the protein.

The term "tauopathy" refers to a class of neurodegenerative diseases associated with the pathological aggregation of tau protein in neurofibrillary or gliofibrillary tangles in the human brain. Primary tauopathies, i.e., conditions in which neurofibrillary tangles (NFT) are predominantly observed, include, but are not limited to, primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, and argyrophilic grain disease.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate.

DETAILED DESCRIPTION OF CERTAIN EMBODIMENTS

Provided herein are bifunctional compounds that bind tau protein and recruit an E3 ligase (e.g., Cereblon) to promote the degradation of tau protein. In one aspect, the disclosure provides compounds of Formula I, and pharmaceutically acceptable salts, solvates, hydrates, polymorphs, co-crystals, tautomers, stereoisomers, isotopically labeled derivatives, prodrugs, and pharmaceutical compositions thereof. The compounds are useful for the treatment and/or prevention of diseases associated with tau protein aggregation (e.g., tauopathies (e.g., AD)) in a subject in need thereof.

Compounds

The compounds described herein interact with tau protein and an E3 ubiquitin ligase (e.g., Cereblon). As described herein, the therapeutic effect may be a result of degradation, modulation, binding, or modification of tau protein by a compound described herein. Without wishing to be bound by any particular theory, the therapeutic effect may be the result of modulation, targeting, binding, or modification of an E3 ubiquitin ligase (e.g., Cereblon) by a compound described herein. The therapeutic effect may be a result of recruitment of an E3 ubiquitin ligase (e.g., Cereblon) by modulation, targeting, binding, or modification of the E3 ubiquitin ligase to ubiquitinate tau protein and mark it for proteasomal degradation, by a compound. A compound may be provided for use in any composition, kit, or method described herein as a pharmaceutically acceptable salt, co-crystal, tautomer, stereoisomer, solvate, hydrate, polymorph, isotopically enriched derivative, or prodrug thereof.

In one aspect, disclosed is a compound of Formula I:

$$T\text{-}L\text{-}E, \qquad \text{I}$$

or a pharmaceutically acceptable salt, co-crystal, tautomer, stereoisomer, solvate, hydrate, polymorph, isotopically enriched derivative, or prodrug thereof, wherein:

T is a tau protein binding moiety;

E is an E3 ubiquitin ligase binding moiety;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, a bond, —O—, —N($R^A$)—, —S—, —C(=O)—, —C(=O)O—, —C(=O)N$R^A$—, —N$R^A$C(=O)—, —N$R^A$C(=O)$R^A$—, —C(=O)$R^A$—, —N$R^A$C(=O)O—, —N$R^A$C(=O)N($R^A$)—, —OC(=O)—, —OC(=O)O—, —OC(=O)N($R^A$)—, —S(O)$_2$N$R^A$—, —N$R^A$S(O)$_2$—, or a combination thereof; and each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, or a nitrogen protecting group when attached to a nitrogen atom, or two $R^A$ groups are joined to form a substituted or unsubstituted heterocyclic ring.

Group T

In certain embodiments, T is any tau protein binding moiety. In certain embodiments, T is any tau protein binding moiety derived from the tau protein binding compounds described in U.S. patent application U.S. Ser. No. 13/447,095, filed May 22, 2012; U.S. Ser. No. 13/035,405, filed Feb. 25, 2011; U.S. Ser. No. 13/881,872, filed Oct. 28, 2011; U.S. Ser. No. 09/378,662, filed Aug. 20, 1999; and U.S. Ser. No. 14/346,914, filed Mar. 24, 2014, each of which is incorporated herein by reference.

In certain embodiments, T is of Formula T-I:

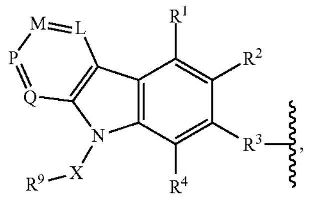

T-I wherein:

L is N or $CR^5$;

M is N or $CR^6$;

P is N or $CR^7$;

Q is N or $CR^8$;

X is a bond or substituted or unsubstituted $C_{1-12}$ alkylene, wherein one or more carbon is optionally replaced with C(O), O, S, $SO_2$, NH, or $NC_{1-6}$ alkyl, optionally substituted with halogen, OH, or $C_{1-6}$ alkyl;

$R^9$ is hydrogen, $—N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is $—(CH_2)_n—O—$, $-A-(CH_2)_n—O—$, $—(CH_2)_n-A-O—$, $-A-O—(CH_2)_n—(C{=}O)NR^A—$, $—(CH_2)_n—S—$, $-A-(CH_2)_n—S—$, $—(CH_2)_n-A-S—$, $-A-S—(CH_2)_n—(C{=}O)NR^A—$, $—(CH_2)_nNR^A$, —, $—(CH_2)_n-A-NR^A—$, $—(CH_2)_n—(C{=}O)NR^A—$, $-A-(CH_2)_n—(C{=}O)NR^A—$, $—(CH_2)_n-A-(C{=}O)NR^A—$, $-A-NR^A—(CH_2)_n—(C{=}O)NR^A—$, $—(CH_2)_n—S(O)_2NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each of $R^1$, $R^2$, and $R^4$-$R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or $—(CH_2)_n—R^{12}$;

$R^{12}$ is hydrogen, $—CH_3$, aryl, or heteroaryl; and n is 0-12;

wherein one or more carbon of $R^{1-8}$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments of Formula T-I:

L is N or $CR^5$;

M is N or $CR^6$;

P is N or $CR^7$;

Q is N or $CR^8$;

X is a bond or substituted or unsubstituted $C_{1-12}$ alkylene, wherein one or more carbon is optionally replaced with C(O), O, S, $SO_2$, NH, or $NC_{1-6}$ alkyl, optionally substituted with halogen, OH, or $C_{1-6}$ alkyl;

$R^9$ is hydrogen, $—N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is $—(CH_2)_n—O—$, $-A-(CH_2)_n—O—$, $—(CH_2)_n-A-O—$, $—(CH_2)_n—S—$, $-A-(CH_2)_n—S—$, $—(CH_2)_n-A-S—$, $—(CH_2)_n—NR^A—$, -A-, $—(CH_2)_n-A-NR^A—$, $—(CH_2)_n—(C{=}O)NR^A—$, $-A-(CH_2)_n—(C{=}O)NR^A—$, $—(CH_2)_n-A-(C{=}O)NR^A—$, $—(CH_2)_n—S(O)_2 NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each of $R^1$, $R^2$, and $R^4$-$R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or $—(CH_2)_n—R^2$;

$R^2$ is hydrogen, $—CH_3$, aryl, or heteroaryl; and n is 0-12;

wherein one or more carbon of $R^{1-8}$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments, L is N or $CR^5$; M is N or $CR^6$; P is $CR^7$; and Q is $CR^8$. In certain embodiments, L is $CR^5$; M is N or $CR^6$; P is $CR^7$; and Q is $CR^8$. In certain embodiments, L is $CR^5$; M is N; P is $CR^7$; and Q is $CR^8$.

In certain embodiments, X is a bond.

In certain embodiments, $R^9$ is hydrogen.

In certain embodiments, $R^3$ is $—(CH_2)_n—NR^A—$, $—(CH_2)_n—(C{=}O)NR^A—$, $—(CH_2)_n$ $S(O)_2NR^A—$, $-A-(CH_2)_n—NR^A—$, $—(CH_2)_n-A-NR^A—$, or $-A-O—(CH_2)_n—(C{=}O)NR^A—$. In certain embodiments, $R^3$ is $—(CH_2)_n—NR^A—$, $—(CH_2)_n—(C{=}O)NR^A—$, $—(CH_2)_n—S(O)_2 NR^A—$, $-A-(CH_2)_n—NR^A—$, or $—(CH_2)_n-A-NR^A—$. In certain embodiments, $R^3$ is $—(CH_2)_n—NR^A—$, $-A-(CH_2)_n—NR^A—$, $—(CH_2)_n-A-NR^A—$, $—(CH_2)_n—(C{=}O)NR^A—$, $-A-(CH_2)_n—(C{=}O)NR^A—$, or $—(CH_2)_n-A-(C{=}O) NR^A—$; and A is substituted or unsubstituted heterocyclylene, substituted or unsubstituted arylene, or substituted or unsubstituted heteroarylene. In certain embodiments, $R^3$ is $—(CH_2)_n—NR^A—$, $-A-(CH_2)_n—NR^A—$, $—(CH_2)_n-A-NR^A—$, $—(CH_2)_n—(C{=}O)NR^A—$, $-A-(CH_2)_n—(C{=}O) NR^A—$, $—(CH_2)_n-A-(C{=}O)NR^A—$, or $-A-O—(CH_2)_n—(C{=}O)NR^A—$; and A is substituted or unsubstituted heterocyclylene, substituted or unsubstituted arylene, or substituted or unsubstituted heteroarylene. In certain embodiments, $R^3$ is $—(CH_2)_n—NR^A—$, $-A-(CH_2)_n—NR^A—$, $—(CH_2)_n-A-NR^A—$, $—(CH_2)_n$ $(C{=}O)NR^A—$, $-A-(CH_2)_n—(C{=}O)NR^A—$, or $—(CH_2)_n-A-(C{=}O)NR^A—$; and A is substituted or unsubstituted heteroarylene. In certain embodiments, $R^3$ is $—(CH_2)_n—NR^A—$, $-A-(CH_2)_n—NR^A—$, $—(CH_2)_n-A-NR^A—$, $—(CH_2)_n—(C{=}O)NR^A—$, $-A-(CH_2)_n—(C{=}O)NR^A—$, $—(CH_2)_n-A-(C{=}O)NR^A—$, or $-A-O—(CH_2)_n—(C{=}O)NR^A—$; and A is substituted or unsubstituted heteroarylene. In certain embodiments, $R^3$ is $-A-(CH_2)_n—NR^A—$, $—(CH_2)_n-A-NR^A—$, or —

$(CH_2)_n$ (C═O)$NR^A$—; and A is substituted or unsubstituted heteroarylene. In certain embodiments, $R^3$ is -A-$(CH_2)_n$—$NR^A$—, —$(CH_2)_n$-A-$NR^A$—, —$(CH_2)_n$—(C═O)$NR^A$—, or -A-O—$(CH_2)_n$—(C═O)$NR^A$—; and A is substituted or unsubstituted heteroarylene. In certain embodiments, $R^3$ is —$(CH_2)_n$—(C═O)$NR^A$—, -A-$(CH_2)_n$—$NR^A$—, or -A-O—$(CH_2)_n$—(C═O)$NR^A$—. In certain embodiments, $R^3$ is —$(CH_2)_n$—(C═O)$NR^A$— or -A-$(CH_2)_n$—$NR^A$—. In certain embodiments, $R^3$ is —$(CH_2)_n$—(C═O)$NR^A$—. In certain embodiments, $R^3$ is -A-$(CH_2)_n$—$NR^A$—. In certain embodiments, $R^3$ is -A-O—$(CH_2)_n$—(C═O)$NR^A$—. In certain embodiments, $R^3$ is —$(CH_2)_n$—(C═O)$NR^A$—, -A-$(CH_2)_n$—$NR^A$—, or -A-O—$(CH_2)_n$—(C═O)$NR^A$—; and A is unsubstituted heteroarylene. In certain embodiments, $R^3$ is —$(CH_2)_n$—(C═O)$NR^A$— or -A-$(CH_2)_n$—$NR^A$—; and A is unsubstituted heteroarylene. In certain embodiments, $R^3$ is —$(CH_2)_n$—(C═O)$NR^A$— or -A-O—$(CH_2)_n$—(C═O) $NR^A$—. In certain embodiments, $R^3$ is -A-$(CH_2)_n$—$NR^A$—; and A is unsubstituted heteroarylene. In certain embodiments, $R^3$ is -A-$(CH_2)_n$—$NR^A$—; and A is unsubstituted pyridinylene, pyrimidinylene, or pyridazinylene. In certain embodiments, $R^3$ is —$(CH_2)_n$—(C═O)$NR^A$— or -A-O—$(CH_2)_n$—(C═O)$NR^A$—; and A is unsubstituted heteroarylene. In certain embodiments, $R^3$ is -A-O—$(CH_2)_n$—(C═O)$NR^A$—; and A is unsubstituted heteroarylene. In certain embodiments, $R^3$ is -A-O—$(CH_2)_n$—(C═O)$NR^A$—; and A is unsubstituted pyridinylene, pyrimidinylene, or pyridazinylene. In certain embodiments, $R^3$ is -A-O—$(CH_2)_n$ —(C═O)$NR^A$—; and A is unsubstituted pyridinylene.

In certain embodiments, each of $R^1$, $R^2$, and $R^4$ are independently hydrogen, OH, halogen, $NH_2$, $CH_3$, $SO_2$, $NO_2$, aryl, heteroaryl, $NHR^{12}$, $N(R^{12})_2C_{3-8}$ cycloalkyl, $N(R^{12})_2$heterocyclyl, or —$(CH_2)_n$—$R^{12}$; and $R^{12}$ is hydrogen, —$CH_3$, aryl, or heteroaryl. In certain embodiments, each of $R^1$, $R^2$, and $R^4$ are independently hydrogen.

In certain embodiments, T is of Formula T-I-a:

T-I-a

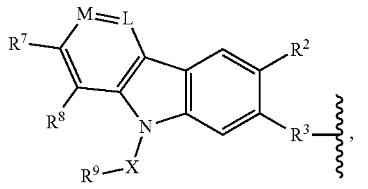

wherein:

L is N or $CR^5$;

M is N or $CR^6$;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2$ $NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^2$;

$R^{12}$ is hydrogen, —$CH_3$, aryl, or heteroaryl; and n is 0-12;

wherein one or more carbon of $R^2$, $R^3$, $R^7$, and $R^8$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments of formula T-I-a:

L is N or $CR^5$;

M is N or $CR^6$;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^{12}$;

$R^2$ is hydrogen, —$CH_3$, aryl, or heteroaryl; and n is 0-12;

wherein one or more carbon of $R^2$, $R^3$, $R^7$, and $R^8$ is optionally replaced with C(O), O, S, $SO_2$, NH, NH—$C_{1-6}$ alkyl, $NC_{1-6}$ alkyl, $NH_2$, or $N(C_{1-6}$ alkyl$)_2$.

In certain embodiments, T is of Formula T-I-b:

T-I-b

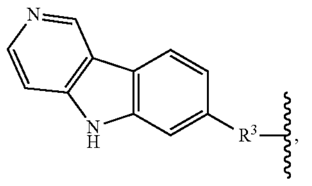

wherein $R^3$ is —$(CH_2)_n$—O—, -A-$(CH_2)_n$—O—, —$(CH_2)_n$ -A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$—(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—.

In certain embodiments of Formula T-1-b, $R^3$ is —$(CH_2)_n$ —O—, -A-$(CH_2)_n$—O—, —$(CH_2)_n$-A-O—, —$(CH_2)_n$—

S—, -A-$(CH_2)_n$—S—, —$(CH_2)_n$-A-S—, —$(CH_2)_n$—$NR^A$—, -A-$(CH_2)_n$—$NR^A$, —$(CH_2)_n$-A-$NR^A$—, —$(CH_2)_n$—(C═O)$NR^A$—, -A-$(CH_2)_n$—(C═O)$NR^A$—, —$(CH_2)_n$ A-(C═)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—.

In certain embodiments of Formula T-I-b, $R^3$ is —$(CH_2)_n$—$NR^A$—, —$(CH_2)_n$—(C═O)$NR^A$—, —$(CH_2)_n$—$S(O)_2NR^A$—, -A-$(CH_2)_n$—$NR^A$—, —$(CH_2)_n$-A-$NR^A$—, or -A-O—$(CH_2)_n$—(C═O)$NR^A$—.

In certain embodiments of Formula T-I-b, $R^3$ is —$(CH_2)_n$—$NR^A$—, —$(CH_2)_n$—(C═O)$NR^A$—, —$(CH_2)_n$—$S(O)_2NR^A$—, -A-$(CH_2)_n$—$NR^A$—, or —$(CH_2)_n$-A-$NR^A$—. In certain embodiments, $R^3$ is —$(CH_2)_n$—(C═O)$NR^A$—, -A-$(CH_2)_n$—$NR^A$—, or -A-O—$(CH_2)_n$—(C═O)$NR^A$—. In certain embodiments, $R^3$ is —$(CH_2)_n$—(C═O)$NR^A$— or -A-$(CH_2)_n$—$NR^A$—. In certain embodiments, $R^3$ is —$(CH_2)_n$ —(C═O)$NR^A$— or -A-O—$(CH_2)_n$—(C═O)$NR^A$—. In certain embodiments, $R^3$ is —$(CH_2)_n$—(C═O)$NR^A$—. In certain embodiments, $R^3$ is -A-$(CH_2)_n$—$NR^A$—. In certain embodiments, $R^3$ is -A-O—$(CH_2)_n$, —(C═O)$NR^A$—. In certain embodiments, $R^3$ is —$(CH_2)_n$—(C═O)$NR^A$—, -A-$(CH_2)_n$—$NR^A$—, or -A-O—$(CH_2)_n$—(C═O)$NR^A$—; and A is unsubstituted heteroarylene. In certain embodiments, $R^3$ is —$(CH_2)_n$—(C═O)$NR^A$— or -A-$(CH_2)_n$ —$NR^A$—; and A is unsubstituted heteroarylene. In certain embodiments, $R^3$ is -A-$(CH_2)_n$—$NR^A$—; and A is unsubstituted heteroarylene. In certain embodiments, $R^3$ is -A-$(CH_2)_n$—$NR^A$—; and A is unsubstituted pyridinylene, pyrimidinylene, or pyridazinylene. In certain embodiments, $R^3$ is —$(CH_2)_n$—(C═O)$NR^A$— or -A-O—$(CH_2)_n$—(C═O)$NR^A$—; and A is unsubstituted heteroarylene. In certain embodiments, $R^3$ is -A-O—$(CH_2)_n$—(C═O)$NR^A$—; and A is unsubstituted heteroarylene. In certain embodiments, $R^3$ is -A-O—$(CH_2)_n$—(C═O)$NR^A$—; and A is unsubstituted pyridinylene, pyrimidinylene, or pyridazinylene. In certain embodiments, $R^3$ is -A-O—$(CH_2)_n$—(C═O)$NR^A$—; and A is unsubstituted pyridinylene.

In certain embodiments, T is of the formula:

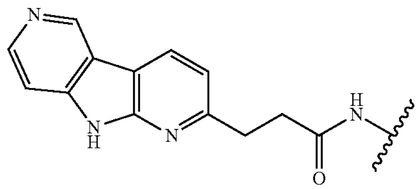
,
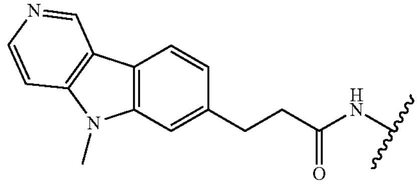
,
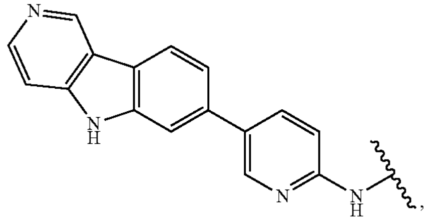
,

-continued

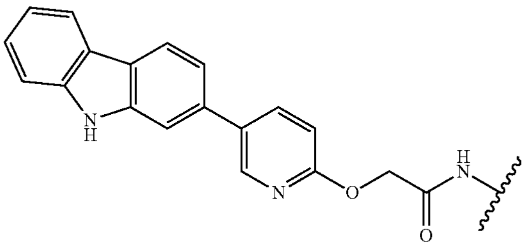
, or
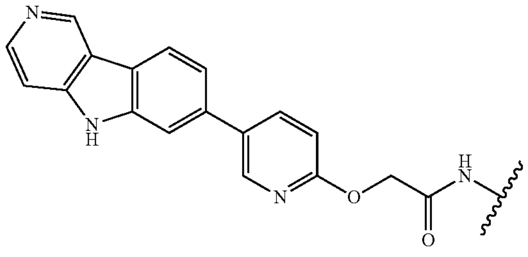
.

In certain embodiments, T is of the formula:

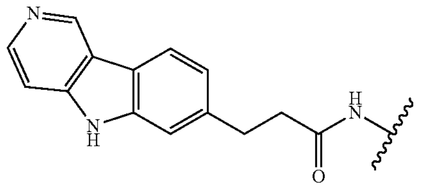
,
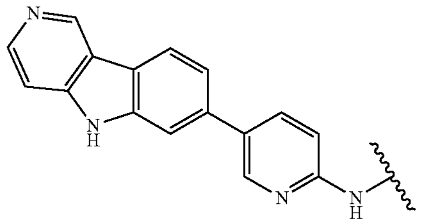
, or
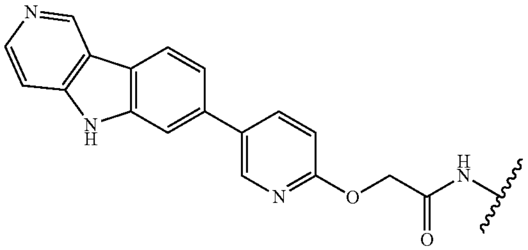
.

In certain embodiments, T is of the formula:

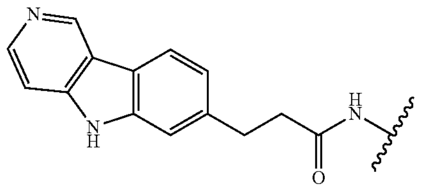
or

-continued

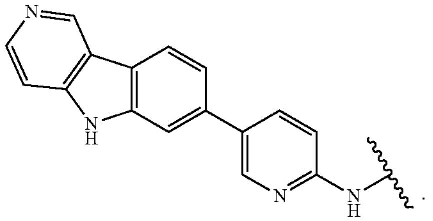

In certain embodiments, T is of the formula:

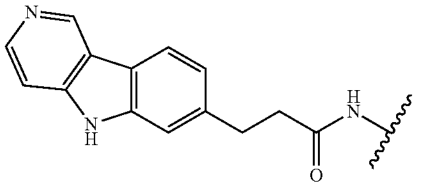

or

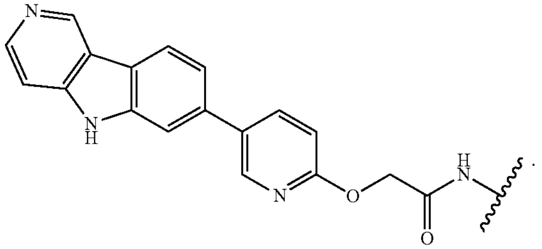

In certain embodiments, T is of the formula:

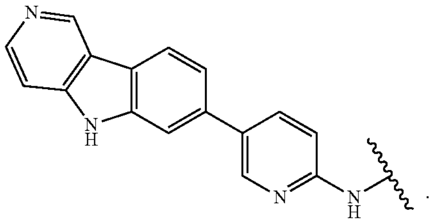 [SMILES: *Nc1ccc(-c2ccc3c(c2)[nH]c2ccncc23)cn1]

In certain embodiments, T is of the formula:

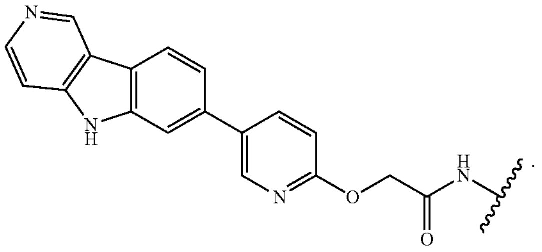 [SMILES: *NC(=O)COc1ccc(-c2ccc3c(c2)[nH]c2ccncc23)cn1]

In certain embodiments, T is of the formula:

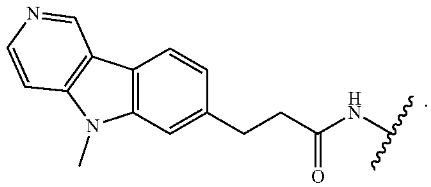 [SMILES: *NC(=O)CCc1ccc2c3cnccc3n(C)c2c1]

In certain embodiments, T is of the formula:

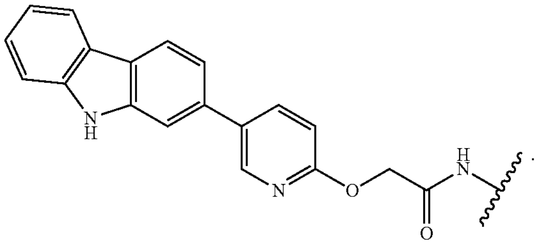 [SMILES: *NC(=O)COc1ccc(-c2ccc3c(c2)[nH]c2ccccc23)cn1]

In certain embodiments, T is of the formula:

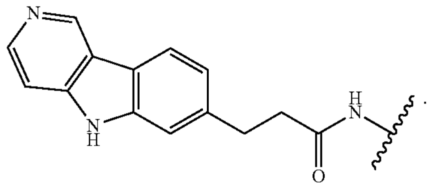 [SMILES: *NC(=O)CCc1ccc2c(c1)[nH]c1ccncc12]

In certain embodiments, T is of Formula T-II:

T-II

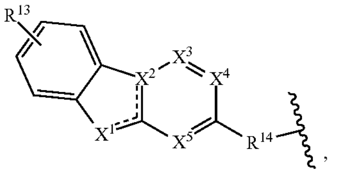

wherein:

$X^1$ is CH, N, NH, O, or S;

$X^2$ is CH, C, or N;

$X^3$ is $CR^{15}$ or N;

$X^4$ is $CR^5$ or N;

$X^5$ is $CR^{15}$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, -A-O—$(CH_2)_n$—(C═O)$NR^A$—; —$(CH_2)_n$—S—, -A-$(CH_2)_n$—S—, —$(CH_2)_n$-A-S—, -A-S—$(CH_2)_n$ —(C═O)$NR^A$—; —$(CH_2)NR^A$—, -A-$(CH_2)_n$ —$NR^A$, —$(CH_2)_n$-A-$NR^A$—, -A-$NR^A$—$(CH_2)_n$—

$(C{=}O)NR^A$—; —$(CH_2)_n$—$(C{=}O)NR^A$—, -A-$(CH_2)_n$—$(C{=}O)NR^A$—, —$(CH_2)_n$-A-$(C{=}O)NR^A$—, —$(CH_2)_n$—$S(O)_2NR^A$—, -A-$(CH_2)_n$—$S(O)_2NR^A$—, or —$(CH_2)_n$-A-$S(O)_2NR^A$—.

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments of Formula T-II:

$X^1$ is CH, N, O, or S;

$X^2$ is CH, C, or N;

$X^3$ is $CR^{15}$ or N;

$X^4$ is $CR^{15}$ or N;

$X^5$ is $CR^{15}$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A(C{=}O)$Oalkyl, —$NR^A(C{=}O)$Oaryl, —$NR^A(C{=}O)$alkyl, —$NR^A(C{=}O)$aryl, —(C=O)Oalkyl, —(C=O)Oaryl, —(C=O)alkyl, —(C=O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—$(C{=}O)NR^A$—, -A-$(CH_2)_n$—$(C{=}O)NR^A$—, —$(CH_2)_n$-A-$(C{=}O)NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments, $X^1$ and $X^2$ are N.

In certain embodiments, at least one of $X^3$, $X^4$, or $X^5$ is N.

In certain embodiments, $X^5$ is N; and $X^3$ and $X^4$ are CH.

In certain embodiments, $R^{14}$ is -A-$(CH_2)_n$—$NR^A$—, -A-$(CH_2)_n$—$(C{=}O)NR^A$—, -A-O—$(CH_2)_n$—$(C{=}O)NR^A$—, or -A-$(CH_2)_n$—$S(O)_2NR^A$—. In certain embodiments, $R^{14}$ is -A-$(CH_2)_n$ $NR^A$—, -A-$(CH_2)_n$, —$(C{=}O)NR^A$—, or -A-$(CH_2)_n$—$S(O)_2NR^A$—. In certain embodiments, $R^{14}$ is -A-$(CH_2)_n$—$NR^A$—, -A-$(CH_2)_n$—$(C{=}O)NR^A$—, or -A-$(CH_2)_n$—$S(O)_2NR^A$—; and A is unsubstituted heterocyclylene. In certain embodiments, $R^{14}$ is -A-$(CH_2)_n$—$(C{=}O)NR^A$—. In certain embodiments, $R^{14}$ is -A-$(CH_2)_n$—$(C{=}O)NR^A$—; and A is unsubstituted heterocyclylene. In certain embodiments, $R^{14}$ is -A-$(CH_2)_n$—$(C{=}O)NR^A$—; and A is unsubstituted piperidinylene or piperazinylene. In certain embodiments, $R^{14}$ is -A-O—$(CH_2)_n$—$(C{=}O)NR^A$—. In certain embodiments, $R^{14}$ is -A-O—$(CH_2)_n$—$(C{=}O)NR^A$—; and A is unsubstituted heteroarylene. In certain embodiments, $R^{14}$ is -A-O—$(CH_2)_n$—$(C{=}O)NR^A$—; and A is unsubstituted pyridinylene, pyrimidinylene, or pyridazinylene. In certain embodiments, $R^{14}$ is -A-O—$(CH_2)_n$—$(C{=}O)NR^A$; and A is unsubstituted pyridinylene.

In certain embodiments, T is of Formula T-II-a:

T-II-a

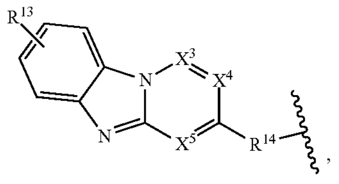

wherein:

$X^3$ is $CR^{15}$ or N;

$X^4$ is $CR^{15}$ or N;

$X^5$ is $CR^{15}$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A(C{=}O)$Oalkyl, —$NR^A(C{=}O)$Oaryl, —$NR^A(C{=}O)$alkyl, —$NR^A(C{=}O)$aryl, —(C=O)Oalkyl, —(C=O)Oaryl, —(C=O)alkyl, —(C=O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, -A-O—$(CH_2)_n$—$(C{=}O)NR^A$—, —$(CH_2)_n$—S—, -A-$(CH_2)_n$—S—, —$(CH_2)_n$-A-S—, -A-S—$(CH_2)_n$ —$(C{=}O)NR^A$—, —$(CH_2)_n$—$NR^A$—, -A-$(CH_2)_n$—$NR^A(CH_2)_n$-A-$NR^A$—, -A-$NR^A$—$(CH_2)_n$—$(C{=}O)NR^A$—, —$(CH_2)_n$—$(C{=}O)NR^A$—, -A-$(CH)_n$ $(C{=}O)NR^A$, —$(CH_2)_n$-A-$(C{=}O)NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments of Formula T-II-a:

$X^3$ is $CR^{15}$ or N;

$X^4$ is $CR^{15}$ or N;

$X^5$ is $CR^{15}$ or N;

each occurrence of $R^{13}$ and $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A(C{=}O)$Oalkyl, —$NR^A(C{=}O)$Oaryl, —$NR^A(C{=}O)$alkyl, —$NR^A(C{=}O)$aryl, —(C=O)Oalkyl, —(C=O)Oaryl, —(C=O)alkyl, —(C=O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—$(C{=}O)NR^A$—, -A-$(CH_2)_n$—$(C{=}O)NR^A$—, —$(CH_2)_n$-A-$(C{=}O)NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene; and n is 0-12;

wherein one or more carbon of $R^{13}$, $R^{14}$, and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments, T is of Formula T-II-b:

T-II-b

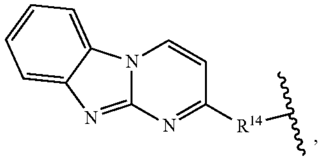

wherein $R^{14}$ is $—(CH_2)_n—O—$, $-A-(CH_2)_n—O—$, $—(CH_2)_n$ $-A-O—$, $-A-O—(CH_2)_n—(C═O)NR^A—$, $—(CH_2)_n—S—$, $-A-(CH_2)_n—S—$, $—(CH_2)_n-A-S—$, $-A-S—(CH_2)_n—(C═O)NR^A—$, $—(CH_2)_n—NR^A—$, $-A-(CH_2)_n$ $NR^A$, $—(CH_2)_n-A-NR^A—$, $-A-NR^A—(CH_2)_n—(C═O)NR^A—$, $—(CH_2)_n—(C═O)NR^A—$, $-A-(CH_2)_n(C═)NR^A$, $—(CH_2)_n-A-(C═O)NR^A—$, $—(CH_2)_n—S(O)_2NR^A—$, $-A-(CH_2)_n—S(O)_2NR^A—$, or $—(CH_2)_n-A-S(O)_2NR^A$-.

In certain embodiments of Formula T-II-b, $R^{14}$ is $—(CH_2)_n$ $—O—$, $-A-(CH_2)_n—O—$, $—(CH_2)_n-A-O—$, $—(CH_2)_n—S—$, $-A-(CH_2)_n—S—$, $—(CH_2)_n-A-S—$, $—(CH_2)_n—NR^A—$, $-A-(CH_2)_n—NR^A—$, $—(CH_2)_n-A-NR^A—$, $—(CH_2)_n—(C═O)NR^A—$, $-A-(CH_2)_n—(C═O)NR^A—$, $—(CH_2)_n-A-(C═O)NR^A—$, $—(CH_2)_n—S(O)_2NR^A—$, $-A-(CH_2)_n—S(O)_2NR^A—$, or $—(CH_2)_n-A-S(O)_2NR^A—$.

In certain embodiments, $R^{14}$ is $-A-(CH_2)_n—NR^A—$, $-A-(CH_2)_n—(C═O)NR^A—$, $-A-O—(CH_2)_n—(C═O)NR^A—$, or $-A-(CH_2)_n—S(O)_2NR^A—$. In certain embodiments, $R^{14}$ is $-A-(CH_2)_n$ $NR^A—$, $-A-(CH_2)_n(C═O)NR^A$, $-A-(CH_2)_n$ $S(O)_2NR^A—$. In certain embodiments, $R^{14}$ is $-A-(CH_2)_n—NR^A—$, $-A-(CH_2)_n—(C═O)NR^A—$, or $-A-(CH_2)_n—S(O)_2NR^A—$; and A is unsubstituted heterocyclylene. In certain embodiments, $R^{14}$ is $-A-(CH_2)_n—(C═O)NR^A—$. In certain embodiments, $R^{14}$ is $-A-(CH_2)_n—(C═O)NR^A—$; and A is unsubstituted heterocyclylene. In certain embodiments, $R^{14}$ is $-A-(CH_2)_n—(C═O)NR^A—$; and A is unsubstituted piperidinylene or piperazinylene. In certain embodiments, $R^{14}$ is $-A-O—(CH_2)_n—(C═O)NR^A—$. In certain embodiments, $R^{14}$ is $-A-O—(CH_2)_n—(C═O)NR^A—$; and A is unsubstituted heteroarylene. In certain embodiments, $R^{14}$ is $-A-O—(CH_2)_n—(C═O)NR^A—$; and A is unsubstituted pyridinylene, pyrimidinylene, or pyridazinylene. In certain embodiments, $R^{14}$ is $-A-O—(CH_2)_n—(C═O)NR^A$; and A is unsubstituted pyridinylene.

In certain embodiments, T is of the formula:

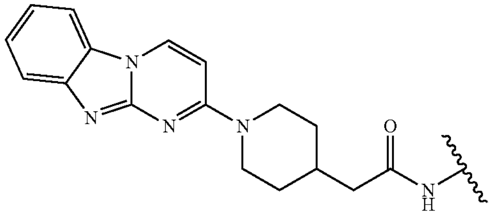

,

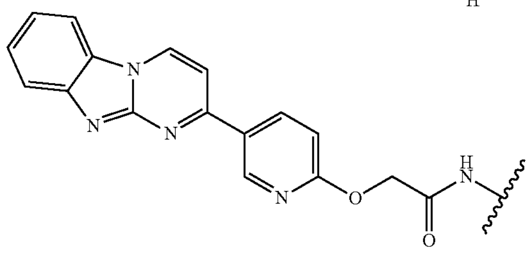

, or

-continued

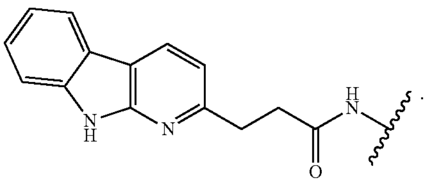

In certain embodiments, T is of the formula:

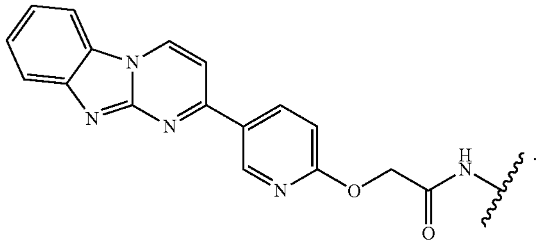 [SMILES: *NC(=O)COc1ccc(-c2ccn3c(n2)nc2ccccc23)cn1]

In certain embodiments, T is of the formula:

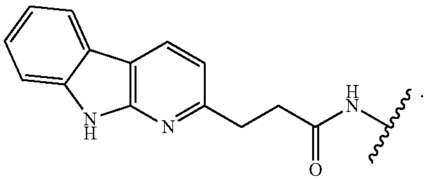 [SMILES: *NC(=O)CCc1ccc2c(n1)[nH]c1ccccc12]

In certain embodiments, T is of the formula:

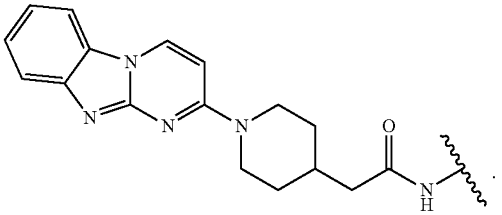 [SMILES: *NC(=O)CC1CCN(c2ccn3c(n2)nc2ccccc23)CC1]

In certain embodiments, T is of formula T-II or T-IV:

T-III

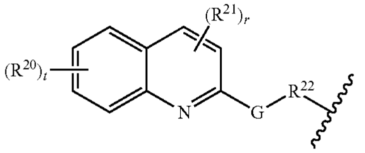

or

T-IV

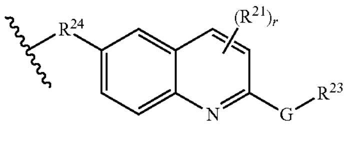

wherein:

each of $R^{20}$ and $R^{21}$ is independently halogen, —OH, —COOH, —$SO_3H$, —$NO_2$, —SH, —$NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$—S$(O)_2NR^A$—;

$R^{23}$ is halogen, —OH, —COOH, —$SO_3H$, —$NO_2$, —SH, —$NR^xR^y$, substituted or unsubstituted alkyl, or substituted or unsubstituted alkoxy;

$R^{24}$ is substituted or unsubstituted alkylene, or substituted or unsubstituted alkoxylene;

$R^x$ and $R^y$ are independently hydrogen, or substituted or unsubstituted alkyl;

n is 0-12;

t is 0, 1, 2, 3, or 4; and r is 0, 1, or 2.

In certain embodiments, T is of formula T-III:

T-III

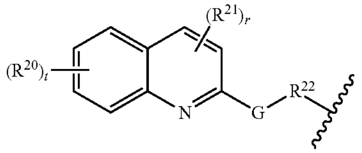

wherein:

$R^{20}$ and $R^{21}$ are independently halogen, —OH, —COOH, —$SO_3H$, —$NO_2$, —SH, —$NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$—S$(O)_2NR^A$—;

$R^x$ and $R^y$ are independently hydrogen, or substituted or unsubstituted alkyl;

n is 0-12;

t is 0, 1, 2, 3, or 4; and r is 0, 1, or 2.

In certain embodiments, T is of formula T-III-a:

T-III-a

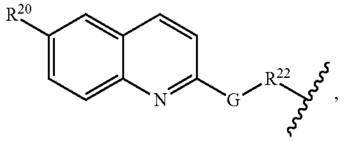

, wherein:

$R^{20}$ is halogen, —OH, —COOH, —$SO_3H$, —$NO_2$, —SH, —$NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$—S$(O)_2NR^A$—;

$R^x$ and $R^y$ are independently hydrogen, or substituted or unsubstituted alkyl; and n is 0-12.

In certain embodiments, $R^{20}$ is unsubstituted alkyl, alkyl substituted with one or more halogen or hydroxy groups, unsubstituted alkoxy, or alkoxy substituted with one or more halogen or hydroxy groups; G is unsubstituted arylene or unsubstituted heteroarylene; and $R^{22}$ is —$(CH_2)_n$—$NR^A$— or —$(CH_2)_n$—(C═O)$NR^A$—.

In certain embodiments, $R^{20}$ is unsubstituted alkyl, alkyl substituted with one or more halogen or hydroxy groups, unsubstituted alkoxy, or alkoxy substituted with one or more halogen or hydroxy groups; G is unsubstituted arylene or unsubstituted heteroarylene; and $R^{22}$ is —$(CH_2)$—$NR^A$—.

In certain embodiments, G is unsubstituted arylene. In certain embodiments, G is unsubstituted phenylene. In certain embodiments, G is unsubstituted heteroarylene. In certain embodiments, G is unsubstituted pyridinylene, pyrimidinylene, pyridazinylene, pyrazolinylene, imidazolylene, oxazolylene, or thiazolylene. In certain embodiments, G is unsubstituted pyridinylene or pyrazolinylene. In certain embodiments, G is unsubstituted pyridinylene. In certain embodiments, G is unsubstituted phenylene, pyridinylene, or pyrazolinylene.

In certain embodiments, $R^{20}$ is unsubstituted alkyl, alkyl substituted with one or more halogen or hydroxy groups, unsubstituted alkoxy, or alkoxy substituted with one or more halogen or hydroxy groups; G is unsubstituted arylene or unsubstituted heteroarylene; and $R^{22}$ is —$(CH_2)_n$—$NR_A$— or —$(CH_2)_n$—(C═O)$NR^A$-.

In certain embodiments, $R^{20}$ is

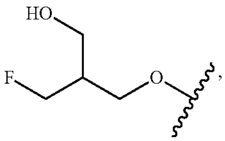,
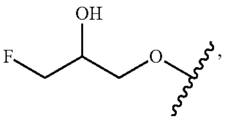 [SMILES: *OCC(O)CF],
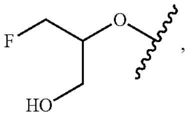, or
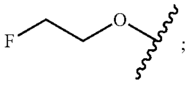;

G is unsubstituted arylene or unsubstituted heteroarylene; and $R^{22}$ is —$(CH_2)_n$—$NR^A$— or —$(CH_2)_n$—(C═O)$NR^A$—.

In certain embodiments, $R^{20}$ is

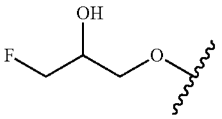 or
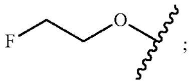;

G is unsubstituted arylene or unsubstituted heteroarylene; and $R^{22}$ is —$(CH_2)_n$—$NR^A$— or —$(CH_2)_n$—(C═O)$NR^A$—.

In certain embodiments, $R^{20}$ is

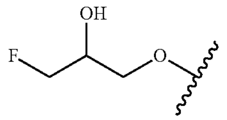 or 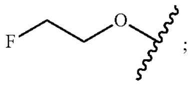 ;

G is unsubstituted arylene or unsubstituted heteroarylene; and $R^{22}$ is $-(CH_2)_n-NR^A-$.

In certain embodiments, $R^{20}$ is

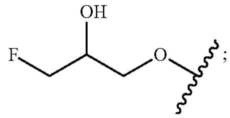 ;

G is unsubstituted arylene or unsubstituted heteroarylene; and $R^{22}$ is $-(CH_2)_n-NR^A-$.

In certain embodiments, $R^{20}$ is

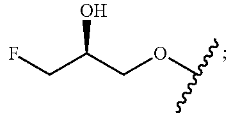 ;

G is unsubstituted arylene or unsubstituted heteroarylene; and $R^{22}$ is $-(CH_2)_n-NR^A-$.

In certain embodiments, T is of the formula:

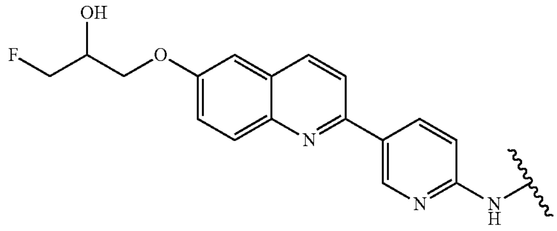 ,

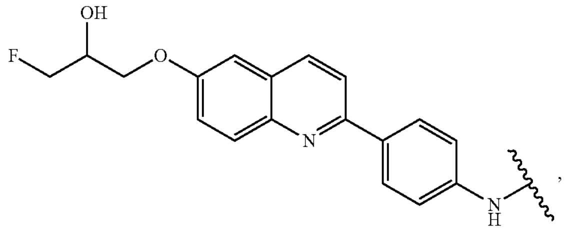 ,

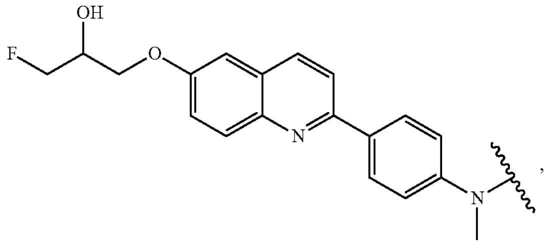 , or

-continued

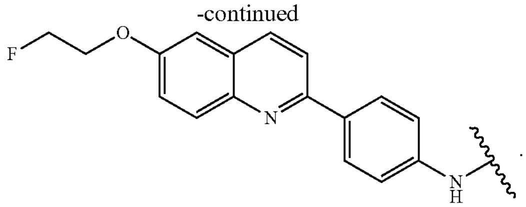 .

In certain embodiments, T is of the formula:

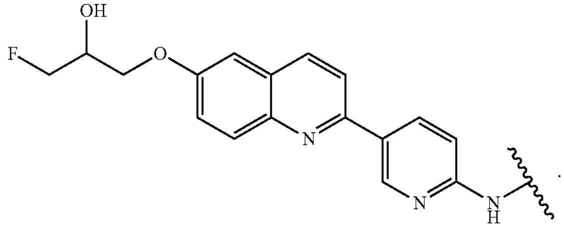 [SMILES: *Nc1ccc(-c2ccc3cc(OCC(O)CF)ccc3n2)cn1] .

In certain embodiments, T is of the formula:

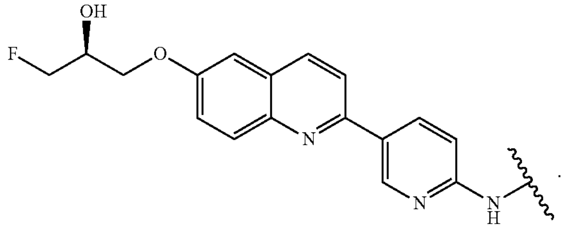 [SMILES: *Nc1ccc(-c2ccc3cc(OC[C@H](O)CF)ccc3n2)cn1] .

In certain embodiments, T is of formula T-IV:

T-IV

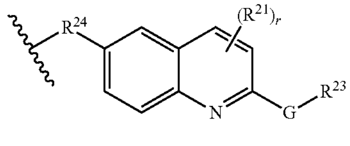

wherein:

$R^{21}$ is halogen, —OH, —COOH, $-SO_3H$, $-NO_2$, —SH, $-NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{23}$ is halogen, —OH, —COOH, $-SO_3H$, $-NO_2$, —SH, $-NR^xR^y$, substituted or unsubstituted alkyl, or substituted or unsubstituted alkoxy;

$R^{24}$ is substituted or unsubstituted alkylene, or substituted or unsubstituted alkoxylene;

$R^x$ and $R^y$ are independently hydrogen, or substituted or unsubstituted alkyl; and r is 0, 1, or 2.

In certain embodiments, T is of formula T-IV-a:

T-IV-a

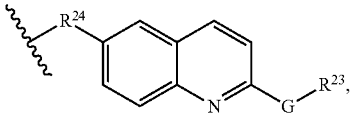

wherein:

G is substituted or unsubstituted heterocyclylene, substituted or unsubstituted arylene, or substituted or unsubstituted heteroarylene;

$R^{23}$ is halogen, —OH, —COOH, —$SO_3H$, —$NO_2$, —SH, —$NR^xR^y$, substituted or unsubstituted alkyl, or substituted or unsubstituted alkoxy;

$R^{24}$ is substituted or unsubstituted alkylene, or substituted or unsubstituted alkoxylene; and $R^x$ and $R^y$ are independently hydrogen, or substituted or unsubstituted alkyl.

In certain embodiments, $R^{24}$ is unsubstituted alkylene, alkylene substituted with one or more halogen or hydroxy groups, unsubstituted alkoxylene, or alkoxylene substituted with one or more halogen or hydroxy groups; G is unsubstituted arylene or unsubstituted heteroarylene; and $R^{23}$ is $NR^xR^y$.

In certain embodiments, G is unsubstituted arylene. In certain embodiments, G is unsubstituted phenylene. In certain embodiments, G is unsubstituted heteroarylene. In certain embodiments, G is unsubstituted pyridinylene, pyrimidinylene, pyridazinylene, pyrazolinylene, imidazolylene, oxazolylene, or thiazolylene. In certain embodiments, G is unsubstituted pyridinylene or pyrazolinylene. In certain embodiments, G is unsubstituted pyridinylene. In certain embodiments, G is unsubstituted phenylene, pyridinylene, or pyrazolinylene.

In certain embodiments, $R^{24}$ is

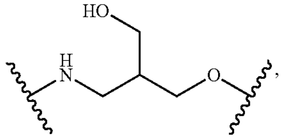,

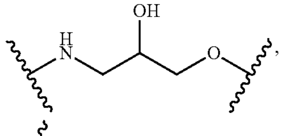,

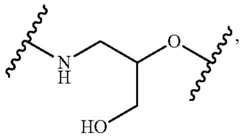, or 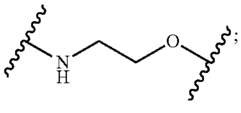;

G is unsubstituted arylene or unsubstituted heteroarylene; and $R^{23}$ is $NR^xR^y$.

In certain embodiments, $R^{24}$ is

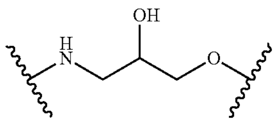 or

-continued

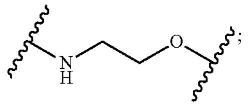;

G is unsubstituted arylene or unsubstituted heteroarylene; and $R^{23}$ is $NR^xR^y$.

In certain embodiments, $R^{24}$ is

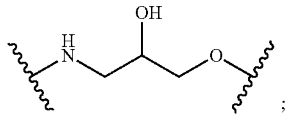 [SMILES: *NCC(O)CO*];

G is unsubstituted arylene or unsubstituted heteroarylene; and $R^{23}$ is $NR^xR^y$.

In certain embodiments, $R^{24}$ is

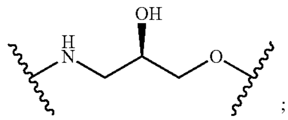 [SMILES: *NC[C@@H](O)CO*];

G is unsubstituted arylene or unsubstituted heteroarylene; and $R^{23}$ is $NR^xR^y$.

In certain embodiments, T is of the formula:

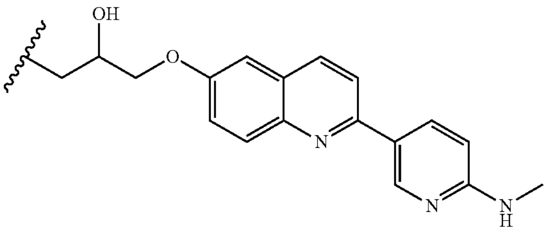,

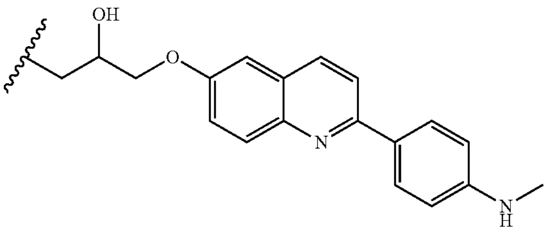,

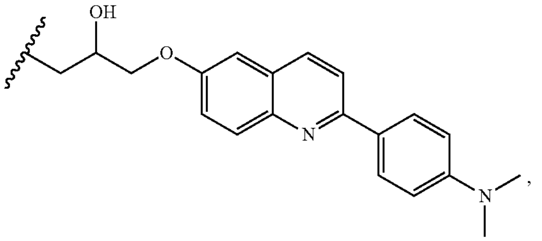, or

-continued
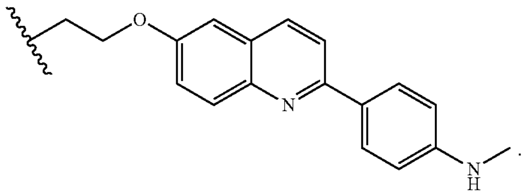
In certain embodiments, T is of the formula:
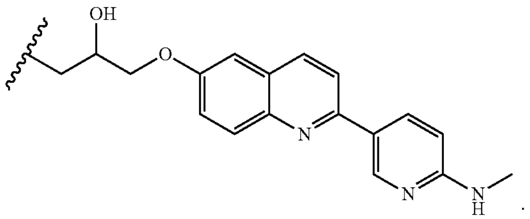 [SMILES: *CC(O)COc1ccc2nc(-c3ccc(NC)nc3)ccc2c1]
In certain embodiments, T is of the formula:
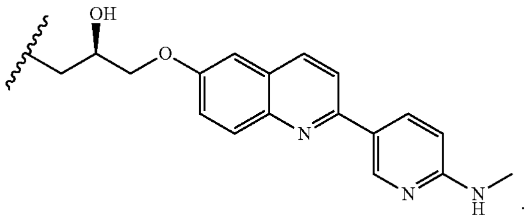 [SMILES: *C[C@@H](O)COc1ccc2nc(-c3ccc(NC)nc3)ccc2c1]
In certain embodiments, T is of the formula:
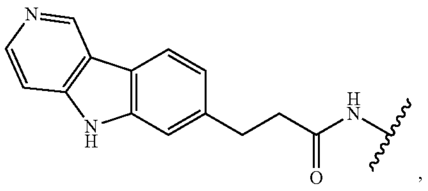
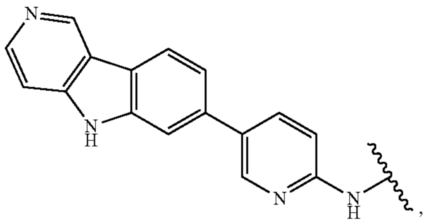
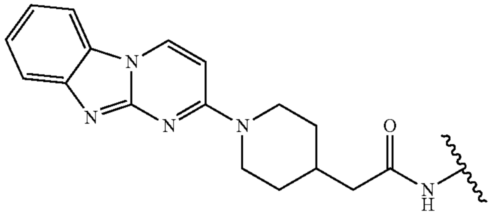
-continued
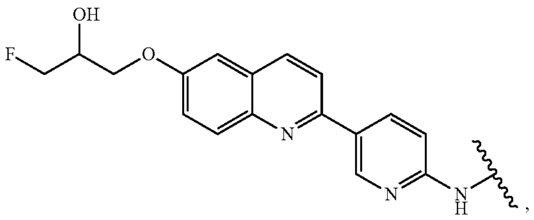
or
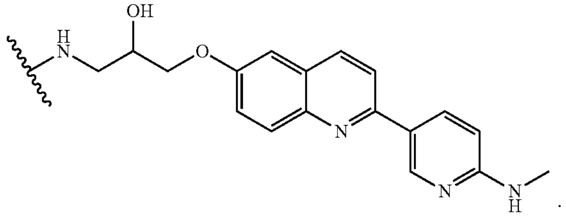
In certain embodiments, T is of the formula:
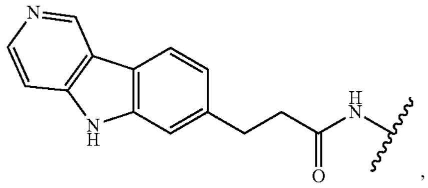
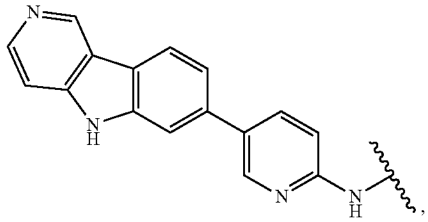
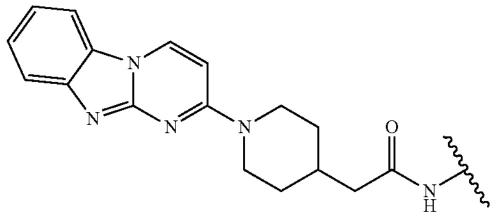
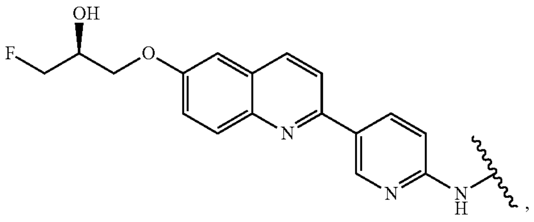
or
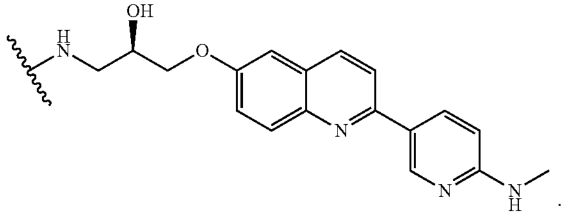

In certain embodiments, T is of the formula:
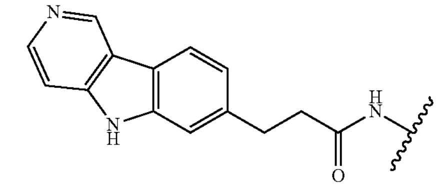
,
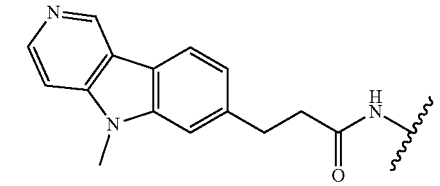
,
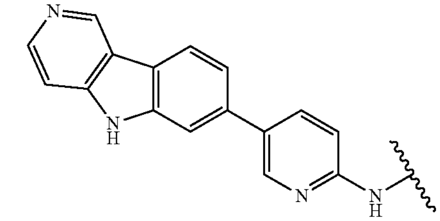
,
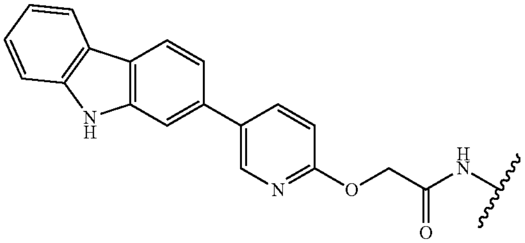
,
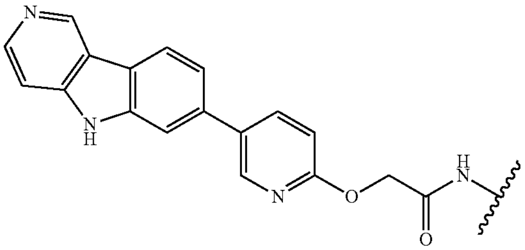
,
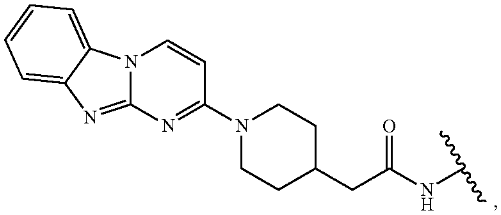
,
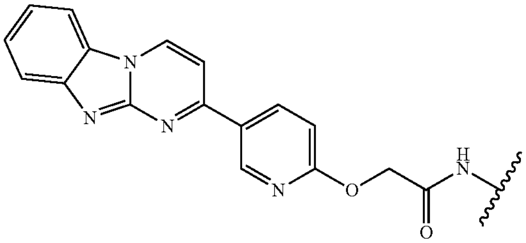
,
-continued
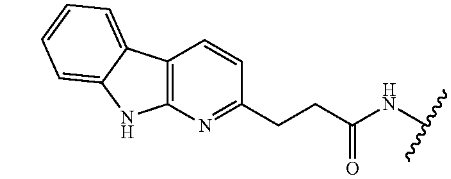
,
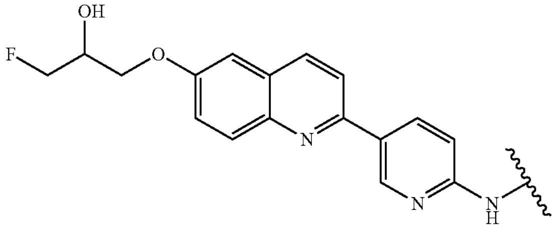
,
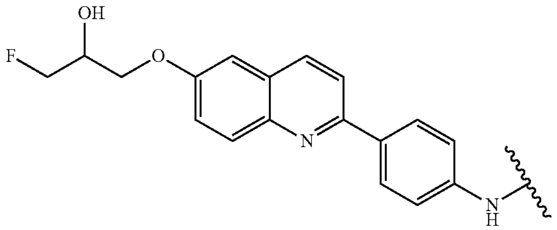
,
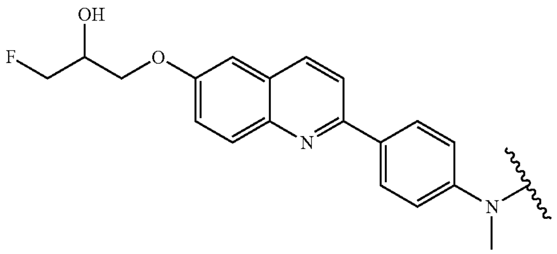
,
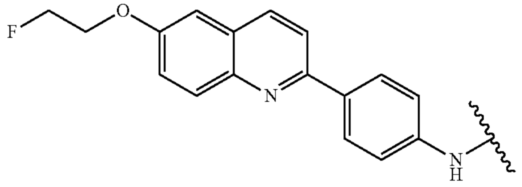
,
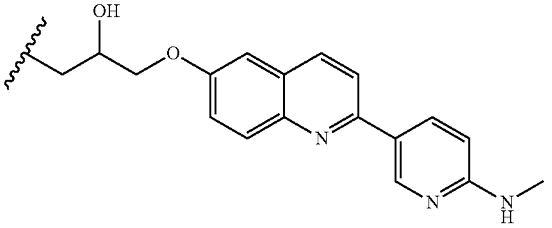
,
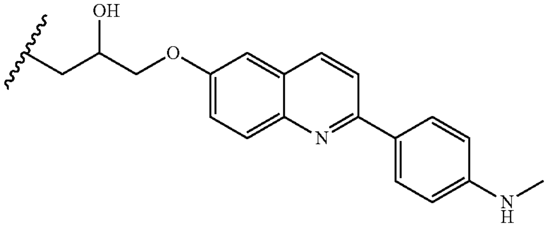
, -continued
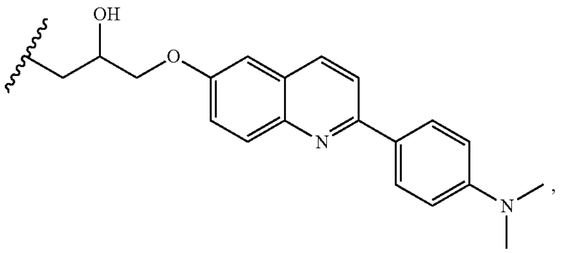
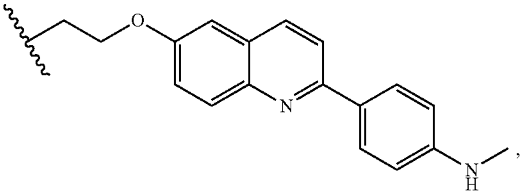
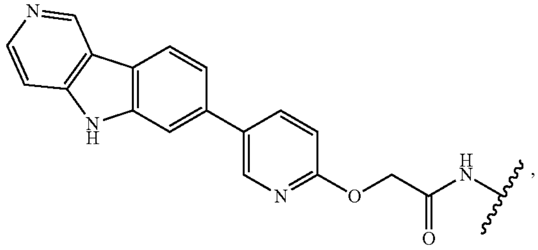
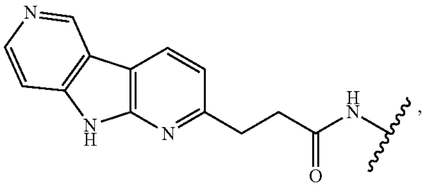
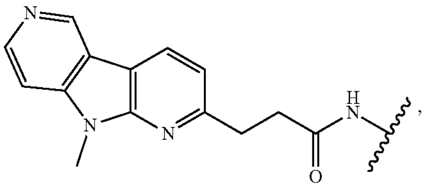
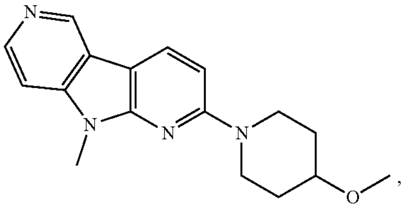
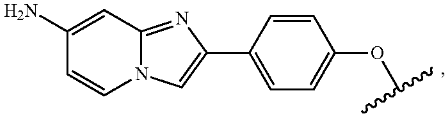
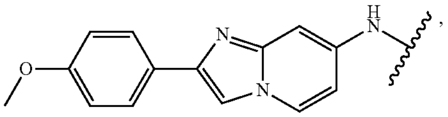
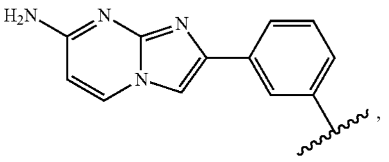
-continued
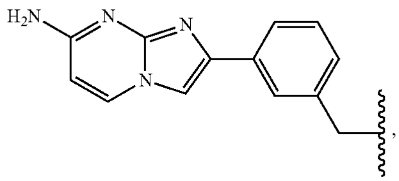
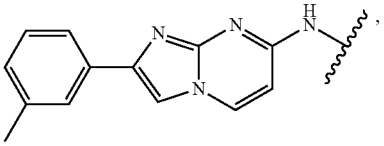
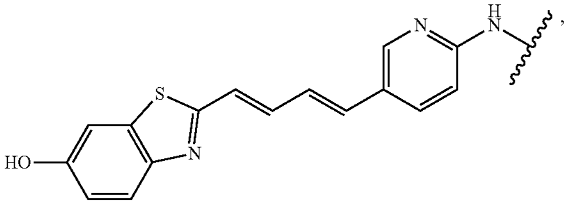
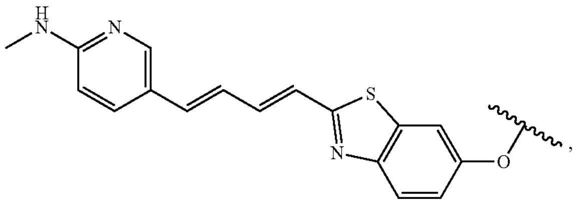
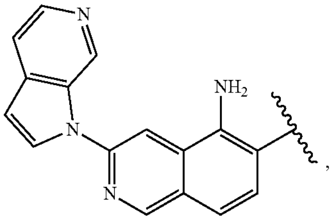
or
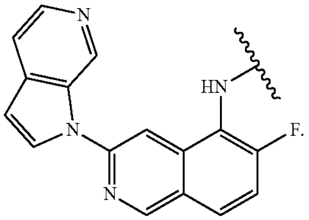
In certain embodiments, T is of the formula:
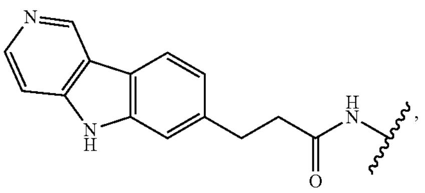
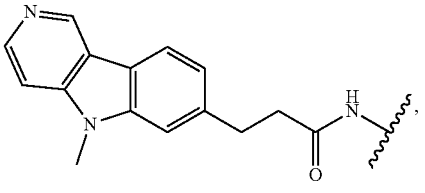

-continued
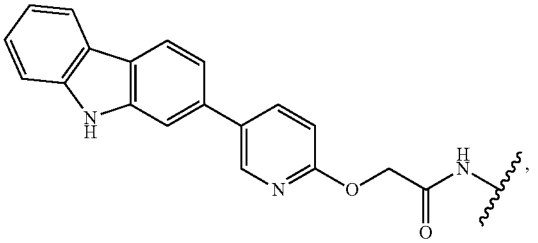
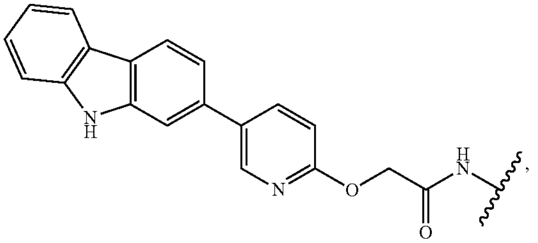
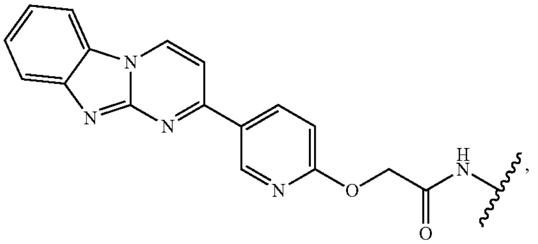
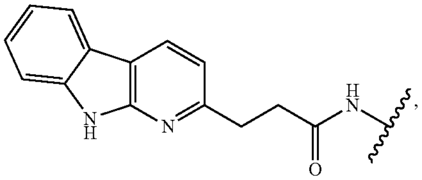
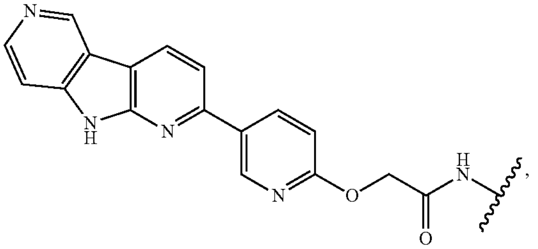
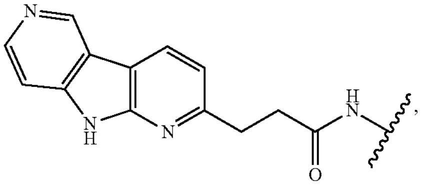
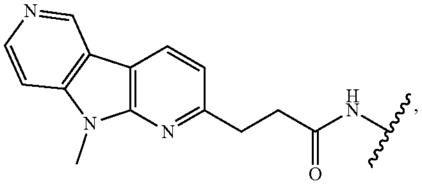
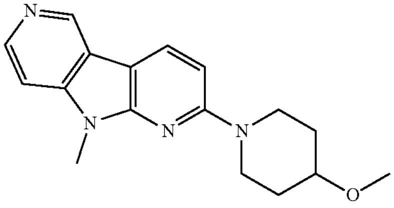
,
-continued
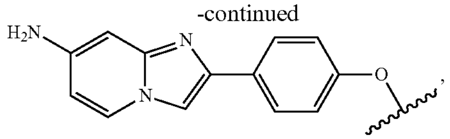
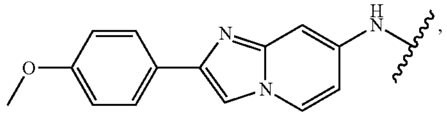
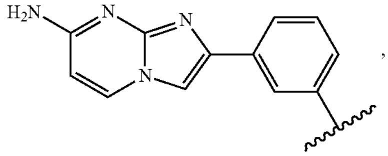
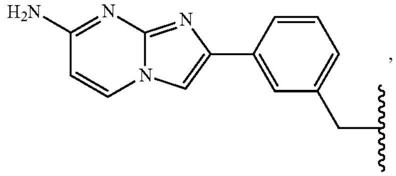
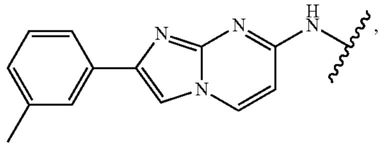
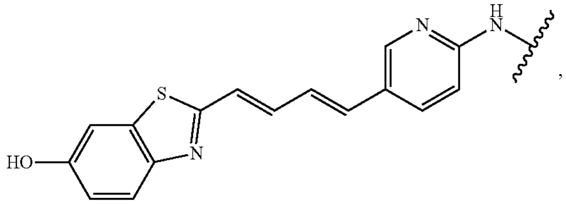
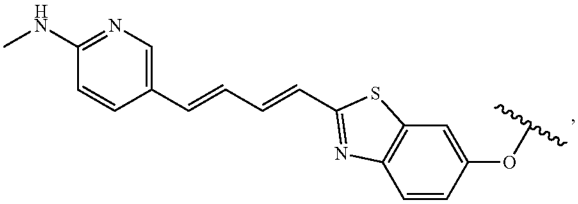
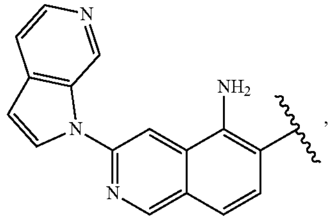
, or
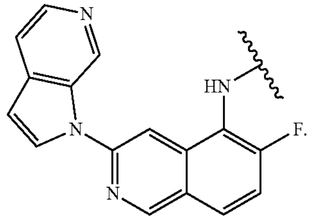
In certain embodiments, the tau binding moiety binds tau protein with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the tau binding moiety selectively binds tau protein over another protein. In some embodiments, the compound of Formula I selectively binds tau protein over amyloid β. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Group L

L is a divalent moiety linking T and E. In certain embodiments, L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, a bond, —O—, —N($R^A$)—, —S—, —C(═O)—, —C(═O)O—, —C(═O)N$R^A$—, —N$R^A$C(═O)—, —N$R^A$C(═O)$R^A$—, —C(═O)$R^A$—, —N$R^A$C(═O)O—, —N$R^A$C(═O)N($R^A$)—, —OC(═O)—, —OC(═O)O—, —OC(═O)N($R^A$)—, —$S(O)_2NR^A$—, —$NR^AS(O)_2$—, or a combination thereof.

In certain embodiments, L is any "L" group recited in U.S. patent application U.S. Ser. No. 14/792,414, filed Jul. 6, 2015, which is incorporated herein by reference. In certain embodiments, L is any "Linker" group recited in U.S. patent application U.S. Ser. No. 14/707,930, filed May 8, 2015, which is incorporated herein by reference. In certain embodiments, L comprises up to 50 atoms, excluding hydrogen atoms. In certain embodiments, L comprises up to 40 atoms, excluding hydrogen atoms. In certain embodiments, L comprises up to 30 atoms, excluding hydrogen atoms. In certain embodiments, L comprises up to 20 atoms, excluding hydrogen atoms. In certain embodiments, L comprises up to 15 atoms, excluding hydrogen atoms. In certain embodiments, L comprises up to 12 atoms, excluding hydrogen atoms. In certain embodiments, L comprises up to 10 atoms, excluding hydrogen atoms. In certain embodiments, L comprises up to 9 atoms excluding hydrogen atoms. In certain embodiments, L comprises up to 6 atoms excluding hydrogen atoms. In certain embodiments, L comprises up to 5 atoms excluding hydrogen atoms. In certain embodiments, L comprises up to 3 atoms excluding hydrogen atoms. In certain embodiments, any of the carbon atoms in L can be substituted.

In certain embodiments, L is substituted or unsubstituted alkylene, substituted or unsubstituted alkenylene, or substituted or unsubstituted heteroalkylene.

In certain embodiments, L is substituted or unsubstituted alkylene, or substituted or unsubstituted heteroalkylene. In certain embodiments, L is a substituted or unsubstituted $C_{1-30}$ alkylene. In certain embodiments, L is a substituted or unsubstituted $C_{1-20}$ alkylene. In certain embodiments, L is a substituted or unsubstituted $C_{1-10}$ alkylene. In certain embodiments, L is a substituted or unsubstituted $C_{1-30}$ heteroalkylene. In certain embodiments, L is a substituted or unsubstituted $C_{1-20}$ heteroalkylene. In certain embodiments, L is a substituted or unsubstituted $C_{1-10}$ heteroalkylene.

In certain embodiments, L is

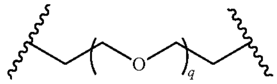,

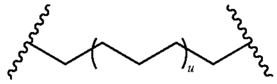, or

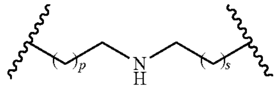;

q is 1-12; u is 1-12; p is 1-10; and s is 1-10.

In certain embodiments, L is

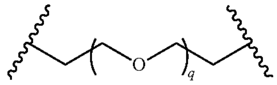 or

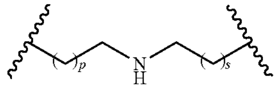;

q is 1-12; p is 1-10; and s is 1-10.

In certain embodiments, L is

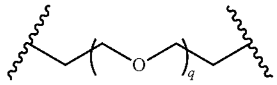 or

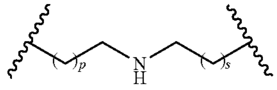;

q is 1-5; p is 2-5; and s is 1-5.

In certain embodiments, L is

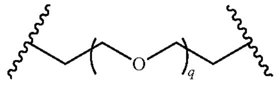;

and q is 1-12. In certain embodiments, L is

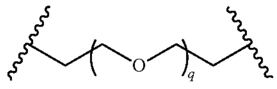;

and q is 1-5. In certain embodiments, L is

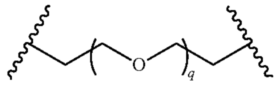;

and q is 2. In certain embodiments, L is

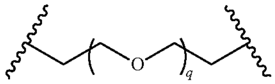;

q; and q is 3. In certain embodiments, L is

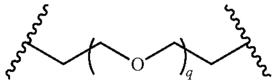;

and q is 4. In certain embodiments, L is

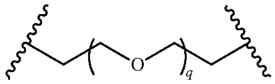;

and q is 5.

In certain embodiments, L is

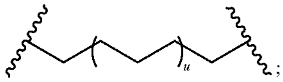;

and u is 1-12. In certain embodiments, L is

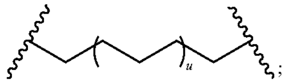;

and u is 1-5.

In certain embodiments, L is

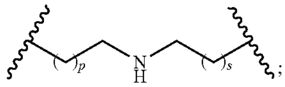;

p is 1-10; and s is 1-10. In certain embodiments, L is

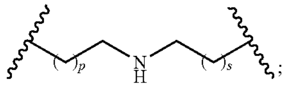;

p is 2-5; and s is 1-5. In certain embodiments, L is

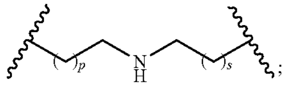;

p is 3; and s is 2.

In certain embodiments, L is an unsubstituted $C_3$-$C_{12}$ alkylene or

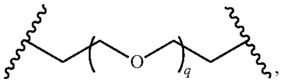, wherein q is 1-12. In certain embodiments, L is an unsubstituted $C_3$-$C_{12}$ alkylene or

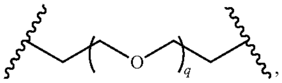, wherein q is 1-11. In certain embodiments, L is an unsubstituted $C_4$-$C_{12}$ alkylene or

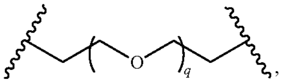, wherein q is 1-11. In certain embodiments, L is an unsubstituted $C_4$-$C_{10}$ alkylene or

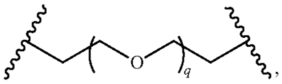, wherein q is 1-11. In certain embodiments, L is an unsubstituted $C_5$-$C_7$ alkylene or

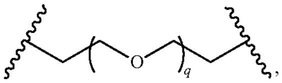, wherein q is 1-11. In certain embodiments, L is an unsubstituted $C_5$-$C_7$ alkylene or

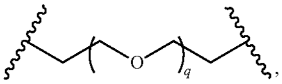, wherein q is 1-6.

In certain embodiments, L is

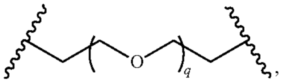, wherein q is 1-12. In certain embodiments, L is

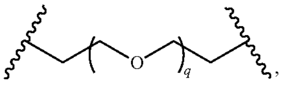, wherein q is 1-6. In certain embodiments, L is

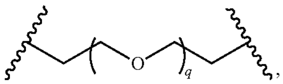

wherein q is 1. In certain embodiments, L is

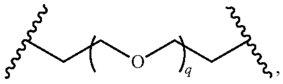

wherein q is 2. In certain embodiments, L is

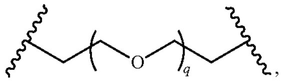

wherein q is 3. In certain embodiments, L is

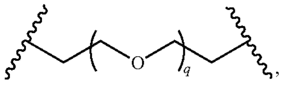

wherein q is 4. In certain embodiments, L is

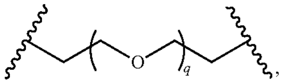

wherein q is 5. In certain embodiments, L is

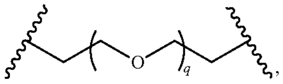

wherein q is 6. In certain embodiments, L is

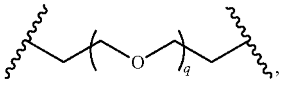

wherein q is 7. In certain embodiments, L is

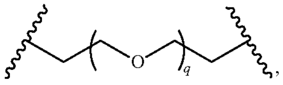

wherein q is 8. In certain embodiments, L is

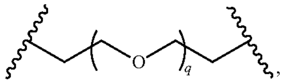

wherein q is 9. In certain embodiments, L is

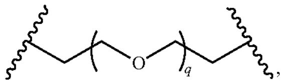

wherein q is 10. In certain embodiments, L is

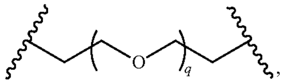

wherein q is 11. In certain embodiments, L is

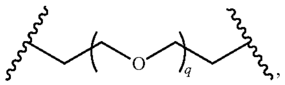

wherein q is 12.

In certain embodiments, L is an unsubstituted $C_3$-$C_{12}$ alkylene. In certain embodiments, L is an unsubstituted $C_4$-$C_{12}$ alkylene. In certain embodiments, L is an unsubstituted $C_4$-$C_{10}$ alkylene. In certain embodiments, L is an unsubstituted $C_5$-$C_7$ alkylene. In certain embodiments, L is an unsubstituted $C_3$ alkylene. In certain embodiments, L is an unsubstituted $C_4$ alkylene. In certain embodiments, L is an unsubstituted $C_5$ alkylene. In certain embodiments, L is an unsubstituted $C_6$ alkylene. In certain embodiments, L is an unsubstituted $C_7$ alkylene. In certain embodiments, L is an unsubstituted $C_8$ alkylene. In certain embodiments, L is an unsubstituted $C_9$ alkylene. In certain embodiments, L is an unsubstituted $C_{10}$ alkylene. In certain embodiments, L is an unsubstituted $C_{11}$ alkylene. In certain embodiments, L is an unsubstituted $C_{12}$ alkylene.

Group $R^4$

In certain embodiments, $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted heterocyclyl, substituted or unsubstituted aryl, substituted or unsubstituted heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted $C_{1-30}$ heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, or substituted or unsubstituted $C_{1-30}$ heteroalkyl. In certain embodiments, $R^A$ is, independently, hydrogen, substituted or unsubstituted $C_{1-6}$ alkyl, or substituted or unsubstituted $C_{1-20}$ heteroalkyl. In certain embodiments, $R^A$ is, independently, hydrogen, or substituted or unsubstituted $C_{1-6}$ alkyl. In certain embodiments, $R^A$ is, independently, hydrogen.

Group E

E is an E3 ubiquitin ligase binding moiety. E is inclusive of all moieties that bind, or can bind, any E3 ubiquitin ligase. For example, in certain embodiments, E is capable of binding an E3 ubiquitin ligase, such as Cereblon or von Hippel-Lindau tumor suppressor (VHL). In certain embodiments, E is capable of binding to multiple different E3 ubiquitin ligases. In certain embodiments, E binds to Cereblon. In certain embodiments, E binds to VHL.

Human Cereblon (CRBN) is a protein of 442 amino acids with an apparent molecular weight of ~51 kDa (GenBank: AAH17419). (For the CRBN protein sequence see: Higgins et al., *Neurology.* 2004, 63, 1927-31. For additional information related to the CRBN structure see Hartmann et al., *PLoS One.* 2015, 10, e0128342.) Human CRBN contains the N-terminal part (237-amino acids from 81 to 317) of ATP-dependent Lon protease domain without the conserved Walker A and Walker B motifs, 11 casein kinase II phosphorylation sites, 4 protein kinase C phosphorylation sites, 1 N-linked glycosylation site, and 2 myristoylation sites. CRBN is widely expressed in testis, spleen, prostate, liver, pancreas, placenta, kidney, lung, skeletal muscle, ovary, small intestine, peripheral blood leukocyte, colon, brain, and retina. CRBN is located in the cytoplasm, nucleus, and peripheral membrane. (Chang et al., *Int. J. Biochem. Mol. Biol.* 2011, 2, 287-94.)

Cereblon is an E3 ubiquitin ligase, and it forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, Cereblon ubiquitination of target proteins results in increased levels of fibroblast growth factor 8 (FGF8) and fibroblast growth factor 10 (FGF10). FGF8, in turn, regulates a number of developmental processes, such as limb and auditory vesicle formation.

In certain embodiments, E is a modulator, binder, inhibitor, or ligand of Cereblon. In certain embodiments, E is a modulator of Cereblon. In certain embodiments, E is a binder of Cereblon. In certain embodiments, E is an inhibitor of Cereblon. In certain embodiments, E is a ligand of Cereblon. In certain embodiments, E is any modulator, binder, inhibitor, or ligand of Cereblon disclosed in U.S. patent application U.S. Ser. No. 14/792,414, filed Jul. 6, 2015, U.S. patent application U.S. Ser. No. 14/707,930, filed May 8, 2015, and International Patent Application, PCT/US2013/054663, filed Aug. 13, 2013, each of which are incorporated herein by reference. In certain embodiments, E is a modulator, binder, inhibitor, or ligand of a Cereblon variant. In certain embodiments, E is a modulator, binder, inhibitor, or ligand of a Cereblon isoform.

In certain embodiments, E comprises a heteroaryl ring. In certain embodiments, E comprises a fused bicyclic heteroaryl ring. In certain embodiments, E comprises a fused bicyclic heteroaryl ring and a heterocyclic ring. In certain embodiments, E comprises a phthalimido group, or an analogue or derivative thereof. In certain embodiments, E comprises a phthalimido-glutarimide group, or an analogue or derivative thereof.

In certain embodiments, E is of Formula E-I:

E-I

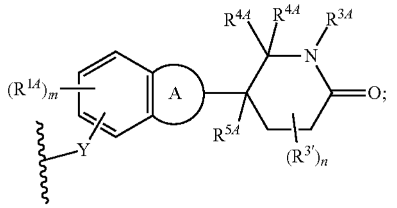

wherein:

A is a substituted or unsubstituted heterocyclyl, or substituted or unsubstituted heteroaryl ring;

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(C{=}O)-(CH_2)_k-O-$, $-NR^B(CH_2)_k-NR^B(C{=}O)-$, or $-(CH_2)_k-NR^B(C{=}O)-$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of Formula E-I:

A is a substituted or unsubstituted heterocyclyl, or substituted or unsubstituted heteroaryl ring;

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(CH_2)_k-NR^B(C{=}O)-$, or $-(CH_2)_k-NR^B(C{=}O)-$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments, Y is $-(CH_2)_k-NR^B-$, $-O(CH_2)_k-(C{=}O)NR^B-$, $-(CH_2)_k-O-$, $-NR^B(C{=}O)-(CH_2)_k-O-$, or $-(CH_2)_k-NR^B(C{=}O)-$. In certain embodiments, Y is $-(CH_2)B-NR^BO(CH_2)_k-(C{=}O)NR^B-$, or $-(CH_2)_k-NR^B(C{=}O)-$. In certain embodiments, Y is $-(CH_2)_k-NR^B-$, $-(CH_2)_k-O-$, or $-NR^B(C{=}O)-(CH_2)_k-O-$. In certain embodiments, Y is $-(CH_2)_k-NH-$. In certain embodiments, Y is $-NH-$. In certain embodiments, Y is $-(CH_2)_k-O-$. In certain embodiments, Y is $-O-$. In certain embodiments, Y is $-NH(C{=}O)-(CH_2)-O-$. In certain embodiments, Y is $-NH-$, $-O-$, or $-NH(C{=}O)-(CH_2)-O-$.

In certain embodiments, E is of Formula E-II or E-III:

E-II

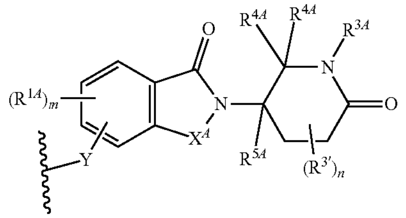

E-III

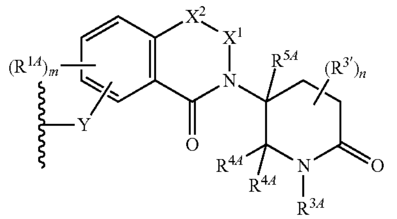

wherein:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(C{=}O)-(CH_2)_k-O-$, $-NR^B(CH_2)_k-NR^B(C{=}O)-$, or $-(CH_2)_k-NR^B(C{=}O)-$;

$X^A$ is C(O) or $C(R^{3A})_2$;

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of Formula E-II or E-III:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(CH_2)_k-NR^B(C{=}O)-$, or $-(CH_2)_k-NR^B(C{=}O)-$;

$X^A$ is C(O) or $C(R^{3A})_2$;

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments, E is of formula E-II:

E-II

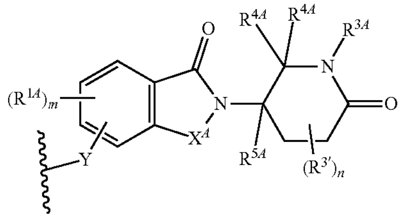

wherein:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(C{=}O)-(CH_2)_k-O-$, $-NR^B(CH_2)_k-NR^B(C{=}O)-$, or $-(CH_2)_k-NR^B(C{=}O)-$;

$X^A$ is C(O) or $C(R^{3A})_2$;

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of formula E-II:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)$ $NR^B$—, —$O(CH_2)_k$—(C═O)$NR^B$—, —$O(CH_2)_k$—$NR^B$(C═O)—, —$NR^B(CH_2)_k$—$NR^B$(C═O)—, or —$(CH_2)_k$—$NR^B$(C═O)—;

$X^A$ is C(O) or $C(R^{3A})_2$;

$X^1$-$X^2$ is $C(R^{3A})$═N or $C(R^{3A})_2$—$C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of Formula E-II:

Y is —$(CH_2)_k$—$NR^B$—, —$O(CH_2)_k$—(C═O)$NR^B$—, —$NR^B$(C═O)—$(CH_2)_k$—O—, or —$(CH_2)_k$—$NR^B$(C═O)—;

$X^A$ is C(O) or $C(R^{3A})_2$;

$X^1$-$X^2$ is $C(R^{3A})$═N or $C(R^{3A})_2$—$C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of Formula E-IT:

Y is —$(CH_2)_k$—$NR^B$—, —$O(CH_2)_k$—(C═O)$NR^B$—, or —$(CH_2)_k$—$NR^B$(C═O);

$X^A$ is C(O) or $C(R^{3A})_2$;

$X^1$-$X^2$ is $C(R^{3A})$═N or $C(R^{3A})_2$—$C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments, E is of Formula E-II-a:

E-II-a

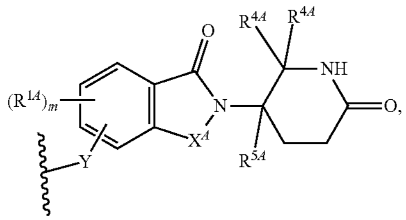

wherein:

Y is —$(CH_2)_k$—$NR^B$—, —$O(CH_2)_k$—(C═O)$NR^B$—, —$NR^B$(C═O)—$(CH_2)_k$—O—, or —$(CH_2)_k$—$NR^B$(C═O)—;

$X^A$ is C(O) or $C(R^{3A})_2$ each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6; and m is 0, 1, 2 or 3.

In certain embodiments of Formula E-II-a:

Y is —$(CH_2)_k$—$NR^B$—, —$O(CH_2)_k$—(C═O)$NR^B$—, or —$(CH_2)_k$—$NR^B$(C═O)—;

$X^A$ is C(O) or $C(R^{3A})_2$;

each $R^B$ is, independently, hydrogen, or substituted or unsubstituted alkyl;

each $R^{1A}$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6; and m is 0, 1, 2 or 3.

In certain embodiments, E is of Formula E-II-b:

E-II-b

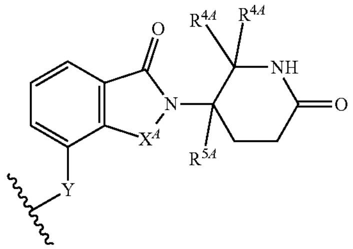

wherein:

Y is —$(CH_2)_k$—$NR^B$—, —$O(CH_2)_k$—(C═O)$NR^B$—, —$NR^B$(C═O)—$(CH_2)_k$—O—, or —$(CH_2)_k$—$NR^B$(C═O)—;

$X^A$ is C(O) or $C(R^{3A})_2$ each $R^B$ is, independently, hydrogen, or substituted or unsubstituted alkyl;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments of Formula E-II-b:

Y is —$(CH_2)_k$—$NR^B$—, —$O(CH_2)_k$—(C═O)$NR^B$—, or —$(CH_2)_k$—$NR^B$(C═O)—;

$X^A$ is C(O) or $C(R^{3A})_2$;

each $R^B$ is, independently, hydrogen, or substituted or unsubstituted alkyl;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments, E is of Formula E-II-c:

E-II-c

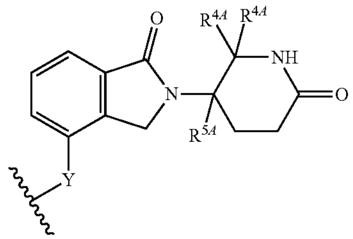

wherein:

Y is —$(CH_2)_k$—$NR^B$—, —$O(CH_2)_k$—(C═O)$NR^B$—, —$NR^B$(C═O)—$(CH_2)_k$—O—, or —$(CH_2)_k$—$NR^B$(C═O)—;

each $R^B$ is, independently, hydrogen, or substituted or unsubstituted alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments of Formula E-II-c:

Y is —$(CH_2)_k$—$NR^B$—, —$O(CH_2)_k$—(C═O)$NR^B$—, or —$(CH_2)_k$—$NR^B$(C═O)—, each $R^B$ is, independently, hydrogen, or substituted or unsubstituted alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments, E is of Formula E-II-d:

E-II-d

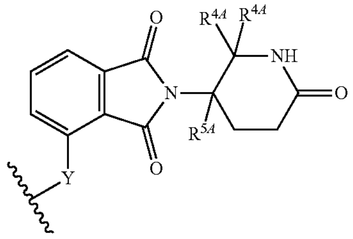

wherein:

Y is —$(CH_2)_k$—$NR^B$—, —$O(CH_2)_k$—(C═O)$NR^B$—, —$NR^B$(C═O)—$(CH_2)_k$—O—, or —$(CH_2)_k$—$NR^B$(C═O)—;

each $R^B$ is, independently, hydrogen, or substituted or unsubstituted alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments of formula E-II-d:

Y is —$(CH_2)_k$—$NR^B$—, —$O(CH_2)_k$—(C═O)$NR^B$—, or —$(CH_2)_k$—$NR^B$(C═O)—;

each $R^B$ is, independently, hydrogen, or substituted or unsubstituted alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments, E is of formula E-II-e:

E-II-e

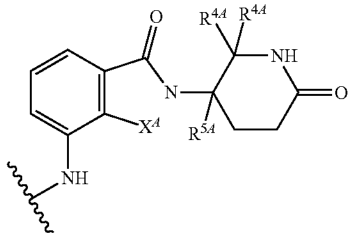

wherein:

$X^A$ is C(O) or $C(R^{3A})_2$;

each $R^4$ is, independently, H or $C_1$-$C_3$ alkyl; or two R A, together with the carbon atom to which they are attached, form a C(O), $C_3$-$C_6$ carbocycle, or a 4-, 5-, or 6-membered heterocycle comprising 1 or 2 heteroatoms selected from N and 0;

each $R^{3A}$ is, independently, H or $C_1$-$C_3$ alkyl; and $R^{5A}$ is H, deuterium, $C_1$-$C_3$ alkyl, F, or Cl.

In certain embodiments, E is of formula E-II-e-1:

E-II-e-1

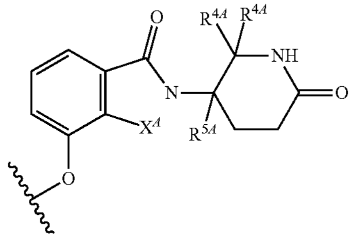

wherein:

$X^{A}$ is C(O) or $C(R^{3A})_2$;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and 0;

each $R^{3A}$ is, independently, H or $C_1$-$C_3$ alkyl; and $R^{5A}$ is H, deuterium, $C_1$-$C_3$ alkyl, F, or Cl.

In certain embodiments, E is of formula E-II-e-1:

E-II-e-2

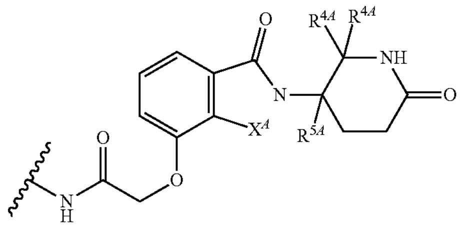

wherein:

$X^{A}$ is C(O) or $C(R^{3A})_2$;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and 0;

each $R^{3A}$ is, independently, H or $C_1$-$C_3$ alkyl; and $R^{5A}$ is H, deuterium, $C_1$-$C_3$ alkyl, F, or Cl.

In certain embodiments, E is of formula E-II-f:

E-II-f

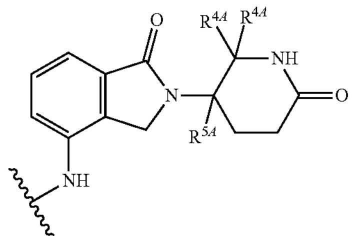

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-II-f-1:

E-II-f-1

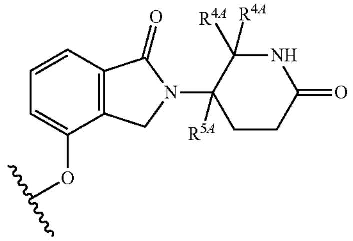

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-TT-f-2:

E-II-f-2

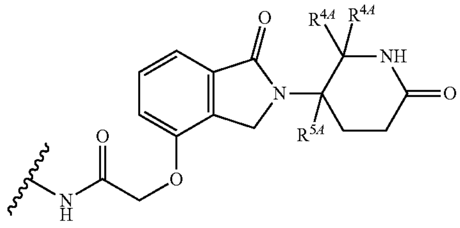

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-II-g:

E-II-g

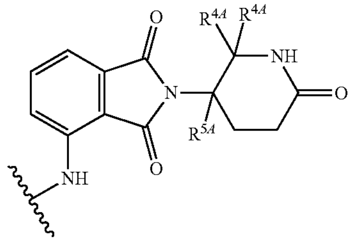

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-II-g-1:

E-II-g-1

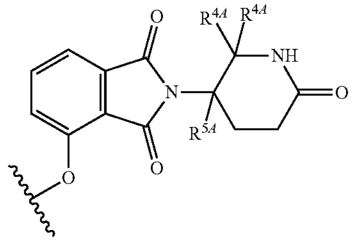

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-II-g-2:

E-II-g-2

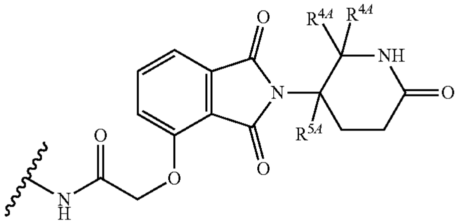

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of Formula E-III:

E-III

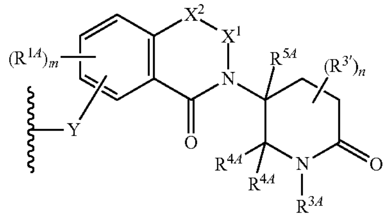

wherein:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(C{=}O)-(CH_2)_k-O-$, $-NR^B(CH_2)_k-NR^B(C{=}O)-$, or $-(CH_2)_k-NR^B(C{=}O)-$;

$X^1-X^2$ is $C(R^{3A}){=}N$ or $C(R^{3A})_2-C(R^{3A})_2$;

each $R^B$ is, independently, hydrogen, or substituted or unsubstituted alkyl;

each $R^A$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments of Formula E-III:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(CH_2)_k-NR^B(C{=}O)-$, or $-(CH_2)_k-NR^B(C{=}O)-$;

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^A$ is, independently, halogen, OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl;

k is 0, 1, 2, 3, 4, 5, or 6;

m is 0, 1, 2 or 3; and n is 1 or 2.

In certain embodiments, Y is $-(CH_2)_k-NR^B-$, $-O(CH_2)_k-(C{=}O)NR^B-$, $-(CH_2)_k-O-$, $-NR^B(C{=}O)-(CH_2)_k-O-$, or $-(CH_2)_k-NR^B(C{=}O)-$. In certain embodiments, Y is $-(CH_2)_k-NR^B-$, $-O(CH_2)_k-(C{=}O)NR^B-$, or $-(CH_2)_k-NR^B(C{=}O)-$. In certain embodiments, Y is $-(CH_2)_k-NR^B-$, $-(CH_2)_k-O-$, or $-NR^B(C{=}O)-(CH_2)_k-O-$. In certain embodiments, Y is $-(CH_2)_k-NH-$. In certain embodiments, Y is $-NH-$. In certain embodiments, Y is $-(CH_2)_k-O-$. In certain embodiments, Y is $-O-$. In certain embodiments, Y is $-NH(C{=}O)-(CH_2)-O-$. In certain embodiments, Y is $-NH-$, $-O-$, or $-NH(C{=}O)-(CH_2)-O-$.

In certain embodiments, E is of formula E-III-a:

E-III-a

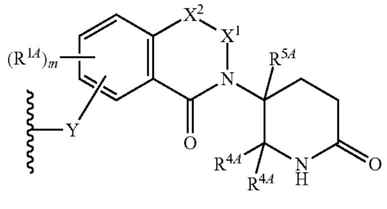

wherein:

Y is $-(CH_2)_k-$, $-(CH_2)_k-O-$, $-O(CH_2)_k-$, $-NR^B(CH_2)_k-$, $-(CH_2)_k-NR^B-$, $-(CH_2)_k-(C{=}O)NR^B-$, $-O(CH_2)_k-(C{=}O)NR^B-$, $-O(CH_2)_k-NR^B(C{=}O)-$, $-NR^B(C{=}O)-(CH_2)_k-O-$, $-NR^B(CH_2)_k-NR^B(C{=}O)-$, or $-(CH_2)_k-NR^B(C{=}O)-$;

$X^1$—$X^2$ is $C(R^{3A})$=N or $C(R^{3A})_2$—$C(R^{3A})_2$;
each $R^B$ is, independently, hydrogen, or substituted or unsubstituted alkyl;
each $R^{1A}$ is, independently, halogen, OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^A$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl;
k is 0, 1, 2, 3, 4, 5, or 6; and
m is 0, 1, 2 or 3.

In certain embodiments of formula E-III-a:
Y is —$(CH_2)_k$—, —$(CH_2)_k$—O—, —$O(CH_2)_k$—, —$NR^B(CH_2)_k$—, —$(CH_2)_k$—$NR^B$—, —$(CH_2)_k$—(C=O)$NR^B$—, —$O(CH_2)_k$—(C=O)$NR^B$—, —$O(CH_2)_k$—$NR^B$(C=O)—, —$NR^B(CH_2)_k$—$NR^B$(C=O)—, or —$(CH_2)_k$—$NR^B$(C=O)—;
$X^1$-$X^2$ is $C(R^{3A})$=N or $C(R^{3A})_2$—$C(R^{3A})_2$;
each $R^B$ is, independently, hydrogen, or substituted or unsubstituted alkyl;
each $R^{1A}$ is, independently, halogen, OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl;
k is 0, 1, 2, 3, 4, 5, or 6; and
m is 0, 1, 2 or 3.

In certain embodiments of formula E-I-a:
Y is —$(CH_2)_k$—$NR^B$—, —$O(CH_2)_k$—(C=O)$NR^B$—, —$NR^B$(C=O)—$(CH_2)_k$—O—, or —$(CH_2)_k$—$NR^B$(C=O)—;
$X^1$—$X^2$ is $C(R^{3A})$=N or $C(R^{3A})_2$—$C(R^{3A})_2$;
each $R^B$ is, independently, hydrogen, or substituted or unsubstituted alkyl;
each $R^{1A}$ is, independently, halogen, OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl;
k is 0, 1, 2, 3, 4, 5, or 6; and
m is 0, 1, 2 or 3.

In certain embodiments of formula E-III-a:
Y is —$(CH_2)_k$—$NR^B$—, —$O(CH_2)_k$—(C=O)$NR^B$—, or —$(CH_2)_k$—$NR^B$(C=O)—;
$X^1$-$X^2$ is $C(R^{3A})$=N or $C(R^{3A})_2$—$C(R^{3A})_2$;
each $R^B$ is, independently, hydrogen, or substituted or unsubstituted alkyl;
each $R^A$ is, independently, halogen, OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl;
k is 0, 1, 2, 3, 4, 5, or 6; and
m is 0, 1, 2 or 3.

In certain embodiments, E is of formula E-111-b:

E-III-b

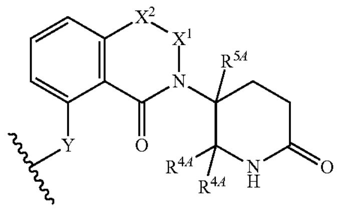

wherein:
Y is —$(CH_2)_k$—$NR^B$—, —$O(CH_2)_k$—(C=O)$NR^B$—, —$NR^B$(C=O)—$(CH_2)_k$—O—, or —$(CH_2)_k$—$NR^B$(C=O)—;
$X^1$-$X^2$ is $C(R^{3A})$=N or $C(R^{3A})_2$—$C(R^{3A})_2$;
each $R^B$ is, independently, hydrogen, or substituted or unsubstituted alkyl;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl; and
k is 0, 1, 2, 3, 4, 5, or 6.

In certain embodiments of formula E-III-b:
Y is —$(CH_2)_k$—$NR^B$—, —$O(CH_2)_k$—(C=O)$NR^B$—, or —$(CH_2)_k$—$NR^B$(C=O)—,
$X^1$-$X^2$ is $C(R^{3A})$=N or $C(R^{3A})_2$—$C(R^{3A})_2$;
each $R^B$ is, independently, hydrogen, or substituted or unsubstituted alkyl;
each $R^{3A}$ is, independently, H or $C_1$-$C_3$ alkyl;
each $R^{4A}$ is, independently, H or $C_1$-$C_3$ alkyl; or two $R^A$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, deuterium, $C_1$-$C_3$ alkyl, F, or Cl; and
k is 0, 1, 2, 3, 4, 5, or 6.

In certain embodiments, E is of formula E-III-c:

E-III-c

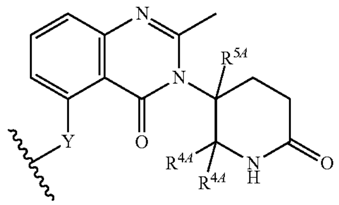

wherein:
Y is —$(CH_2)_k$—$NR^B$—, —$O(CH_2)_k$—(C=O)$NR^B$—, —$NR^B$(C=O)—$(CH_2)_k$—O—, or —$(CH_2)_k$—$NR^B$(C=O)—;
$X^1$-$X^2$ is $C(R^{3A})$=N or $C(R^{3A})_2$—$C(R^{3A})_2$;
each $R^B$ is, independently, hydrogen, or substituted or unsubstituted alkyl;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments of formula E-III-c:

Y is $-(CH_2)_k-NR^B-$, $-O(CH_2)_k-(C{=}O)NR^B-$, or $-(CH_2)_k-NR^B(C{=}O)-$;

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, deuterium, $C_1$-$C_3$ alkyl, F, or Cl; and k is 0, 1, 2, 3, 4, 5, or 6.

In certain embodiments, E is of formula E-III-d:

E-III-d

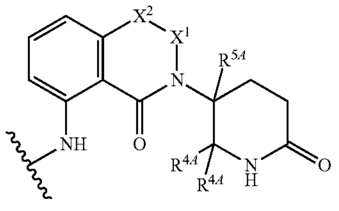

wherein:

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-III-d-1:

E-III-d-1

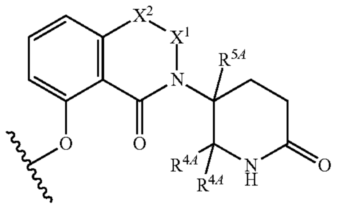

wherein:

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-III-d-2:

E-III-d-2

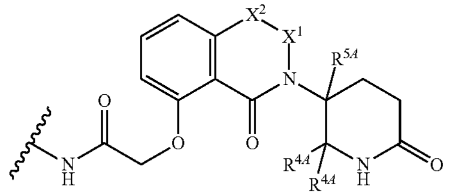

wherein:

$X^1$-$X^2$ is $C(R^{3A}){=}N$ or $C(R^{3A})_2-C(R^{3A})_2$;

each $R^B$ is, independently, hydrogen, or substituted or unsubstituted alkyl;

each $R^{3A}$ is, independently, H or $C_1$-$C_3$ alkyl;

each $R^4$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-III-e:

E-III-e

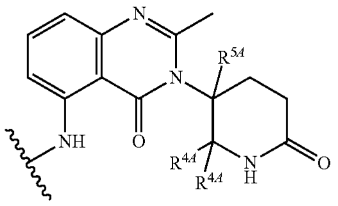

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-III-e-1:

E-III-e-1

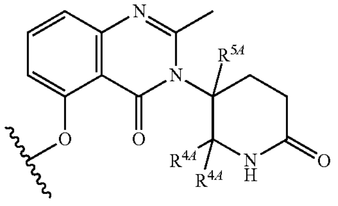

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is of formula E-III-e-2:

E-III-e-2

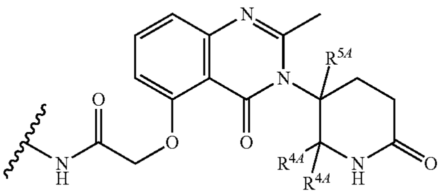

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, deuterium, $C_1$-$C_3$ alkyl, F, or Cl.

In certain embodiments, E is thalidomide, lenalidomide, pomalidomide, CC-885 (Matyskiela et al., *Nature* 2016, 535, 252-257), 3-(5-amino-2-methyl-4-oxoquinazolin-3(4H)-yl)piperidine-2,6-dione, or an analogue or derivative thereof.

In certain embodiments, E is

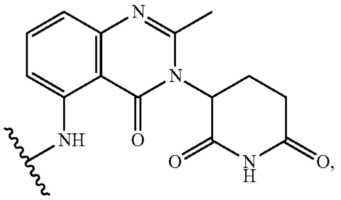

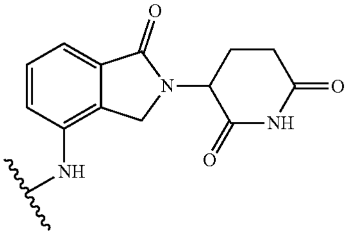

or

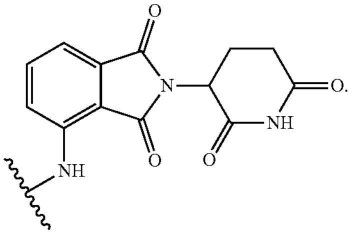

In certain embodiments, E is

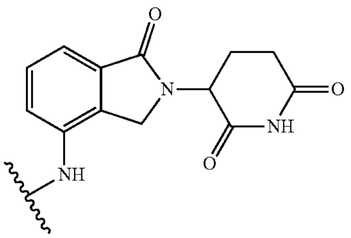

or

-continued

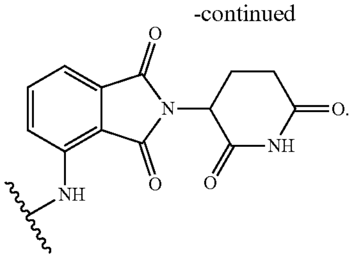

In certain embodiments, E is

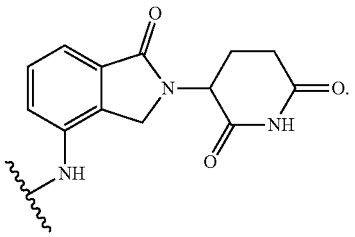 [SMILES: *Nc1cccc2c1CN(C1CCC(=O)NC1=O)C2=O]

In certain embodiments, E is

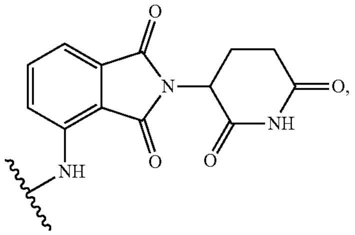

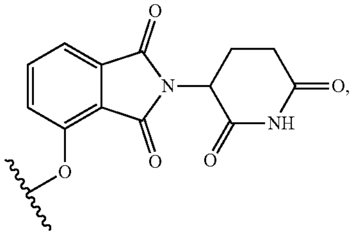 [SMILES: *Oc1cccc2c1C(=O)N(C1CCC(=O)NC1=O)C2=O]

or

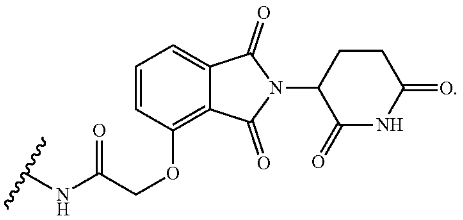 [SMILES: *NC(=O)COc1cccc2c1C(=O)N(C1CCC(=O)NC1=O)C2=O]

In certain embodiments, E is

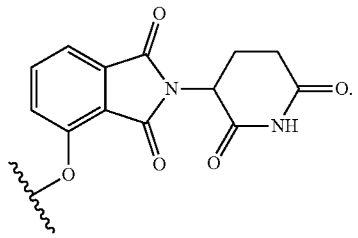

In certain embodiments, E is

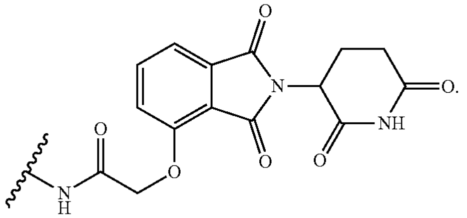

In certain embodiments, E is

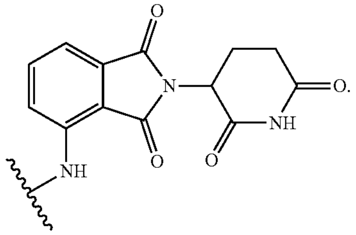 [SMILES: *Nc1cccc2c1C(=O)N(C1CCC(=O)NC1=O)C2=O]

The von Hippel-Lindau tumor suppressor (VHL) is an E3 ubiquitin ligase. VHL comprises the substrate recognition subunit/E3 ubiquitin ligase complex VCB, which includes elongins B and C, and a complex including Cullin-2 and Rbx1. The primary substrate of VHL is Hypoxia Inducible Factor 1α (HIF-1α), a transcription factor that upregulates genes, such as the pro-angiogenic growth factor VEGF and the red blood cell-inducing cytokine, erythropoietin, in response to low oxygen levels. VCB is a known target in cancer, chronic anemia, and ischemia.

The full-length von Hippel-Lindau tumor suppressor protein (VHL) contains 213 amino acids. (For the VHL protein sequence see: Duan et al., *Proc. Natl. Acad. Sci. U.S.A.* 1995, 92, 6459-63. For additional information related to the VHL structure see Stebbins et al., *Science* 1999, 284, 455-61 and Minervini et al., *Sci. Rep.* 2015, 5, 12605.) A second VHL-gene product arises by internal translation initiation from the codon 54 methionine, producing a 160 amino-acid protein ("pVHL19"). VHL has two main structural domains: an N-terminal domain composed mainly of β-sheets (β-domain) and a smaller C-terminal domain between amino acids 155-192 composed mainly of a helices (α-domain). The α-domain consists of three a helices that combines with a fourth a helix donated by elongin C. The β-domain is on the opposite side of the a domain and is free to contact other protein.

In certain embodiments, E is a modulator, binder, inhibitor, or ligand of VHL. In certain embodiments, E is a modulator of VHL. In certain embodiments, E is a binder of VHL. In certain embodiments, E is an inhibitor of VHL. In certain embodiments, E is a ligand of Cereblon. In certain embodiments, E is any ligand of VHL listed in Galdeano, C. et al. *J. Med. Chem.* 2014, 57, 8657, which is incorporated herein by reference. In certain embodiments, E is a modulator, binder, inhibitor, or ligand of a VHL variant. In certain embodiments, E is a modulator, binder, inhibitor, or ligand of a VHL isoform. In certain embodiments, E is a modulator, binder, inhibitor, or ligand of a VHL gene-product (e.g., pVHL19).

In certain embodiments, E comprises a peptide backbone structure. In certain embodiments, E is of the formula:

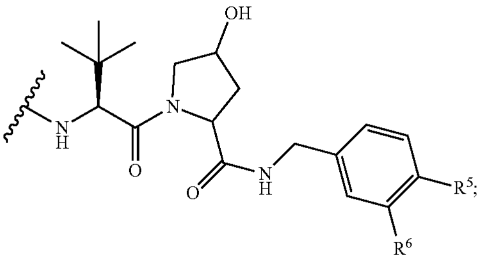

wherein $R^5$ is a heteroaryl ring, and $R^6$ is hydrogen or $C_{1-4}$ alkyl. In certain embodiments, $R^5$ is a 5-membered heteroaryl ring comprising at least one nitrogen. In certain embodiments, $R^5$ is substituted or unsubstituted oxazolinyl, or substituted or unsubstituted thiazolinyl.

In certain embodiments, E is of the formula:

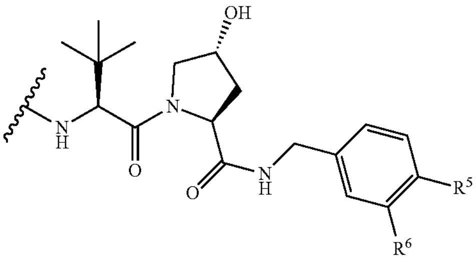

or

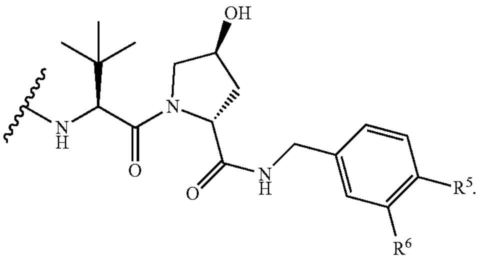

In certain embodiments, E is of the formula:

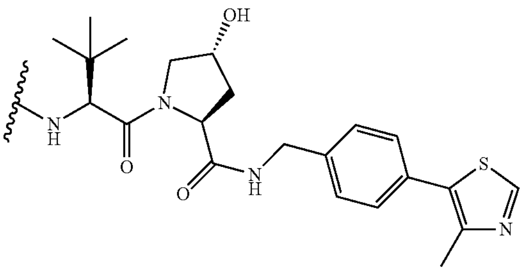

or

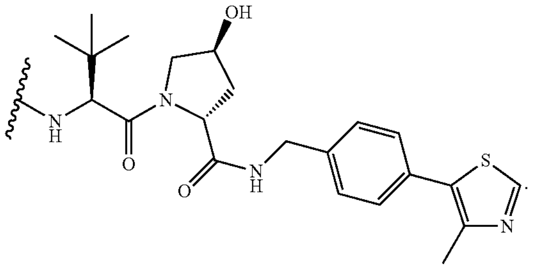

In certain embodiments, E is of the formula:

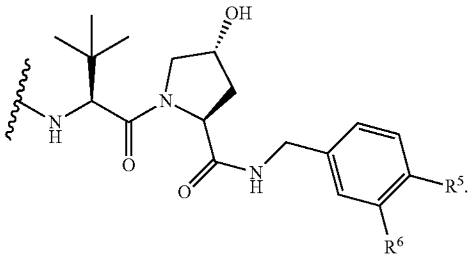

In certain embodiments, E is of the formula:

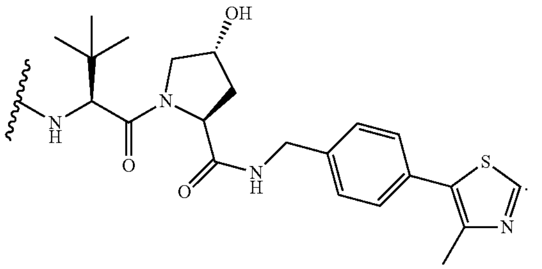

In certain embodiments, E is of the formula:

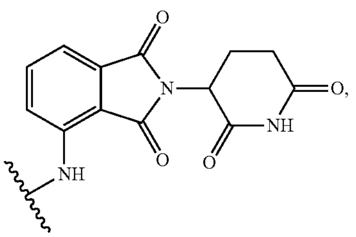

-continued

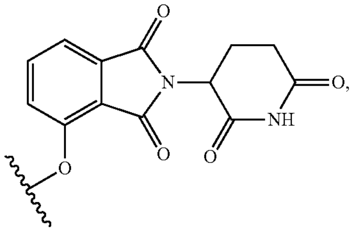

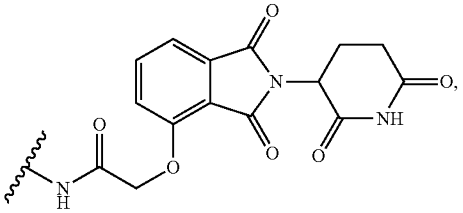

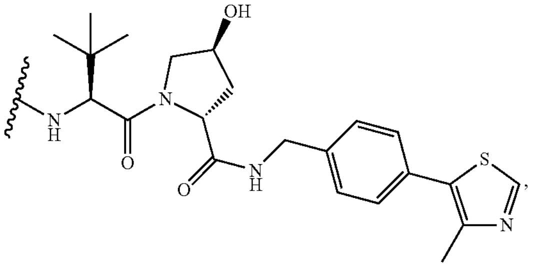

or

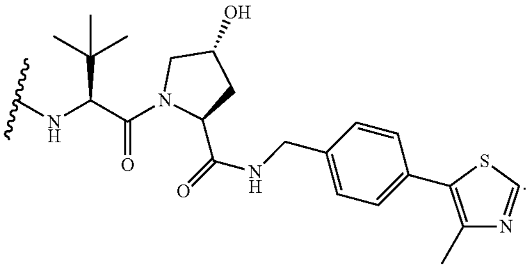 [SMILES: *N[C@H](C(=O)N1C[C@H](O)C[C@H]1C(=O)NCc1ccc(-c2scnc2C)cc1)C(C)(C)C]

In certain embodiments, E is of the formula:

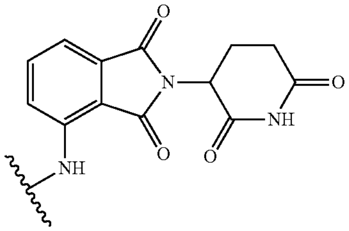

or

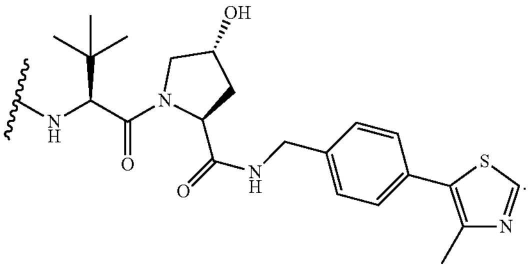

In certain embodiments, the E3 ligase binding moiety binds an E3 ubiquitin ligase with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety binds Cereblon with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety binds VHL with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety selectively binds an E3 ubiquitin ligase as compared to another protein. In some embodiments, the E3 ligase binding moiety selectively binds Cereblon over another protein. In some embodiments, the E3 ligase binding moiety selectively binds Cereblon over another E3 ubiquitin ligase. In some embodiments, the E3 ligase binding moiety selectively binds VHL over another protein. In some embodiments, the E3 ligase binding moiety selectively binds VHL over another E3 ubiquitin ligase. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Further Embodiments of Formula I

In certain embodiments, the compound of Formula I is a compound of Formula I-a:

I-a

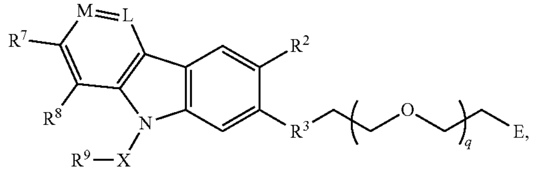

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

L is N or $CR^5$;

M is N or $CR^6$

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_1$-6alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$ $NR^A$—, —$(CH_2)_n$-A-$NR^A$—, -A-$NR^A$—$(CH_2)_n$ —(C═O)$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—; A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^{12}$ $R^2$ is hydrogen, —$CH_3$, aryl, or heteroaryl;

n is 0-12; and q is 1-6;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}$ alkyl$)_2$.

In certain embodiments of the compound of Formula I-a,

E is an E3 ubiquitin ligase binding moiety;

L is N or $CR^5$;

M is N or $CR^6$

X is a bond or substituted or unsubstituted $C_{1-2}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}$ alkyl$)_2$, aryl, heteroaryl, or a protecting group, wherein the aryl and heteroaryl are optionally substituted with halogen, $SO_2$, $NH_2$, or $C_{1-6}$alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^{12}$ $R^2$ is hydrogen, —$CH_3$, aryl, or heteroaryl;

n is 0-12; and q is 1-5;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-a, L is $CR^5$;

M is N;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}\ alkyl)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—; A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^2)_2C_{3-8}$ cycloalkyl, $N(R^{12})_2$heterocyclyl, or —$(CH_2)_n$—$R^2$;

$R^{12}$ is hydrogen, —$CH_3$, aryl, or heteroaryl;

n is 0-12; and q is 1-6;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-a, L is $CR^5$;

M is N;

X is a bond or substituted or unsubstituted $C_{1-12}$ alkylene, wherein one or more carbon is optionally replaced with C(O), O, S, $SO_2$, NH, or $NC_{1-6}$ alkyl optionally substituted with halogen, OH, or $C_{1-6}$ alkyl;

$R^9$ is hydrogen, —$N_3$, alkynyl, OH, halogen, $NH_2$, $N(C_{1-6}\ alkyl)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^2)_2C_{3-8}$ cycloalkyl, $N(R^{12})_2$heterocyclyl, or —$(CH_2)_n$—$R^2$;

$R^{12}$ is hydrogen, —$CH_3$, aryl, or heteroaryl;

n is 0-12; and q is 1-5;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-a, L is $CR^5$;

M is N;

X is a bond;

$R^9$ is hydrogen, —$N_3$, alkynyl, OH, halogen, $NH_2$, $N(C_{1-6}\ alkyl)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or —$(CH_2)_n$—$R^{12}$ $R^{12}$ is hydrogen, —$CH_3$, aryl, or heteroaryl;

n is 0-12; and q is 1-6;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-a, L is $CR^5$;

M is N;

X is a bond;

$R^9$ is hydrogen, —$N_3$, alkynyl, OH, halogen, $NH_2$, $N(C_{1-6}\ alkyl)_2$, aryl, heteroaryl, or a protecting group, wherein the aryl and heteroaryl are optionally substituted with halogen, $SO_2$, $NH_2$, or $C_{1-6}$ alkyl optionally substituted with halogen or $C_{3-8}$ cycloalkyl;

$R^3$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^2$, $N(R^{12})_2C_{3-8}$ cycloalkyl, $N(R^{12})_2$heterocyclyl, or —$(CH_2)_n$—$R^2$;

$R^{12}$ is hydrogen, —$CH_3$, aryl, or heteroaryl;

n is 0-12; and q is 1-5;

wherein one or more carbon of $R^2$, $R^3$, $R^7$, and $R^8$ is optionally replaced with C(O), 0, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-a, L is $CR^5$;

M is N;

X is a bond;

$R^9$ is hydrogen;

$R^3$ is $—(CH_2)_n—O—$, $-A-(CH_2)_n—O—$, $—(CH_2)_n-A-O—$, $-A-O—(CH_2)_n—(C{=}O)NR^A—$, $—(CH_2)_n—S—$, $-A-(CH_2)_n—S—$, $—(CH_2)_n-A-S—$, $-A-S—(CH_2)_n$ $—(C{=}O)NR^A—$, $—(CH_2)_n—NR^A—$, $-A-(CH_2)_n—NR^A—$, $—(CH_2)_n-A-NR^A—$, $-A-NR^A—(CH_2)_n—(C{=}O)NR^A—$, $—(CH_2)_n—(C{=}O)NR^A—$, $-A-(CH_2)_n—(C{=}O)NR^A—$, $—(CH_2)_n-A-(C{=}O)NR^A—$, $—(CH_2)_n—S(O)_2NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or $—(CH_2)_n—R^2$;

$R^{12}$ is hydrogen, $—CH_3$, aryl, or heteroaryl;

n is 0-12; and q is 1-6;

wherein one or more carbon of $R^2$, $R^3$, $R^7$, and $R^8$ is optionally replaced with C(O), 0, S, $SO_2$, NH, $NC_{1-6}$ alkyl, $NH—C_{1-6}$ alkyl, $NH_2$, or $N(C_{1-6}$ alkyl$)_2$.

In certain embodiments of the compound of Formula I-a,

L is $CR^5$;

M is N;

X is a bond;

$R^9$ is hydrogen;

$R^3$ is $—(CH_2)_n—O—$, $-A-(CH_2)_n—O—$, $—(CH_2)_n-A-O—$, $—(CH_2)_n—S—$, $-A-(CH_2)_n—S—$, $—(CH_2)_n-A-S—$, $—(CH_2)_n$ $—NR^A—$, $-A-(CH_2)_n—NR^A—$, $—(CH_2)_n-A-NR^A—$, $—(CH_2)_n—(C{=}O)NR^A—$, $-A-(CH_2)_n—(C{=}O)NR^A—$, $—(CH_2)_n-A-(C{=}O)NR^A—$, $—(CH_2)_n—S(O)_2NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each $R^2$, $R^7$, and $R^8$ are independently hydrogen, OH, halogen, $NH_2$, $CH_3$, $SO_2$, $NO_2$, a leaving group, a protecting group, aryl, heteroaryl, $NHR^{12}$, $N(R^{12})_2C_{3-8}$ cycloalkyl, $N(R^{12})_2$heterocyclyl, or $—(CH_2)_n—R^2$;

$R^{12}$ is hydrogen, $—CH_3$, aryl, or heteroaryl;

n is 0-12; and q is 1-5;

wherein one or more carbon of $R^2$, $R^3$, $R^7$, and $R^8$ is optionally replaced with C(O), 0, S, $SO_2$, NH, $NC_{1-6}$ alkyl, $NH—C_{1-6}$ alkyl, $NH_2$, or $N(C_{1-6}$ alkyl$)_2$.

In certain embodiments of the compound of Formula I-a,

L is $CR^5$;

M is N;

X is a bond;

$R^9$ is hydrogen;

$R^3$ is $—(CH_2)_n—O—$, $-A-(CH_2)_n—O—$, $—(CH_2)_n-A-O—$, $-A-O—(CH_2)_n—(C{=}O)NR^A—$, $—(CH_2)_n—S—$, $-A-(CH_2)_n—S—$, $—(CH_2)_n-A-S—$, $-A-S—(CH_2)_n$ $—(C{=}O)NR^A—$, $—(CH_2)_n—NR^A—$, $-A-(CH_2)_n—NR^A—$, $—(CH_2)_n-A-NR^A—$, $-A-NR^A—(CH_2)_n—(C{=}O)NR^A—$, $—(CH_2)_n—(C{=}O)NR^A—$, $-A-(CH_2)_n$ $—(C{=}O)NR^A—$, $—(CH_2)_n-A-(C{=}O)NR^A—$, $—(CH_2)_n—S(O)_2NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each $R^2$, $R^7$, and $R^8$ is hydrogen;

n is 0-12; and q is 1-6;

wherein one or more carbon of $R^3$ is optionally replaced with C(O), O, S, $SO_2$, NH, or $NC_{1-6}$ alkyl.

In certain embodiments of the compound of Formula I-a,

L is CR;

M is N;

X is a bond;

$R^9$ is hydrogen;

$R^3$ is $—(CH_2)_n—O—$, $-A-(CH_2)_n—O—$, $—(CH_2)_n-A-O—$, $—(CH_2)_n—S—$, $-A-(CH_2)_n—S—$, $—(CH_2)_n-A-S—$, $—(CH_2)_n—NR^A—$, $-A-(CH_2)_n—NR^A—$, $—(CH_2)_n-A-NR^A—$, $—(CH_2)_n—(C{=}O)NR^A—$, $-A-(CH_2)_n—(C{=}O)NR^A—$, $—(CH_2)_n-A-(C{=}O)NR^A—$, $—(CH_2)_n—S(O)_2NR^A—$, $-A-(CH_2)_n—S(O)_2NR^A—$, or $—(CH_2)_n-A-S(O)_2NR^A—$;

A is substituted or unsubstituted heterocyclylene, substituted or unsubstituted arylene, or substituted or unsubstituted heteroarylene;

each $R^2$, $R^7$, and $R^8$ is hydrogen;

n is 0-12; and q is 1-5;

wherein one or more carbon of $R^3$ is optionally replaced with C(O), O, S, $SO_2$, NH, or $NC_{1-6}$ alkyl.

In certain embodiments of the compound of Formula I-a,

L is $CR^5$;

M is N;

X is a bond;

$R^9$ is hydrogen;

$R^3$ is $-A-(CH_2)_n—NR^A—$, $—(CH_2)_n-A-NR^A—$, or $—(CH_2)_n—(C{=}O)NR^A—$;

A is substituted or unsubstituted arylene, or substituted or unsubstituted heteroarylene;

each $R^2$, $R^7$, and $R^8$ is hydrogen;

n is 0-12; and q is 1-6.

In certain embodiments of the compound of Formula I-a,

L is $CR^5$;

M is N;

X is a bond;

$R^9$ is hydrogen;

$R^3$ is $-A-(CH_2)_n—NR^A—$, $—(CH_2)_n-A-NR^A—$, or $—(CH_2)_n—(C{=}O)NR^A—$;

A is substituted or unsubstituted arylene, or substituted or unsubstituted heteroarylene;

each $R^2$, $R^7$, and $R^8$ is hydrogen;

n is 0-12; and q is 1-5.

In certain embodiments of the compound of Formula I-a,

L is $CR^5$;

M is N;

X is a bond;

$R^9$ is hydrogen;

$R^3$ is $-A-O—(CH_2)_n—(C{=}O)NR^A—$ or $—(CH_2)_n—(C{=}O)NR^A—$;

A is substituted or unsubstituted heteroarylene;

each $R^2$, $R^7$, and $R^8$ is hydrogen;

n is 0-12; and q is 1-6.

In certain embodiments of the compound of Formula I-a,

L is $CR^5$;

M is N;

X is a bond;

$R^9$ is hydrogen;

$R^3$ is $-A-(CH_2)_n—NR^A—$;

A is substituted or unsubstituted heteroarylene;

each $R^2$, $R^7$, and $R^8$ is hydrogen;

n is 0-12; and q is 1-6.

In certain embodiments of the compound of Formula I-a,

L is $CR^5$;

M is N;

X is a bond;

$R^9$ is hydrogen;

$R^3$ is $-A-(CH_2)_n-NR^A-$;

A is substituted or unsubstituted heteroarylene;

each $R^2$, $R^7$, and $R^8$ is hydrogen;

n is 0-12; and q is 1-5.

In certain embodiments of the compound of Formula I-a,

L is $CR^5$;

M is N;

X is a bond;

$R^9$ is hydrogen;

$R^3$ is $-(CH_2)_n-(C{=}O)NR^A-$;

each $R^2$, $R^7$, and $R^8$ is hydrogen;

n is 0-12; and q is 1-6.

In certain embodiments of the compound of Formula I-a,

L is $CR^5$;

M is N;

X is a bond;

$R^9$ is hydrogen;

$R^3$ is $-(CH_2)_n-(C{=}O)NR^A$;

each $R^2$, $R^7$, and $R^8$ is hydrogen;

n is 0-12; and q is 1-5.

In certain embodiments of the compound of Formula I-a,

L is $CR^5$;

M is N;

X is a bond;

$R^9$ is hydrogen;

$R^3$ is $-A-O-(CH_2)_n-(C{=}O)NR^A-$;

each $R^2$, $R^7$, and $R^8$ is hydrogen;

n is 0-12; and q is 1-6.

In certain embodiments, the compound of Formula I is a compound of Formula I-b:

I-b

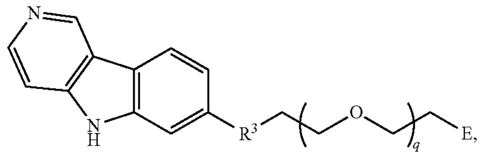

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

$R^3$ is $-(CH_2)_n-O-$, $-A-(CH_2)_n-O-$, $-(CH_2)_n-A-O-$, $-A-O-(CH_2)_n-(C{=}O)NR^A-$, $-(CH_2)_n-S-$, $-A-(CH_2)_n-S-$, $-(CH_2)_n-A-S-$, $-A-S-(CH_2)_n-(C{=}O)NR^A-$, $-(CH_2)_n-NR^A-$, $-A-(CH_2)_n-NR^A-$, $-(CH_2)_n-A-NR^A-$, $-(CH_2)_n-(C{=}O)NR^A-$, $-A-(CH_2)_n-(C{=}O)NR^A-$, $-(CH_2)_n-A-(C{=}O)NR^A-$, $-(CH_2)_n-S(O)_2NR^A-$, $-A-(CH_2)_n-S(O)_2NR^A-$, or $-(CH_2)_n-A-S(O)_2NR^A-$;

A is substituted or unsubstituted heterocyclylene, substituted or unsubstituted arylene, or substituted or unsubstituted heteroarylene;

n is 0-12; and q is 1-6;

wherein one or more carbon of $R^3$ is optionally replaced with C(O), O, S, $SO_2$, NH, or $NC_{1-6}$ alkyl.

In certain embodiments of the compound of Formula I-b,

E is an E3 ubiquitin ligase binding moiety;

$R^3$ is $-(CH_2)_n-O-$, $-A-(CH_2)_n-O-$, $-(CH_2)_n-A-O-$, $-(CH_2)_n-S-$, $-A-(CH_2)_n-S-$, $-(CH_2)_n-A-S-$, $-(CH_2)_n-NR^A-$, $-A-(CH_2)_n-NR^A-$, $-(CH_2)_n-A-NR^A-$, $-(CH_2)_n-(C{=}O)NR^A-$, $-A-(CH_2)_n-(C{=}O)NR^A-$, $-(CH_2)_n-A-(C{=}O)NR^A-$, $-(CH_2)_n-S(O)_2NR^A-$, $-A-(CH_2)_n-S(O)_2NR^A-$, or $-(CH_2)_n-A-S(O)_2NR^A-$;

A is substituted or unsubstituted heterocyclylene, substituted or unsubstituted arylene, or substituted or unsubstituted heteroarylene;

n is 0-12; and q is 1-5;

wherein one or more carbon of $R^3$ is optionally replaced with C(O), O, S, $SO_2$, NH, or $NC_{1-6}$ alkyl.

In certain embodiments of the compound of Formula I-b, $R^3$ is $-A-(CH_2)_n-NR^A-$, $-(CH_2)_n-A-NR^A-$, or $-(CH_2)_n-(C{=}O)NR^A-$;

A is substituted or unsubstituted arylene, or substituted or unsubstituted heteroarylene;

n is 0-12; and q is 1-6.

In certain embodiments of the compound of Formula I-b, $R^3$ is $-A-(CH_2)_n-NR^A-$, $-(CH_2)_n-A-NR^A-$, or $-(CH_2)_n-(C{=}O)NR^A-$;

A is substituted or unsubstituted arylene, or substituted or unsubstituted heteroarylene;

n is 0-12; and q is 1-5.

In certain embodiments of the compound of Formula I-b, $R^3$ is $-A-O-(CH_2)_n-(C{=}O)NR^A-$ or $-(CH_2)_n-(C{=}O)NR^A-$;

A is substituted or unsubstituted heteroarylene;

n is 0-12; and q is 1-6.

In certain embodiments of the compound of Formula I-b, $R^3$ is $-A-(CH_2)_n-NR^A-$;

A is substituted or unsubstituted heteroarylene;

n is 0-12; and q is 1-6.

In certain embodiments of the compound of Formula I-b, $R^3$ is $-A-(CH_2)_n-NR^A-$;

A is substituted or unsubstituted heteroarylene;

n is 0-12; and q is 1-5.

In certain embodiments of the compound of Formula I-b, $R^3$ is $-(CH_2)_n-(C{=}O)NR^A-$;

n is 0-12; and q is 1-6.

In certain embodiments of the compound of Formula I-b, $R^3$ is $-(CH_2)_n-(C{=}O)NR^A$;

n is 0-12; and q is 1-5.

In certain embodiments, the compound of Formula I-b is a compound of Formula I-b-1:

I-b-1

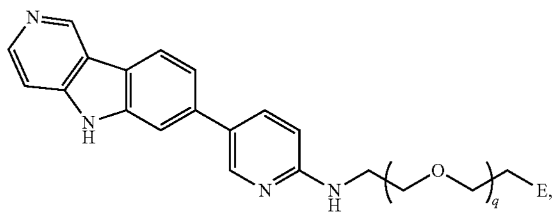

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-6.

In certain embodiments of the compound of Formula I-b-1, E is an E3 ubiquitin ligase binding moiety; and q is 1-5.

In certain embodiments, the compound of Formula I-b is a compound of Formula I-b-2:

I-b-2

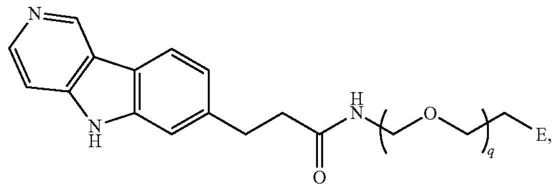

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-6.

In certain embodiments of the compound of Formula I-b-2, E is an E3 ubiquitin ligase binding moiety; and q is 1-5.

In certain embodiments, the compound of Formula I-b is a compound of Formula I-b-3:

I-b-3

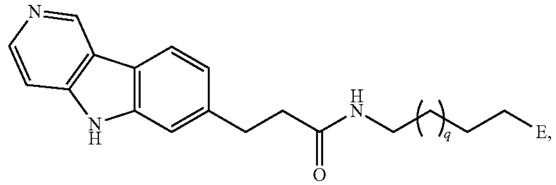

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-4.

In certain embodiments, the compound of Formula I-b is a compound of Formula I-b-4:

I-b-4

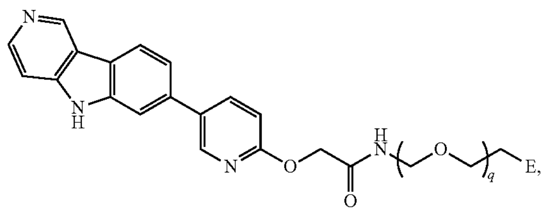

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-6.

In certain embodiments, the compound of Formula I-b is a compound of Formula I-b-5:

I-b-5

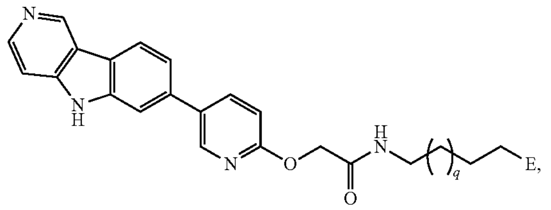

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-4.

In certain embodiments, the compound of Formula I is a compound of Formula I-c:

(I-c)

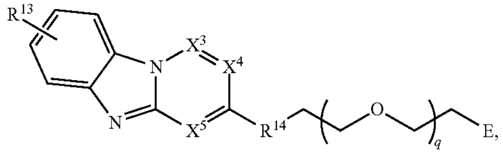

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

$X^3$ is $CR^{15}$ or N;

$X^4$ is $CR^{15}$ or N;

$X^5$ is $CR^{15}$ or N;

each occurrence of $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)$—$NR^A$—, —$(CH_2)_n$-A-$NR^A$—, -A-$NR^A$—$(CH_2)_n$ —(C═O)$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-6;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments of the compound Formula I-c,

E is an E3 ubiquitin ligase binding moiety;

$X^3$ is $CR^{15}$ or N;

$X^4$ is $CR^{15}$ or N;

$X^5$ is $CR^{15}$ or N;

each occurrence of $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-5;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$ In certain embodiments of the compound of Formula I-c, $X^3$ is $CR^{15}$;

$X^4$ is $CR^{15}$;

$X^5$ is N;

each occurrence of $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—,-A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene or substituted or unsubstituted heteroarylene;

n is 0-12; and q is 1-6;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-c, $X^3$ is $CR^{15}$;

$X^4$ is $CR^{15}$;

$X^5$ is N;

each occurrence of $R^{15}$ is independently hydrogen, halogen, hydroxy, nitro, cyano, amino, substituted or unsubstituted alkyl, aralkyl, alkylamino, cycloalkylamino, aminoalkyl, arylamino, aminoaryl, alkoxy, —$NR^A$(C═O)Oalkyl, —$NR^A$(C═O)Oaryl, —$NR^A$(C═O)alkyl, —$NR^A$(C═O)aryl, —(C═O)Oalkyl, —(C═O)Oaryl, —(C═O)alkyl, —(C═O)aryl, aryl, heteroaryl, cycloalkyl, or heterocyclyl;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$— $NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene or substituted or unsubstituted heteroarylene;

n is 0-12; and q is 1-5;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\ alkyl)_2$.

In certain embodiments of the compound of Formula I-c, $X^3$ is $CR^{15}$;

$X^4$ is $CR^{15}$;

$X^5$ is N;

each occurrence of $R^{15}$ is hydrogen;

$R^{14}$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—, -A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$, —$(CH_2)_n$-A-$NR^A$—, -A-$NR^A$—$(CH_2)_n$ —(C═O)$NR^A$—, —$(CH_2)_n$—(C═O)$NR^A$—, -A-$(CH_2)_n$—(C═O)$NR^A$, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-6;

wherein one or more carbon of $R^{14}$ is optionally replaced with C(O), O, S, $SO_2$, NH, or $NC_{1-6}$ alkyl.

In certain embodiments of the compound of Formula I-c, $X^3$ is $CR^{15}$;

$X^4$ is $CR^{15}$;

$X^5$ is N;

each occurrence of $R^{15}$ is hydrogen;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-

$(CH_2)_n$—(C═O)$NR^A$—, —$(CH_2)_n$-A-(C═O)$NR^A$—, —$(CH_2)_n$—$S(0)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-5;

wherein one or more carbon of $R^{14}$ is optionally replaced with C(O), O, S, $SO_2$, NH, or $NC_{1-6}$ alkyl.

In certain embodiments of the compound of Formula I-c, $X^3$ is $CR^{15}$;

$X^4$ is $CR^{15}$;

$X^5$ is N;

each occurrence of $R^{15}$ is hydrogen;

$R^{14}$ is -A-$(CH_2)_n$—(C═O)$NR^A$— or —$(CH_2)_n$-A-(C═O)$NR^A$—;

A is substituted or unsubstituted heterocyclylene, substituted or unsubstituted arylene or substituted or unsubstituted heteroarylene;

n is 0-12; and q is 1-5;

wherein one or more carbon of $R^{14}$ is optionally replaced with C(O), O, S, $SO_2$, NH, or $NC_{1-6}$ alkyl.

In certain embodiments of the compound of Formula I-c, $X^3$ is $CR^5$;

$X^4$ is $CR^{15}$;

$X^5$ is N;

each occurrence of $R^{15}$ is hydrogen;

$R^{14}$ is -A-$(CH_2)_n$—(C═O)$NR^A$—;

A is substituted or unsubstituted heterocyclylene, substituted or unsubstituted arylene, or substituted or unsubstituted heteroarylene;

n is 0-12; and q is 1-5.

In certain embodiments of the compound of Formula I-c, $X^3$ is $CR^{15}$;

$X^4$ is $CR^{15}$;

$X^5$ is N;

each occurrence of $R^{15}$ is hydrogen;

$R^{14}$ is -A-$(CH_2)_n$—(C═O)$NR^A$—;

A is substituted or unsubstituted heterocyclylene;

n is 0-12; and q is 1-5.

In certain embodiments of the compound of Formula I-c, $X^3$ is $CR^{15}$;

$X^4$ is $CR^{15}$;

$X^5$ is N;

each occurrence of $R^{15}$ is hydrogen;

$R^{14}$ is -A-O—$(CH_2)_n$—(C═O)$NR^A$;

A is substituted or unsubstituted heteroarylene;

n is 0-12; and q is 1-6.

In certain embodiments, the compound of Formula I is a compound of Formula I-d:

I-d

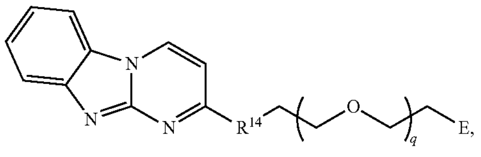

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

$R^{14}$ is —$(CH_2)_n$—O—, -A-$(CH_2)_n$—O—, —$(CH_2)_n$-A-O—, -A-O—$(CH_2)_n$—(C═O)$NR^A$—, —$(CH_2)_n$—S—,-A-$(CH_2)_n$—S—, —$(CH_2)_n$-A-S—, -A-S—$(CH_2)_n$ —(C═O)$NR^A$—, —$(CH_2)_n$—$NR^A$—, -A-$(CH_2)_n$—$NR^A$—, —$(CH_2)_n$-A-$NR^A$—, -A-$NR^A$—$(CH_2)_n$—(C═O)$NR^A$—, —$(CH_2)_n$—(C═O)$NR^A$—, -A-$(CH_2)_n$—(C═O)$NR^A$, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-6;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\text{ alkyl})_2$.

In certain embodiments of the compound of Formula I-d,

E is an E3 ubiquitin ligase binding moiety;

$R^{14}$ is —$(CH_2)_n$—O—, -A-$(CH_2)_n$—O—, —$(CH_2)_n$-A-O—, —$(CH_2)_n$—S—, -A-$(CH_2)_n$—S—, —$(CH_2)_n$-A-S—, —$(CH_2)_n$—$NR^A$—, -A-$(CH_2)_n$—$NR^A$—, —$(CH_2)_n$-A-$NR^A$—, —$(CH_2)_n$—(C═O)$NR^A$—, -A-$(CH_2)_n$—(C═O)$NR^A$—, —$(CH_2)_n$-A-(C═O)$NR^A$—, —$(CH_2)_n$—$S(O)_2NR^A$—, -A-$(CH_2)_n$—$S(O)_2NR^A$—, or —$(CH_2)_n$-A-$S(O)_2NR^A$—;

A is substituted or unsubstituted heterocyclylene, substituted or unsubstituted arylene, or substituted or unsubstituted heteroarylene;

n is 0-12; and q is 1-5;

wherein one or more carbon of $R^{14}$ and $R^{15}$ is optionally replaced with C(O), O, S, $SO_2$, NH, $NC_{1-6}$ alkyl, NH—$C_{1-6}$ alkyl, $NH_2$, or $N(C_{1-6}\text{ alkyl})_2$.

In certain embodiments of the compound of Formula I-d, $R^{14}$ is -A-$(CH_2)_n$—(C═O)$NR^A$— or —$(CH_2)_n$-A-(C═O)$NR^A$—;

A is substituted or unsubstituted heterocyclylene, substituted or unsubstituted arylene, or substituted or unsubstituted heteroarylene;

n is 0-12; and q is 1-5;

wherein one or more carbon of $R^{14}$ is optionally replaced with C(O), O, S, $SO_2$, NH, or $NC_{1-6}$ alkyl.

In certain embodiments of the compound of Formula I-d, $R^{14}$ is -A-$(CH_2)_n$—(C═O)$NR^A$—;

A is substituted or unsubstituted heterocyclylene, substituted or unsubstituted arylene or substituted or unsubstituted heteroarylene;

n is 0-12; and q is 1-5.

In certain embodiments of the compound of Formula I-d, $R^{14}$ is -A-$(CH_2)_n$—(C═O)$NR^A$—;

A is substituted or unsubstituted heterocyclylene;

n is 0-12; and q is 1-5.

In certain embodiments of the compound of Formula I-d, $R^{14}$ is -A-O—$(CH_2)_n$—(C═O)$NR^A$—;

A is substituted or unsubstituted heteroarylene;

n is 0-12; and q is 1-6.

In certain embodiments, the compound of Formula I-d is a compound of Formula I-d-1:

I-d-1

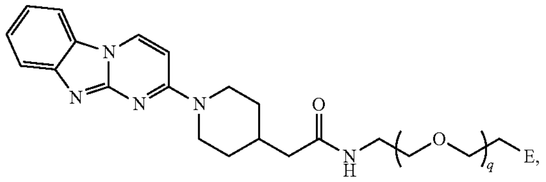

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-6.

In certain embodiments of the compound of Formula I-d-1, E is an E3 ubiquitin ligase binding moiety; and q is 1-5.

In certain embodiments, the compound of Formula I is a compound of Formula I-e:

I-e

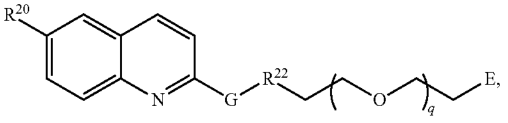

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

$R^{20}$ is halogen, —OH, —COOH, —$SO_3H$, —$NO_2$, —SH, —$NR^xR^y$, substituted or unsubstituted alkyl, or substituted or unsubstituted alkoxy;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$—S$(O)_2NR^A$—;

$R^x$ and $R^y$ are independently hydrogen, or substituted or unsubstituted alkyl;

n is 0-12; and q is 1-5.

In certain embodiments of the compound of Formula I-e, $R^{20}$ is unsubstituted alkyl, alkyl substituted with one or more halogen or hydroxy groups, unsubstituted alkoxy, or alkoxy substituted with one or more halogen or hydroxy groups;

G is substituted or unsubstituted heterocyclylene, substituted or unsubstituted arylene, or substituted or unsubstituted heteroarylene;

$R^{22}$ is —$(CH_2)_n$—O—, —$(CH_2)_n$—S—, —$(CH_2)_n$—$NR^A$—, —$(CH_2)_n$—(C═O)$NR^A$—, or —$(CH_2)_n$—S$(O)_2NR^A$—;

n is 0-12; and q is 1-5.

In certain embodiments of the compound of Formula I-e, $R^{20}$ is unsubstituted alkyl, alkyl substituted with one or more halogen or hydroxy groups, unsubstituted alkoxy, or alkoxy substituted with one or more halogen or hydroxy groups;

G is substituted or unsubstituted heterocyclylene, substituted or unsubstituted arylene, or substituted or unsubstituted heteroarylene;

$R^{22}$ is —$(CH_2)_n$—$NR^A$— or —$(CH_2)_n$—(C═O)$NR^A$—;

n is 0-12; and q is 1-5.

In certain embodiments of the compound of Formula I-e, $R^{20}$ is unsubstituted alkyl, alkyl substituted with one or more halogen or hydroxy groups, unsubstituted alkoxy, or alkoxy substituted with one or more halogen or hydroxy groups;

G is unsubstituted arylene or unsubstituted heteroarylene;

$R^{22}$ is —$(CH_2)_n$—$NR^A$— or —$(CH_2)_n$—(C═O)$NR^A$—;

n is 0-12; and q is 1-5.

In certain embodiments of the compound of Formula I-e, $R^{20}$ is unsubstituted alkyl, alkyl substituted with one or more halogen or hydroxy groups, unsubstituted alkoxy, or alkoxy substituted with one or more halogen or hydroxy groups;

G is unsubstituted arylene or unsubstituted heteroarylene;

$R^{22}$ is —$(CH_2)_n$—$NR^A$—;

n is 0-12; and q is 1-5.

In certain embodiments of the compound of Formula I-e, $R^{20}$ is unsubstituted alkyl, alkyl substituted with one or more halogen or hydroxy groups, unsubstituted alkoxy, or alkoxy substituted with one or more halogen or hydroxy groups;

G is unsubstituted heteroarylene;

$R^{22}$ is —$(CH_2)_n$—$NR^A$—;

n is 0-12; and q is 1-5.

In certain embodiments of the compound of Formula I-e, $R^{20}$ is alkoxy substituted with one or more halogen or hydroxy groups;

G is unsubstituted heteroarylene;

$R^2$ is —$(CH_2)_n$—$NR^A$—;

n is 0-12; and q is 1-5.

In certain embodiments, the compound of Formula T-e is a compound of Formula I-e-1:

I-e-1

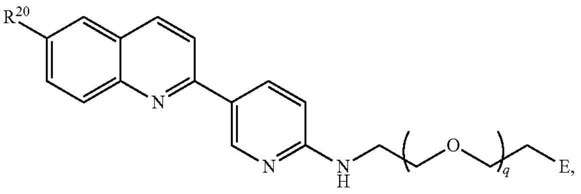

or a pharmaceutically acceptable salt, co-crystal, tautomer, stereoisomer, solvate, hydrate, polymorph, isotopically enriched derivative, or prodrug thereof, wherein $R^{20}$ is alkoxy substituted with one or more halogen or hydroxy groups; E is an E3 ubiquitin ligase binding moiety; and q is 1-5.

In certain embodiments, the compound of Formula I-e is a compound of Formula I-e-2:

I-e-2

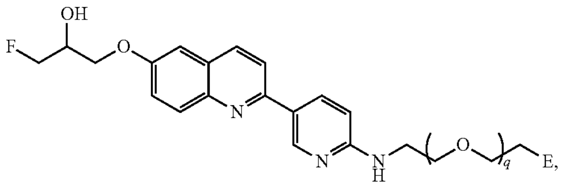

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-5.

In certain embodiments, the compound of Formula I-e is a compound of Formula I-e-3:

I-e-3

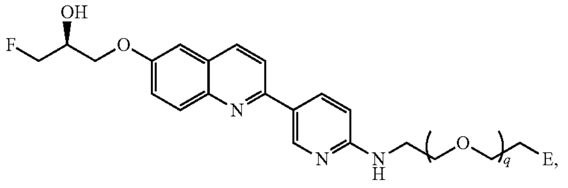

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-5.

In certain embodiments, the compound of Formula I is a compound of Formula I-f:

I-f

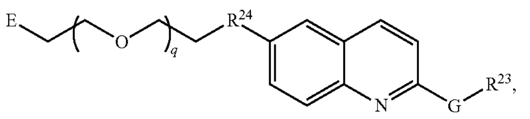

or a pharmaceutically acceptable salt, co-crystal, tautomer, stereoisomer, solvate, hydrate, polymorph, isotopically enriched derivative, or prodrug thereof, wherein:

E is an E3 ubiquitin ligase binding moiety;

G is substituted or unsubstituted heterocyclylene, substituted or unsubstituted arylene, or substituted or unsubstituted heteroarylene;

$R^{23}$ is halogen, —OH, —COOH, —$SO_3H$, —$NO_2$, —SH, —$NR^xR^y$, substituted or unsubstituted alkyl, or substituted or unsubstituted alkoxy;

$R^{24}$ is unsubstituted alkylene, alkylene substituted with one or more halogen or hydroxy groups, unsubstituted alkoxylene, or alkoxylene substituted with one or more halogen or hydroxy groups;

$R^x$ and $R^y$ are independently hydrogen, or substituted or unsubstituted alkyl; and q is 1-5.

In certain embodiments of the compound of Formula I-f,

G is substituted or unsubstituted heterocyclylene, substituted or unsubstituted arylene, or substituted or unsubstituted heteroarylene;

$R^{23}$ is —$NR^xR^y$;

$R^{24}$ is unsubstituted alkylene, alkylene substituted with one or more halogen or hydroxy groups, unsubstituted alkoxylene, or alkoxylene substituted with one or more halogen or hydroxy groups;

$R^x$ and $R^y$ are independently hydrogen, or substituted or unsubstituted alkyl; and q is 1-5.

In certain embodiments of the compound of Formula I-f,

G is substituted or unsubstituted heterocyclylene, substituted or unsubstituted arylene, or substituted or unsubstituted heteroarylene;

$R^{23}$ is —$NR^xR^y$;

$R^{24}$ is substituted or unsubstituted alkylene, or substituted or unsubstituted alkoxylene;

$R^x$ and $R^y$ are independently hydrogen, or substituted or unsubstituted alkyl; and q is 1-5.

In certain embodiments of the compound of Formula I-f,

G is substituted or unsubstituted heterocyclylene, substituted or unsubstituted arylene, or substituted or unsubstituted heteroarylene;

$R^2$ is —$NR^xR^y$;

$R^{24}$ is substituted or unsubstituted alkoxylene;

$R^x$ and $R^y$ are independently hydrogen, or substituted or unsubstituted alkyl; and q is 1-5.

In certain embodiments of the compound of Formula I-f,

G is substituted or unsubstituted heterocyclylene, substituted or unsubstituted arylene, or substituted or unsubstituted heteroarylene;

$R^3$ is —$NR^xR^y$;

$R^{24}$ is alkoxylene substituted with one or more halogen or hydroxy groups;

$R^x$ and $R^y$ are independently hydrogen, or substituted or unsubstituted alkyl; and q is 1-5.

In certain embodiments of the compound of Formula I-f,

G is substituted or unsubstituted heteroarylene;

$R^2$ is —$NR^xR^y$;

$R^{24}$ is alkoxylene substituted with one or more halogen or hydroxy groups;

$R^x$ and $R^y$ are independently hydrogen, or substituted or unsubstituted alkyl; and q is 1-5.

In certain embodiments of the compound of Formula I-f,

G is unsubstituted heteroarylene;

$R^{23}$ is —$NR^xR^y$;

$R^{24}$ is alkoxylene substituted with one or more halogen or hydroxy groups;

$R^x$ and $R^y$ are independently hydrogen, or substituted or unsubstituted alkyl; and q is 1-5.

In certain embodiments, the compound of Formula I-f is a compound of Formula I-f-1:

I-f-1

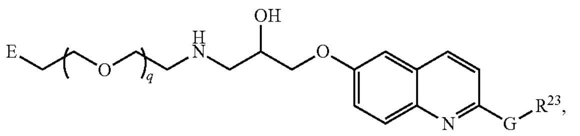

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; G is unsubstituted heteroarylene; $R^2$ is —$NR^xR^y$; $R^x$ and $R^y$ are independently hydrogen, or substituted or unsubstituted alkyl; and q is 1-5.

In certain embodiments, the compound of Formula I-f is a compound of Formula I-f-2:

I-f-2

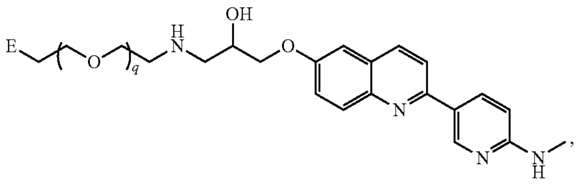

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-5.

In certain embodiments, the compound of Formula I-f is a compound of Formula I-f-3:

I-f-3

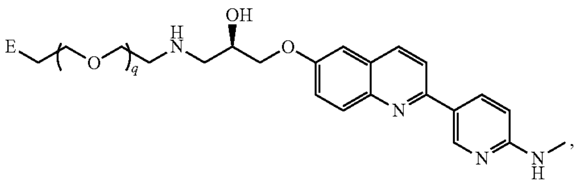

or a pharmaceutically acceptable salt, co-crystal, tautomer, stereoisomer, solvate, hydrate, polymorph, isotopically enriched derivative, or prodrug thereof, wherein E is an E3 ubiquitin ligase binding moiety; and q is 1-5.

In certain embodiments, the compound of Formula I is a compound of Formula I-g:

I-g

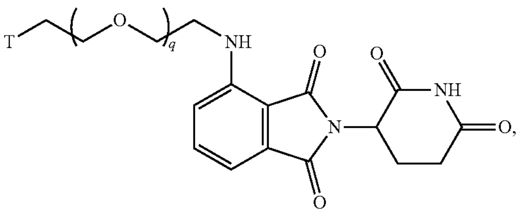

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-6.

In certain embodiments, the compound of Formula I is a compound of Formula I-h:

I-h

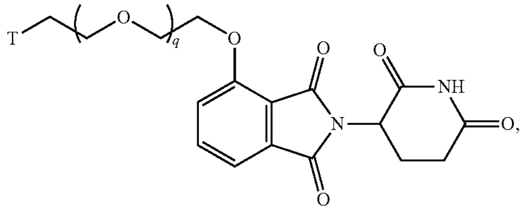

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-6.

In certain embodiments, the compound of Formula I is a compound of Formula I-i:

I-i

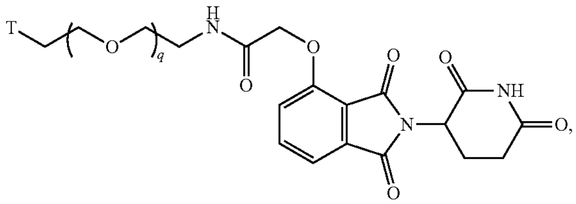

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-6.

In certain embodiments, the compound of Formula I is a compound of Formula I-j:

I-j

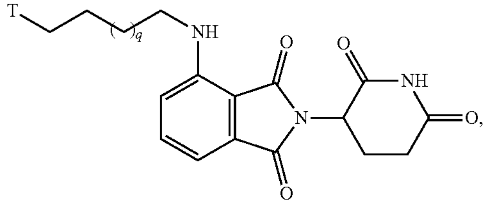

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-4.

In certain embodiments, the compound of Formula I is a compound of Formula I-k:

I-k

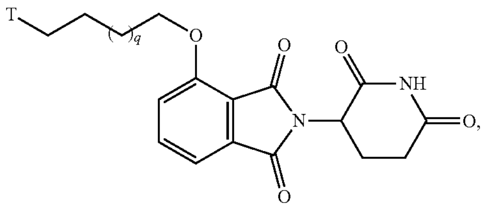

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-4.

In certain embodiments, the compound of Formula I is a compound of Formula I-1:

I-l

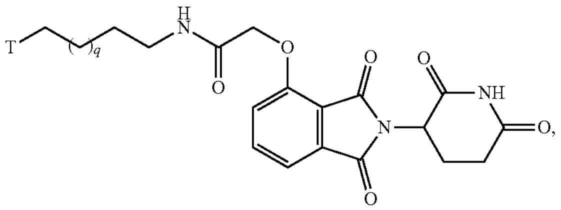

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-4.

In certain embodiments, the compound of Formula I is a compound of Formula I-m:

I-m

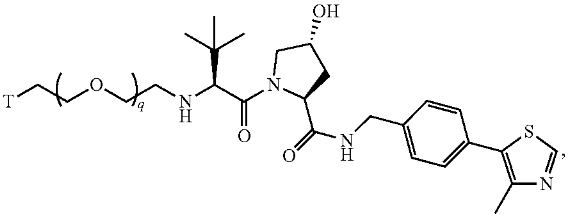

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-6.

In certain embodiments, the compound of Formula I is a compound of Formula I-n:

I-n

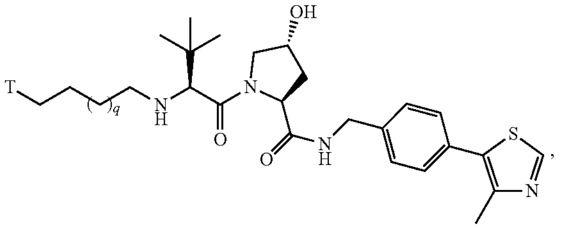

or a pharmaceutically acceptable salt, co-crystal, tautomer, stereoisomer, solvate, hydrate, polymorph, isotopically enriched derivative, or prodrug thereof, wherein:

T is a tau protein binding moiety; and q is 1-4.

In certain embodiments, the compound of Formula I is a compound of Table 1, or a pharmaceutically acceptable salt, co-crystal, tautomer, stereoisomer, solvate, hydrate, polymorph, isotopically enriched derivative, or prodrug thereof.

TABLE 1

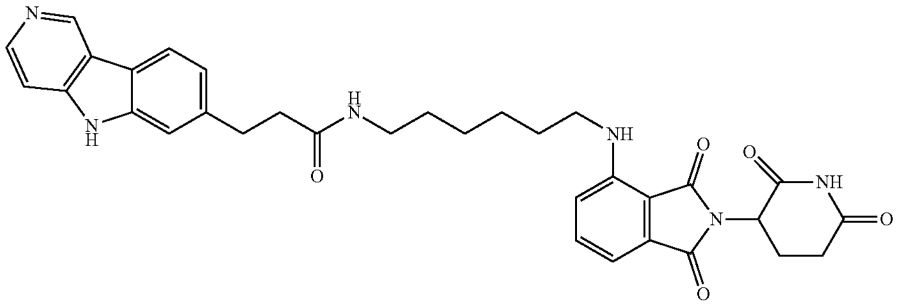 [SMILES: O=C(CCc1ccc2c(c1)[nH]c1ccncc12)NCCCCCCNc1cccc2c1C(=O)N(C1CCC(=O)NC1=O)C2=O]

TABLE 1-continued
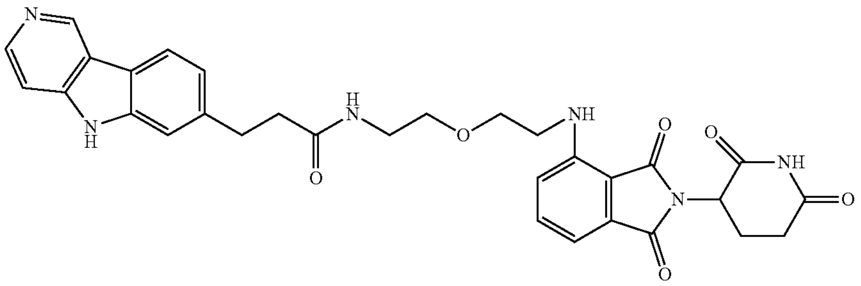 [SMILES: O=C(CCc1ccc2c(c1)[nH]c1ccncc12)NCCOCCNc1cccc2c1C(=O)N(C1CCC(=O)NC1=O)C2=O]
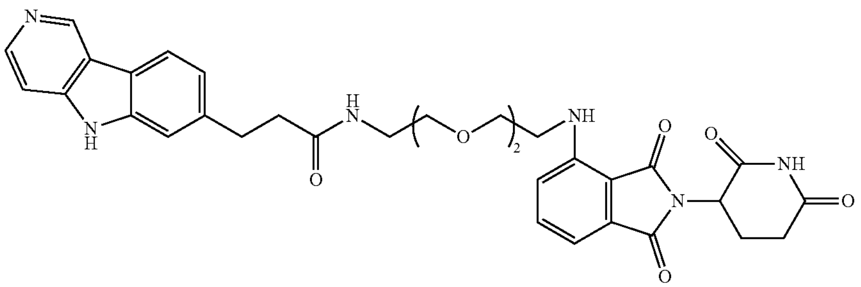
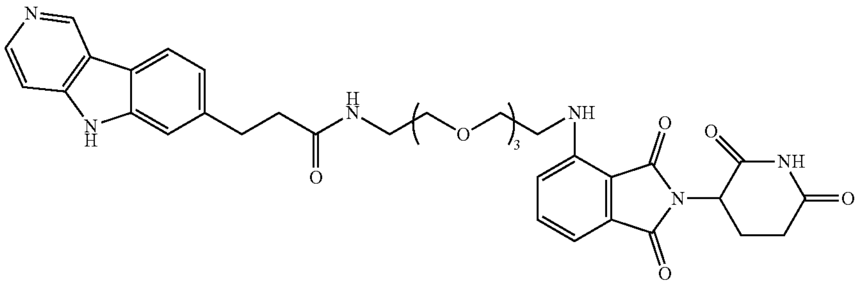
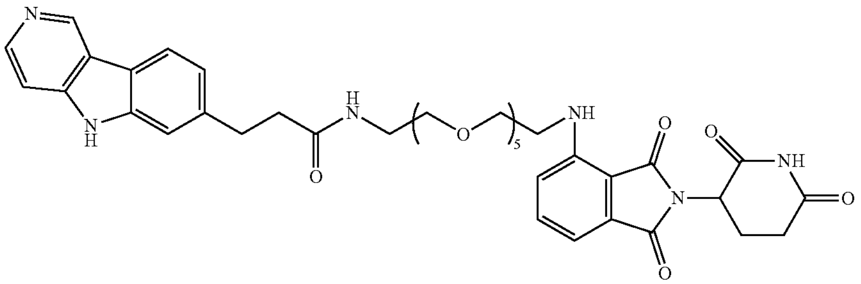
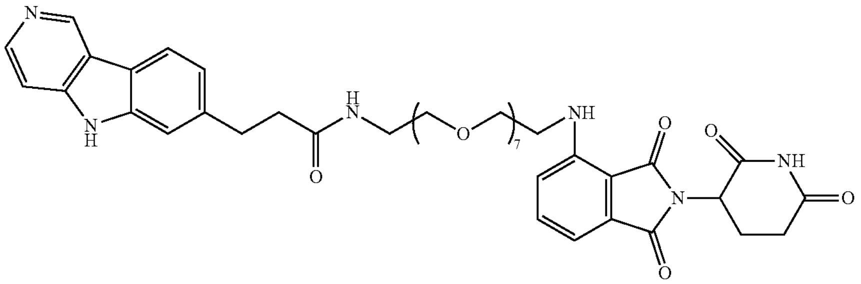

TABLE 1-continued
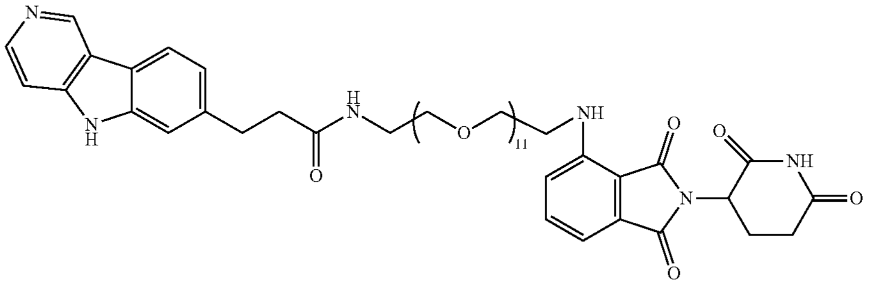
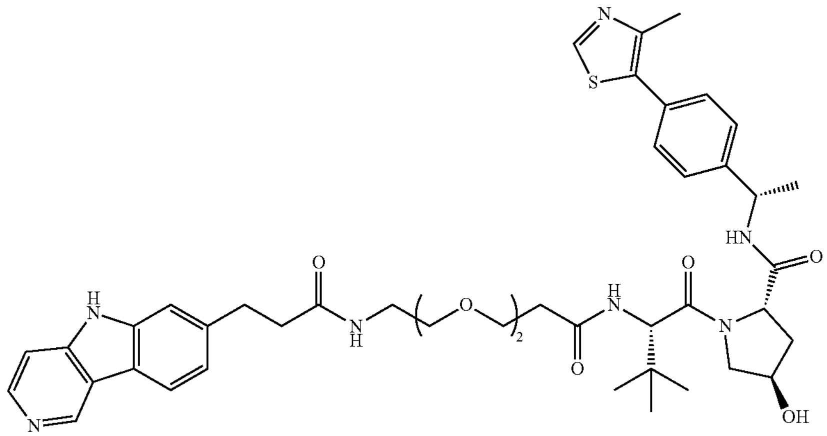
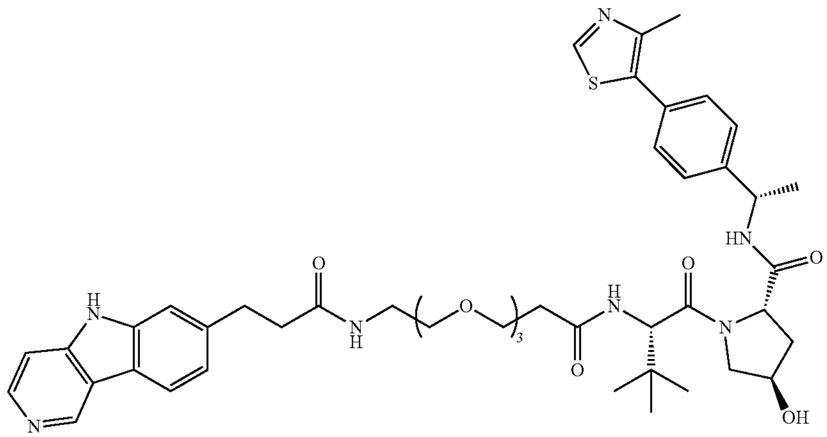
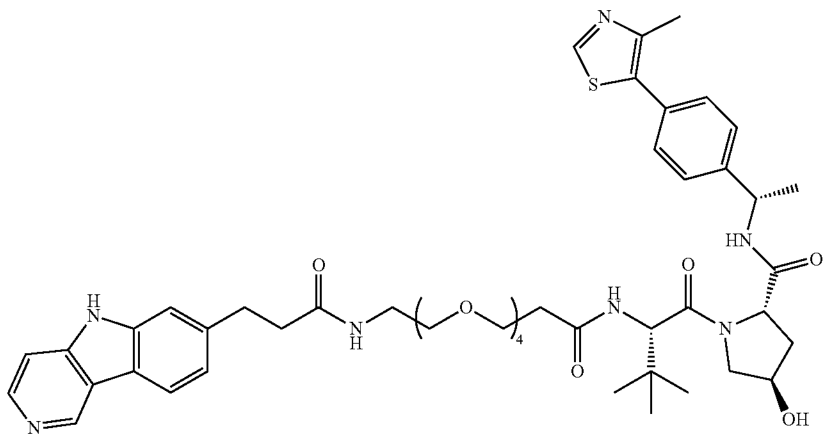

TABLE 1-continued
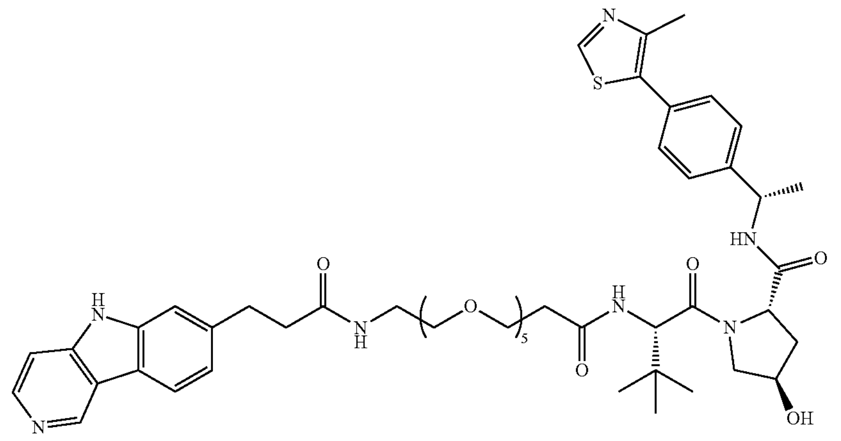
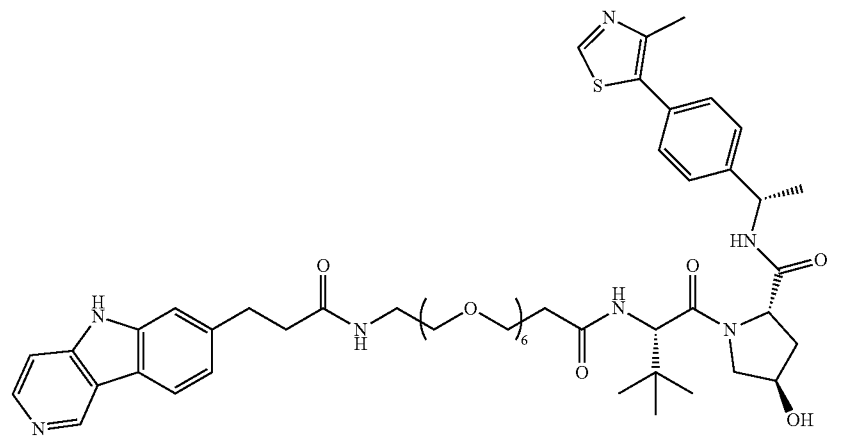
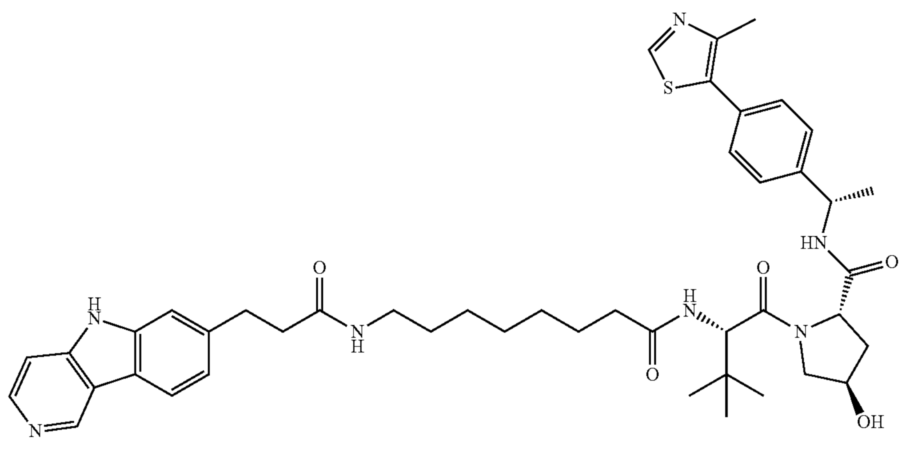 [SMILES: Cc1ncsc1-c1ccc([C@H](C)NC(=O)[C@@H]2C[C@@H](O)CN2C(=O)[C@@H](NC(=O)CCCCCCCNC(=O)CCc2ccc3c(c2)[nH]c2ccncc23)C(C)(C)C)cc1]

TABLE 1-continued
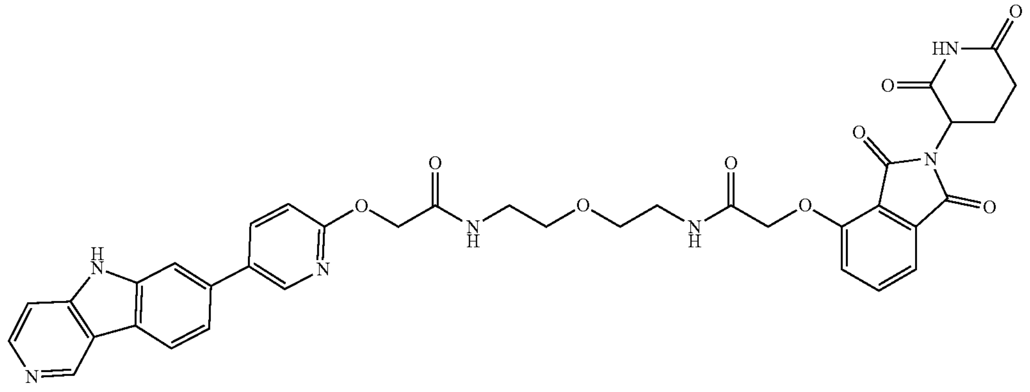 [SMILES: O=C(COc1ccc(-c2ccc3c(c2)[nH]c2ccncc23)cn1)NCCOCCNC(=O)COc1cccc2c1C(=O)N(C1CCC(=O)NC1=O)C2=O]
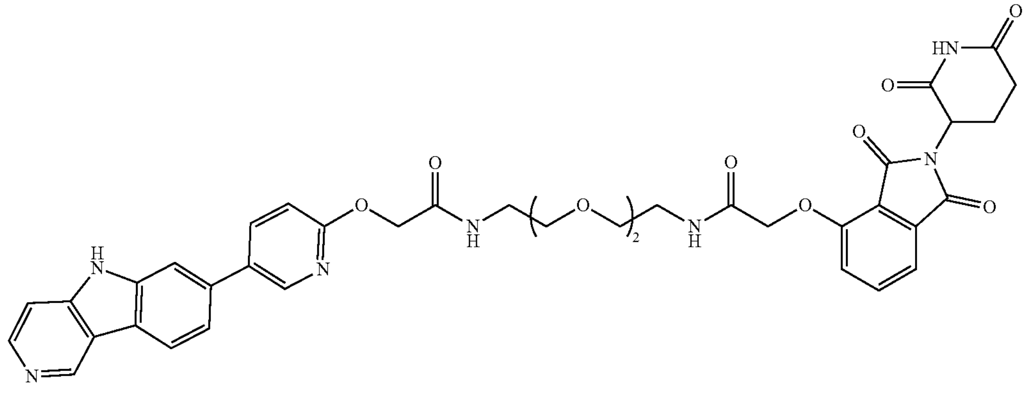
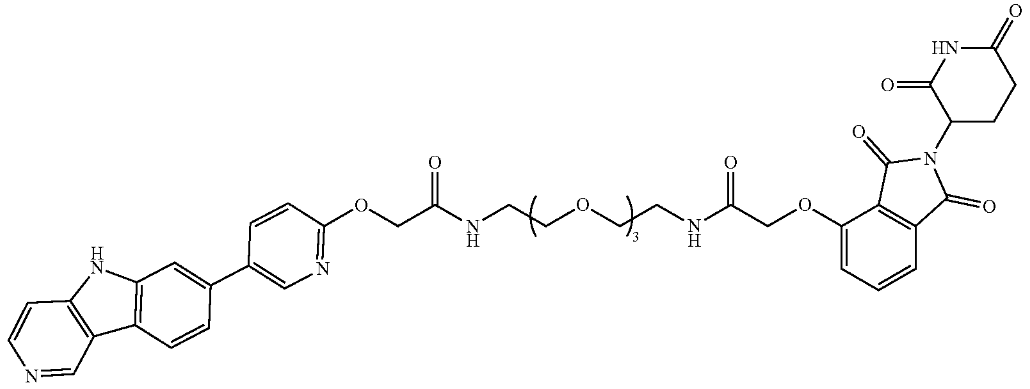
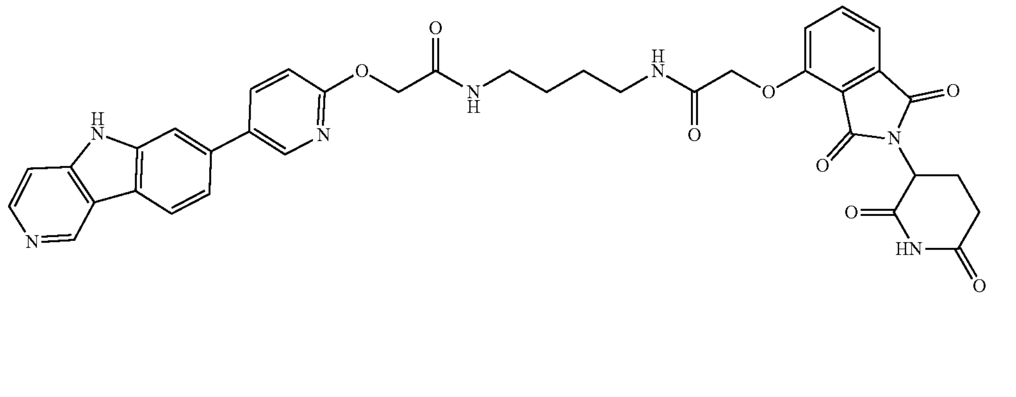 [SMILES: O=C(COc1ccc(-c2ccc3c(c2)[nH]c2ccncc23)cn1)NCCCCNC(=O)COc1cccc2c1C(=O)N(C1CCC(=O)NC1=O)C2=O]

TABLE 1-continued
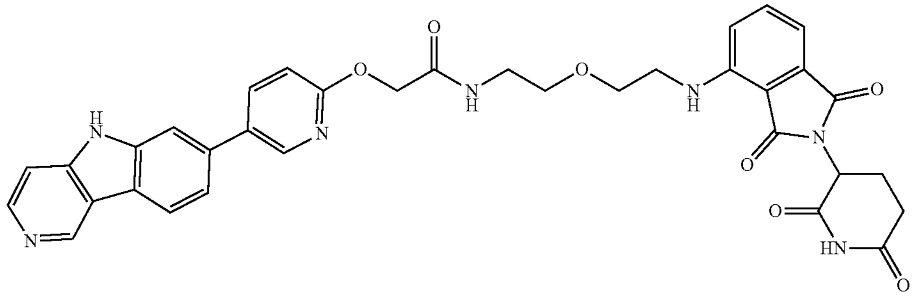 [SMILES: O=C(COc1ccc(-c2ccc3c(c2)[nH]c2ccncc23)cn1)NCCOCCNc1cccc2c1C(=O)N(C1CCC(=O)NC1=O)C2=O]
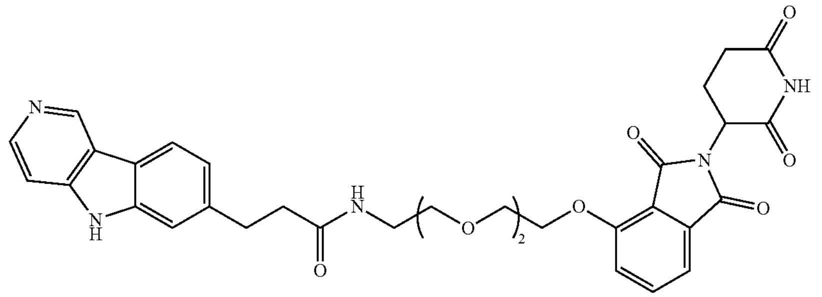
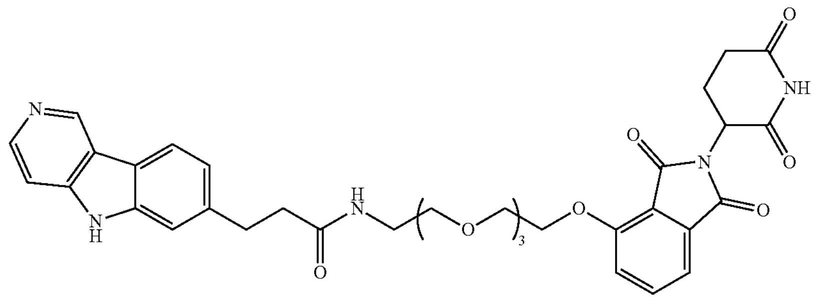
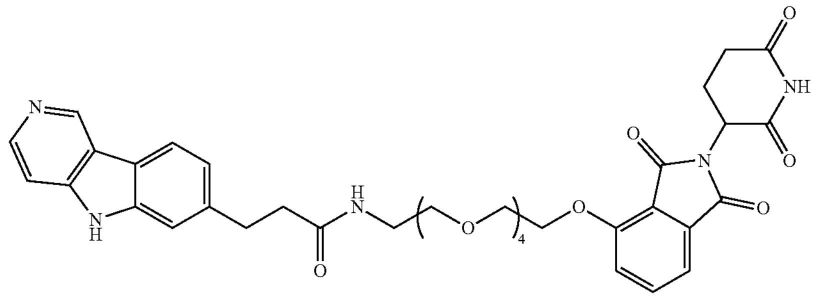
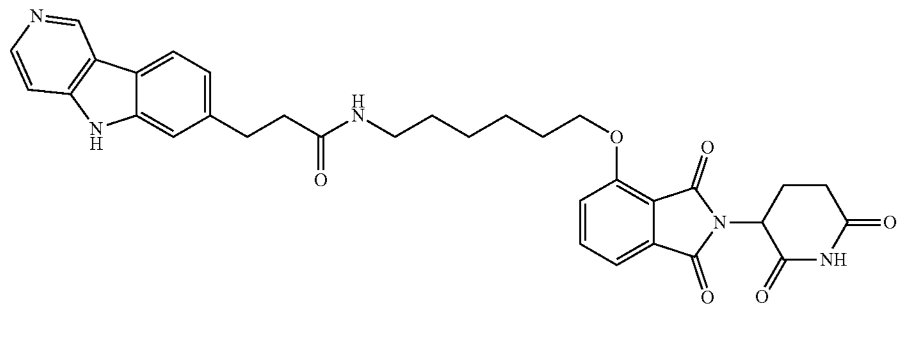 [SMILES: O=C(CCc1ccc2c(c1)[nH]c1ccncc12)NCCCCCCOc1cccc2c1C(=O)N(C1CCC(=O)NC1=O)C2=O]

TABLE 1-continued
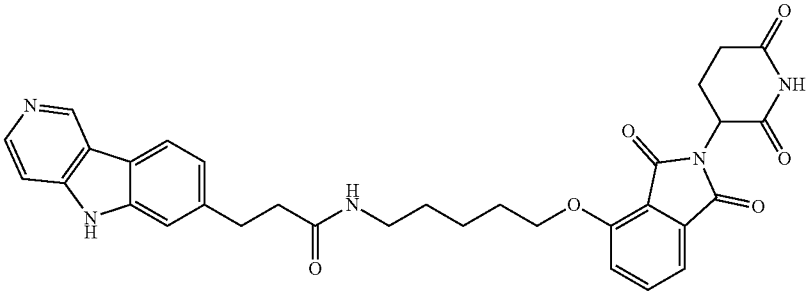 [SMILES: O=C(CCc1ccc2c(c1)[nH]c1ccncc12)NCCCCCOc1cccc2c1C(=O)N(C1CCC(=O)NC1=O)C2=O]
In certain embodiments, the compound of Formula i is a compound of Table 2, or a pharmaceutically acceptable salt, co-crystal, tautomer, stereoisomer, solvate, hydrate, polymorph, isotopically enriched derivative, or prodrug thereof.
TABLE 2
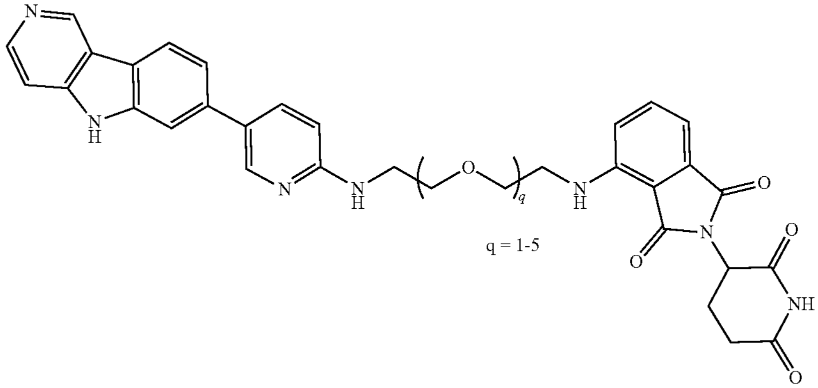
q = 1-5
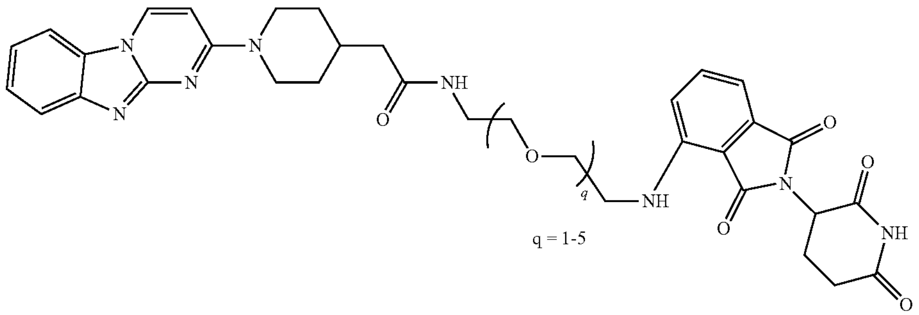
q = 1-5
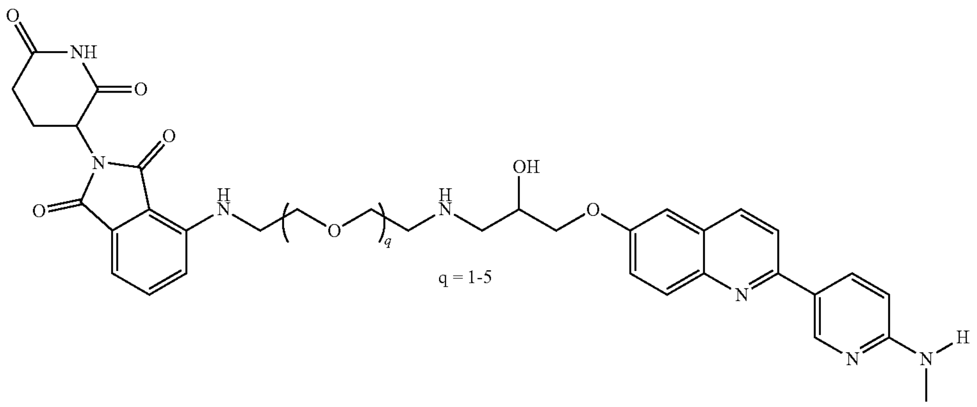
q = 1-5

TABLE 2-continued

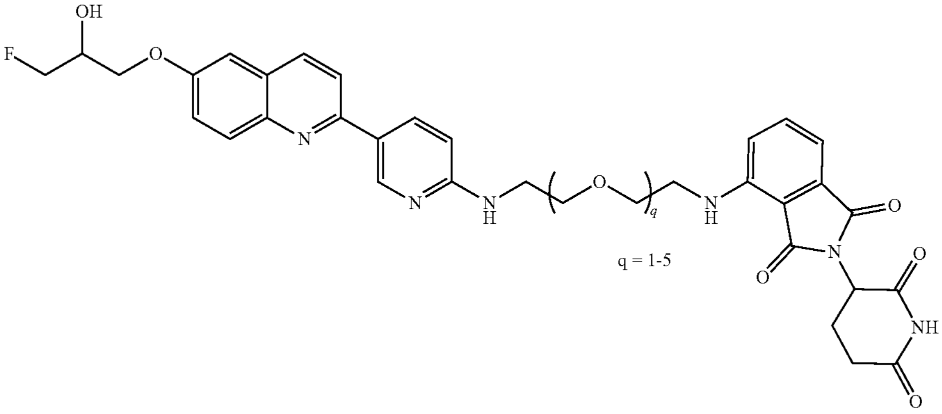

q = 1-5

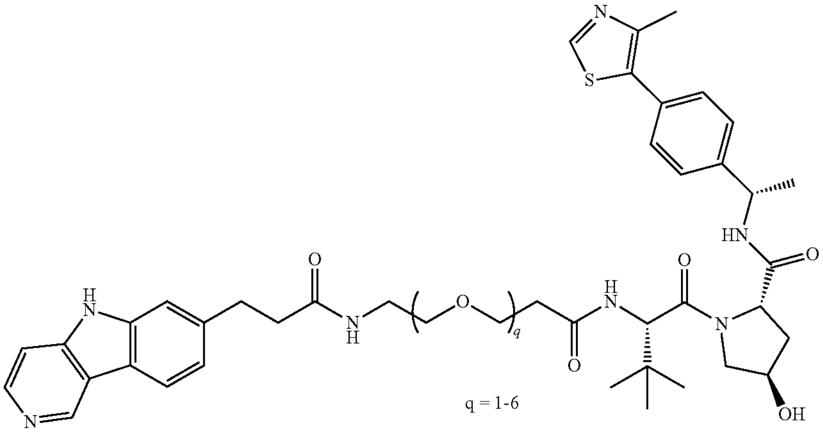

q = 1-6

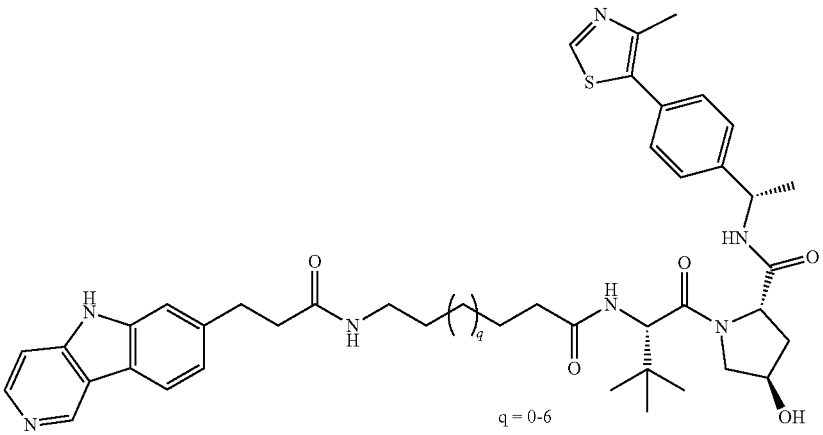

q = 0-6

In certain embodiments, the compound of Formula I comprises a radionuclide. In certain embodiments, the compound of Formula I is substituted with a radionuclide. In certain embodiments, the compound of Formula I is enriched with a radionuclide. In certain embodiments, the compound of Formula I is useful as an imaging agent (e.g., for use in positron emission tomography). The radionuclide, such as a halogen atom, for example, may be readily introduced into the compound using a number of different methods well known in the art. Accordingly, the radiolabeled compounds of Formula I may be prepared using standard methods known in the art for preparing such radiolabeled compounds having a particular substituent, wherein the compound may be incorporated with a particular radionuclide selected from the group consisting of $^{11}C$, $^{13}N$, $^{15}O$, $^{18}F$, $^{123}I$, $^{124}I$, $^{125}I$, $^{131}I$, and $^{77}Br$.

In certain embodiments, the compound of Formula I binds tau protein with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I selectively binds tau protein over another protein. In some embodiments, the compound of Formula I selectively binds tau protein over amyloid β. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula I binds an E3 ubiquitin ligase with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I binds Cereblon with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I selectively binds an E3 ubiquitin ligase as compared to another protein. In some embodiments, the compound of Formula I selectively binds Cereblon over another protein. In some embodiments, the compound of Formula I selectively binds Cereblon over another E3 ubiquitin ligase. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula I promotes the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of tau protein at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 rnM or less, 4 nM or less, 3 nM or less, 2 nM or less, or 1 nM or less.

In certain embodiments, the compound of Formula I increases the rate of tau protein degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formula I, or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula I, or a pharmaceutically acceptable salt thereof, and a pharmaceutically acceptable excipient.

In certain embodiments, the compound of Formula I is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a neurological disorder in a subject in need thereof. In certain embodiments, the effective amount is an amount effective for preventing a neurological disorder in a subject in need thereof. In certain embodiments, the effective amount is an amount effective for treating a neurodegenerative disease in a subject in need thereof. In certain embodiments, the effective amount is an amount effective for preventing a neurodegenerative disease in a subject in need thereof. In certain embodiments, the effective amount is an amount effective for treating a tauopathy in a subject in need thereof. In certain embodiments, the effective amount is an amount effective for preventing a tauopathy in a subject in need thereof. In certain embodiments, the effective amount is an amount effective for reducing the risk of developing a disease (e.g., neurological disorder, neurodegenerative disease, or tauopathy) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for promoting the degradation of at least about 10%, at least about 20%, at least about 30%, at least about 40%, at least about 50%, at least about 60%, at least about 70%, at least about 80%, at least about 90%, at least about 95%, at least about 98%, or at least about 99% of tau protein. In certain embodiments, the effective amount is an amount effective for promoting the degradation of tau protein by a range between a percentage described in this paragraph and another percentage described in this paragraph, inclusive.

The present disclosure provides pharmaceutical compositions comprising a compound that interacts with tau protein and/or an E3 ubiquitin ligase (e.g., Cereblon) for use in treating a neurological disorder in a subject in need thereof. In certain embodiments, the composition is for use in treating a neurodegenerative disease. In certain embodiments, the composition is for use in treating a tauopathy. In certain embodiments, the composition is for use in treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the composition is for use in treating Alzheimer's disease.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., neurological disorder, neurodegenerative disease, and/or tauopathy). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™, polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazelnut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., neurological disorder, neurodegenerative disease, or tauopathy) in a subject in need thereof. In certain embodiments, the kits are useful for preventing a disease (e.g., neurological disorder, neurodegenerative disease, or tauopathy) in a subject in need thereof. In certain embodiments, the kits are useful for reducing the risk of developing a disease (e.g., neurological disorder, neurodegenerative disease, or tauopathy) in a subject in need thereof. In certain embodiments, the kits are useful for promoting the degradation of tau protein in a subject or cell. In certain embodiments, the kits are useful for imaging and/or detecting a neurological disorder in any human tissue (e.g., through use of a radiolabeled compound of Formula I). In certain embodiments, the kits are useful for promoting the degradation of tau protein in a subject or cell. In certain embodiments, the kits are useful for imaging and/or detecting a neurological disorder in the central nervous system (e.g., through use of a radiolabeled compound of Formula I). In certain embodiments, the kits are useful for promoting the degradation of tau protein in a subject or cell. In certain embodiments, the kits are useful for imaging and/or detecting a neurological disorder in the brain (e.g., through use of a radiolabeled compound of Formula I). In certain embodiments, the kits are useful for imaging and/or detecting pathological aggregation of tau protein in any human tissue (e.g., through use of a radiolabeled compound of Formula I). In certain embodiments, the kits are useful for imaging and/or detecting pathological aggregation of tau protein in the central nervous system (e.g., through use of a radiolabeled compound of Formula I). In certain embodiments, the kits are useful for imaging and/or detecting pathological aggregation of tau protein in the brain (e.g., through use of a radiolabeled compound of Formula I).

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., neurological disorder, neurodegenerative disease, or tauopathy) in a subject in need thereof. In certain embodiments, the kits and instructions provide for preventing a disease (e.g., neurological disorder, neurodegenerative disease, or tauopathy) in a subject in need thereof. In certain embodiments, the kits and instructions provide for reducing the risk of developing a disease (e.g., neurological disorder, neurodegenerative disease, or tauopathy) in a subject in need thereof. In certain embodiments, the kits and instructions provide for promoting the degradation of tau protein in a subject or cell. In certain embodiments, the kits and instructions provide for diagnosing a neurological disorder in the central nervous system (e.g., through use of a radiolabeled compound of Formula I). In certain embodiments, the kits and instructions provide for imaging and/or detecting a neurological disorder in the central nervous system (e.g., through use of a radiolabeled compound of Formula I). In certain embodiments, the kits and instructions provide for imaging and/or detecting pathological aggregation of tau protein in the central nervous system (e.g., through use of a radiolabeled compound of Formula I). A kit described herein may include one or more additional pharmaceutical agents described herein as a separate composition.

Methods of Treatment

Major neuropathology observations of postmortem examination of Alzheimer's disease (AD) brains confirm the presence of AD through the detection of intracellular neurofibrillary tangles (NFT). NFTs derive from filaments of aggregated hyperphosphorylated tau proteins. The presence and severity of NFTs generally but not always correlates with the severity of dementia and cognitive impairment, and it has become clear that the pathological process of AD begins before the presentation of the clinical symptoms of dementia and the late stage NFTs. Therefore, reduction and/or elimination of aberrant tau species preceding NFTs, or NFTs themselves, by tau protein degradation is an attractive method for the treatment of AD and other tauopathies.

Immunomodulatory agents, including thalidomide and lenalidomide, bind Cereblon. Accordingly, use of a bifunctional compound that binds tau protein and an E3 ubiquitin ligase (e.g., Cereblon) provides a strategy for treating diseases associated with tau protein aggregation, also known as tauopathies.

The present disclosure provides methods for treating neurological disorders. In certain embodiments, the application provides a method of treating neurodegenerative disease. In certain embodiments, the application provides a method of treating a tauopathy. In certain embodiments, the application provides a method of treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the application provides a method of treating Alzheimer's disease.

The present disclosure provides methods for preventing neurological disorders. In certain embodiments, the application provides a method of preventing neurodegenerative disease. In certain embodiments, the application provides a method of preventing a tauopathy. In certain embodiments, the application provides a method of preventing primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the application provides a method of preventing Alzheimer's disease.

In certain embodiments, the application provides a method of promoting the degradation of tau protein (e.g., in a cell). In certain embodiments, the application provides a method of promoting the degradation of tau protein in a subject in need thereof. In certain embodiments, the application provides a method of binding an E3 ubiquitin ligase and promoting the degradation of tau protein. In certain embodiments, the E3 ubiquitin ligase targeted is Cereblon.

In certain embodiments, the methods comprise administering to a subject in need thereof (e.g., a subject with a neurodegenerative disease) a compound that interacts with tau protein, for example, a compound that is a modulator of tau protein, a binder of tau protein, a compound that modifies tau protein, or a compound that promotes the degradation of tau protein. The compound may also be an inhibitor of an E3 ubiquitin ligase, a modulator of an E3 ubiquitin ligase, a binder of an E3 ubiquitin ligase, a compound that modifies an E3 ubiquitin ligase, or a compound that disrupts the interaction of the E3 ubiquitin ligase with another protein. In certain embodiments, the methods comprise administering a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof.

The present disclosure also provides a compound of Formula I, or a pharmaceutically acceptable salt, co-crystal, tautomer, stereoisomer, solvate, hydrate, polymorph, isotopically enriched derivative, or prodrug, or composition thereof, for use in the treatment of a neurological disorder. In certain embodiments, the neurological disorder is a neurodegenerative disease. In certain embodiments, the neurodegenerative disease is a tauopathy. In certain embodiments, the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the tauopathy is Alzheimer's disease.

The present disclosure also provides uses of a compound of Formula I, or a pharmaceutically acceptable salt, co-crystal, tautomer, stereoisomer, solvate, hydrate, polymorph, isotopically enriched derivative, or prodrug, or composition thereof, in the manufacture of a medicament for the treatment of a neurological disorder. In certain embodiments, the neurological disorder is a neurodegenerative disease. In certain embodiments, the neurodegenerative disease is a tauopathy. In certain embodiments, the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the tauopathy is Alzheimer's disease.

In certain embodiments, the methods of the disclosure comprise administering to the subject an effective amount of a compound of Formula I, or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula I, or at different times than the compound of Formula I. For example, the compound of Formula I and any additional pharmaceutical agent(s) may be on the same dosing schedule or different dosing schedules. All or some doses of the compound of Formula I may be administered before all or some doses of an additional pharmaceutical agent, after all or some does an additional pharmaceutical agent, within a dosing schedule of an additional pharmaceutical agent, or a combination thereof. The timing of administration of the compound of Formula I and additional pharmaceutical agents may be different for different additional pharmaceutical agents.

In certain embodiments, the additional pharmaceutical agent comprises an agent useful in the treatment of a neurological disorder. In certain embodiments, the additional pharmaceutical agent is useful in the treatment of a neurodegenerative disease. In certain embodiments, the additional pharmaceutical agent is useful in the treatment of a tauopathy. In certain embodiments, the additional pharmaceutical agent is useful in the treatment of primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the additional pharmaceutical agent is useful in the treatment of a non-Hodgkin's lymphoma. In certain embodiments, the additional pharmaceutical agent is useful in the treatment of Alzheimer's disease.

In another aspect, the present disclosure provides methods for promoting the degradation of tau protein, the method comprising administering to the subject a compound of Formula I, or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding an E3 ubiquitin ligase and promoting the degradation of tau protein, the method comprising administering to the subject a compound of Formula I, or a pharmaceutically acceptable salt, co-crystal, tautomer, stereoisomer, solvate, hydrate, polymorph, isotopically enriched derivative, or prodrug, or composition thereof. In certain embodiments, the E3 ubiquitin ligase is Cereblon.

Diagnostic Methods

The pathological development of tauopathies often begin before presentation of clinical symptoms, thus in vivo imaging of aberrant and/or aggregated tau protein may be useful for the early and accurate diagnosis of neurological disease. In particular, the pathological process of AD begins before the presentation of the clinical symptoms of dementia, and in vivo imaging of aberrant tau and NFTs may be useful for the early and accurate diagnosis of AD. Quantitative evaluation of tau pathology could also be helpful for tracking and predicting severity of dementia, because the formation of neuritic pathology correlates with clinical severity of dementia. The compounds of the present disclosure recognize pathological forms of tau, which includes forms containing excessively phosphorylated tau protein as a constituent ingredient as well as aberrant high-molecular weight species formed from tau and other post-translational modifications, and thus the compounds can be used as a probe for the detection of aberrant tau relevant to neurodegeneration. Thus, imaging techniques in conjunction with novel treatments that prevent or reduce the pathological formation of neurofibrillary pathology would be useful for the evaluation of treatment efficacy.

In certain embodiments, the present disclosure relates to radiolabeled compounds of Formula I as imaging agents. These imaging agents are useful as they contain tau protein binding moieties that interact with and bind to tau protein, providing the ability to image aggregated tau protein in vivo. As the compounds of Formula I lead to the degradation of tau protein by regular administration, progression of the therapeutic effect of the compounds of Formula I may be monitored through the use of radiolabeled forms of the compounds or other known imaging agents for tau protein.

In certain embodiments, the imaging is achieved by employing a fluorescence imaging technique or a nuclear imaging technique selected from the group consisting of positron emission tomography (PET) and single photon emission computed tomography (SPECT), the fluorescence imaging technique and/or nuclear imaging technique for monitoring or visualizing a distribution of the radiolabeled or tagged compound within the central nervous system or within a portion thereof (e.g., the brain).

PET and SPECT utilize radiolabeled compounds. PET and SPECT are sensitive techniques and require small quantities of radiolabeled compounds, or tracers. The labeled compounds are transported, accumulated and converted in vivo in exactly the same way as the corresponding non-radioactively compound. Tracers, or probes, can be radiolabeled with a radionuclide useful for PET imaging, such as $^{11}C$, $^{13}N$, $^{15}O$, $^{18}F$, $^{64}Cu$ and 124, or with a radionuclide useful for SPECT imaging, such as $^{99}Tc$, $^{77}Br$, $^{61}Cu$, $^{153}Gd$, $^{123}I$, $^{125}I$, $^{131}I$ and $^{32}P$.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

The present disclosure provides methods for detecting a neurological disorder, the method comprising contacting a compound of Formula I, or a pharmaceutically acceptable salt thereof, or a pharmaceutical composition comprising a compound of Formula I, with tissue of the central nervous system. In certain embodiments, the neurological disorder is a neurodegenerative disease. In certain embodiments, the neurodegenerative disease is a tauopathy. In certain embodiments, the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the tauopathy is Alzheimer's disease.

The present disclosure provides methods for detecting pathological aggregation of tau protein in the central nervous system (e.g., brain), the method comprising contacting a compound of Formula I, or a pharmaceutically acceptable salt thereof, or a pharmaceutical composition comprising a compound of Formula I, with tissue of the central nervous system. In certain embodiments, contacting includes administration of the compound of Formula I, or a pharmaceutically acceptable salt thereof, to a subject and allowing the compound to distribute into the central nervous system.

The present disclosure also provides methods for imaging tau protein in a subject, the method comprising administering a compound of Formula I, or a pharmaceutically acceptable salt thereof, or a pharmaceutical composition comprising a compound of Formula I, to a subject. In certain embodiments, the methods comprise imaging pathological aggregation of tau protein in the central nervous system (e.g., brain).

The present disclosure also provides methods for diagnosing a neurological disorder in a subject, the method comprising contacting a compound of Formula I, or a pharmaceutically acceptable salt thereof, or a pharmaceutical composition comprising a compound of Formula I, with tissue of the central nervous system. In certain embodiments, the neurological disorder is a neurodegenerative disease. In certain embodiments, the neurodegenerative disease is a tauopathy. In certain embodiments, the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease. In certain embodiments, the tauopathy is Alzheimer's disease.

In certain embodiments, the tissue of the central nervous system is brain tissue. In certain embodiments, the compound is contacted with the tissue in vivo. In other embodiments, the compound is contacted with the tissue in vitro. In certain embodiments, the compound contacts the tissue after administration of the compound to a subject and allowing the compound to distribute into the central nervous system.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Compounds of Formula I may be prepared using the synthetic schemes and procedures described in detail below.

Preparation of Synthetic Intermediates

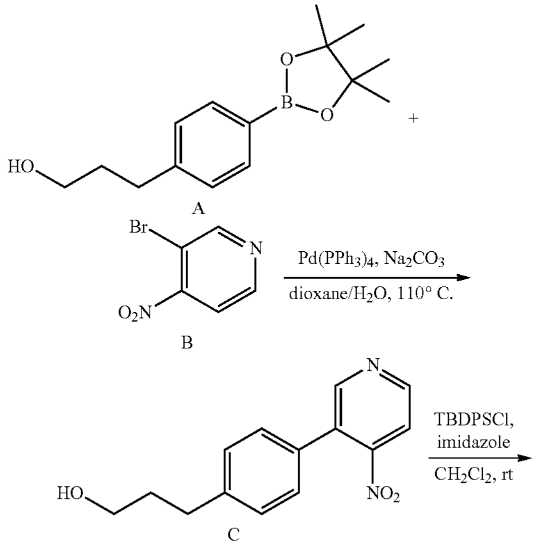

-continued

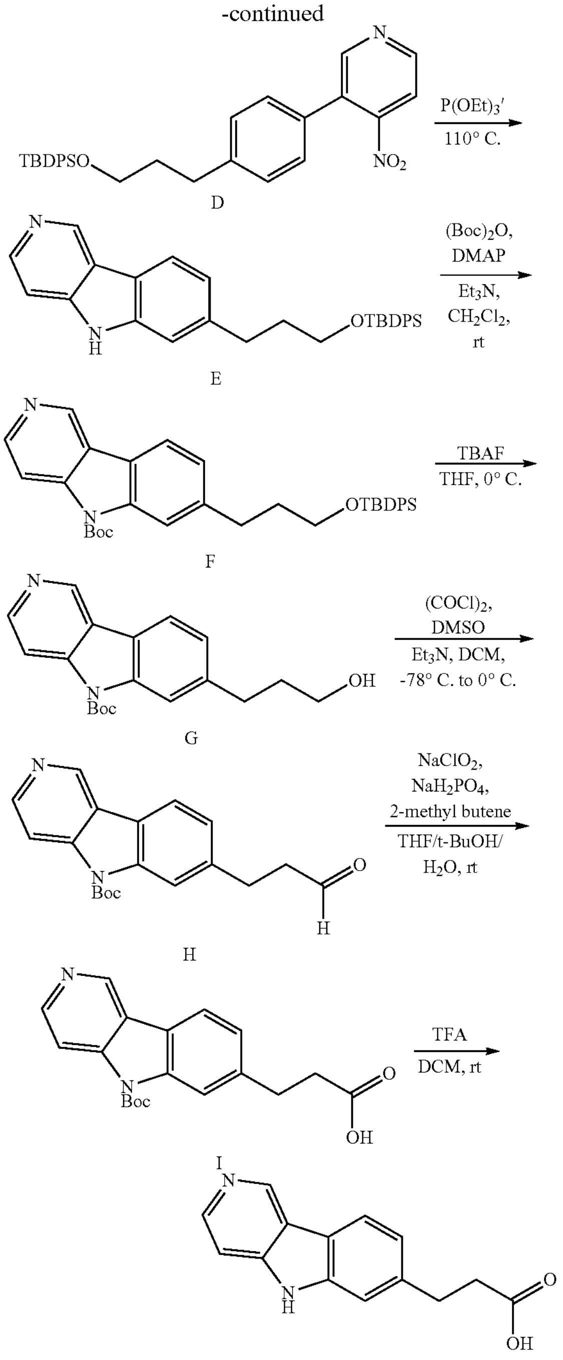

3-(4-(4-Nitropyridin-3-yl)phenyl)propan-1-ol (C): A solution of 3-(4-(4,4,5,5-tetramethyl-1,3,2-dioxaborolan-2-yl) phenyl)propan-1-ol (A) (1.65 g, 6.29 mmol), 3-bromo-4-nitropyridine (B) (1.16 g, 5.72 mmol), $Na_2CO_3$ (1.52 g, 14.3 mmol), and $Pd(PPh_3)_4$(330 mg, 0.286 mmol) in 1,4-dioxane (40 mL) and $H_2O$ (10 mL) was stirred at 110° C. for 16 h before it was quenched with $NH_4Cl$ (sat. aq., 100 mL). The resulting mixture was extracted with $CH_2Cl_2$ (3×80 mL), the combined organic phases were dried over anhydrous $Na_2SO_4$ and concentrated under reduced pressure. The residue was purified by flash column chromatography to give the title compound (950 mg, 3.68 mmol, 64% yield).

3-(4-(3-((tert-Butyldiphenylsilyl)oxy)propyl)phenyl)-4-nitropyridine (D): To a stirred solution of C (950 mg, 3.68 mmol) in $CH_2Cl_2$ (35 mL) at 25° C. was added imidazole (751 mg, 11.04 mmol) and TBDPSCI (2.01 g, 7.36 mmol). After stirring at this temperature for 3 h, the reaction was quenched with $NH_4Cl$ (sat. aq., 100 mL). The resulting mixture was extracted with $CH_2Cl_2$ (2×50 mL), the combined organic phases were washed with brine (100 mL), dried over anhydrous $Na_2SO_4$ and concentrated under reduced pressure. The residue was purified by flash column chromatography to give the title compound (1.62 g, 3.26 mmol, 89% yield).

7-(3-((tert-Butyldiphenylsilyl)oxy)propyl)-5H-pyrido[4,3-b]indole (E): A solution of D (1.62 g, 3.26 mmol) in $P(OEt)_3$ (20 mL) was stirred at 110° C. for 3 h before it was concentrated under reduced pressure. The residue was purified by flash column chromatography to give the title compound (1.32 g, 2.84 mmol, 87% yield).

tert-Butyl 7-(3-((tert-butyldiphenylsilyl)oxy)propyl)-5H-pyrido[4,3-b]indole-5-carboxylate (F): To a stirred solution of E (1.32 g, 2.84 mmol) and DMAP (213 mg, 1.75 mmol) in $CH_2Cl_2$(30 mL) at 25° C. was added $Et_3N$ (1.06 g, 10.47 mmol) and $(Boc)_2O$ (1.52 g, 6.98 mmol). After stirring at this temperature for 2 h, the reaction was quenched with $NH_4Cl$ (sat. aq., 100 mL). The resulting mixture was extracted with $CH_2Cl_2$ (2×50 mL), the combined organic phases were washed with brine (100 mL), dried over anhydrous $Na_2SO_4$ and concentrated under reduced pressure. The residue was purified by flash column chromatography to give the title compound (1.42 g, 2.52 mmol, 89% yield).

tert-Butyl 7-(3-hydroxypropyl)-5H-pyrido[4,3-b]indole-5-carboxylate (G): To a stirred solution of F (1.42 g, 2.52 mmol) in THF (25 mL) at 0° C. was added TBAF (1.0 M in THF, 3.8 mL, 3.8 mmol) dropwise. After stirring at this temperature for 2 h, the reaction was quenched with acetic acid (0.2 mL). The mixture was concentrated under reduced pressure. The residue was purified by flash column chromatography to give the title compound (670 mg, 2.05 mmol, 81% yield).

tert-butyl 7-(3-oxopropyl)-5H-pyrido[4,3-b]indole-5-carboxylate (H): To a stirred solution of DMSO (1.30 g, 16.6 mmol) in $CH_2Cl_2$ (7 mL) at −78° C. was added oxalyl chloride (783 mg, 6.16 mmol) in $CH_2Cl_2$ (6 mL) dropwise. After stirring at this temperature for 0.5 h, a solution of G (670 mg, 2.05 mmol) in $CH_2Cl_2$ (6 mL) was added dropwise. The mixture was stirred at this temperature for 2 h followed by the addition of $Et_3N$ (1.035 g, 10.25 mmol) dropwise. The reaction mixture was slowly warmed to 0° C. over 1 h, and was quenched with $NH_4Cl$ (sat. aq., 30 mL). The resulting mixture was extracted with $CH_2Cl_2$ (2×30 mL), the combined organic phases were washed with brine (100 mL), dried over anhydrous $Na_2SO_4$ and concentrated under reduced pressure to provide the title compound. The crude product of H was used in the next step without further purification.

3-(5-(tert-Butoxycarbonyl)-5H-pyrido[4,3-b]indol-7-yl) propanoic acid (I): To a stirred solution of the above residue of H in THE (10 mL), t-BuOH (5 mL) and $H_2O$ (5 mL) at 25° C. was added $NaH_2PO_4H_2O$ (2.55 g, 18.5 mmol), 2-methyl-butene (5 mL) and sodium chlorite (1.64 g, 18.5 mmol). After stirring at this temperature for 2 h, the reaction was diluted with $H_2O$ (50 mL). The resulting mixture was extracted with $CH_2Cl_2$ (2×50 mL), the combined organic phases were dried over anhydrous $Na_2SO_4$ and concentrated under reduced pressure to provide the title compound. The crude product of I was used in the next step without further purification.

3-(5H-Pyrido[4,3-b]indol-7-yl)propanoic acid (J): A solution of the crude product of I in $CH_2Cl_2$ (12 mL) and TFA (6 mL) was stirred at 25° C. for 12 h before it was concentrated under reduced pressure. The residue was dissolved in NaOH (0.5 M, aq., 20 mL) and was extracted with $CH_2Cl_2$ (4×15 mL). The water phase was added HCl (aq., 1.0 M) dropwise to adjust the pH to 6-7. The resulting mixture was extracted with $CHCl_3$/i-PrOH (4/1, 3×30 mL), the combined organic phases were dried over anhydrous $Na_2SO_4$ and concentrated under reduced pressure to afford the title compound (357 mg, 1.48 mmol, 73% yield over 3 steps).

Preparation of Exemplary Compounds

N-(6-((2-(2,6-Dioxopiperidin-3-yl)-1,3-dioxoisoindolin-4-yl)amino)hexyl)-3-(5H-pyrido[4,3-b]indol-7-yl)propanamide (1; QC-01-178))

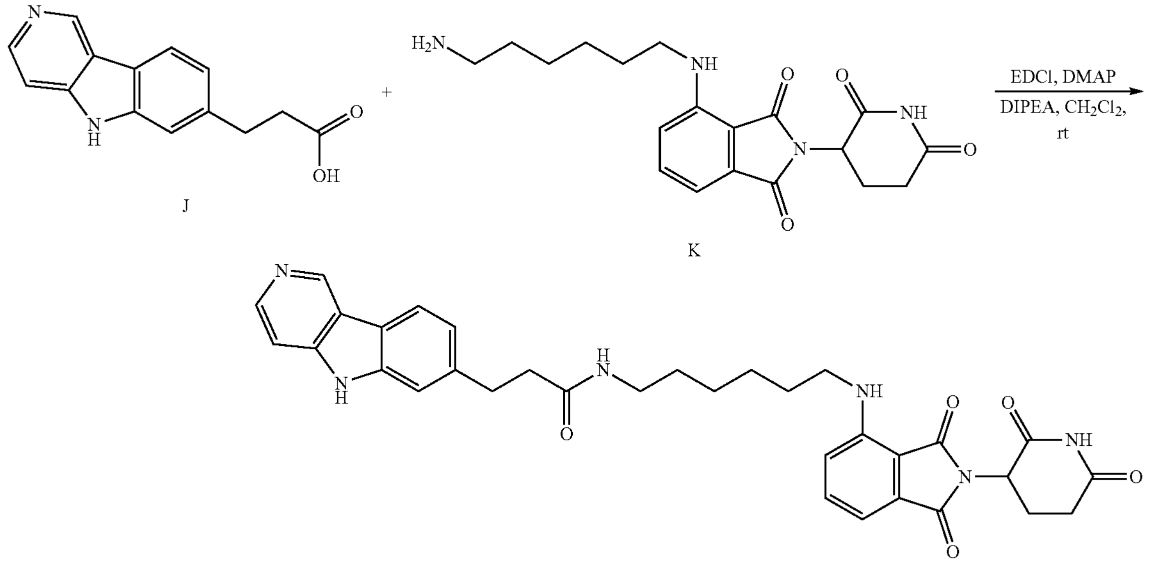

J

K 1
(QC-01-178)

N-(6-((2-(2,6-Dioxopiperidin-3-yl)-1,3-dioxoisoindolin-4-yl)amino)hexyl)-3-(5H-pyrido[4,3-b]indol-7-yl)propanamide (1): To a stirred solution of carboxylic acid J (6.8 mg, 0.02 mmol), EDCI (11.5 mg, 0.06 mmol), DMAP (2.2 mg, 0.02 mmol) and DIPEA (14.3 mg, 0.12 mmol) in $CH_2Cl_2$ (0.6 mL) at 25° C. was added 4-((6-aminohexyl)amino)-2-(2,6-dioxopiperidin-3-yl)isoindoline-1,3-dione (K) (9.7 mg, 0.26 mmol). The resulting reaction mixture was stirred at this temperature for 4 h, and then concentrated under reduced pressure. The residue was purified by reverse-phase HPLC to give the title compound as the TFA salt (9.6 mg, 0.014 mmol, 70% yield). $^1H$ NMR (500 MHz, DMSO) δ 13.03 (s, 1H), 11.10 (s, 1H), 9.68 (s, 1H), 8.61 (d, J=6.8 Hz, 1H), 8.33 (d, J=8.1 Hz, 1H), 7.96 (d, J=6.7 Hz, 1H), 7.80 (t, J=5.6 Hz, 1H), 7.59 (s, 1H), 7.57 (dd, J=8.5, 7.2 Hz, 1H), 7.36 (dd, J=8.2, 1.0 Hz, 1H), 7.03 (d, J=3.9 Hz, 1H), 7.02 (d, J=2.3 Hz, 1H), 6.46 (t, J=5.1 Hz, 1H), 5.05 (dd, J=12.8, 5.4 Hz, 1H), 3.20 (dd, J=12.4, 6.5 Hz, 2H), 3.06-3.00 (m, 4H), 2.89 (ddd, J=17.0, 13.9, 5.4 Hz, 1H), 2.66-2.52 (m, 2H), 2.48 (t, J=7.6 Hz, 2H), 2.06-2.01 (m, 1H), 1.49-1.43 (m, 2H), 1.37-1.31 (m, 2H), 1.29-1.23 (m, 2H), 1.22-1.16 (m, 2H).

Example compounds 2-7 were prepared in an analogous manner to compound 1, employing the corresponding amine starting materials and carboxylic acid J.

| | Structure/Name | Characterization |
|---|---|---|
| 2 | 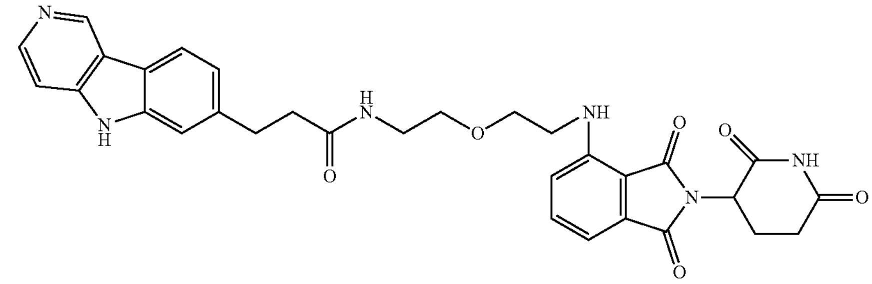 [SMILES: O=C(CCc1ccc2c(c1)[nH]c1ccncc12)NCCOCCNc1cccc2c1C(=O)N(C1CCC(=O)NC1=O)C2=O] QC-01-179 N-(2-(2-((2-(2,6-dioxopiperidin-3-yl)-1,3-dioxoisoindolin-4-yl)amino)ethoxy)ethyl)-3-(5H-pyrido[4,3-b]indol-7-yl)propanamide | $^1H$ NMR (500 MHz, DMSO) δ 13.00 (s, 1H), 11.08 (s, 1H), 9.65 (s, 1H), 8.61 (d, J = 6.8 Hz, 1H), 8.31 (d, J = 8.1 Hz, 1H), 7.95 (d, J = 6.7 Hz, 1H), 7.88 (t, J = 5.6 Hz, 1H), 7.58 (s, 1H), 7.55 (dd, J = 8.4, 7.2 Hz, 1H), 7.34 (dd, J = 8.2, 1.0 Hz, 1H), 7.06 (d, J = 8.6 Hz, 1H), 7.02 (d, J = 7.0 Hz, 1H), 6.53 (t, J = 5.6 Hz, 1H), 5.02 (dd, J = 12.9, 5.4 Hz, 1H), 3.54 (t, J = 5.4 Hz, 2H), 3.42 (t, J = 5.8 Hz, 2H), 3.39-3.36 (m, 2H), 3.23-3.19 (m, 2H), 3.04 (t, J = 7.5 Hz, 2H), 2.83 (ddd, J = 17.4, 14.1, 5.3 Hz, 1H), 2.56-2.48 (m, 4H), 2.02-1.97 (m, 1H). |

-continued

| | Structure/Name | Characterization |
|---|---|---|
| 3 | 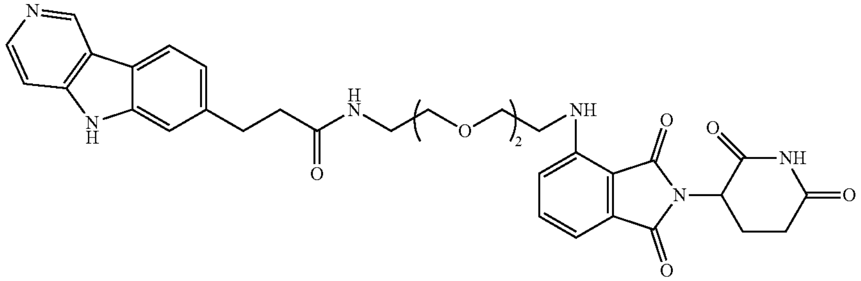<br>QC-01-175<br>N-(2-(2-(2-((2-(2,6-dioxopiperidin-3-yl)-1,3-dioxoisoindolin-4-yl)amino)ethoxy)ethoxy)ethyl)-3-(5H-pyrido[4,3-b]indol-7-yl)propanamide | $^1$H NMR (500 MHz, DMSO) δ 13.04 (s, 1H), 11.09 (s, 1H), 9.67 (s, 1H), 8.62 (d, J = 6.6 Hz, 1H), 8.31 (d, J = 8.1 Hz, 1H), 7.96 (d, J = 6.7 Hz, 1H), 7.90 (t, J = 5.6 Hz, 1H), 7.58 (s, 1H), 7.56 (dd, J = 8.3, 7.4 Hz, 1H), 7.33 (d, J = 7.4 Hz, 1H), 7.11 (d, J = 8.6 Hz, 1H), 7.01 (d, J = 7.0 Hz, 1H), 6.57 (t, J = 5.7 Hz, 1H), 5.05 (dd, J = 12.7, 5.4 Hz, 1H), 3.58 (t, J = 5.7 Hz, 2H), 3.52-3.50 (m, 2H), 3.47-3.42 (m, 6H), 3.20-3.17 (m, 2H), 3.03 (t, J = 7.6 Hz, 2H), 2.87 (ddd, J = 16.9, 13.8, 5.3 Hz, 1H), 2.60-2.55 (m, 1H), 2.54-2.47 (m, 3H), 2.01 (ddd, J = 10.0, 6.7, 4.0 Hz, 1H). |
| 4 | 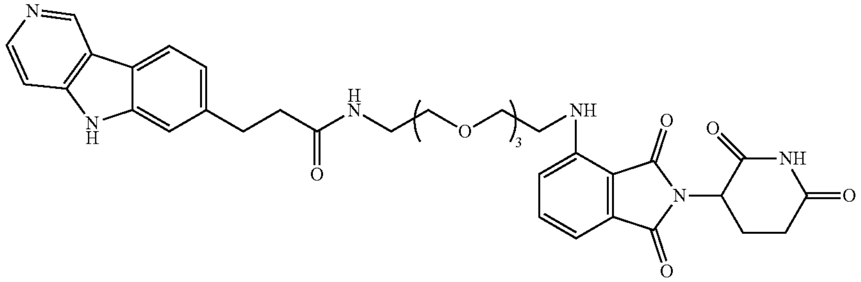<br>QC-01-208<br>N-(2-(2-(2-(2-((2-(2,6-dioxopiperidin-3-yl)-1,3-dioxoisoindolin-4-yl)amino)ethoxy)ethoxy)ethoxy)ethyl)-3-(5H-pyrido[4,3-b]indol-7-yl)propanamide | $^1$H NMR (500 MHz, DMSO) δ 13.02 (s, 1H), 11.09 (s, 1H), 9.67 (s, 1H), 8.62 (d, J = 6.7 Hz, 1H), 8.32 (d, J = 8.1 Hz, 1H), 7.96 (d, J = 6.7 Hz, 1H), 7.91 (t, J = 5.6 Hz, 1H), 7.59 (s, 1H), 7.56 (dd, J = 8.4, 7.2 Hz, 1H), 7.34 (d, J = 9.0 Hz, 1H), 7.11 (d, J = 8.6 Hz, 1H), 7.02 (d, J = 7.0 Hz, 1H), 6.57 (br s, 1H), 5.05 (dd, J = 12.8, 5.4 Hz, 1H), 3.60 (t, J = 5.4 Hz, 2H), 3.55-3.53 (m, 2H), 3.50-3.48 (m, 2H), 3.46-3.42 (m, 6H), 3.35 (t, J = 5.8 Hz, 2H), 3.19-3.16 (m, J = 5.7 Hz, 2H), 3.03 (t, J = 7.6 Hz, 2H), 2.88 (ddd, J = 17.0, 13.9, 5.4 Hz, 1H), 2.60-2.56 (m, 1H), 2.54-2.47 (m, 3H), 2.06-1.96 (m, 1H). |
| 5 | 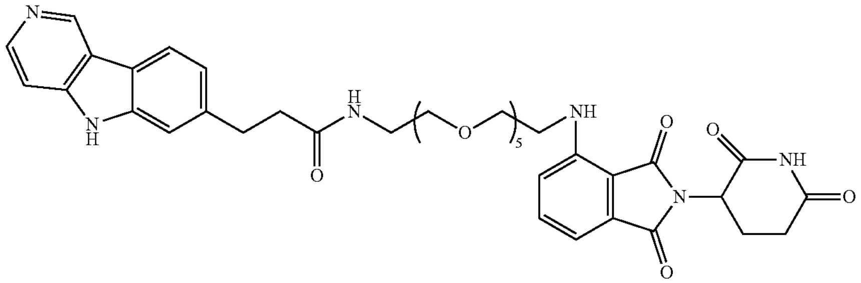<br>QC-01-176<br>N-(17-(2-((2-(2,6-dioxopiperidin-3-yl)-1,3-dioxoisoindolin-4-yl)amino)-3,6,9,12,15-pentaoxaheptadecyl)-3-(5H-pyrido[4,3-b]indol-7-yl)propanamide | $^1$H NMR (500 MHz. DMSO) δ 13.01 (s, 1H), 9.67 (s, 1H), 8.62 (d, J = 6.8 Hz, 1H), 8.32 (d, J = 8.1 Hz, 1H), 7.96 (d, J = 6.7 Hz, 1H), 7.91 (t, J = 5.6 Hz, 1H), 7.59 (s, 1H), 7.56 (dd, J = 8.5, 7.2 Hz, 1H), 7.35 (dd, J = 8.2, 1.1 Hz, 1H), 7.12 (d, J = 8.6 Hz, 1H), 7.02 (d, J = 6.9 Hz, 1H), 6.58 (t, J = 5.7 Hz, 1H), 5.05 (dd, J = 12.8, 5.4 Hz, 1H), 3.60 (t, J = 5.5 Hz, 2H), 3.56-3.54 (m, 2H), 3.52-3.37 (m, 16H), 3.35 (t, J = 5.9 Hz, 3H), 3.20-3.16 (m, 2H), 3.04 (t, J = 7.6 Hz, 2H), 2.91-2.84 (m, 1H), 2.60-2.60 (m, 1H), 2.53-2.47 (m, 3H), 2.04-2.00 (m, 1H). |
| 6 | 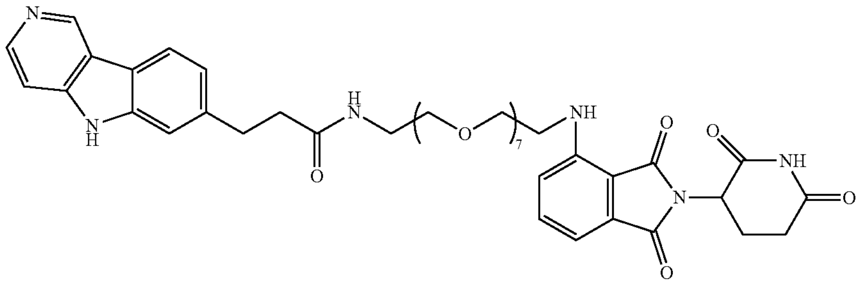<br>QC-02-001<br>N-(23-(2-((2-(2,6-dioxopiperidin-3-yl)-1,3-dioxoisoindolin-4-yl)amino)-3,6,9,12,15,18,21-heptaoxatricosyl)-3-(5H-pyrido[4,3-b]indol-7-yl)propanamide | $^1$H NMR (500 MHz, DMSO) δ 13.03 (s, 1H), 11.09 (s, 1H), 9.67 (s, 1H), 8.62 (d, J = 6.8 Hz, 1H), 8.32 (d, J = 8.1 Hz, 1H), 7.97 (d, J = 6.7 Hz, 1H), 7.92 (t, J = 5.6 Hz, 1H), 7.59 (s, 1H), 7.57 (dd, J = 9.5, 8.2 Hz, 1H), 7.35 (dd, J = 8.2, 1.1 Hz, 1H), 7.13 (d, J = 8.6 Hz, 1H), 7.03 (d, J = 7.0 Hz, 1H), 6.59 (t, J = 5.6 Hz, 1H), 5.05 (dd, J = 12.8, 5.4 Hz, 1H), 3.61 (t, J = 5.4 Hz, 2H), 3.56-3.54 (m, 2H), 3.52-3.43 (m, 20H), 3.35 (t, J = 5.8 Hz, 2H), 3.20-3.16 (m, 1H), 3.04 (t, J = 7.6 Hz, 1H), 2.88 (ddd, J = 16.9, 13.8, 5.4 Hz, 1H), 2.60-2.56 (m, 1H), 2.54-2.47 (m, 3H), 2.04-1.99 (m, 1H). |

-continued

| | Structure/Name | Characterization |
|---|---|---|
| 7 | 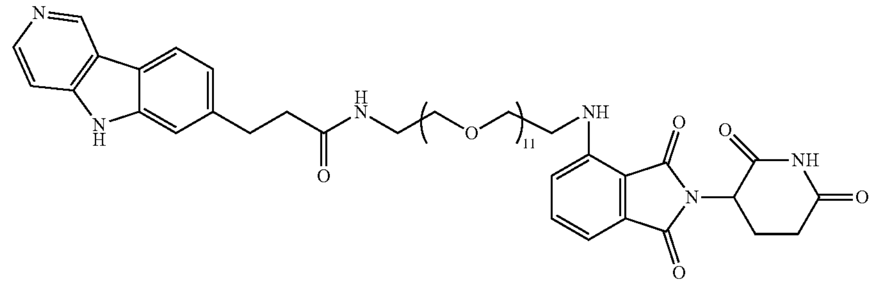 QC-02-004 N-(35-(2-((2-(2,6-dioxopiperidin-3-yl)-1,3-dioxoisoindolin-4-yl)amino)-3,6,9,12,15,18,21,24,27,30,33-undecaoxapentatriacontyl)-3-(5H-pyrido[4,3-b]indol-7-yl)propanamide | $^1$H NMR (500 MHz, DMSO) δ 13.02 (s, 1H), 11.09 (s, 1H), 9.68 (s, 1H), 8.62 (d, J = 6.7 Hz, 1H), 8.32 (d, J = 8.1 Hz, 1H), 7.97 (d, J = 6.7 Hz, 1H), 7.92 (t, J = 5.6 Hz, 1H), 7.59 (s, 1H), 7.57 (dd, J = 8.6, 7.3 Hz, 1H), 7.35 (d, J = 8.1 Hz, 1H), 7.13 (d, J = 8.6 Hz, 1H), 7.03 (d, J = 7.0 Hz, 1H), 6.59 (br s, 1H), 5.05 (dd, J = 12.8, 5.4 Hz, 1H), 3.61 (t, J = 5.4 Hz, 2H), 3.57-3.55 (m, 2H), 3.53-3.43 (m, 36H), 3.35 (t, J = 5.8 Hz, 2H), 3.18 (q, J = 5.7 Hz, 2H), 3.04 (t, J = 7.6 Hz, 2H), 2.88 (ddd, J = 16.9, 13.8, 5.4 Hz, 1H), 2.60-2.56 (m, 1H), 2.52 (dd, J = 18.3, 13.8 Hz, 3H), 2.04-2.00 (m, 1H). |

(2S,4R)-1-[(2S)-3,3-Dimethyl-2-(3-{2-[2-(3-{5H-pyrido[4,3-b]indol-7-yl}propanamido)ethoxy]ethoxy}propanamido)butanoyl]-4-hydroxy-N-[(1S)-1-[4-(4-methyl-1,3-thiazol-5-yl)phenyl]ethyl]pyrrolidine-2-carboxamide (8; FMF-05

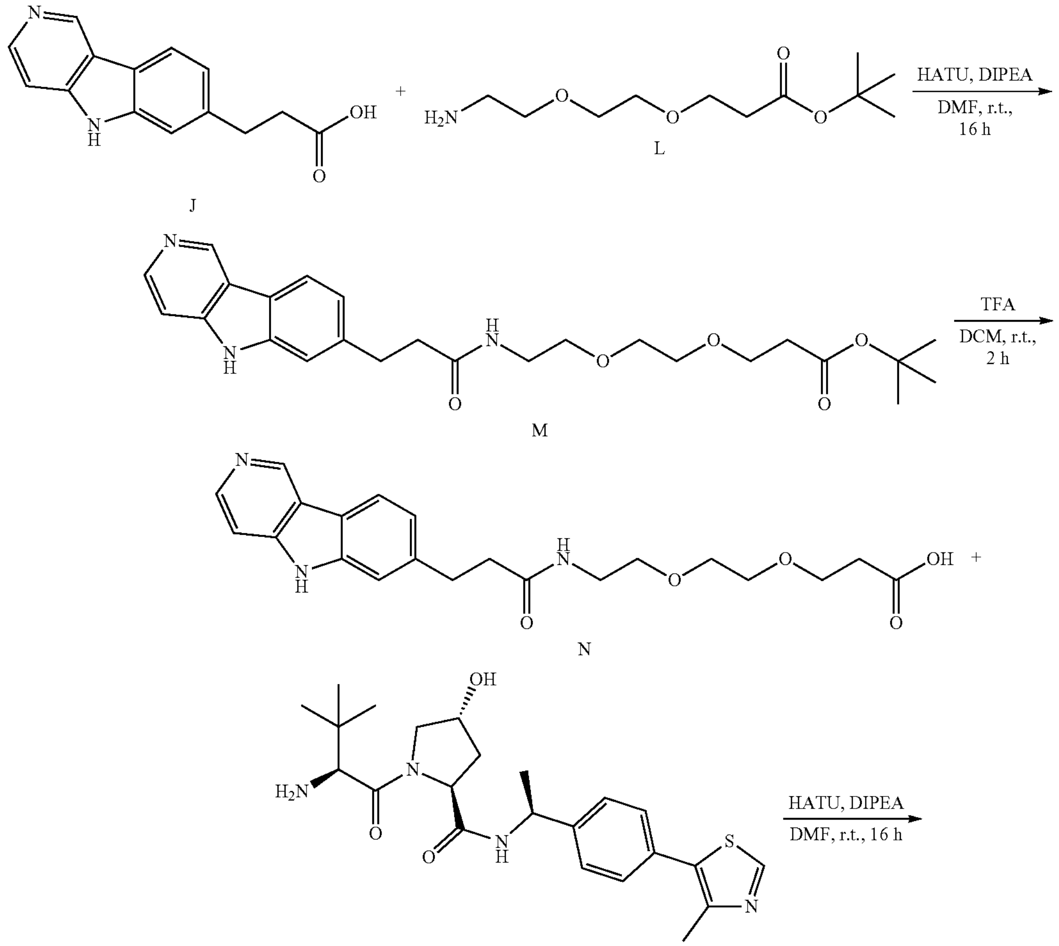

J L M N O

-continued

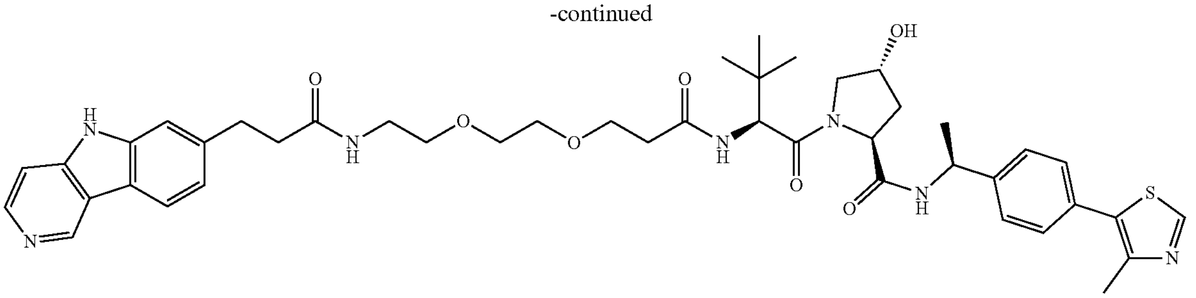

8
(FMF-05-129-1)

(M): To a stirred solution of carboxylic acid 10 (30 mg, 0.125 mmol), HATU (53 mg, 1.38 mmol) and DIPEA (70 µL, 0.375 mmol) in DMF (5 mL) at 25° C. was added the corresponding primary amine (33 mg, 0.138 mmol). The reaction mixture was stirred for 16 h, diluted with 0.1 N aqueous NaOH (15 mL) and extracted with $CH_2Cl_2$ (3×20 mL). The combined organic phases were dried over anhydrous $Na_2SO_4$ and concentrated under reduced pressure. The residue was purified by flash column chromatography (0-5% MeOH in DCM) to give compound M (18 mg, 0.040 mmol, 32% yield). MS (ESI) m/z 456 $(M+H)^+$ (N): A solution of M (18 mg, 0.04 mmol) in $CH_2Cl_2$(2 mL) and TFA (1 mL) was stirred at 25° C. for 12 h before it was concentrated under reduced pressure to give compound N (20 mg, 0.04 mmol, quant. yield). MS (ESI) m/z 400 $(M+H)^+$ (2S,4R)-1-[(2S)-3,3-Dimethyl-2-(3-{2-[2-(3-{5H-pyrido[4,3-b]indol-7-yl}propanamido)ethoxy]ethoxy}propanamido)butanoyl]-4-hydroxy-N-[(1S)-1-[4-(4-methyl-1,3-thiazol-5-yl)phenyl]ethyl]pyrrolidine-2-carboxamide (8): Compound O (25 mg, 0.06 mmol) was added to a stirred solution of carboxylic acid N (20 mg, 0.04 mmol), HATU (27 mg, 0.07 mmol) and DIPEA (35 µL, 0.18 mmol) in DMF (2 mL) at 25° C. The reaction mixture was stirred for 16 h, diluted with saturated aqueous $NaHCO_3$ (15 mL) and extracted with $CH_2Cl_2$(3×20 mL). The combined organic phases were dried over anhydrous $Na_2SO_4$ and concentrated under reduced pressure. The residue was purified by reverse-phase HPLC to give compound 8 (FMF-05-129-1) (10 mg, 0.01 mmol, 25% yield). $^1$H NMR (500 MHz, DMSO-$d_6$) δ 9.67 (s, 1H), 8.99 (s, 1H), 8.82 (d, J=6.1 Hz, 1H), 8.37 (dd, J=9.9, 7.9 Hz, 2H), 7.97 (t, J=5.6 Hz, 1H), 7.86 (d, J=9.3 Hz, 1H), 7.75 (d, J=6.1 Hz, 1H), 7.49 (dd, J=8.1, 1.3 Hz, 1H), 7.44 (dd, J=8.2, 1.7 Hz, 3H), 7.40-7.37 (m, 3H), 4.91 (h, J=7.0 Hz, 1H), 4.50 (dd, J=26.0, 9.0 Hz, 1H), 4.43 (t, J=8.1 Hz, 1H), 4.36-4.25 (m, 2H), 3.66-3.56 (m, 3H), 3.54 (s, 6H), 3.51-3.35 (m, 6H), 3.21 (q, J=5.8 Hz, 2H), 3.09 (t, J=7.6 Hz, 2H), 2.82 (s, 5H), 2.59-2.52 (m, 2H), 2.46 (s, 4H), 2.34 (dt, J=14.8, 6.2 Hz, 1H), 2.19-1.97 (m, 1H), 1.76 (dddd, J=38.8, 13.3, 8.9, 4.4 Hz, 1H), 1.38 (d, J=7.0 Hz, 4H), 1.07 (s, 4H), 0.93 (d, J=5.1 Hz, 9H). MS (ESI) m/z 827 $(M+H)^+$ Example compounds 9-14 were prepared in an analogous manner to compound 8, employing the corresponding amine starting materials and carboxylic acid J.

| | Structure/Name | Characterization |
|---|---|---|
| 9 | 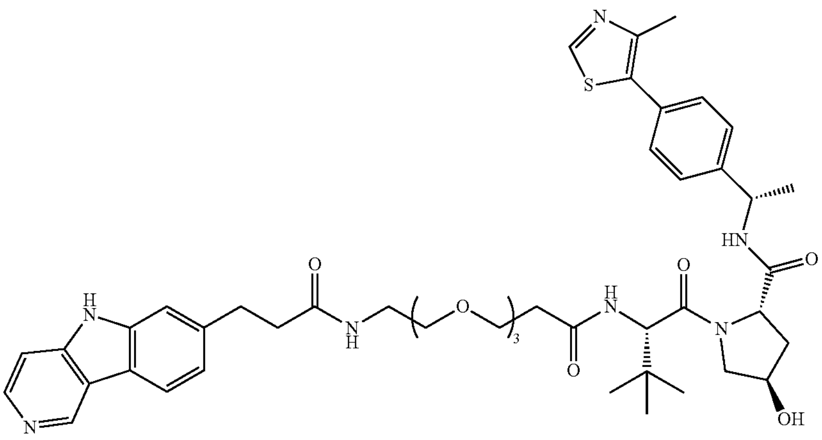 FMF-05-129-2 (2S,4R)-1-[(2S)-3,3-dimethyl-2-[3-(2-{2-[2-(3-{5H-pyrido[4,3-b]indol-7-yl}propanamido)ethoxy]ethoxy}ethoxy)propanamido]butanoyl]-4-hydroxy-N [(1S)-1-[4-(4-methyl-1,3-thiazol-5-yl)phenyl]ethyl]pyrrolidine-2-carboxamide | $^1$H NMR (500 MHz, DMSO-$d_6$) δ 13.02 (s, 1H), 9.69 (s, 1H), 8.99 (s, 1H), 8.63 (d, J = 6.8 Hz, 1H), 8.36 (dd, J = 20.7, 7.9 Hz, 2H), 7.98 (d, J = 6.7 Hz, 1H), 7.93 (t, J = 5.6 Hz, 1H), 7.86 (d, J = 9.3 Hz, 1H), 7.60 (s, 1H), 7.47-7.41 (m, 2H), 7.41-7.30 (m, 3H), 4.92 (p, J = 7.0 Hz, 1H), 4.53 (d, J = 9.3 Hz, 1H), 4.43 (t, J = 8.1 Hz, 1H), 4.29 (d, J = 4.4 Hz, 1H), 3.59 (dddd, J = 18.5, 15.9, 7.8, 5.3 Hz, 4H), 3.51-3.38 (m, 8H), 3.37 (t, J = 5.9 Hz, 2H), 3.25-3.14 (m, 2H), 3.05 (t, J = 7.6 Hz, 2H), 2.46 (s, 3H), 2.35 (dt, J = 14.7, 6.1 Hz, 1H), 2.06-1.97 (m, 1H), 1.80 (ddd, J = 12.9, 8.5, 4.6 Hz, 1H), 1.37 (d, J = 7.0 Hz, 3H), 0.93 (d, J = 5.1 Hz, 9H). MS (ESI) m/z 871 $(M + H)^+$ |

-continued

| | Structure/Name | Characterization |
|---|---|---|
| 10 | 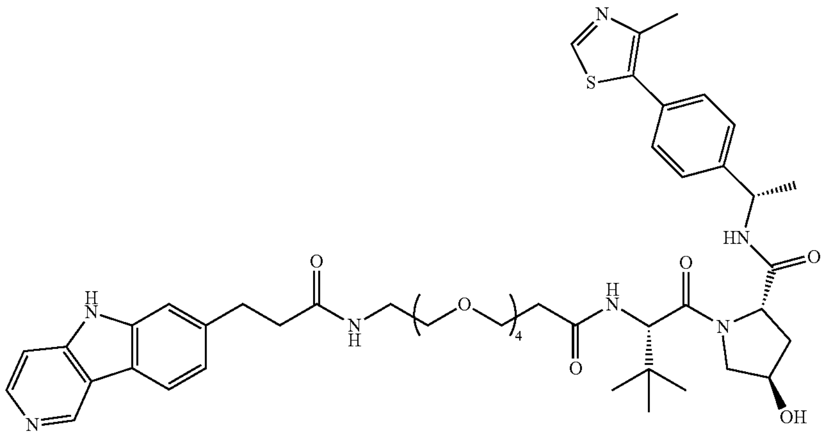 FMF-05-129-3 (2S,4R)-1-[(2S)-3,3-dimethyl-2-[1-(3-{5H-pyrido[4,3-b]indol-7-yl}propanamido)-3,6,9,12-tetraoxapentadecan-15-amido]butanoyl]-4-hydroxy-N-[(1S)-1-[4-(4-methyl-1,3-thiazol-5-yl)phenyl]ethyl]pyrrolidine-2-carboxamide | $^1$H NMR (500 MHz, DMSO-$d_6$) δ 13.04 (s, 1H), 9.69 (s, 1H), 8.99 (s, 1H), 8.68-8.56 (m, 1H), 8.36 (dd, J = 21.4, 7.9 Hz, 2H), 7.98 (d, J = 6.8 Hz, 1H), 7.95-7.80 (m, 2H), 7.65-7.55 (m, 1H), 7.48-7.30 (m, 5H), 4.92 (p, J = 7.0 Hz, 1H), 4.53 (d, J = 9.4 Hz, 1H), 4.43 (t, J = 8.1 Hz, 1H), 4.28 (s, 1H), 3.65-3.55 (m, 4H), 3.55-3.41 (m, 14H), 3.41-3.31 (m, 2H), 3.19 (qd, J = 5.7, 2.1 Hz, 2H), 3.05 (t, J = 7.6 Hz, 2H), 2.95 (s, 3H), 2.79 (s, 3H), 2.46 (d, J = 2.8 Hz, 3H), 2.38-2.26 (m, 1H), 2.02 (td, J = 9.5, 8.2, 4.5 Hz, 1H), 1.96 (s, 3H), 1.80 (ddd, J = 12.9, 8.5, 4.6 Hz, 1H), 1.47 (s, 1H), 1.43-1.32 (m, 3H), 0.94 (s, 9H). MS (ESI) m/z 915 $(M + H)^+$ |
| 11 | 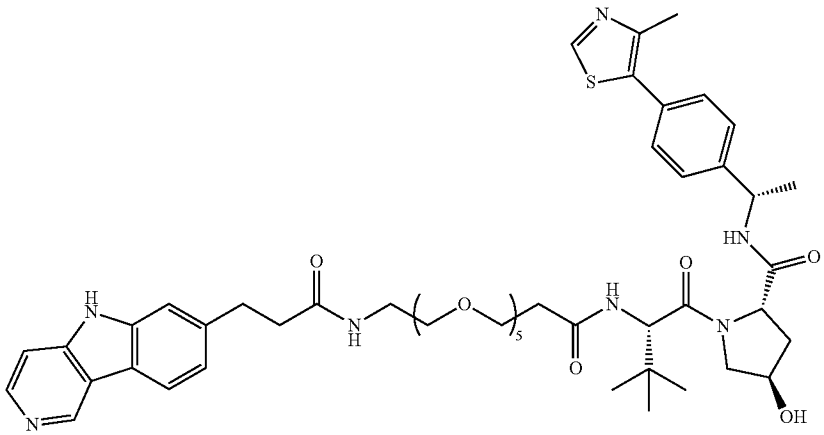 FMF-05-129-4 (2S,4R)-1-[(2S)-3,3-dimethyl-2-[1-(3-{5H-pyrido[4,3 b]indol-7-yl}propanamido)-3,6,9,12,15,18-hexaoxahenicosan-21-amido]butanoyl]-4-hydroxy-N-[(1S)-1-[4-(4-methyl-1,3-thiazol-5-yl)phenyl]ethyl]pyrrolidine-2 -carboxamide | $^1$H NMR (500 MHz, DMSO-$d_6$) δ 9.80 (s, 1H), 9.00 (d, J = 1.3 Hz, 1H), 8.90 (d, J = 6.3 Hz, 1H), 8.47 (d, J = 7.6 Hz, 1H), 8.39 (dd, J = 15.6, 7.9 Hz, 2H), 7.97 (t, J = 5.7 Hz, 1H), 7.88 (dd, J = 20.7, 7.8 Hz, 2H), 7.53 (dd, J = 8.1, 1.3 Hz, 1H), 7.45-7.43 (m, 4H), 7.39-7.35 (m, 3H), 6.96 (d, J = 6.0 Hz, 1H), 4.97-4.84 (m, 2H), 4.57-4.39 (m, 3H), 4.37-4.25 (m, 2H), 4.19 (d, J = 6.1 Hz, 1H), 3.86 (d, J = 11.4 Hz, 1H), 3.61 (ddt, J = 14.1, 11.1, 2.7 Hz, 3H), 3.55 (s, 6H), 3.52-3.46 (m, 15H), 3.43-3.37 (m, 2H), 3.26-3.19 (m, 2H), 3.10 (t, J = 7.6 Hz, 2H), 2.83 (s, 6H), 2.59-2.52 (m, 2H), 2.46 (s, 5H), 2.35 (dt, J = 14.6, 6.1 Hz, 1H), 2.15 (dd, J = 13.1, 8.0 Hz, 1H), 2.02 (ddd, J = 12.2, 8.2, 2.2 Hz, 1H), 1.76 (dddd, J = 38.8, 13.2, 8.9, 4.4 Hz, 1H), 1.38 (dd, J = 7.0, 1.7 Hz, 5H), 1.07 (s, 5H), 0.93 (d, J = 6.0 Hz, 9H). MS (ESI) m/z 959 $(M + H)^+$ |
| 12 | 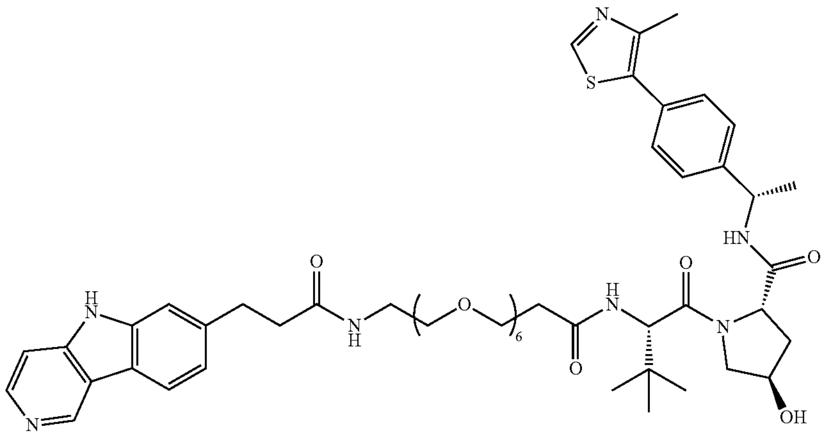 | $^1$H NMR (500 MHz, DMSO-$d_6$) δ 11.11 (s, 1H), 9.81 (s, 1H), 9.00 (d, J = 3.3 Hz, 1H), 8.91-8.85 (m, 1H), 8.40 (dd, J = 14.9, 7.9 Hz, 2H), 8.01 (t, J = 5.6 Hz, 1H), 7.88 (dd, J = 20.0, 7.8 Hz, 2H), 7.55-7.46 (m, 1H), 7.45-7.42 (m, 2H), 7.39 (dq, J = 8.7, 2.2 Hz, 2H), 4.96-4.87 (m, 1H), 4.56-4.46 (m, 1H), 4.43 (t, J = 8.0 Hz, 1H), 4.30-4.23 (m, 1H), 3.55 (s, 5H), 3.52-3.42 (m, 14H), 3.38 (t, J = 5.8 Hz, 1H), 3.21 (d, J = 5.0 Hz, 2H), 3.15 (d, J = 20.9 Hz, 2H), 3.10 (t, J = 7.6 Hz, 1H), 2.83 (s, 5H), 2.46 (s, 3H), 1.41-1.34 (m, 4H), 1.00 (s, 3H), 0.94 (s, 9H). MS (ESI) m/z 1003 $(M + H)^+$ |

-continued

| | Structure/Name | Characterization |
|---|---|---|
| | FMF-05-129-5<br>(2S,4R)-1-[(2S)-3,3-dimethyl-2-[1-(3-{5H-pyrido[4,3-b]indol-7-yl}propanamido)-3,6,9,12,15,18-hexaoxahenicosan-21-amido]butanoyl]-4-hydroxy-N-[(1S)-1-[4-(4-methyl-1,3-thiazol-5-yl)phenyl]ethyl]pyrrolidine-2-carboxamide | |
| 13 | 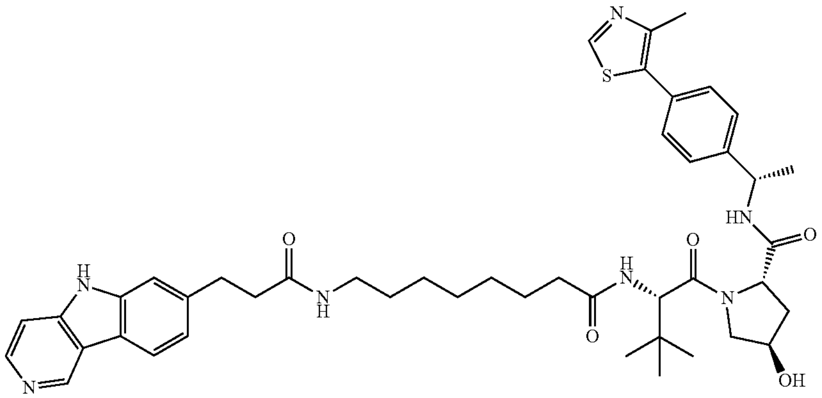 [SMILES: Cc1ncsc1-c1ccc([C@H](C)NC(=O)[C@@H]2C[C@@H](O)CN2C(=O)[C@@H](NC(=O)CCCCCCCNC(=O)CCc2ccc3c(c2)[nH]c2ccncc23)C(C)(C)C)cc1]<br>FMF-06-066-1<br>(2S,4R)-1-((S)-2-(8-(3-(5H-pyrido[4,3-b]indol-7-yl)propanamido)octanamido)-3,3-dimethylbutanoyl)-4-hydroxy-N-((S)-1-(4-(4-methylthiazol-5-yl)phenyl)ethyl)pyrrolidine-2-carboxamide | $^1$H NMR (500 MHz, DMSO-$d_6$) δ 13.05 (s, 1H), 9.69 (s, 1H), 8.99 (s, 1H), 8.63 (d, J = 6.8 Hz, 1H), 8.37 (d, J = 7.7 Hz, 1H), 8.33 (d, J = 8.1 Hz, 1H), 7.97 (d, J = 6.7 Hz, 1H), 7.84-7.74 (m, 2H), 7.59 (s, 1H), 7.45-7.42 (m, 2H), 7.40-7.36 (m, 3H), 4.92 (p, J = 7.2 Hz, 1H), 4.51 (d, J = 9.3 Hz, 1H), 4.43 (t, J = 8.0 Hz, 1H), 4.29 (s, 1H), 4.07-3.96 (m, 2H), 3.07-2.98 (m, 5H), 2.55 (s, 1H), 2.46 (d, J = 2.3 Hz, 4H), 2.25-2.16 (m, 1H), 2.10-1.95 (m, 3H), 1.80 (ddd, J = 12.8, 8.5, 4.6 Hz, 1H), 1.38 (dd, J = 6.8, 3.8 Hz, 5H), 1.24 (s, 3H), 1.08-0.97 (m, 3H), 0.93 (s, 9H). MS (ESI) m/z 809 (M + H)$^+$ |
| 14 | 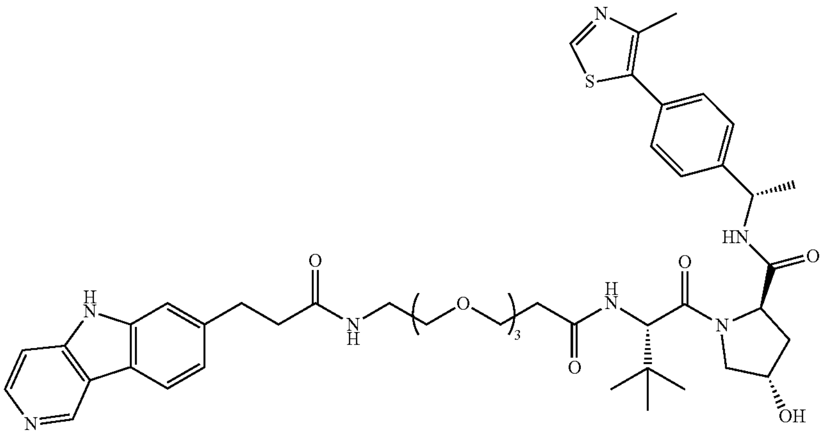<br>FMF-06-064-1<br>(2R,4S)-1-((S)-2-(tert-butyl)-4,17-dioxo-19-(5H-pyrido[4,3-b]indol-7-yl)-7,10,13-trioxa-3,16-diazanonadecanoyl)-4-hydroxy-N-((S)-1-(4-(4-methylthiazol-5-yl)phenyl)ethyl)pyrrolidine-2-carboxamide | $^1$H NMR (500 MHz, DMSO-$d_6$) δ 13.07 (s, 1H), 9.68 (s, 1H), 8.99 (d, J = 6.4 Hz, 2H), 8.62 (d, J = 6.8 Hz, 1H), 8.33 (d, J = 8.2 Hz, 1H), 8.07 (d, J = 7.9 Hz, 1H), 7.99-7.96 (m, 2H), 7.59 (s, 1H), 7.44 (d, J = 3.5 Hz, 4H), 7.38-7.33 (m, 1H), 4.92 (dt, J = 14.5, 7.1 Hz, 2H), 4.45-4.27 (m, 4H), 3.38-3.31 (m, 2H), 3.04 (t, J = 7.8 Hz, 2H), 2.79 (s, 2H), 2.47-2.43 (m, 5H), 2.29 (dt, J = 13.4, 6.2 Hz, 2H), 2.11-1.86 (m, 4H), 1.31 (d, J = 7.2 Hz, 3H), 1.24 (s, 3H), 1.10 (t, J = 7.0 Hz, 1H), 1.00 (d, J = 2.1 Hz, 5H), 0.96 (d, J = 3.1 Hz, 9H). MS (ESI) m/z 871 (M + H)$^+$ |

2-{[2-(2,6-dioxopiperidin-3-yl)-1,3-dioxo-2,3-dihydro-1H-isoindol-4-yl]oxy}-N-{2-[2-(2-{2-[(5-{5H-pyrido[4,3-b]indol-7-yl}pyridin-2-yl)oxy]acetamido}ethoxy)ethoxy]ethyl}acetamide (15; FMF-05-183-1)
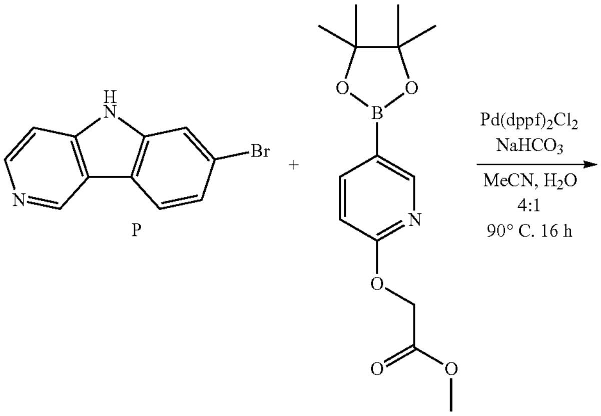
P Q
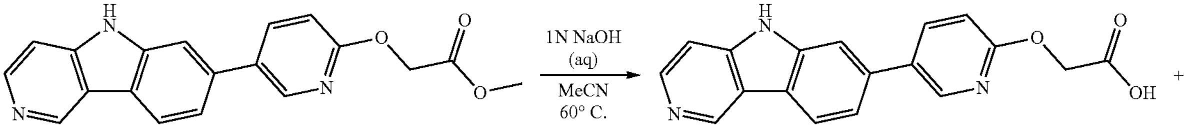
R S
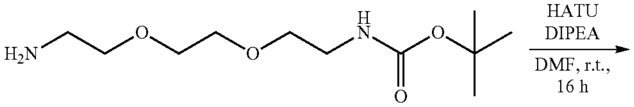
T
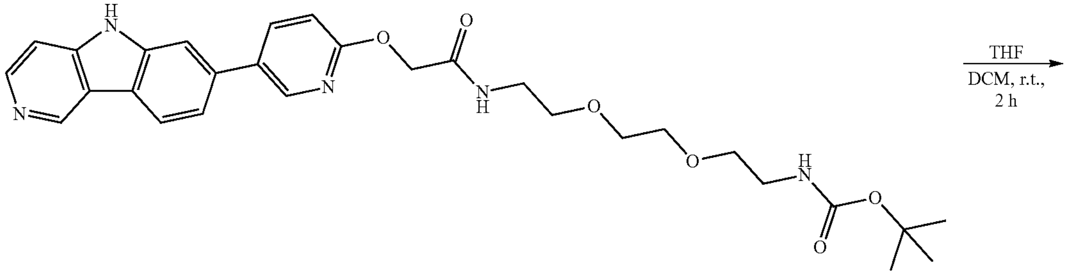
U -continued

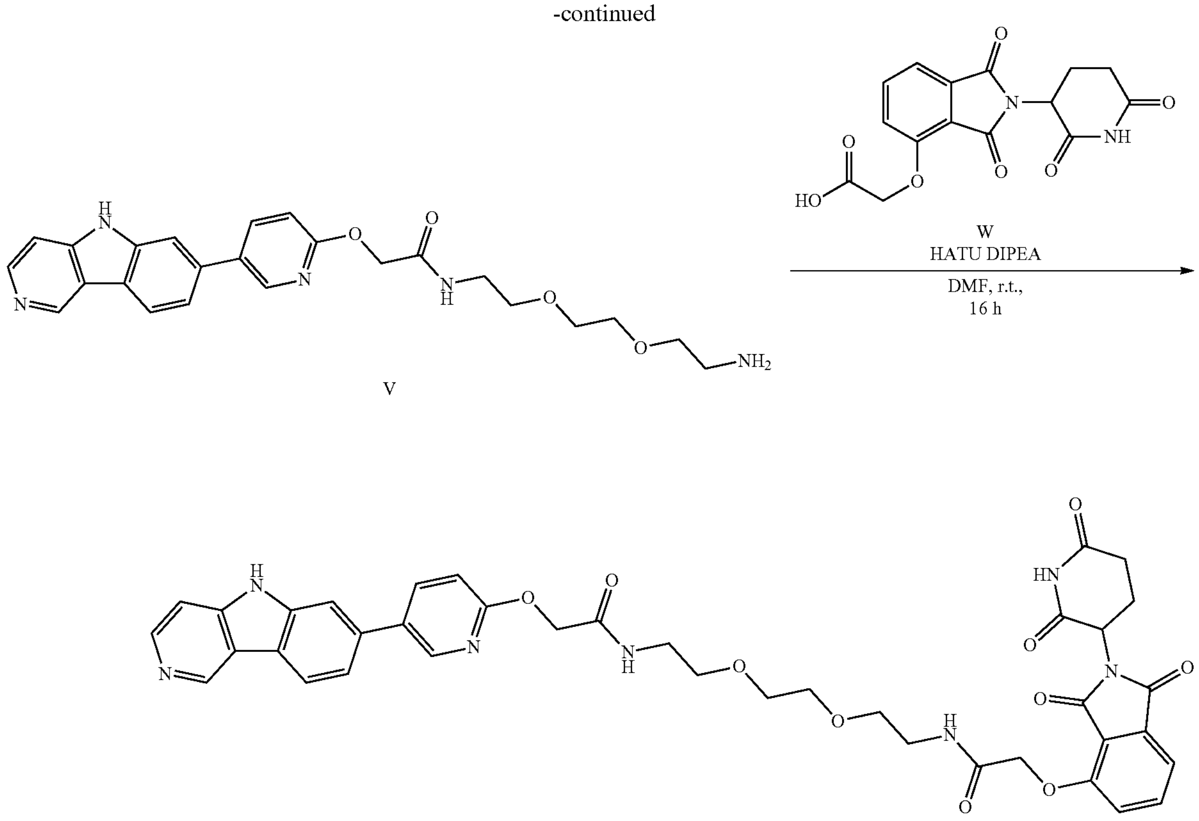

15
(FMF-05-183-1)

(R): Compound P (500 mg, 2.02 mmol), compound Q (655 mg, 2.23 mmol), $NaHCO_3$ (510 mg, 6.06 mmol), and $Pd(dppf)_2Cl_2$ (70 mg) in MeCN and $H_2O$ (4:1, 10 mL) were stirred at 90° C. for 30 min. The reaction mixture was cooled to r.t., diluted with $H_2O$ (50 mL), and extracted with DCM (3×100 mL). The organics were combined and concentrated in vacuo. The resulting solid was washed with cold DCM (3 mL) to afford compound R as a white powder, which was used without further purification (340 mg, 1.02 mmol, 51%). MS (ESI) m/z 334 $(M+H)^+$ (S): Compound R (340 mg, 1.02 mmol) was dissolved in MeCN (1 mL) and 1 N aqueous NaOH (1 mL), and stirred at 60° C. for 16 h. The reaction mixture was cooled to 0° C. and acidified to pH 5 with conc. HCl (36%). The resulting precipitate was filtered off to afford the compound S as a white solid which was used without further purification. (309 mg, 0.97 mmol, 95%). $^1H$ NMR (500 MHz, DMSO-$d_6$) δ 9.58 (s, 1H), 8.62 (d, J=4.3 Hz, 1H), 8.55 (d, J=2.4 Hz, 1H), 8.42 (d, J=8.2 Hz, 2H), 8.16 (dd, J=8.8, 2.6 Hz, 1H), 7.89 (s, 1H), 7.75 (d, J=6.1 Hz, 1H), 7.66 (d, J=8.3 Hz, 1H), 7.41 (dd, J=8.4, 4.3 Hz, 1H), 7.03 (d, J=8.6 Hz, 1H), 4.89 (s, 2H). MS (ESI) m/z 320 $(M+H)^+$ (U): Compound S (50 mg, 0.15 mmol), compound T (42 mg, 0.17 mmol), HATU (72 mg, 0.19 mmol), DIPEA (61 uL, 0.47 mmol), and DMF (3 mL) were stirred at 60° C. for 30 mins, cooled to r.t. and stirred for 16 h. The reaction mixture was diluted with sat. aq. $NaHCO_3$ (30 mL) and extracted with DCM (3×50 mL). The combined organic phases were dried over anhydrous $Na_2SO_4$ and concentrated under reduced pressure. The residue was purified by flash column chromatography (0-15% MeOH in DCM) to afford compound U (36 mg, 0.065 mmol, 44%). $^1H$ NMR (500 MHz, Methanol-$d_4$) δ 9.20 (s, 1H), 8.43 (d, J=2.5 Hz, 1H), 8.37 (d, J=5.8 Hz, 1H), 8.20 (d, J=8.2 Hz, 1H), 8.03 (dd, J=8.6, 2.6 Hz, 1H), 7.67 (d, J=1.4 Hz, 1H), 7.50-7.45 (m, 2H), 7.02 (d, J=8.6 Hz, 1H), 3.58 (dd, J=6.6, 4.4 Hz, 6H), 3.48 (q, J=5.4 Hz, 4H), 3.37 (s, 2H), 3.33 (p, J=1.7 Hz, 1H), 3.21 (t, J=5.8 Hz, 2H), 1.42 (s, 9H). MS (ESI) m/z 550 $(M+H)^+$ (V): Compound U (41 mg, 0.07 mmol), TFA (1 mL) and DCM (1 mL) were stirred at r.t. for 2 h. The reaction mixture was concentrated under reduced pressure to afford compound V as a TFA salt (42 mg, 0.07 mmol) which was used without further purification. MS (ESI) m/z 450 $(M+H)^+$ 2-{[2-(2,6-dioxopiperidin-3-yl)-1,3-dioxo-2,3-dihydro-1H-isoindol-4-yl]oxy}-N-{2-[2-(2-{2-[(5-{5H-pyrido[4,3-b]indol-7-yl}pyridin-2-yl)oxy]acetamido}ethoxy)ethoxy]ethyl}acetamide: Compound V (42 mg, 0.07 mmol), compound W (27 mg, 0.08 mmol), HATU (32 mg, 0.08 mmol), and DIPEA (40 uL, 0.21 mmol) were stirred in DMF (1 mL) at r.t. for 16 h. The reaction mixture was filtered and purified by HPLC to afford compound 15 (FMF-05-183-1) as a TFA salt (35 mg, 0.04, 54%). $^1H$ NMR (500 MHz, DMSO-$d_6$) δ 13.24 (s, 1H), 11.12 (s, 1H), 9.76 (s, 1H), 8.67 (d, J=6.7 Hz, 1H), 8.59 (d,J=2.6 Hz, 1H), 8.52 (d, J=8.2 Hz, 1H), 8.21 (dd, J=8.6, 2.6 Hz, 1H), 8.09 (t, JP=5.7 Hz, 1H), 8.04-7.99 (m, 3H), 7.81-17.77 (m, 211), 7.47 (d, J=7.2 Hz, 1H), 7.38 (d, J=8.5 Hz, 1H), 7.07 (d, J=8.6 Hz, 1)), 5.11 (dd, J 12.8, 5.5 Hz, 1H), 4.79 (d, J 11.1 Hz, 4H), 3.52 (s, 41), 3.46 (dt, J=7.9, 5.8 Hz, 4H), 3.30 (dq, J=17.7, 5.8 Hz, 4H), 2.94-2.83 (m, 1H), 2.62-2.56 (m, 1H), 2.04 (dtd, J=13.0, 5.4, 2.3 Hz, 1H), 1.30-1.16 (m, 1H). MS (ESI) m/z 765 $(M+H)^+$ Example Compounds 16-18 were Prepared in an Analogous Manner to Compound 15, Employing the Corresponding Amine Starting Materials and Carboxylic Acid S

| | Structure/Name | Characterization |
| --- | --- | --- |
| 16 | 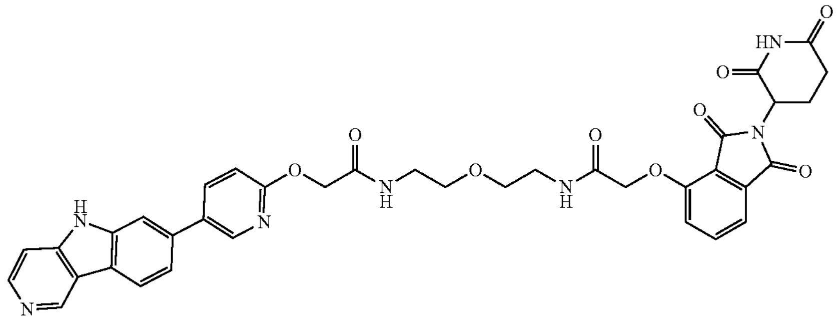 [SMILES: O=C(COc1ccc(-c2ccc3c(c2)[nH]c2ccncc23)cn1)NCCOCCNC(=O)COc1cccc2c1C(=O)N(C1CCC(=O)NC1=O)C2=O] FMF-05-182-1 2-{[2-(2,6-dioxopiperidin-3-yl)-1,3-dioxo-2,3-dihydro-1H-isoindol-4-yl]oxy}-N-[2-(2-{2-[(5-{5H-pyrido[4,3-b]indol-7-yl}pyridin-2-yl)oxy]acetamido}ethoxy)ethyl]acetamide | $^1$H NMR (500 MHz, DMSO-d$_6$) δ 13.20 (s, 1H), 11.11 (s, 1H), 9.75 (s, 1H), 8.66 (d, J = 6.6 Hz, 1H), 8.58 (d, J = 2.6 Hz, 1H), 8.51 (d, J = 8.2 Hz, 1H), 8.19 (dd, J = 8.6, 2.6 Hz, 1H), 8.08 (t, J = 5.7 Hz, 1H), 8.03-7.97 (m, 3H), 7.81-7.77 (m, 2H), 7.46 (d, J = 7.3 Hz, 1H), 7.38 (d, J = 8.5 Hz, 1H), 7.06 (d, J = 8.6 Hz, 1H), 5.11 (dt, J = 12.6, 5.2 Hz, 1H), 4.79 (d, J = 8.5 Hz, 4H), 3.47 (t, J = 5.8 Hz, 4H), 3.31 (p, J = 5.9 Hz, 4H), 2.89 (ddd, J = 16.7, 13.7, 5.4 Hz, 1H), 2.63-2.56 (m, 1H), 2.06-2.00 (m, 1H), 1.22-1.11 (m, 1H). MS (ESI) m/z 721 (M + H)$^+$ |
| 17 | 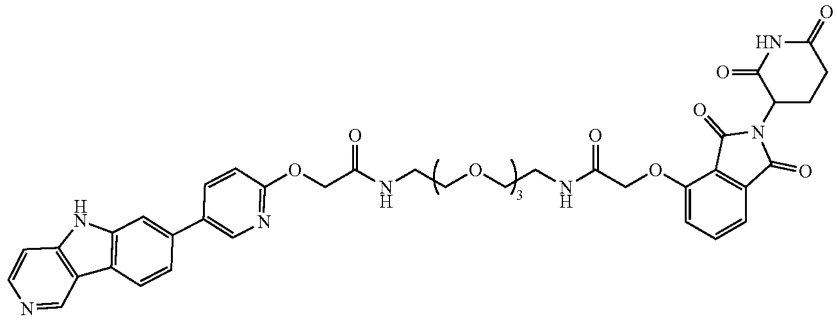 FMF-05-184-1 2-{[2-(2,6-dioxopiperidin-3-yl)-1,3-dioxo-2,3-dihydro-1H-isoindol-4-yl]oxy}-N-(2-{2-[2-(2-{2-[(5-{5H-pyrido[4,3-b]indol-7-yl}pyridin-2-yl)oxy]acetamido}ethoxy)ethoxy]ethoxy}ethyl]acetamide | $^1$H NMR (500 MHz, DMSO-d$_6$) δ 13.20 (s, 1H), 11.12 (s, 1H), 9.75 (s, 1H), 8.66 (d, J = 6.7 Hz, 1H), 8.60 (d, J = 2.7 Hz, 1H), 8.51 (d, J = 8.2 Hz, 1H), 8.21 (dd, J = 8.7, 2.6 Hz, 1H), 8.09 (t, J = 5.8 Hz, 1H), 8.04-7.94 (m, 3H), 7.82-7.72 (m, 2H), 7.48 (d, J = 7.2 Hz, 1H), 7.39 (d, J = 8.5 Hz, 1H), 7.07 (d, J = 8.7 Hz, 1H), 5.15-5.07 (m, 1H), 4.79 (d, J = 11.4 Hz, 4H), 3.50 (d, J = 4.6 Hz, 7H), 3.44 (t, J = 5.5 Hz, 3H), 3.29 (dq, J = 15.7, 5.8 Hz, 3H), 2.95-2.84 (m, 1H), 2.63-2.57 (m, 1H), 2.04 (ddd, J = 10.5, 5.7, 3.3 Hz, 1H), 1.22-1.15 (m, 3H). MS (ESI) m/z 709 (M + H)$^+$ |
| 18 | 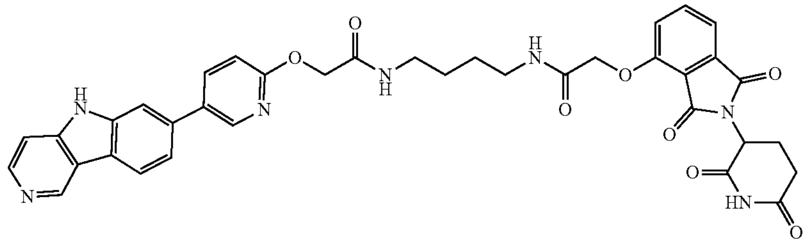 [SMILES: O=C(COc1ccc(-c2ccc3c(c2)[nH]c2ccncc23)cn1)NCCCCNC(=O)COc1cccc2c1C(=O)N(C1CCC(=O)NC1=O)C2=O] FMF-05-185-1 2-{[2-(2,6-dioxopiperidin-3-yl)-1,3-dioxo-2,3-dihydro-1H-isoindol-4-yl]oxy}-N-(4-{2-[(5-{5H-pyrido[4,3-b]indol-7-yl}pyridin-2-yl)oxy]acetamido}ethoxy)butyl]acetamide | $^1$H NMR (500 MHz, DMSO-d$_6$) δ 11.11 (s, 1H), 9.71 (s, 1H), 8.64 (d, J = 6.7 Hz, 1H), 8.59 (d, J = 2.7 Hz, 1H), 8.48 (d, J = 8.2 Hz, 1H), 8.20 (dd, J = 8.6, 2.6 Hz, 1H), 8.07 (t, J = 5.7 Hz, 1H), 8.00-7.92 (m, 3H), 7.80-7.74 (m, 2H), 7.45 (d, J = 7.3 Hz, 1H), 7.36-7.33 (m, 1H), 7.08-7.05 (m, 1H), 5.14-5.08 (m, 1H), 4.76 (d, J = 19.9 Hz, 3H), 3.19-3.10 (m, 4H), 2.90 (ddd, J = 18.5, 13.8, 5.4 Hz, 1H), 2.67-2.60 (m, 1H), 2.09-2.00 (m, 1H), 1.44 (d, J = 3.8 Hz, 4H), 1.22-1.10 (m, 2H). MS (ESI) m/z 704 (M + H)$^+$ |

N-[2-(2-{[2-(2,6-dioxopiperidin-3-yl)-1,3-dioxo-2,3-dihydro-1H-isoindol-4-yl]amino}ethoxy)ethyl]-2-[(5-{5H-pyrido[4,3-b]indol-7-yl}pyridin-2-yl)oxy] acetamide (19; FMF-05-167-1)

19

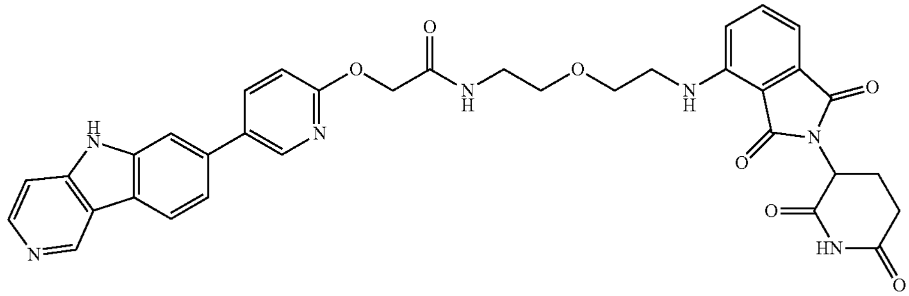

(FMF-05-167-1)

The title compound was prepared in an analogous manner to compound 1, employing the corresponding amine starting materials and compound S. Compound S (50 mg, 0.15 mmol), the corresponding amine (61 mg, 0.17 mmol), HATU (18 mg, 0.05 mmol), and DIPEA (30 uL, 0.15 mmol) were stirred in DMF (1 mL) at r.t. for 16 h. The reaction mixture was filtered and purified by HPLC to afford compound 19 (FMF-05-167-1) as a TFA salt (7 mg, 0.009, 23%). $^1$H NMR (500 MHz, DMSO-$d_6$) δ 13.19 (s, 1H), 11.09 (s, 1H), 9.77 (d, J=3.6 Hz, 1H), 8.68 (d, J=6.7 Hz, 1H), 8.59 (d, J=2.6 Hz, 1H), 8.52 (dd, J=8.2, 4.4 Hz, 1H), 8.22-8.18 (m, 1H), 8.09 (t, J=5.7 Hz, 1H), 8.04-7.99 (m, 2H), 7.82-7.77 (m, 1H), 7.58-7.54 (m, 1H), 7.12 (d, J=8.6 Hz, 1H), 7.06 (d, J=8.6 Hz, 1H), 7.01 (d, J=7.0 Hz, 1H), 6.60 (t, J=6.0 Hz, 1H), 5.09-4.98 (m, 1H), 4.81 (s, 1H), 3.66-3.57 (m, 4H), 3.54-3.43 (m, 4H), 3.31 (q, J=5.9 Hz, 1H), 3.15 (qd, J=7.4, 4.3 Hz, 2H), 2.60-2.54 (m, 1H), 2.06-1.97 (m, 1H), 1.35 (d, J=28.5 Hz, 1H). MS (ESI) m/z 663 $(M+H)^+$ N-{2-[2-(2-{[2-(2,6-dioxopiperidin-3-yl)-1,3-dioxo-2,3-dihydro-1H-isoindol-4-yl]oxy}ethoxy)ethoxy]ethyl}-3-{5H-pyrido[4,3-b]indol-7-yl}propanamide (20; FMF-06-038-1)

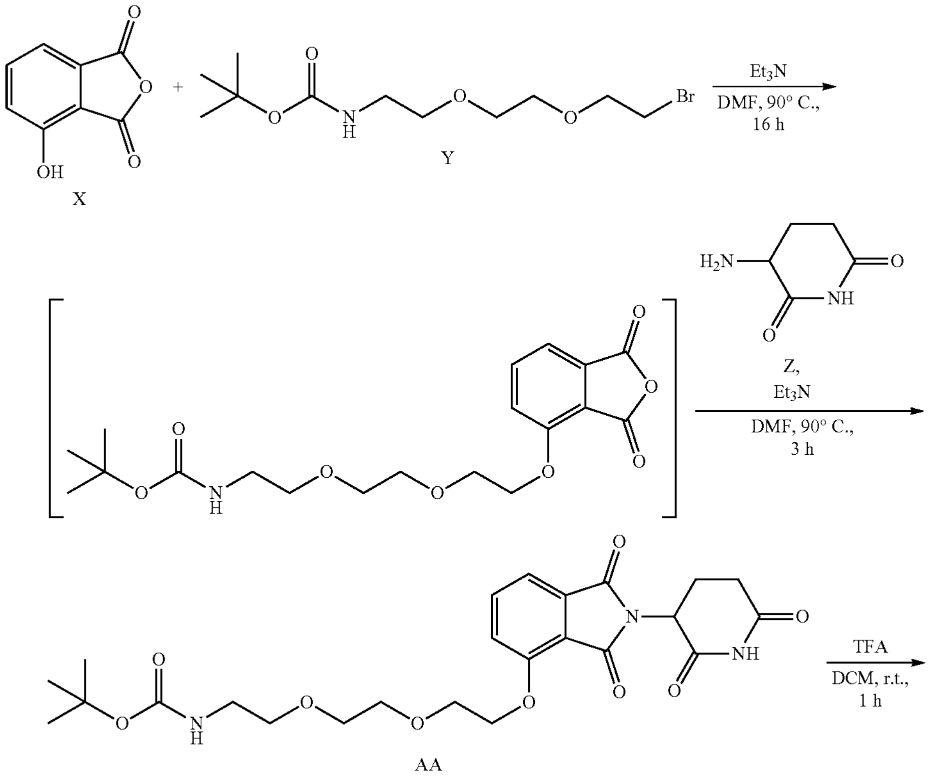

-continued

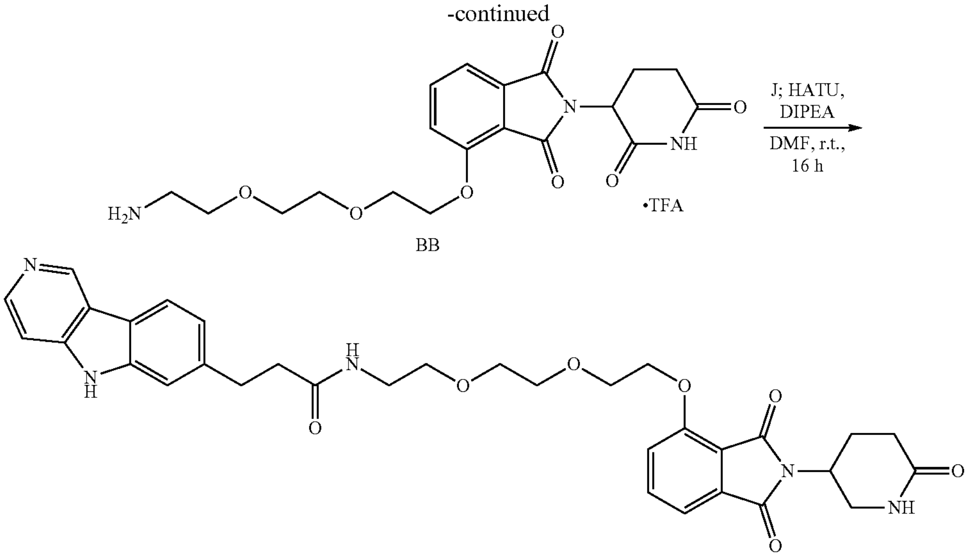

BB 20
(FMF-06-038-1)

(AA): Compound X (100 mg, 0.61 mmol), compound Y (256 mg, 0.92 mmol), and $Et_3N$ (430 uL, 3.06 mmol) were stirred in DMF (2 mL) at 90° C. for 16 h. The reaction mixture was cooled to room temperature and filtered. The precipitate was washed with EtOAc (20 mL) and the combined filtrate and organics were concentrated under reduced pressure to 2 mL volume. $Et_3N$ (430 uL, 3.06 mmol) and compound Z (250 mg, 0.53 mmol) were added to the concentrated filtrates and the reaction mixture heated at 90° C. for 3 h. The reaction was concentrated under reduced pressure and purified by flash chromatography to afford the title compound (270 mg, 0.57 mmol, 93%). $^1$H NMR (500 MHz, DMSO-$d_6$) δ 11.10 (s, 1H), 7.82 (dd, J=8.5, 7.2 Hz, 1H), 7.56-7.51 (m, 1H), 7.46 (d, J=7.2 Hz, 1H), 6.77-6.70 (m, 1H), 5.09 (dd, J=12.8, 5.5 Hz, 1H), 4.37-4.33 (m, 2H), 3.84-3.79 (m, 2H), 3.64 (dd, J=5.8, 3.8 Hz, 2H), 3.54-3.48 (m, 4H), 3.37 (d, J=6.2 Hz, 2H), 3.06 (q, J=5.8 Hz, 3H), 2.60 (ddd, J=17.0, 4.4, 2.4 Hz, 1H), 2.03 (dtd, J=13.0, 5.3, 2.2 Hz, 1H), 1.36 (s, 9H). MS (ESI) m/z 506 $(M+H)^+$ (BB): Compound AA (156 mg, 0.31 mmol) was dissolved in 2 mL DCM and 2 mL TFA, and stirred at r.t. for 2 h. The reaction mixture was concentrated under reduced pressure to afford the compound BB (161 mg, 0.31 mmol, 100%), which was used without further purification. MS (ESI) m/z 406 $(M+H)^+$ N-{2-[2-(2-{[2-(2,6-dioxopiperidin-3-yl)-1,3-dioxo-2,3-dihydro-1H-isoindol-4-yl]oxy}ethoxy)ethoxy]ethyl}-3-{5H-pyrido[4,3-b]indol-7-yl}propanamide: Compound BB (10 mg, 0.042 mmol), Compound J (24 mg, 0.046 mmol), HATU (20 mg, 0.05 mmol), and DIPEA (26 uL, 0.126 mmol) were dissolved in DMF (2 mL) and stirred at r.t. for 4 h. The reaction mixture was filtered and purified by HPLC to afford compound 20 (FMF-06-038-1) as a TFA salt. (3 mg, 0.004 mmol, 10%). $^1$H NMR (500 MHz, DMSO-$d_6$) δ 13.05 (s, 1H), 11.10 (s, 1H), 9.68 (s, 1H), 8.62 (d, J=6.7 Hz, 1H), 8.32 (d, J=8.1 Hz, 1H), 7.97 (d, J=6.7 Hz, 1H), 7.93 (q, J=5.6 Hz, 1H), 7.81-7.77 (m, 1H), 7.59 (d, J=4.2 Hz, 1H), 7.51 (d, J=8.6 Hz, 1H), 7.45-7.41 (m, 1H), 7.37-7.32 (m, 1H), 5.08 (dd, J=12.8, 5.3 Hz, 1H), 4.33-4.27 (m, 2H), 3.64-3.59 (m, 6H), 3.17-3.13 (m, 6H), 3.07-3.02 (m, 2H), 2.90-2.84 (m, 2H), 2.61-2.57 (m, 1H), 2.06-2.01 (m, 1H). MS (ESI) m/z 626 $(M-H)^-$ Example Compounds 21-24 were Prepared in an Analogous Manner to Compound 20, Employing the Corresponding Amine Starting Materials and Carboxylic Acid J

| | Structure/Name | Characterization |
|---|---|---|
| 21 | 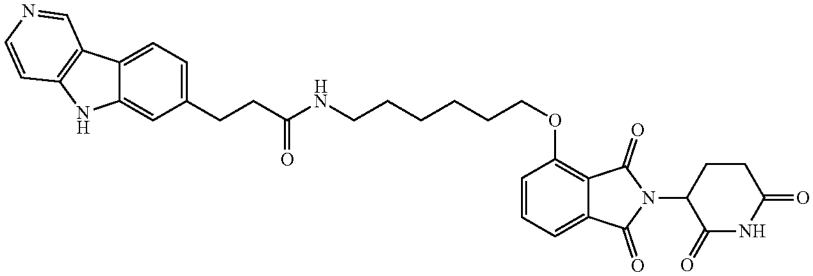 [SMILES: O=C(CCc1ccc2c(c1)[nH]c1ccncc12)NCCCCCCOc1cccc2c1C(=O)N(C1CCC(=O)NC1=O)C2=O] FMF-06-049-1 N-(6-{[2-(2,6-dioxopiperidin-3-yl)-1,3-dioxo-2,3-dihydro-1H-isoindol-4-yl]oxy}hexyl)-3-{5H-pyrido[4,3-b]indol-7-yl}propanamide | $^1$H NMR (500 MHz, DMSO-$d_6$) δ 13.04 (s, 1H), 11.10 (s, 1H), 9.67 (s, 1H), 8.61 (d, J = 6.7 Hz, 1H), 8.33 (d, J = 8.0 Hz, 1H), 7.97 (d, J = 6.6 Hz, 1H), 7.81 (dd, J = 8.4, 7.2 Hz, 1H), 7.70 (s, 1H), 7.60 (s, 1H), 7.46 (dd, J = 13.7, 7.9 Hz, 2H), 7.36 (dd, J = 8.3, 1.3 Hz, 1H), 5.08 (dd, J = 12.8, 5.5 Hz, 1H), 4.23-3.99 (m, 3H), 3.03 (dq, J = 12.4, 6.6, 5.9 Hz, 4H), 2.77 (d, J = 12.2 Hz, 2H), 1.64 (t, J = 7.5 Hz, 1H), 1.53 (d, J = 7.2 Hz, 1H), 1.46 (dd, J = 15.6, 6.6 Hz, 1H), 1.37-1.33 (m, 5H), 1.23 (d, J = 11.1 Hz, 2H), 1.11-1.04 (m, 3H). MS (ESI) m/z 596 $(M + H)^+$ |

-continued

| | Structure/Name | Characterization |
|---|---|---|
| 22 | 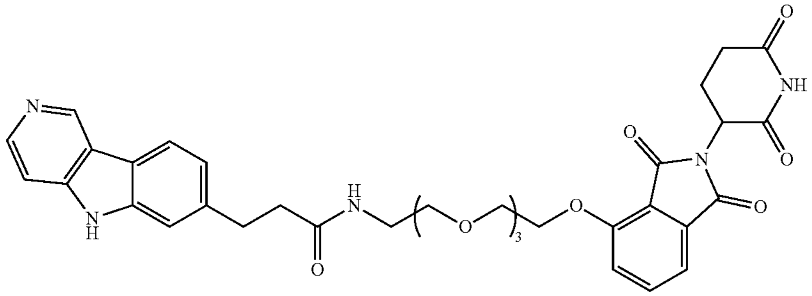 FMF-06-050-2 N-(2-{2-[2-(2-{[2-(2,6-dioxopiperidin-3-yl)-1,3-dioxo-2,3-dihydro-1H-isoindol-4-yl]oxy}ethoxy)ethoxy]ethoxy}ethyl)-3-{5H-pyrido[4,3-b]indol-7-yl}propanamide | MS (ESI) m/z 672 (M + H)+ |
| 23 | 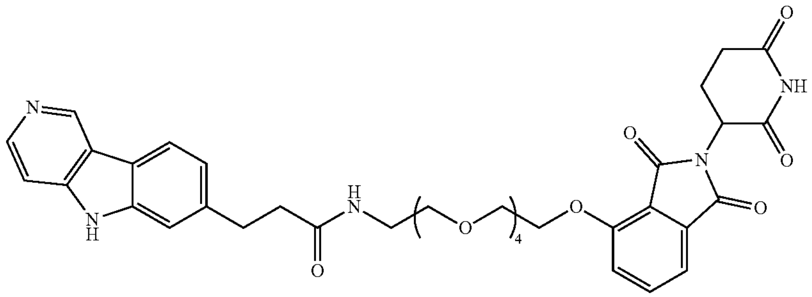 FMF-06-052-1 N-(14-{[2-(2,6-dioxopiperidin-3-yl)-1,3-dioxo-2,3-dihydro-1H-isoindol-4-yl]oxy}-3,6,9,12-tetraoxatetradecan-1-yl)-3-{5H-pyrido[4,3-b]indol-7-yl}propanamide | $^1$H NMR (500 MHz, DMSO-$d_6$) δ 12.98 (s, 1H), 11.10 (s, 1H), 9.66 (s, 1H), 8.61 (s, 1H), 8.32 (dd, J = 11.7, 8.1 Hz, 1H), 7.92 (t, J = 5.7 Hz, 1H), 7.80 (dd, J = 8.5, 7.3 Hz, 1H), 7.58 (s, 1H), 7.51 (d, J = 8.5 Hz, 1H), 7.45 (d, J = 7.3 Hz, 1H), 7.33 (dd, J = 8.1, 1.4 Hz, 1H), 5.08 (dd, J = 12.8, 5.4 Hz, 1H), 4.33 (t, J = 4.7 Hz, 2H), 3.79 (t, J = 4.6 Hz, 2H), 3.63 (dd, J = 5.8, 3.7 Hz, 2H), 3.58-3.41 (m, 13H), 3.18 (q, J = 5.7 Hz, 2H), 3.04 (t, J = 7.7 Hz, 2H), 2.06-1.99 (m, 0H), 1.26-1.23 (m, 2H), 1.18-0.82 (m, 2H). MS (ESI) m/z 716 (M + H)+ |
| 24 | 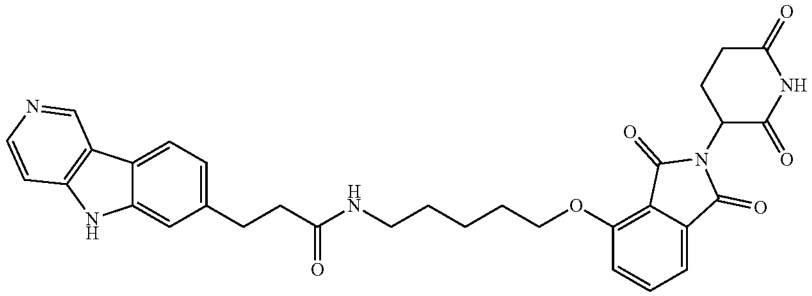 [SMILES: O=C(CCc1ccc2c(c1)[nH]c1ccncc12)NCCCCCOc1cccc2c1C(=O)N(C1CCC(=O)NC1=O)C2=O] FMF-06-53-1 N-(5-{[2-(2,6-dioxopiperidin-3-yl)-1,3-dioxo-2,3-dihydro-1H-isoindol-4-yl]oxy}pent)-3-{5H-pyrido[4,3-b]indol-7-yl}propanamide | $^1$H NMR (500 MHz, DMSO-$d_6$) δ 13.12 (s, 1H), 11.10 (s, 1H), 9.66 (s, 1H), 8.60 (d, J = 6.8 Hz, 1H), 8.33 (d, J = 8.1 Hz, 1H), 7.95 (d, J = 6.9 Hz, 1H), 7.85 (t, J = 5.7 Hz, 1H), 7.79 (dd, J = 8.4, 7.3 Hz, 1H), 7.59 (s, 1H), 7.43 (dd, J = 7.9, 4.3 Hz, 2H), 7.35 (dd, J = 8.2, 1.4 Hz, 1H), 5.06 (dd, J = 12.7, 5.4 Hz, 1H), 4.07 (t, J = 6.4 Hz, 2H), 3.08-3.01 (m, 4H), 2.92-2.85 (m, 4H), 1.67 (p, J = 6.6 Hz, 2H), 1.41 (p, J = 6.9 Hz, 2H), 1.33 (p, J = 7.6 Hz, 1H), 1.29-1.21 (m, 4H). MS (ESI) m/z 582 (M + H)+ |

Tau Degradation Assays

Assays were performed to demonstrate the ability of the exemplary compounds to degrade tau in human cells. Compounds employed as controls in the experiments described below include the following:

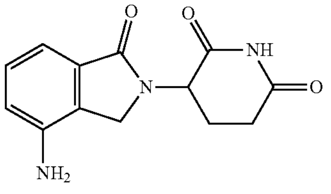

lenalidomide

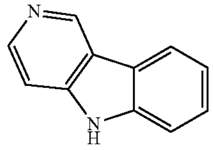

T-807 core

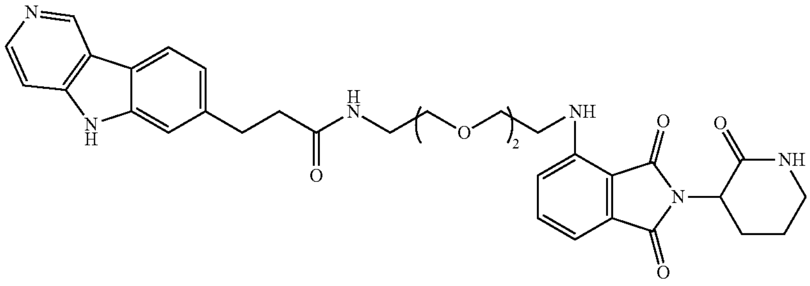

QC-03-075

Example compounds 1-12 were evaluated for their ability to degrade tau protein in cultured human differentiated frontotemporal lobar dementia (FTD) neurons. Several exemplary compounds significantly degraded hyperphosphorylated tau and total tau in human tau-A152T neurons (5-week differentiated) and tau-P301L neurons (8-week differentiated) after treatment of the neurons with the compounds for 24 hours (FIGS. 1, 2, and 8-10). For each condition, 1 well of differentiated neuronal cells (6 well-plate) was washed and collected in PBS, pelleted and lysed in RIPA buffer (Boston Bio-Products) with 2% SDS (Sigma), protease inhibitors (Roche Complete Mini tablets), and phosphatase inhibitors (Sigma), followed by sonication in a water sonicator (Bransonic Ultrasonic Baths, Thomas Scientific) for 5 min, and centrifugation at 20,000 g for 15 min. Supernatants were transferred to new tubes, total protein concentration was quantified with the Pierce BCA Protein Assay Kit (Thermo), and SDS-PAGE gels were loaded with 10 μg total protein per well (pre-boiled samples). Western blots were performed with the Novex NuPAGE SDS-PAGE Gel System (Invitrogen). All samples were resolved in 7% Tris-Acetate gels with Tris-Acetate running buffer (Invitrogen). Blots were probed with antibodies against total tau (TAU5) and phosphosrylated tau (Ser396), along with β-actin as a loading control; followed by corresponding HRP-linked secondary antibodies (Cell Signaling Technology), and SuperSignal West Pico Chemiluminescent Substrate (Thermo) detection. Membranes were exposed to autoradiographic film (LabScientific) and films were scanned using an Epson Perfection V800 Photo Scanner. Protein band intensities (pixel mean intensity) were quantified using Adobe Photoshop CS5 Histogram function. Whereas the vehicle alone (DMSO) had no effect on tau, varying degrading activity was observed amongst the compounds, however with overall similar relative levels of degrading activity between tau-A152T neurons and tau-P301L neurons. Compounds were added at the doses indicated of either 0.1, 1, 5, or 10 μM. Lenalidomide (1 μM or 10 μM) was also evaluated as a control in some experiments since it binds CRBN but should not engage tau, as confirmed by having no effect on tau levels.

Figure 3:
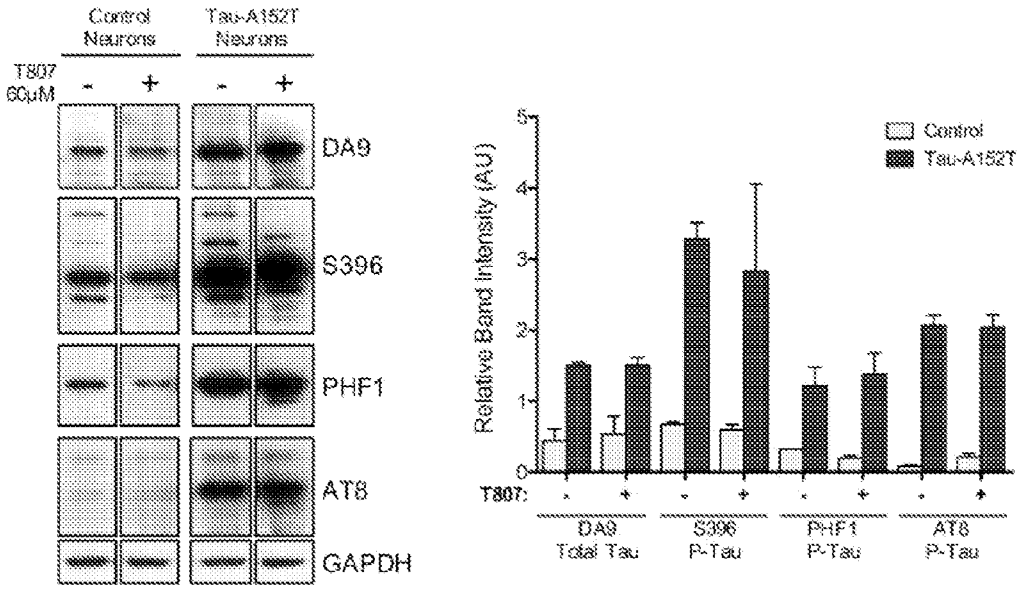
FIG. 3 is a series of western blot stains showing the effect of T807, a known tau-binding compound, on levels of tau protein in non-mutant human neurons (control) and human tau-A152T neurons. The graph on the right shows the quantification of the blots. No significant tau lowering activity of T807 was observed in either cell line.
Figure 4A:
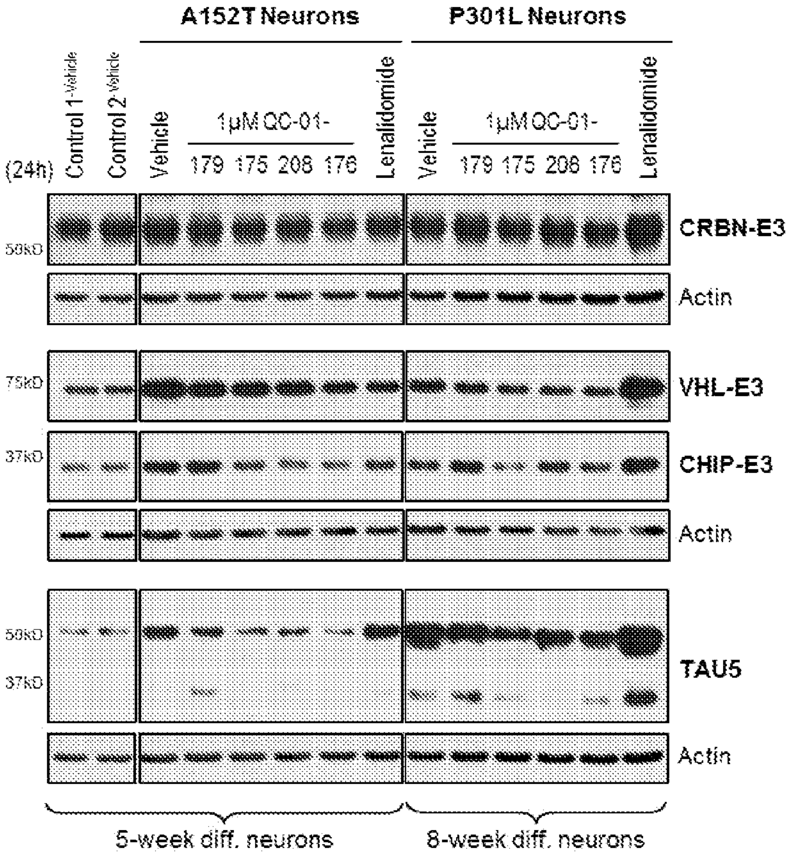
FIG. 4A is a series of western blot stains showing the effect of exemplary compounds on levels of E3 ubiquitin ligases Cereblon (CRBN), von Hippel-Lindau tumor suppressor (VHL), and C terminus of HSC70-Interacting Protein (CHIP) in human tau-A152T and tau-P301 L neurons, after 24 h treatment.
Figure 4B:
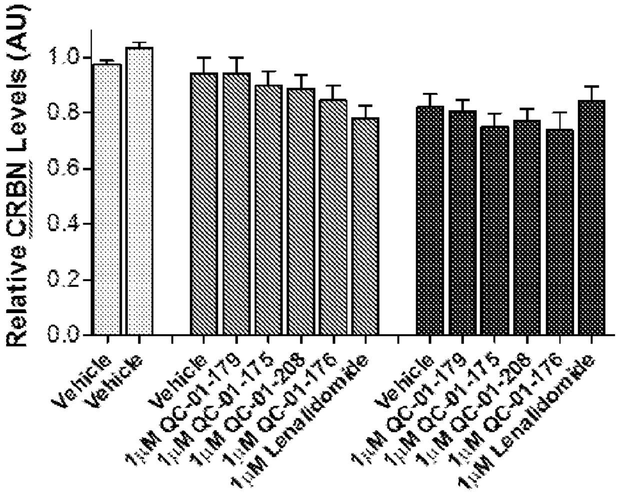
FIG. 4B is a series of bar graphs quantifying CRBN from the western blots in FIG. 4A; CRBN levels in the tau-A152T neurons are on the left (medium grey bars) and CRBN levels in the tau-P301L neurons are on the right (black bars).
Figure 4C:
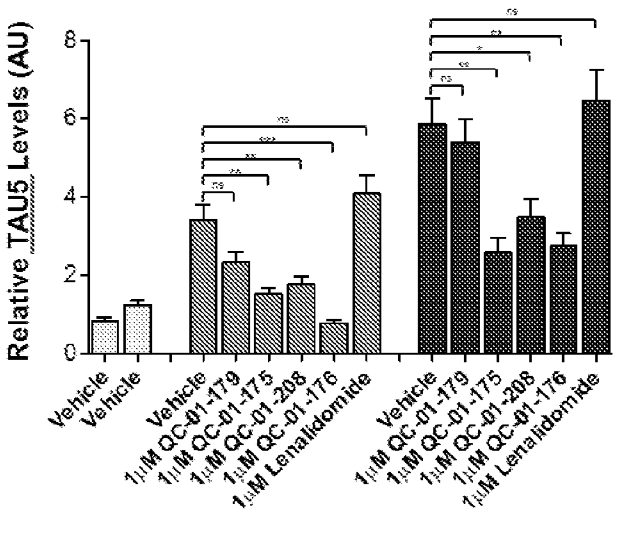
FIG. 4C is a series of bar graphs quantifying total tau from the western blots in FIG. 4A; Tau5 (total tau) levels in the tau-A152T neurons are on the left (medium grey bars) and Tau5 levels in the tau-P301L neurons are on the right (black bars).
Figure 4D:
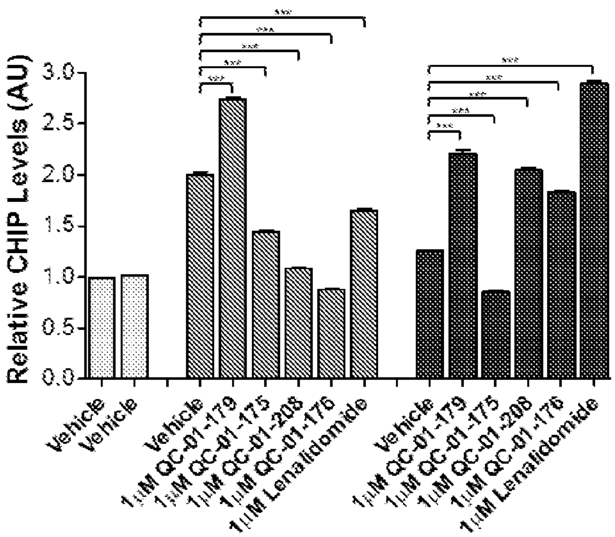
FIG. 4D is a series of bar graphs quantifying CHIP from the western blots in FIG. 4A; CHIP levels in the tau-A152T neurons are on the left (medium grey bars) and CHIP levels in the tau-P301L neurons are on the right (black bars).
Figure 4E:
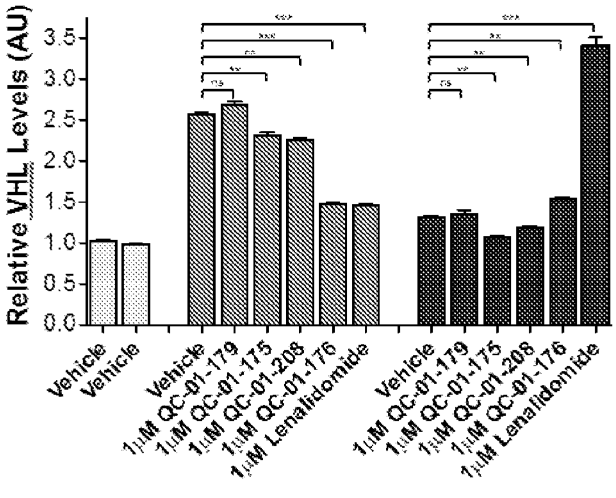
FIG. 4E is a series of bar graphs quantifying VHL from the western blots in FIG. 4A; VHL levels in the tau-A152T neurons are on the left (medium grey bars) and VHL levels in the tau-P301L neurons are on the right (black bars).

The effect of the tau binding moiety, T807, was also evaluated in a control experiment since it should not recruit tau to CRBN as it does not bind CRBN. Four-week differentiated neurons, both non-mutant (8330-8) and tau-A152T (19-5-RC6) were employed. The neurons were treated with T807 for 24 hours (at 10 μg/mL=59.4 μM). One well of differentiated neuronal cells (6 well-plate, treated or untreated) was washed and collected in PBS, pelleted and directly lysed in 200 μL of Sample Buffer (New England Biolabs) supplemented with 3X DTT, boiled for 15 min and 10 μL of each lysate was run by SDS-PAGE in a 4-12% Bis-Tris Gel, with MOPS running buffer. Blots were probed with antibodies to total tau (DA9) and phosphorylated tau (Ser396, PHF1, AT8) along with GAPDH as a loading control. The results of this experiment showed that T807 had no effect on tau levels and did not degrade tau (FIG. 3). Complementarily, FIG. 5 also showed no effect of T807 on tau and phosphorylated tau, when treated concomitantly with other exemplary compounds at the same dose of 1 μM.

Example compounds 2-5 were reevaluated for their ability to degrade tau protein in human FTD neurons as well as evaluate their effect on E3 ubiquitin ligases CRBN, VHL, and CHIP (FIG. 4A-E). For each control and treatment, 1 well of differentiated neuronal cells (6 well-plate) was washed and collected in PBS, pelleted and lysed in RIPA buffer (Boston Bio-Products) with 2% SDS (Sigma), protease inhibitors (Roche Complete Mini tablets), and phosphatase inhibitors (Sigma), followed by sonication in a water sonicator (Bransonic Ultrasonic Baths, Thomas Scientific) for 5 min, and centrifugation at 20,000 g for 15 min. Supernatants were transferred to new tubes, total protein concentration was quantified with the Pierce BCA Protein Assay Kit (Thermo), and SDS-PAGE gels were loaded with 10 μg total protein per well (pre-boiled samples). Western blots were performed with the Novex NuPAGE SDS-PAGE Gel System (Invitrogen), with gradient 4-12% Bis-Tris gels with MOPS running buffer (Invitrogen). Blots were probed with antibodies to CRBN, VHL, CHIP and total tau (TAU5), along with β-actin as a loading control; followed by corresponding HRP-linked secondary antibodies (Cell Signaling Technology), and SuperSignal West Pico Chemiluminescent Substrate (Thermo) detection. Membranes were exposed to autoradiographic film (LabScientific) and films were scanned using an Epson Perfection V800 Photo Scanner. Protein band intensities (pixel mean intensity) were quantified using Adobe Photoshop CS5 Histogram function. Whereas the vehicle alone (DMSO) had no effect on tau, several of the compounds significantly degraded hyperphosphorylated tau and total tau in human tau-A152T neurons (5-week differentiated) and tau-P301 L neurons (8-week differentiated). Lenalidomide was also evaluated as a control, and it had no effect on tau levels. In addition, the exemplary compounds did not have an effect on CRBN, but did have an effect on VHL and CHIP. The assay also confirmed significant tau accumulation in A152T and P301L neurons. In FTD neurons (A152T and P301L), tau accumulation leads to disruption of specific proteostasis pathways, which include upregulation of CHIP and VHL. For CHIP, the compounds with highest potency for tau degradation also caused a decrease in CHIP levels. This may be an indication that CRBN is a stable and useful target for degraders of tau protein in human neurons.

Figure 5A:
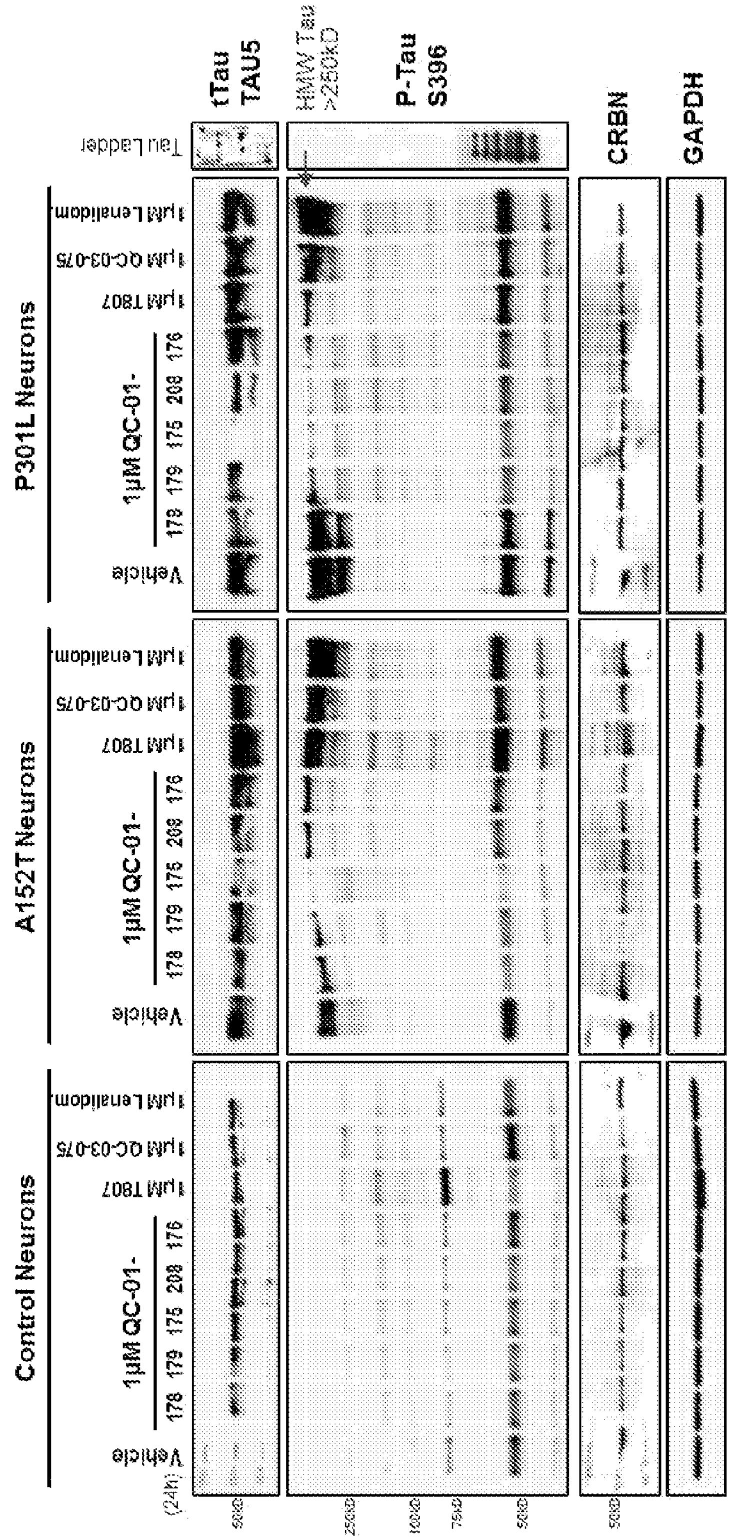
FIG. 5A is a series of western blot stains showing the effect of exemplary compounds on levels of tau protein in human non-mutant (control), human tau-A152T, and human tau-P301L neurons at 6 weeks of differentiation.
Figure 5B:
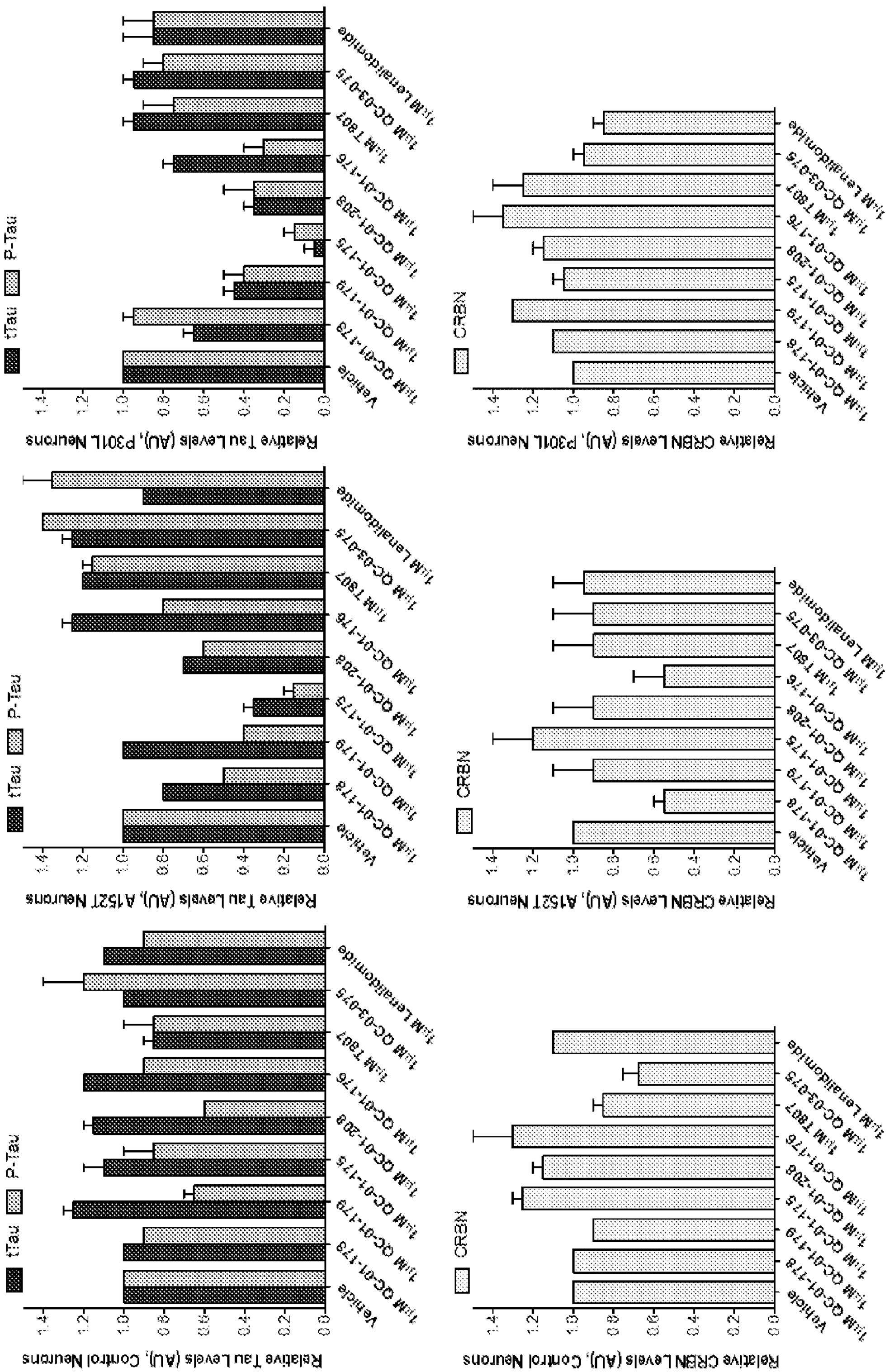
FIG. 5B is a series of bar graphs quantifying total tau, hyperphosphorylated tau (upper graphs), and CRBN (bottom graphs) from the western blots in FIG. 5A.
Figure 5C:
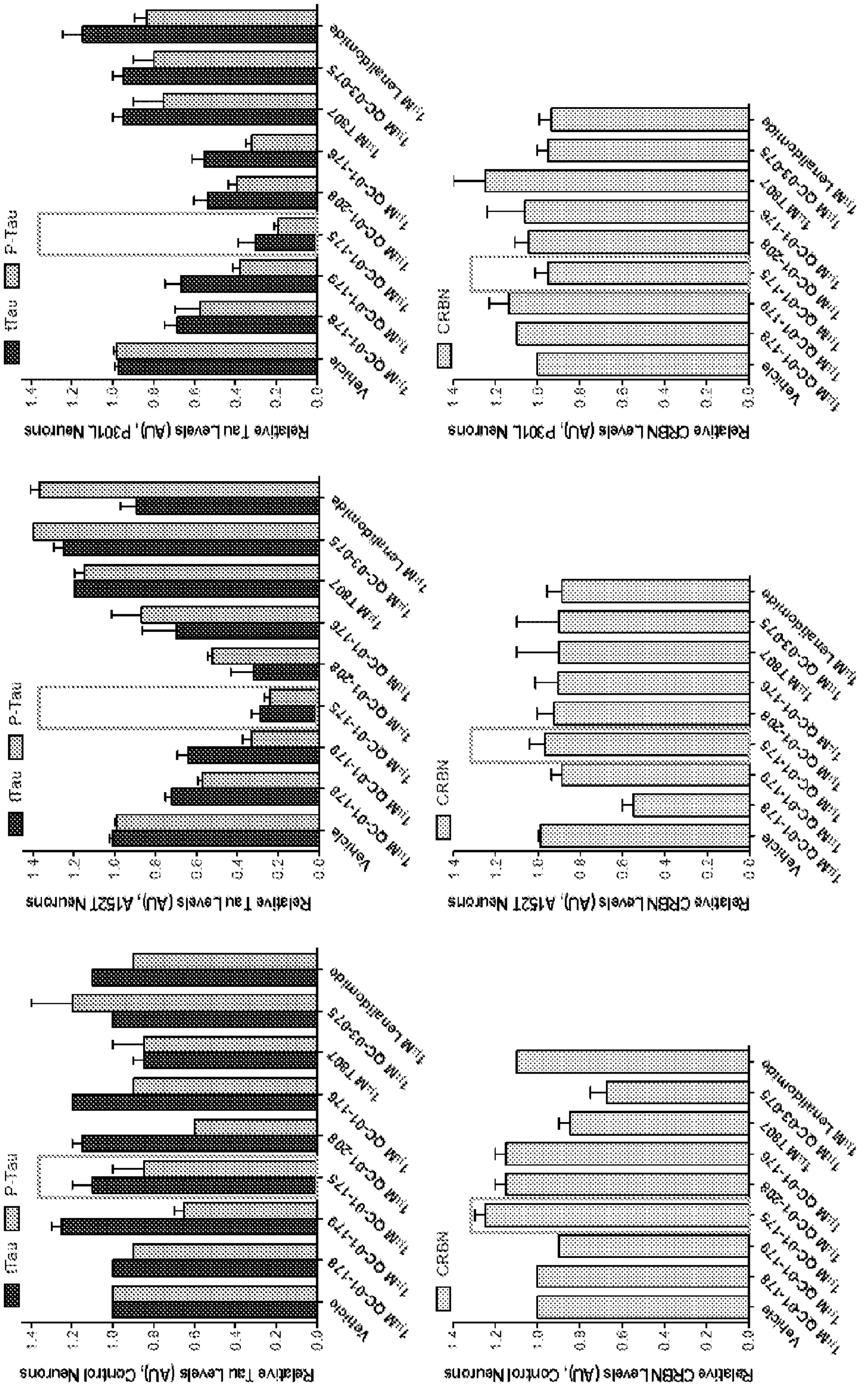
FIG. 5C is a series of bar graphs quantifying total tau, hyperphosphorylated tau (upper graphs), and CRBN (bottom graphs) from an average of three experiments of the western blots as represented in FIG. 5A.

Example compounds 2-5 were again evaluated in tau degradation assays in non-mutant control, A152T and P301L neurons (6-week differentiated). Non-mutant neurons were employed as a negative control since derivatives of T807 should not recognize non-disease states of tau based upon how the series was identified, using selection for binding to pathological forms of tau in post-mortem brain lysates and tissue slices. In addition, T807, lenalidomide, and QC-03-075 were employed as controls along with the vehicle (DMSO). As QC-03-075 does not bind to CRBN it should act as a negative control. For each condition, 1 well of differentiated neuronal cells (6 well-plate) was washed and collected in PBS, pelleted and lysed in RIPA buffer (Boston Bio-Products) with 2% SDS (Sigma), protease inhibitors (Roche Complete Mini tablets), and phosphatase inhibitors (Sigma), followed by sonication in a water sonicator (Bransonic Ultrasonic Baths, Thomas Scientific) for 5 min, and centrifugation at 20,000 g for 15 min. Supernatants were transferred to new tubes, total protein concentration was quantified with the Pierce BCA Protein Assay Kit (Thermo), and SDS-PAGE gels were loaded with 10 μg total protein per well (pre-boiled samples). Western blots were performed with the Novex NuPAGE SDS-PAGE Gel System (Invitrogen) and samples were resolved in 7% Tris-Acetate gels with Tris-Acetate running buffer (Invitrogen). Blots were probed with antibodies to total tau (TAU5), phospho-tau (S396) and CRBN along with GAPDH as a loading control; followed by corresponding HRP-linked secondary antibodies (Cell Signaling Technology), and SuperSignal West Pico Chemiluminescent Substrate (Thermo) detection. Membranes were exposed to autoradiographic film (LabScientific) and films were scanned using an Epson Perfection V800 Photo Scanner. Protein band intensities (pixel mean intensity) were quantified using Adobe Photoshop CS5 Histogram function. Assay results again confirmed the ability of the exemplary compounds to be effective degraders of pathological forms of tau while having little effect on levels of tau in non-mutant tau neurons (FIG. 5A-C). These results were confirmed by three biological replicates (FIG. 5C).

Figure 6A:
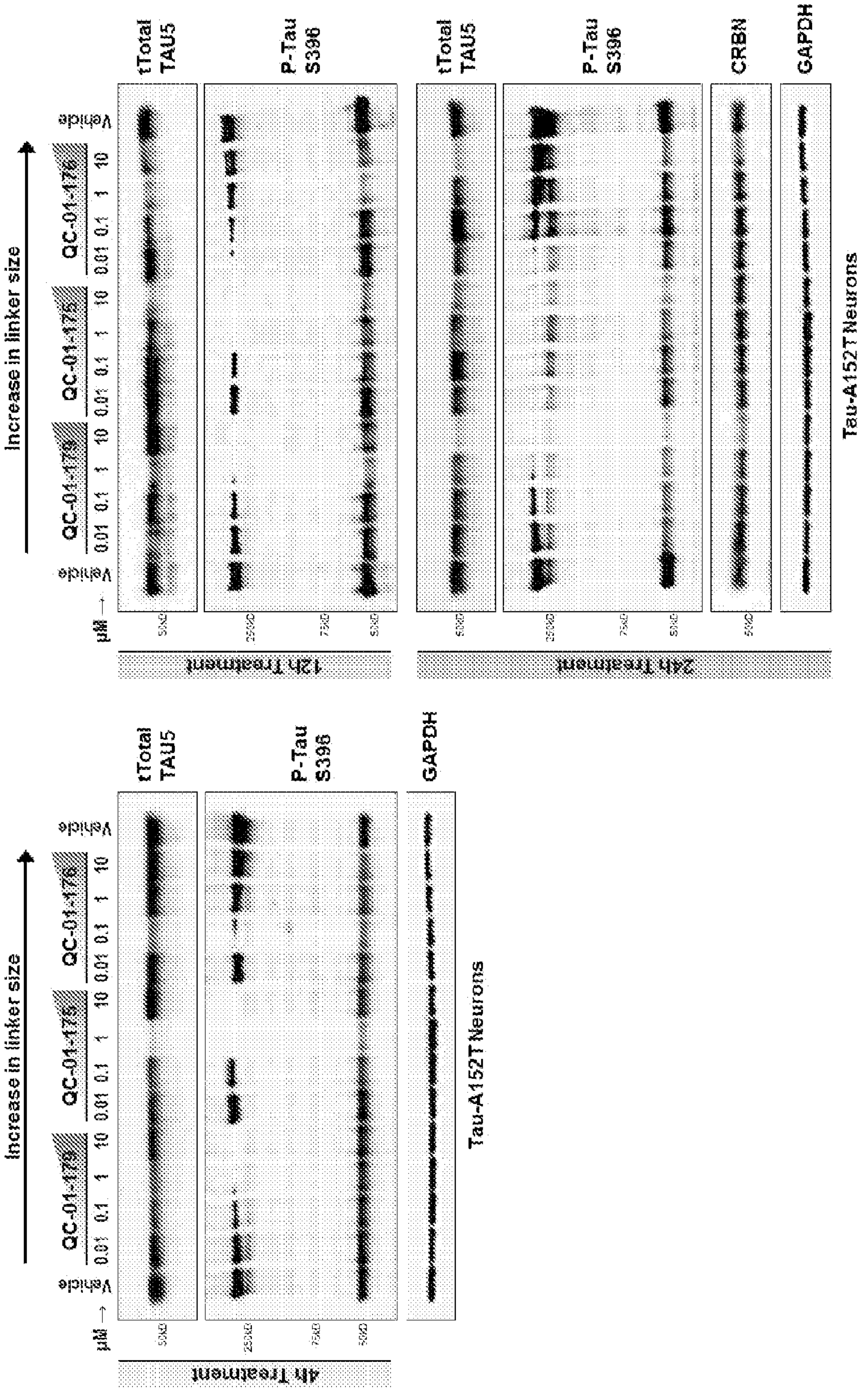
FIG. 6A is a series of western blot stains showing the effect of exemplary compounds in 6-week differentiated human tau-A152T neurons.
Figure 6B:
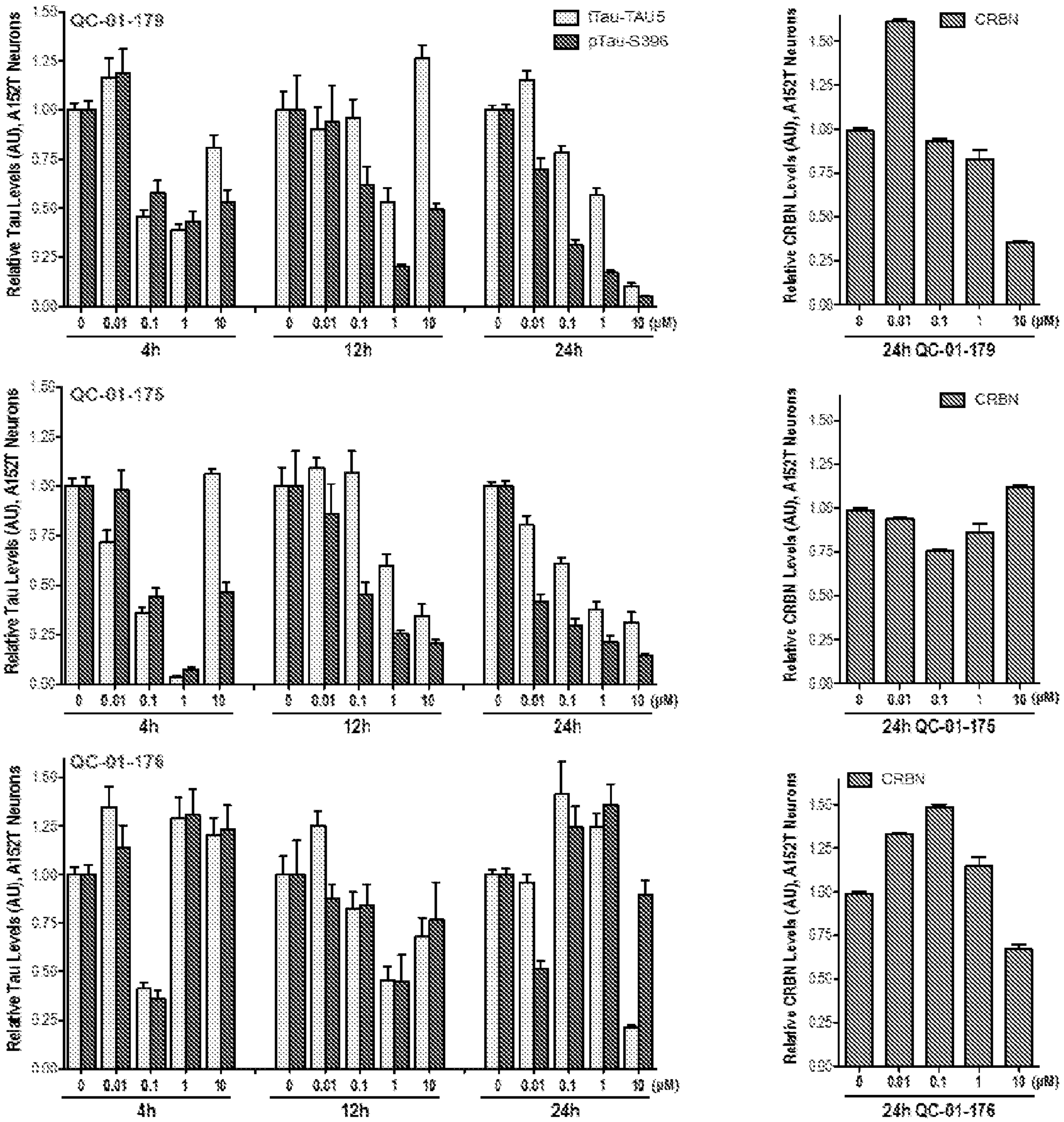
FIG. 6B is a series of bar graphs quantifying total tau, hyperphosphorylated tau, and CRBN from the western blots in FIG. 6A.

Example compounds 2, 3, and 5 were evaluated to determine time and dose-dependency effect on the degradation of tau in 6-week differentiated A152T neurons (FIG. 6A-B). For each condition, one well of differentiated neuronal cells (6 well-plate, treated or untreated) was washed and collected in PBS, pelleted and directly lysed in 150 μL of Sample Buffer (New England Biolabs) supplemented with 3X DTT, boiled for 15 min and 10 μL of each lysate was run by SDS-PAGE in a Novex NuPAGE SDS-PAGE System (Invitrogen) with 7% Tris-Acetate gels and Tris-Acetate running buffer (Invitrogen). Blots were probed with antibodies to total tau (TAU5), and phospho-tau (5396), along with GAPDH as a loading control; followed by HRP-linked secondary antibodies (Cell Signaling Technology), and SuperSignal West Pico Chemiluminescent Substrate (Thermo) detection. Membranes were exposed to autoradiographic film (LabScientific) and films were scanned using an Epson Perfection V800 Photo Scanner. Protein band intensities (pixel mean intensity) were quantified using Adobe Photoshop CS5 Histogram function. Upon compound treatment, no toxicity or detachment were detected. The results confirmed the findings of the previous assays described above and showed that compounds 2 and 3 have a dose dependent effect on tau after treatment for 24 hours.

Figure 7:
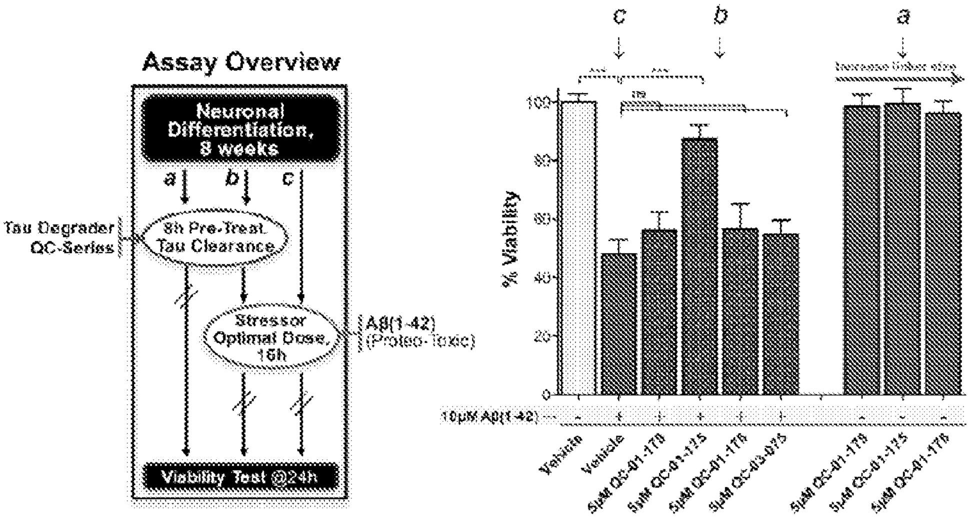
FIG. 7 is a bar graph quantifying the results of neuronal cell viability assays for the ability of exemplary compounds to provide protection from toxic stimuli associated with neurodegeneration, here chosen to be β-amyloid (1-42) peptide, as a functional readout of having effectively degraded tau (at 8 weeks of differentiation). As shown by Silva et al. (*Stem Cell Reports,* 2016, 7(3), 325-40; doi: 10.1016/j.stemcr.2016.08.001) reduction of viability due to β-amyloid (1-42) exposure is dependent on tau. Left, schematic of experimental design, right, graph of viability.
Figures 8A, 8B:
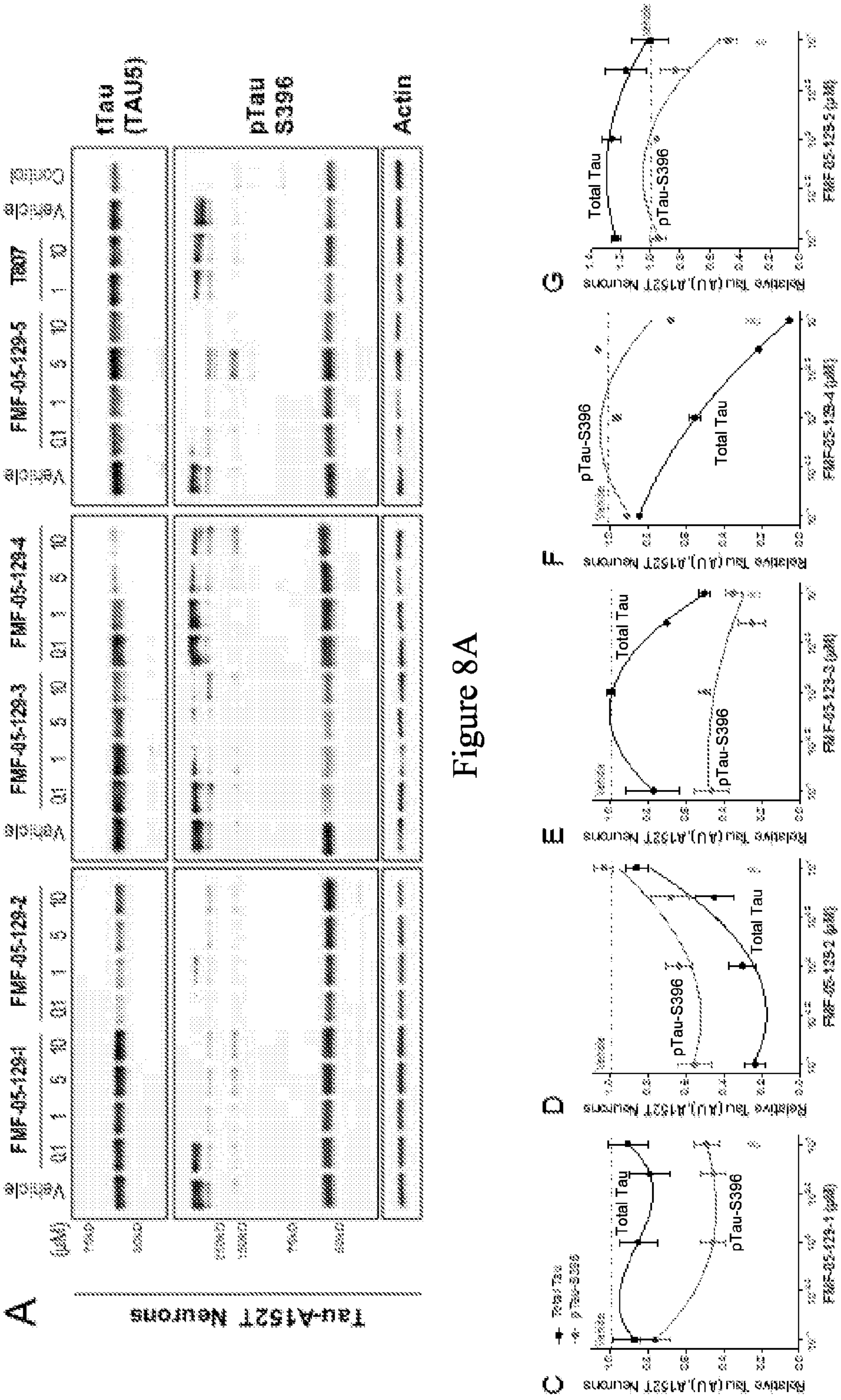
FIG. 8A is a series of western blot stains showing the effect of exemplary compounds and T-807 on levels of tau protein in a human tau-A152T neuronal model, after 24 h treatment. The control is a non-mutant neuron (8330-8-RC1).
FIG. 8B is a series of graphs quantifying the total tau and hyperphosphorylated tau from the western blots in FIG. 8A.
Figure 9A:
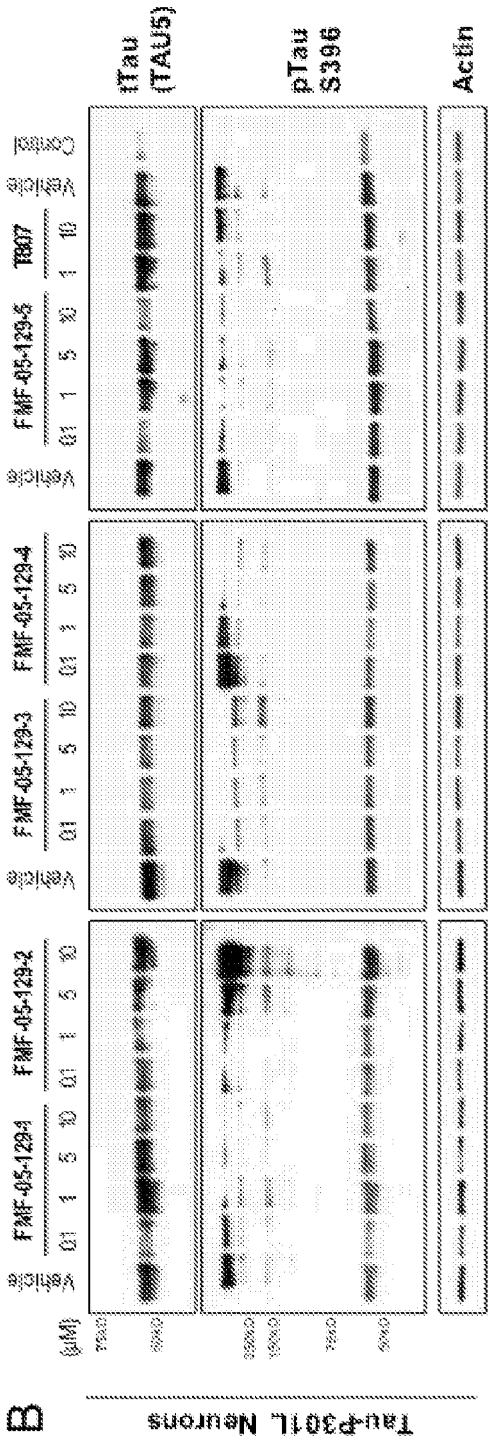
FIG. 9A is a series of western blot stains showing the effect of exemplary compounds and T-807 on levels of tau protein in a human tau-P301L neuronal model, after 24 h treatment. The control is a non-mutant neuron (CTR2-L17-RC2).
Figure 9B:
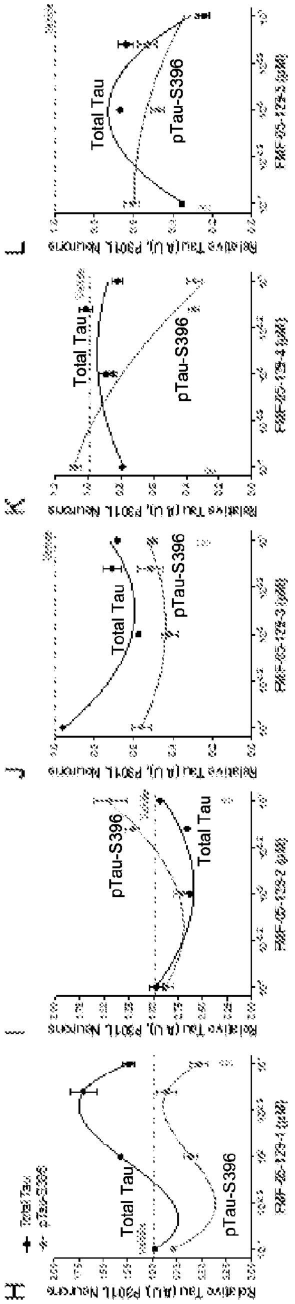
FIG. 9B is a series of graphs quantifying the total tau and hyperphosphorylated tau from the western blots in FIG. 9A.
Figure 10:
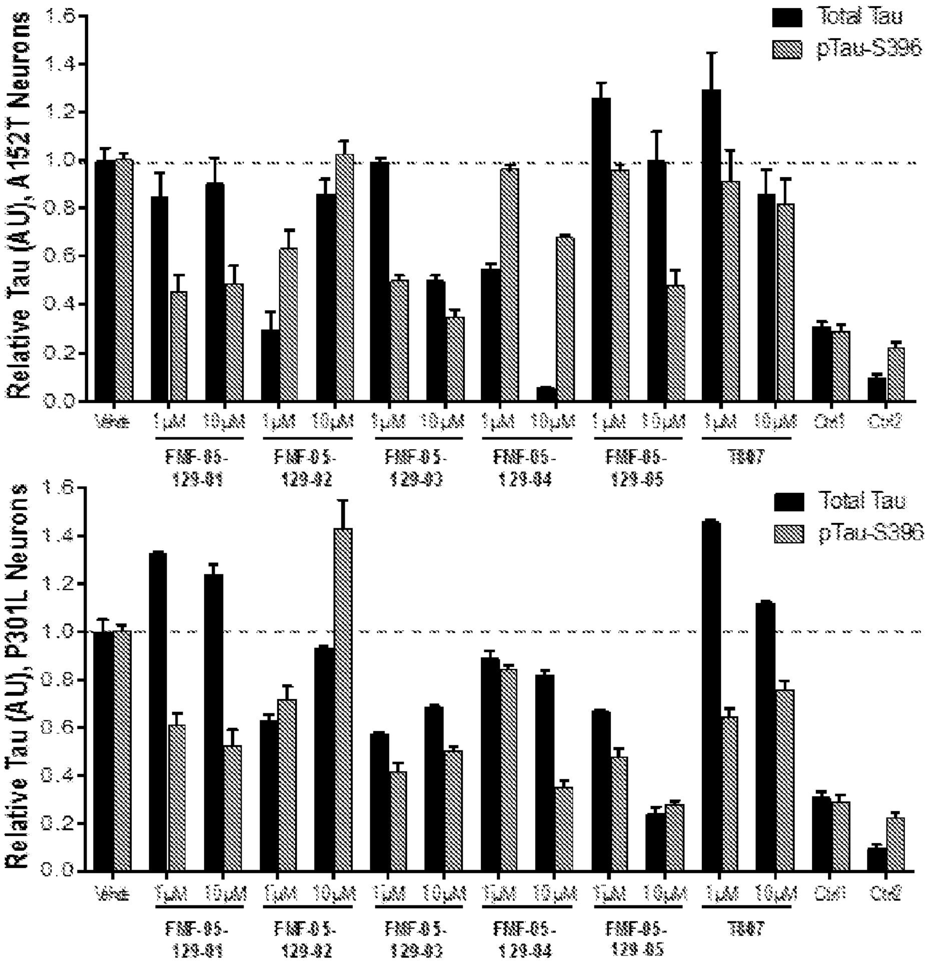
FIG. 10 is a series of bar graphs quantifying the total tau and hyperphosphorylated tau from the western blots in FIGS. 8A and 9A.

Example compounds 2, 3, and 5 were also evaluated for their ability to rescue stress vulnerability in A152T neurons differentiated for 8 weeks. QC-03-075 was employed as negative control. Compound 3 showed that it is effective at rescuing stress vulnerability caused by exposure of neurons to 10 μM β-amyloid (1-42) peptide for 16 h, when these neurons were pre-treated with Compound 3 for 8 h prior to stress exposure (FIG. 7). The results also demonstrated that example Compounds 2, 3, and 5 had no effect on neuronal viability (FIG. 7) as for Silva et al. (*Stem Cell Reports,* 2016, 7(3), 325-40; doi: 10.1016/j.stemcr.2016.08.001) reduction of viability due to β-amyloid (1-42) exposure is dependent on tau levels.

In vivo Assay

To determine whether the compounds of the present disclosure are capable of crossing the blood brain barrier (BBB), a key property for use of these compounds as CNS therapeutics, compound 3 was administered to mice in a pharmacokinetic study of plasma and brain tissue. A stable formulation compatible with chronic administration was prepared prior to administration, and analytical methods for measuring concentration of the compound in plasma and brain tissue were developed. Mice were additionally monitored for tolerability for up to 24 hours.

Animal Husbandry: Male CD-1 mice were group housed during a 2-3 day acclimation prior to the study at an animal room environment with a controlled environment (target conditions: temperature 18-26° C., relative humidity 30-70%, 12 hours artificial light and 12 hours dark). All animals had access to Certified Rodent Diet and water ad libitum.

Formulation & Dosing: Compound 3 (QC-01-175) was formulated at 5.00 mg/mL in 20% PEG400 in water producing a clear, stable solution. For intraperitoneal (IP) dosing, the dose formulation was administered with a dose volume determined by the animals' body weight collected on the morning of dosing day.

Sample Collection & Processing:

Blood Samples: A blood sample (about 0.03 mL per time point) was collected from each mouse into polypropylene tubes at each timepoint. All blood samples were transferred into pre-chilled commercial EDTA-K2 tubes or pre-chilled plastic microcentrifuge tubes containing 2 μL of EDTA-K2 as anti-coagulant and placed on wet ice until centrifugation. Each collected blood sample was centrifuged for 15 minutes at 4° C. and 3000 g for plasma collection. Plasma from each mouse was transferred into a pre-labeled polypropylene tube in dry ice at each time point. After terminal collection, all plasmas were stored at approximately −80° C. until bioanalysis.

Brain Samples: Whole brain was dissected at each designated time point and rinsed twice cold in deionized water before processing. They were then blotted on filter paper, weighed and homogenized with 5-fold of cold 15 mM PBS/MeOH (V:V, 2:1) using mechanical method. The samples were kept with ice water when homogenizing, and further stored at −80° C. until bioanalysis.

Bioanalytical Method Development: A LC-MS/MS method was developed and used for the quantitative determination of test compound concentration in blood and brain with a calibration curve applied to determine the limits of quantification.

In Vivo Sample Analysis: Plasma and brain concentration versus time data along with $C^{max}$, $T_{max}$, $T_{1/2}$, and $AUC_{(0-t)}$ was analyzed by non-compartmental approaches using the Phoenix WinNonlin 6.3 software program.

Results: As summarized in Table 3, Compound 3 was capable of brain penetration when systemically administered to male CD-1 mice via intraperitoneal injection (n=3 per group) at a dose of 30 mg/kg in a vehicle of 20% PEG400/water. Additionally, mice were monitored for up to 24 hours and no adverse effects were observed.

TABLE 3

In vivo pharmacokinetic profile of compound 3

| | Mean Plasma | Mean Brain |
|---|---|---|
| $C_{max}$ (ng/mL) | 4640 | 56.4 |
| $T_{max}$ (h) | 1.00 | 0.500 |
| $T_{1/2}$ (h) | 7.23 | 0.766 |
| $AUC_{0-last}$ (ng · h/mL) | 6938 | 74.3 |

Compound 3 was well tolerated and is capable of crossing the blood-brain barrier. The dose achieved in brain is within the concentration range estimated from the ex vivo cellular studies to allow efficient tau degradation.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound having a structure:

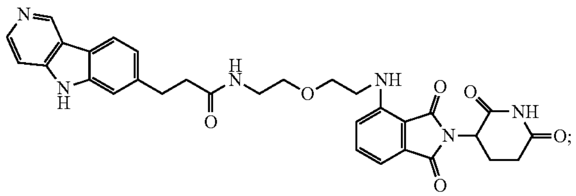

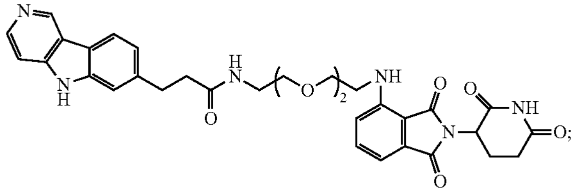

-continued

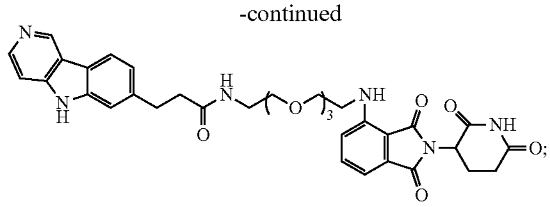

; or

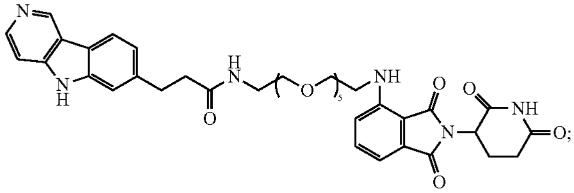

;

or a pharmaceutically acceptable salt thereof.

2. A radiolabeled compound comprising the compound of claim 1, or a pharmaceutically acceptable salt thereof, enriched with a radionuclide.

3. A pharmaceutical composition comprising a compound of claim 1, or a pharmaceutically acceptable salt thereof, and a pharmaceutically acceptable excipient.

4. A method of treating a neurological disorder in a subject in need thereof, the method comprising administering a compound of claim 1, or a pharmaceutically acceptable salt thereof, to the subject in need thereof.

5. The method of claim 4, wherein the neurological disorder is a neurodegenerative disease.

6. The method of claim 5, wherein the neurodegenerative disease is a tauopathy.

7. The method of claim 6, wherein the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, lipofuscinosis, Huntington's disease, Alzheimer's disease, or argyrophilic grain disease.

8. A method of promoting the degradation of tau protein in a subject in need thereof, the method comprising administering a compound of claim 1, or a pharmaceutically acceptable salt thereof, to the subject in need thereof.

9. A method of detecting a neurological disorder, the method comprising contacting a compound of claim 2, or a pharmaceutically acceptable salt thereof, with a tissue.

10. A method of detecting pathological aggregation of tau protein, the method contacting a compound of claim 2, or a pharmaceutically acceptable salt thereof, with a tissue.

11. A method of diagnosing a neurological disorder in a subject, the method comprising contacting a compound of claim 2, or a pharmaceutically acceptable salt thereof, with a tissue of the subject.

12. The method of claim 9, wherein the tissue is tissue of the central nervous system.

13. The method of claim 12, wherein the tissue of the central nervous system is brain tissue.

* * * * *